United States Patent
Anthony

(10) Patent No.: US 6,609,523 B1
(45) Date of Patent: Aug. 26, 2003

(54) COMPUTER BASED BUSINESS MODEL FOR A STATISTICAL METHOD FOR THE DIAGNOSIS AND TREATMENT OF BPPV

(76) Inventor: Philip F. Anthony, 901 Hemphill, Fort Worth, TX (US) 76104

( * ) Notice: Subject to any disclaimer, the term of this patent is extended or adjusted under 35 U.S.C. 154(b) by 287 days.

(21) Appl. No.: 09/695,600

(22) Filed: Oct. 24, 2000

Related U.S. Application Data

(63) Continuation-in-part of application No. 09/570,002, filed on May 12, 2000, now abandoned.
(60) Provisional application No. 60/175,554, filed on Jan. 11, 2000, and provisional application No. 60/161,426, filed on Oct. 26, 1999.

(51) Int. Cl.[7] .............................................. A61B 19/00

(52) U.S. Cl. ..................................................... 128/897

(58) Field of Search ..................... 128/897–98; 600/300, 600/301

(56) References Cited

U.S. PATENT DOCUMENTS

| | | | |
|---|---|---|---|
| 4,984,579 A | * 1/1991 | Burgert et al. ............... | 128/897 |
| 5,471,382 A | 11/1995 | Tallman et al. | |
| 5,660,176 A | 8/1997 | Iliff | |
| 5,764,923 A | 6/1998 | Tallman et al. | |
| 6,029,670 A | * 2/2000 | Anthony ..................... | 128/897 |

OTHER PUBLICATIONS

Fife T: Recognition and Management of Horizontal Canal Benign Positional Vertigo. Am J Otolaryngology 19:345–351, 1998.
Takegoshi H, Ito K, Mizuno M, Mizutani J. Horizontal variant of benign paroxysmal positional vertigo. Equilibrium Research (Japan) 1996;55:12–9.
Brandt T, Daroff R., Physical Therapy for Benign Paroxysmal Positional Vertigo. Arch. Otolaryng 106: Aug., 1980, pp. 484–485.
Semont A, Freyss G, Vitte E. Curing BPPV with a liberatory maneuver. Adv. Otorhinolaryng 1988; 42:290–3.
Norre M. Rational of Rehabilitation Treatment for Vertigo. Am J Otol,8:31–35, 198.
Norre M. Rehabilitation Treatment for Vertigo and Related Syndromes. CRC Critical Reviews of Physical Medicine, 2:101–120, 1990.
Norre M and Beckers, A. Vestibular Habituation Training. Specificity of Adequate Exercise. Arch Otolaryng Head Neck Surgery, 114:883–886, 1988.
Epley J. Caveats in particle repositioning for treatment of canalithiasis (BPPV), Operative Techniques in Otolaryngology–Head and Neck Surgery vol. 8, No. 2 (Jun.) 1997, pp. 68–76.
Epley J. The canalith repositioning procedure: For treatment of benign paroxysmal positional vertigo. Otolaryngology Head and Neck Surgery 107:3 Sep. 1992, pp. 399–404.

Harvey S, Hain T, Adameic J. Modified Liberatory Maneuver: Effective Treatment for Benign Paroxysmal Positional Vertigo Laryngoscope 104 Oct., 1994, pp. 1206–1212.
Katsarkas A. Paroxysmal Positional Vertigo: An Overview and the deposits repositioning maneuver. Am J Otolaryngology 16:6, pp. 725–730.
Lempert T, Wolsley C, Davies R, Gresty M, Bronstein A. Three hundred sixty–degree rotation of posterior semicircular canal for treatment of benign positional vertigo: A placebo–controlled trial. Neurology 49;Sep. 97, pp, 729–33.
McClure J. Horizontal canal BPV. The Jour Otolaryng 14:130–135.
Nutti D, Vannucchi P, Pagnini O. Benign Paroxysmal Positional Vertigo of the Horizontal Canal: a form of canalithiasis with variable clinical features. J Vestib Res 1996;6:176–84.
Herdman S. Treatment of Benign Paroxysmal Positional Vertigo. Physical Therapy 70:6 Jun. 1990:381–388.
Jacobson GP,Newman CW. The development of the Dizziness Handicap Inventory. Arch Otolaryngol Head Neck Surg vol. 116, Apr. 1990 pp 424–427.
Fielder H, Denholm SW, Lyons RA, Fielder CP. Measurement of health status in patients with vertigo. Clinics of Otolaryngology 1996;21:122–126.
McKenna L, Hallam RS, Hinchcliffe R. Clinics of Otolaryngology 1991;16:452–456. The problems of psychological disturbance in neurotology patients.
Goldberg D (1978). Manual of the General Health Questionnaire. National Foundation for Educational Research Slough (Apparently a British general health questionnaire).

(List continued on next page.)

Primary Examiner—John P. Lacyk
(74) Attorney, Agent, or Firm—Arthur F Zobal

(57) ABSTRACT

A computational statistical determination is made as to whether a person suffers from benign paroxysmal positional vertigo (BPPV) based upon answers provided by a person to questions stored in a computer. The person answers questions about the characteristics of his or her vertigo, dizziness or imbalance symptoms. Based on proprietary information about the predictive value of each question, and the relationships between the questions, the person is given a statement of the chance of his or her having BPPV which would be responsive to a head maneuver designed to clear gravity sensitive crystals from a sensitive semicircular canal (SCC) area to a less sensitive area of the inner ear. Based on this determination, the person 1) is offered for sale an apparatus for further diagnosis and an apparatus to relieve his BPPV symptoms by self-treatment or 2) he may be told to go to a healthcare provider for treatment. For self-treatment, the 1) apparatus guides the person's head positioning to allow the diagnosis of which SCC is involved (if the user provided question answers do not specifically indicate the involved SCC), and 2) guide the person's head through a head maneuver to clear the gravity sensitive crystals from the position sensitive SCC to a less sensitive area of the inner ear.

14 Claims, 156 Drawing Sheets-

OTHER PUBLICATIONS

Yardley L, Owen N, Nazareth I, Luxon L. The prevalence and presentation of dizziness in a general practice community sample of working age people. British Journal of General Practice 1998;48:1131–1135.

Abu–Arafeh I, Russell G. Paroxysmal vertigo as a migraine equivalent in children: a population based study. The Journal Cephalgia 1995;15:22–25. Oslo.

Honrubia V, Bell TS, Harris MR, Baloh RW, Fische LM. Quantitative evaluation of dizziness characeristics and impact on quality of life. American Journal of Otology 1996;17:595–602.

Savundra PA, Sutherland R, Freeman J, Carter J, Coelho A, Davies RA, Luxon LN. Cawthorne–Cooksey exercises in relaxation therapy in the management of vertigo due to labyrinthine dysfunction. Journal of Audiology and Medicine in Press 1997.

Busis S. Neurotologic diagnoses. Acta Otolaryngologica (Stockholm). Supplement 209, 1965. (FAX'ed req to cpy whole thing on Nov. 29, 1999 to circ desk).

Sheehy JL. The dizzy patient. Archives of Otolaryngol 1967;86:44–45.

Mira E, Buizza A, Magenes G, Manfrin M, Schmid R. Expert systems as diagnostic aid in otoneurology. Otorhinolaryngology (Journal of for Oto–Rhino–Laryngology and Its Related Specialties.) 1990;52:96–103.

Mira E, Schmid R, Zanocco P, et al: Nouveaux supports informatises a l'exploration de la fonction vestibulaire. II. Un systeme expert pour la classification des vertiges. Acta Oto–Rhino–Laryng Belg 1987;41:1010–1020.

Schmid R, Zanocco P, Buizza A, et al: An Expert system for the classification of dizziness and vertigo; in Fox J, Fieschi M, Engelbrecht R (eds): AIME 87, Lecture Notes in Medical Informatics, Berlin, Springer, 1987, vol. 33, pp 45–53.

Mira E, Schmidt R, Zanocco P, Buizza A, Magenes G, Manfrin M. A computer based consultation system (Expert system) for the classification and diagnosis of dizziness. Advances in Oto–Rhino–Laryngology 1988;42:77–80.

Auramo Y, Juloha M, Pyykko I. The expert system for the computer aided diagnosis of dizziness and vertigo. Medical Informatics 1993; 18,#4:293–305.

Kentala E, Pyykko Y, Auramo Y, Juhola M. Reasoning in Expert System ONE for Vertigo Work Up. Acta Otolaryngol (Stockh) 1995; Suppl 520: 207–208.

Kentala E. Characteristics of Six Otologic Diseases Involving Vertigo. Am J Otol. 1996;17:883–892.

Gavilan C, Gallegro J, Gavilan J. 1990, Carrusel: An expert system for vestibular disorders. Acta Otolaryngologica, 110, 161–167. (ask Linda at TCOM interlibrary loans to reorder on Nov. 29, 1999).

* cited by examiner

Fig. 53
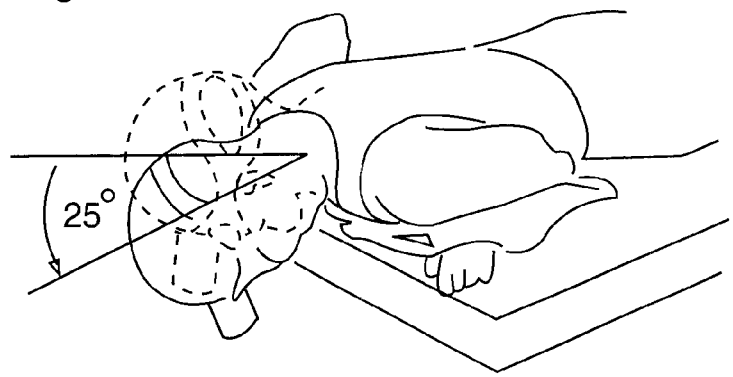
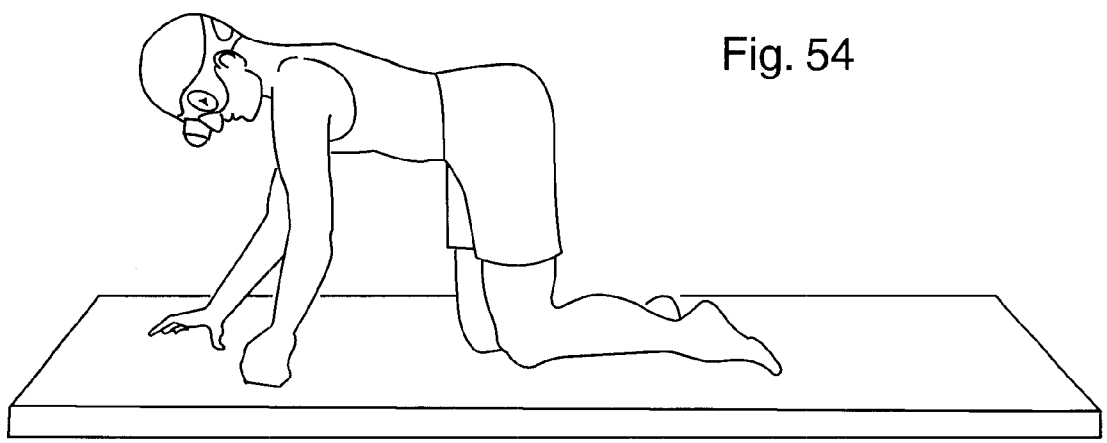
Fig. 54

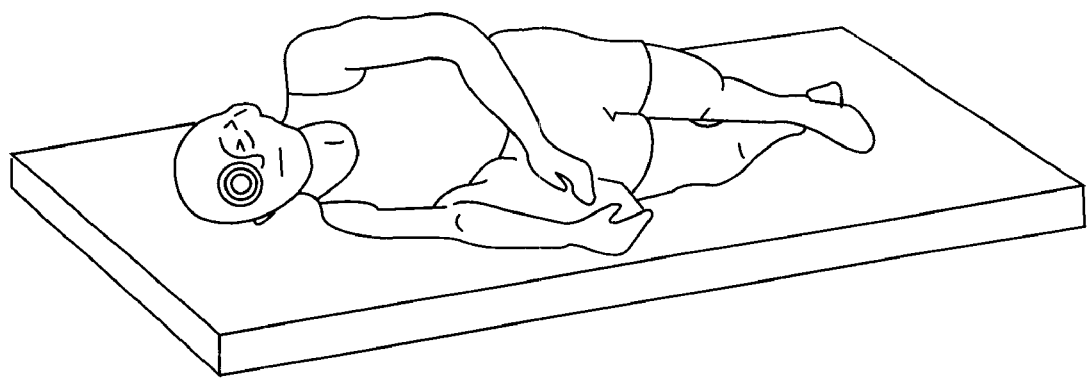
Fig. 66
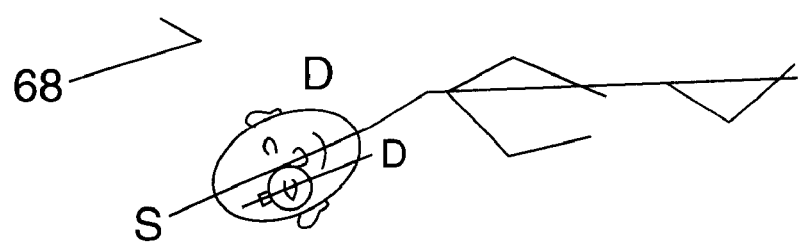
Fig. 67

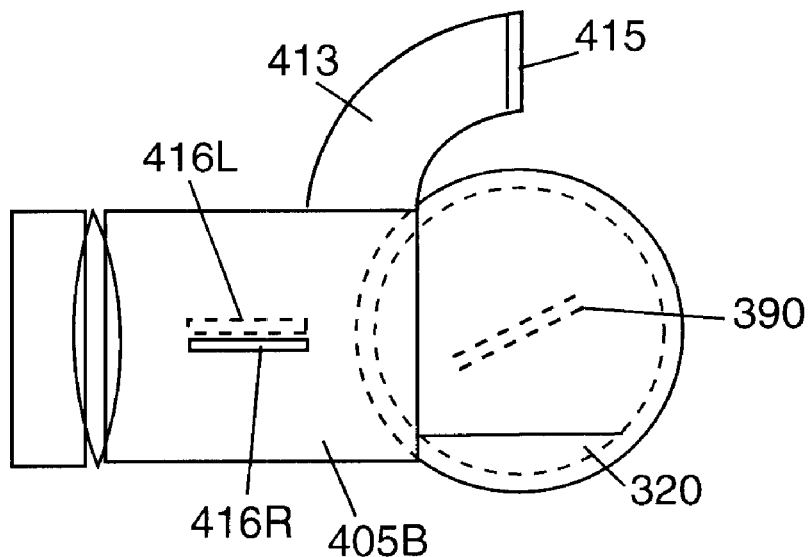
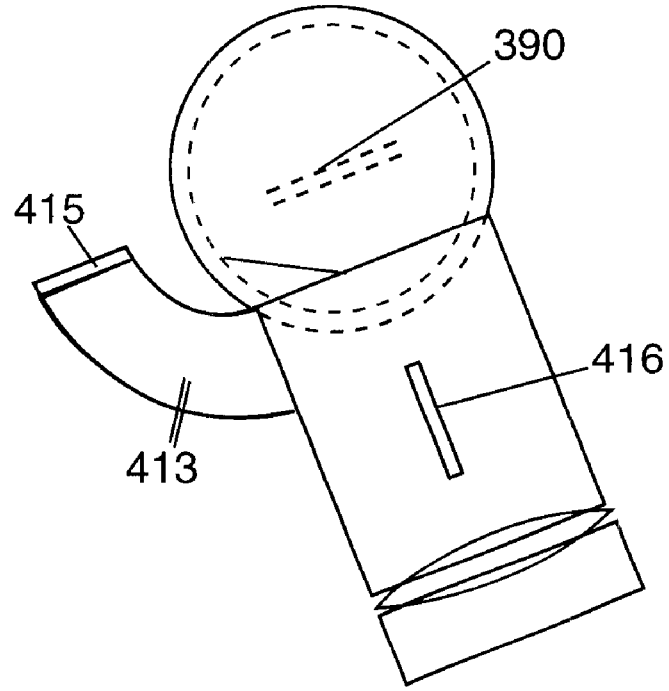

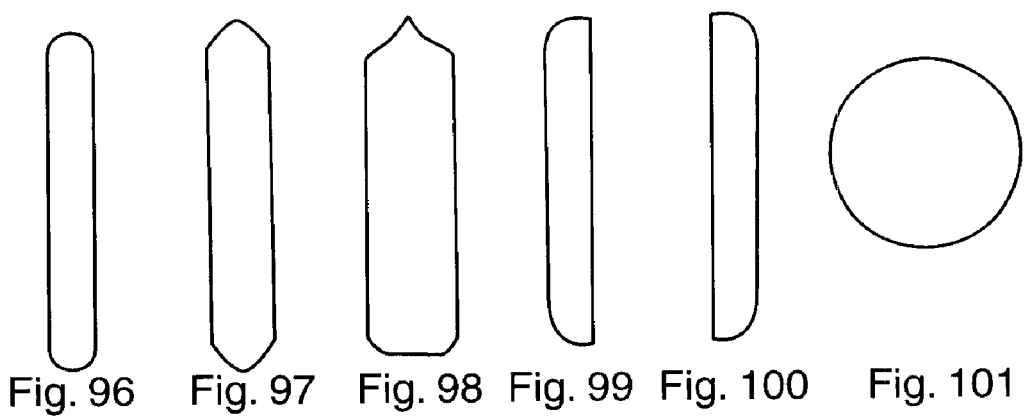
Fig. 96  Fig. 97  Fig. 98  Fig. 99  Fig. 100  Fig. 101
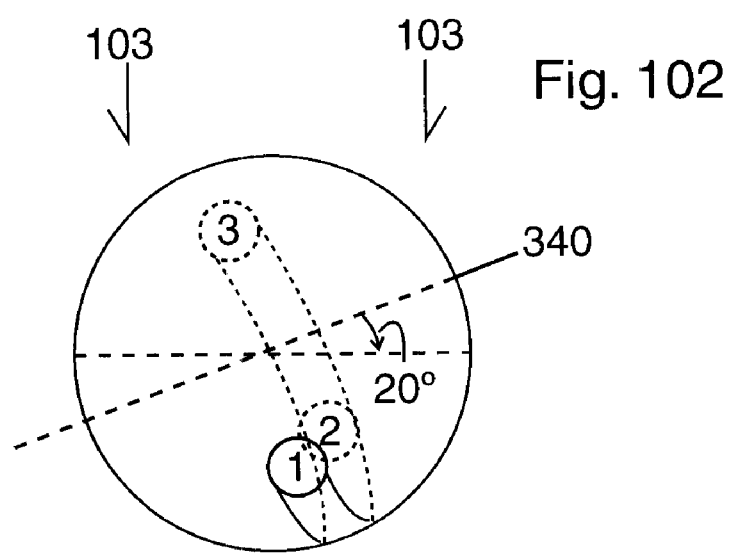

Fig.138
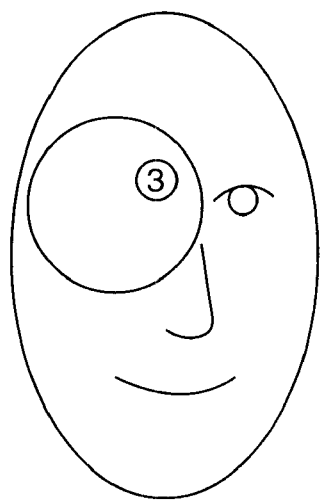
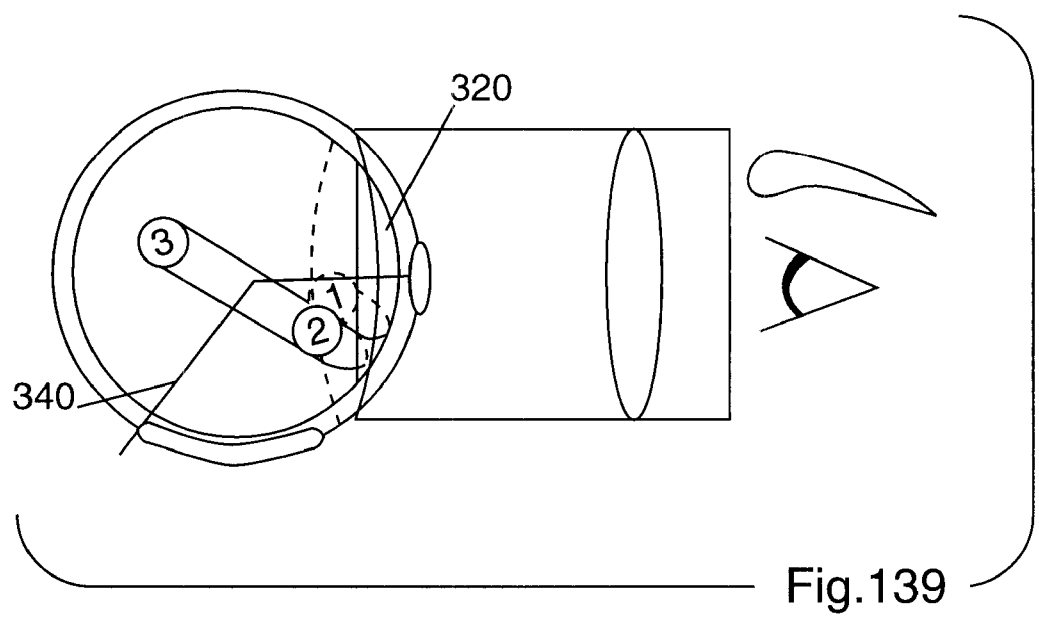
Fig.139

Fig. 149
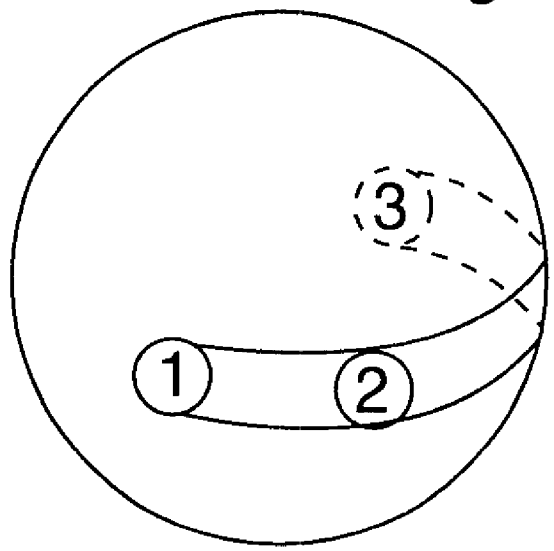
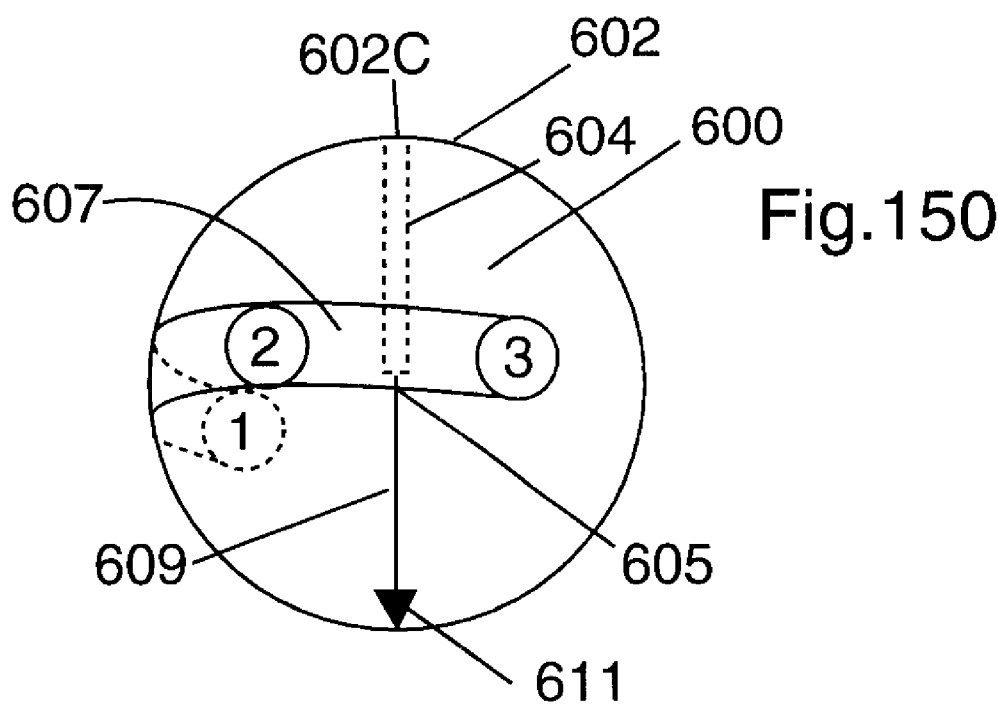
Fig. 150

Fig. 157
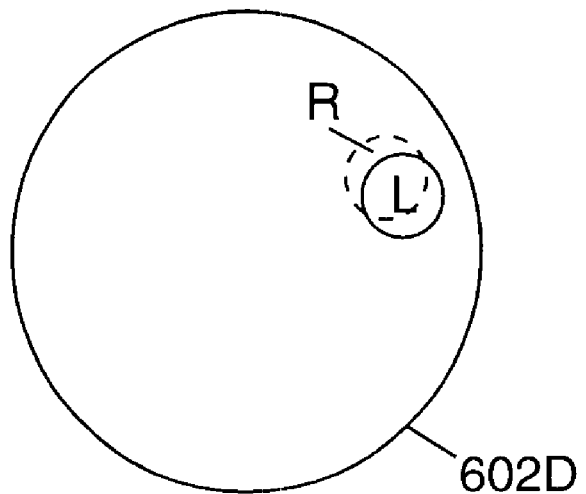
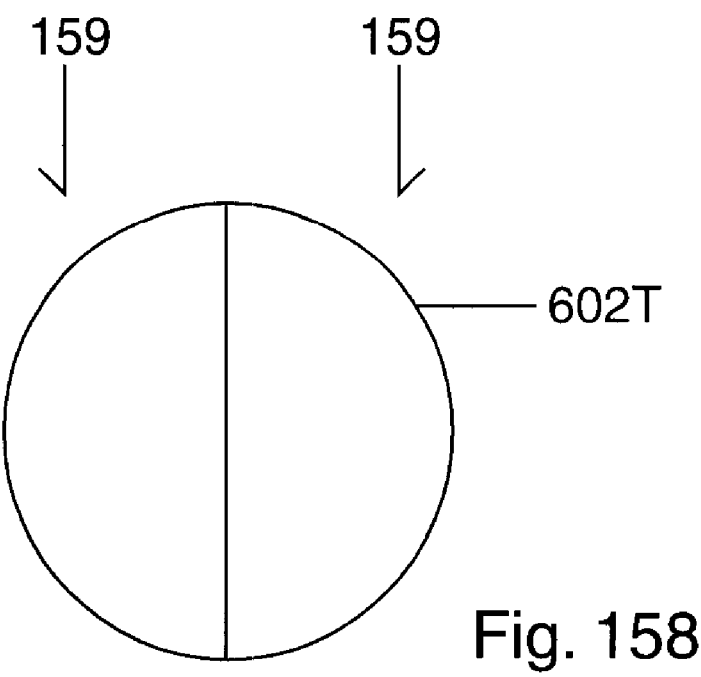
Fig. 158

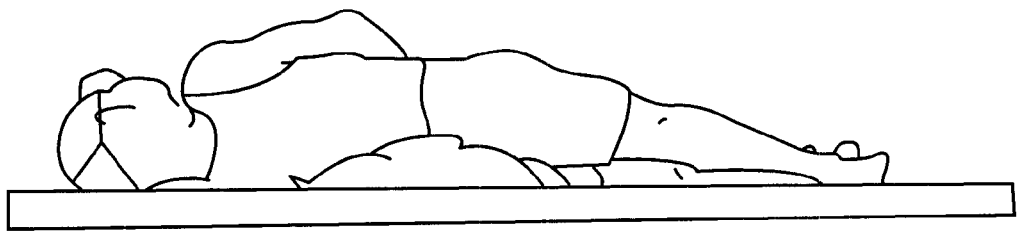
Fig. 207A
Fig. 207B
Fig. 208A
Fig. 208B

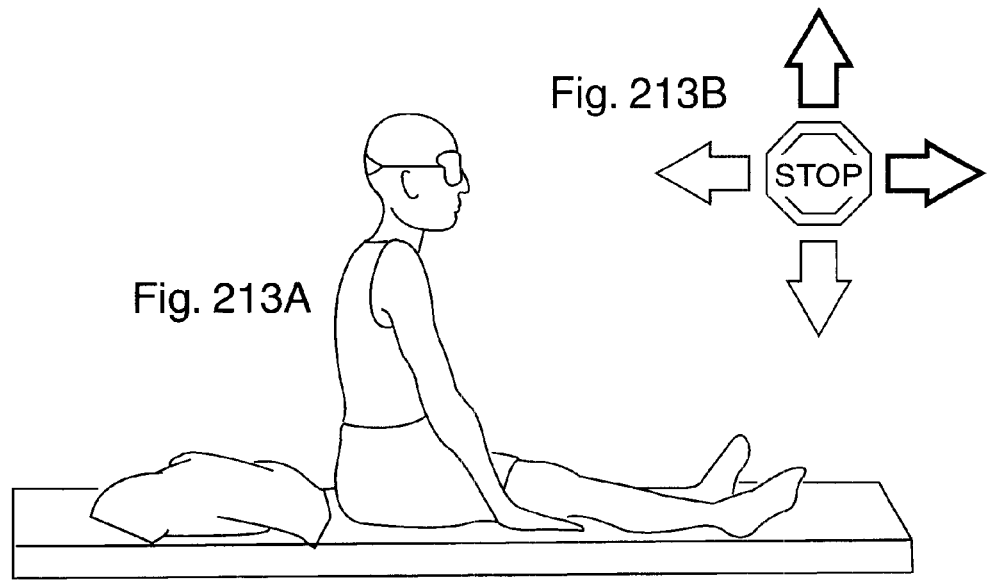
Fig. 213B
Fig. 213A
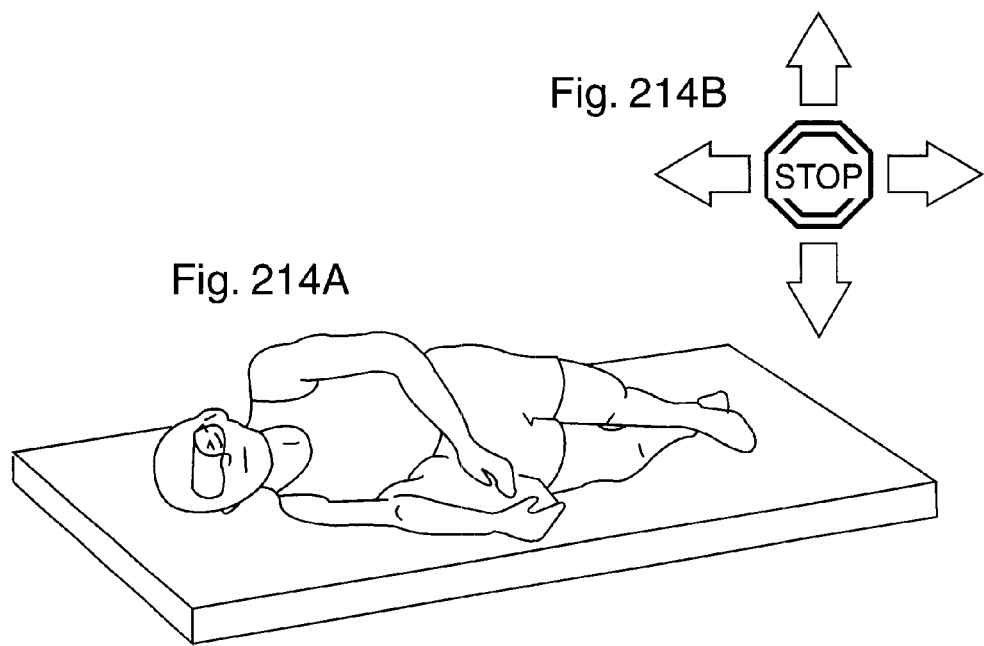
Fig. 214B
Fig. 214A

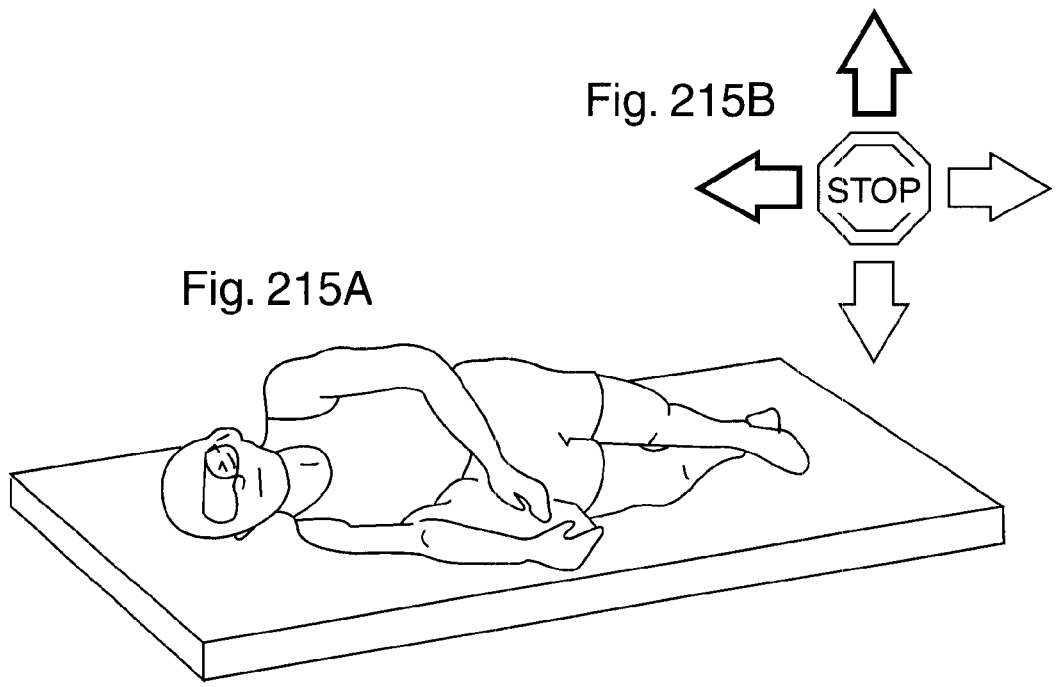
Fig. 215B
Fig. 215A
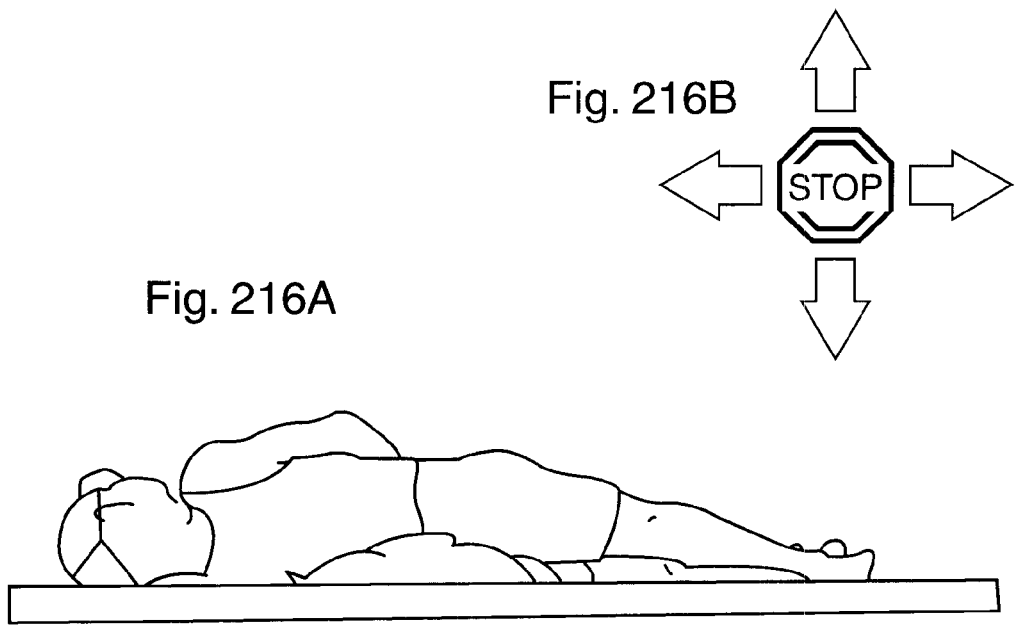
Fig. 216B
Fig. 216A

Fig. 217A
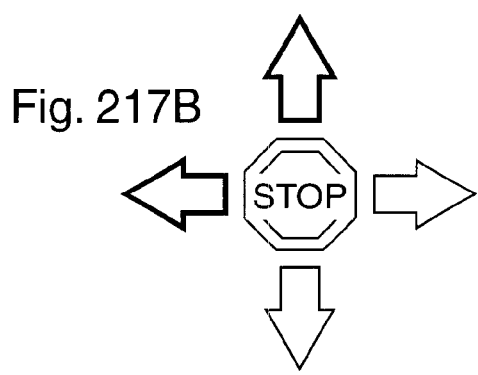
Fig. 217B
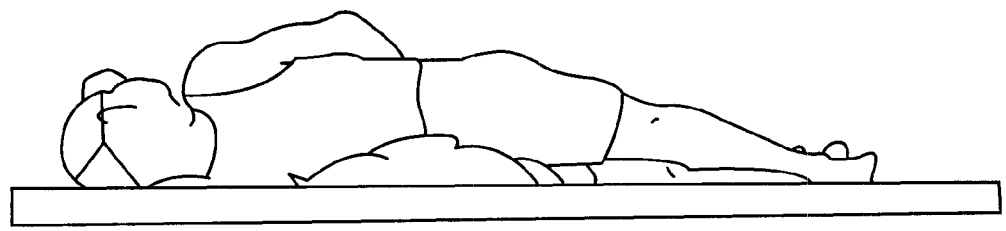
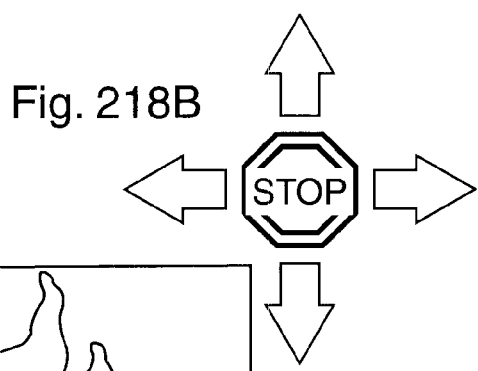
Fig. 218B
Fig. 218A
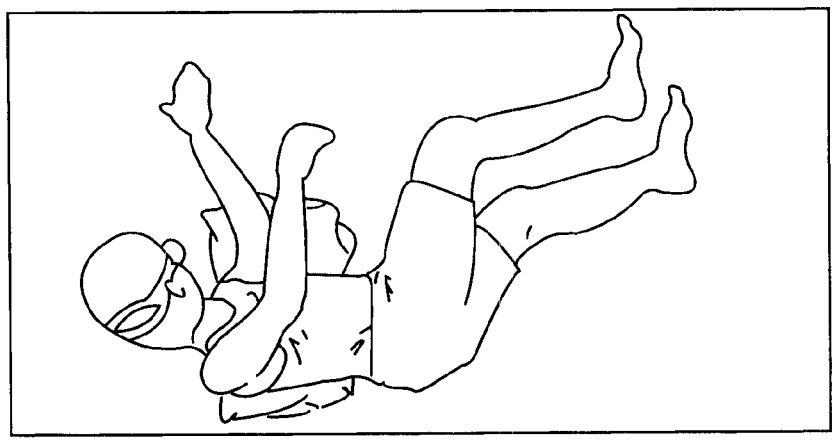

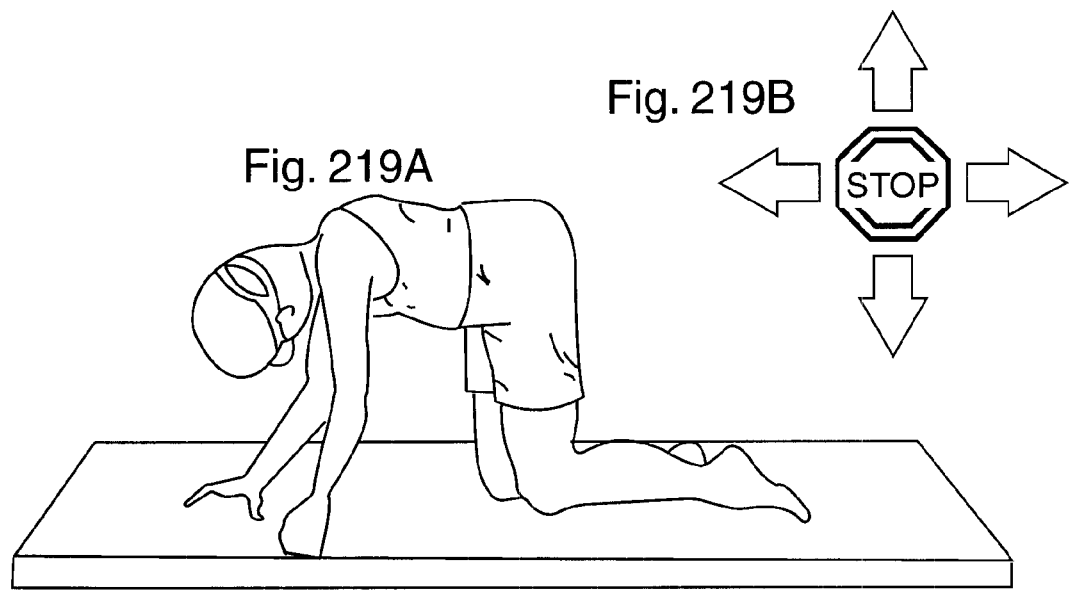
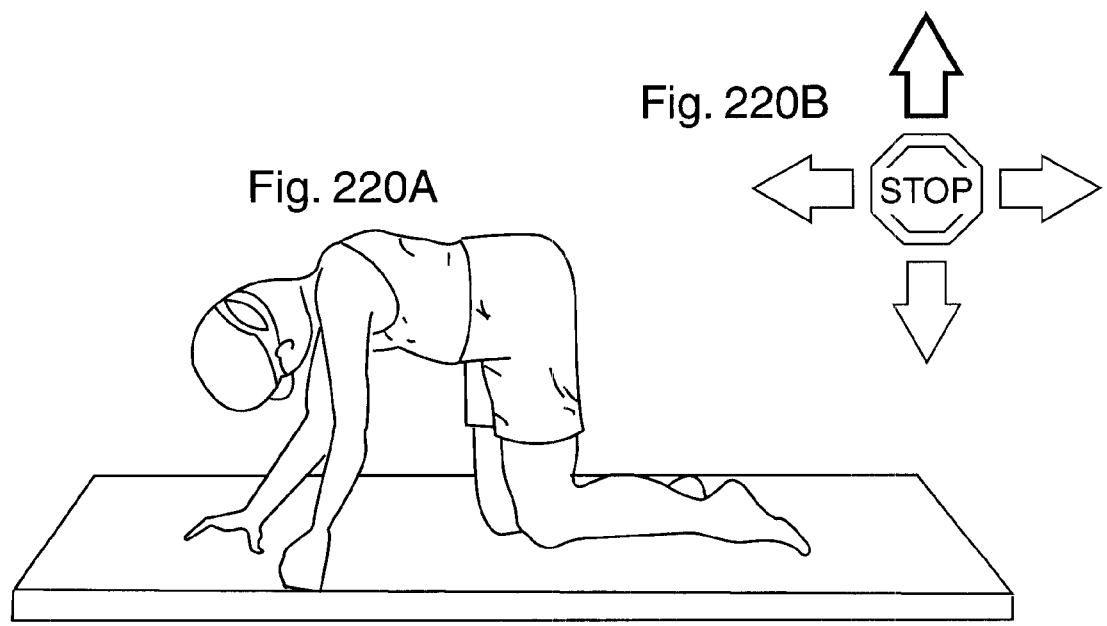

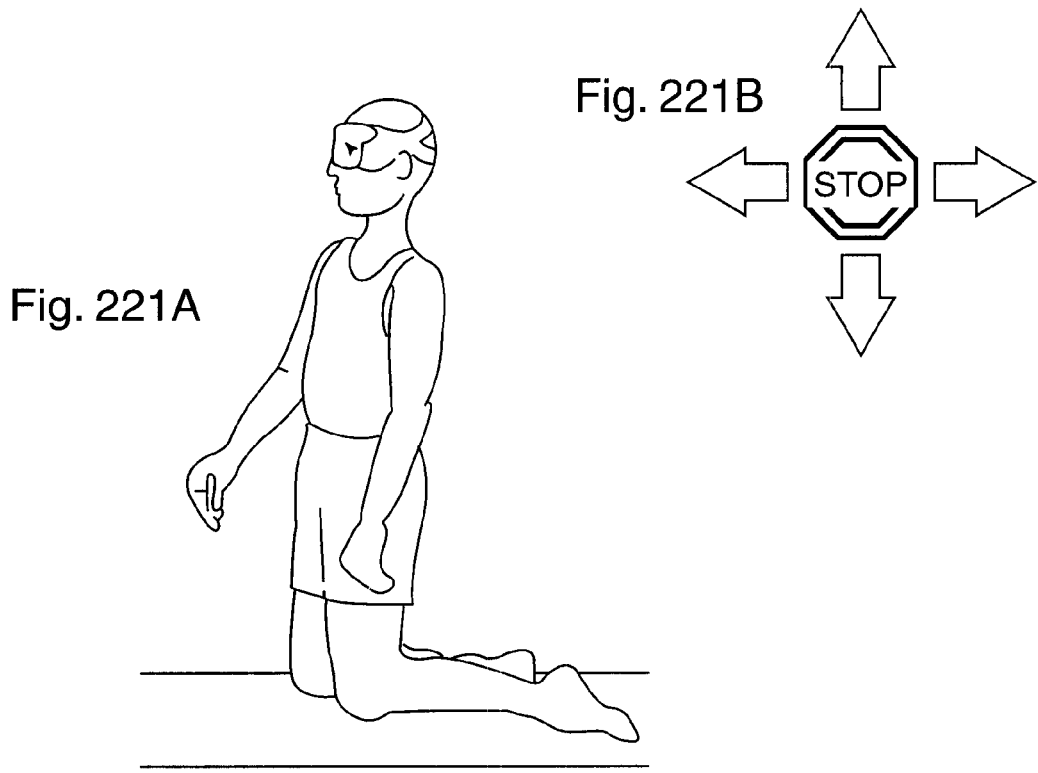
Fig. 221A
Fig. 221B
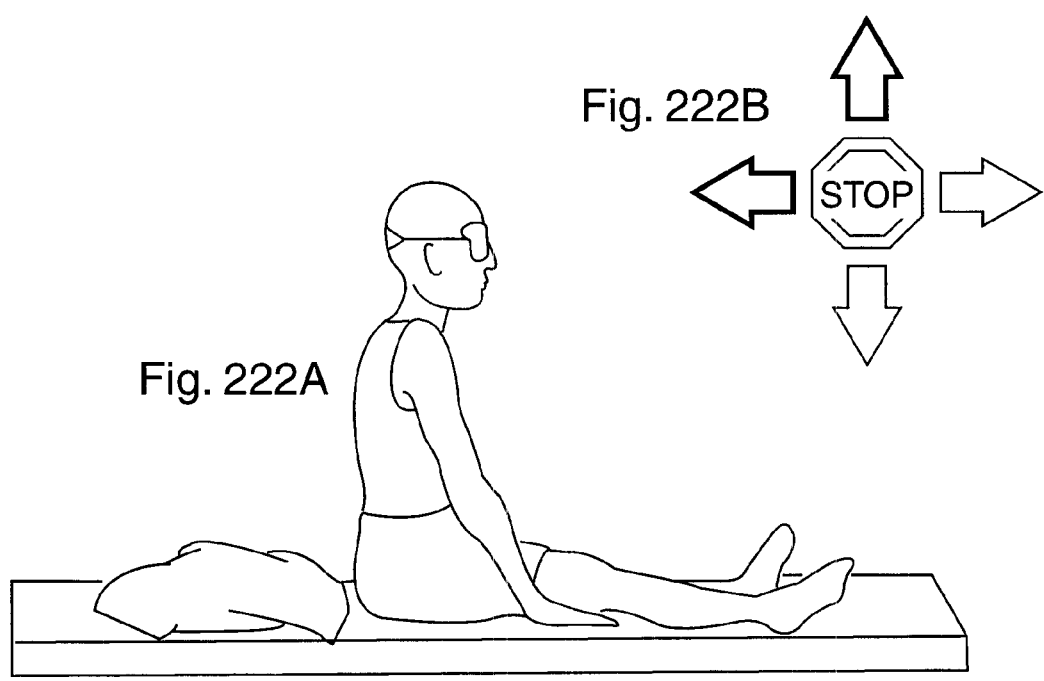
Fig. 222A
Fig. 222B

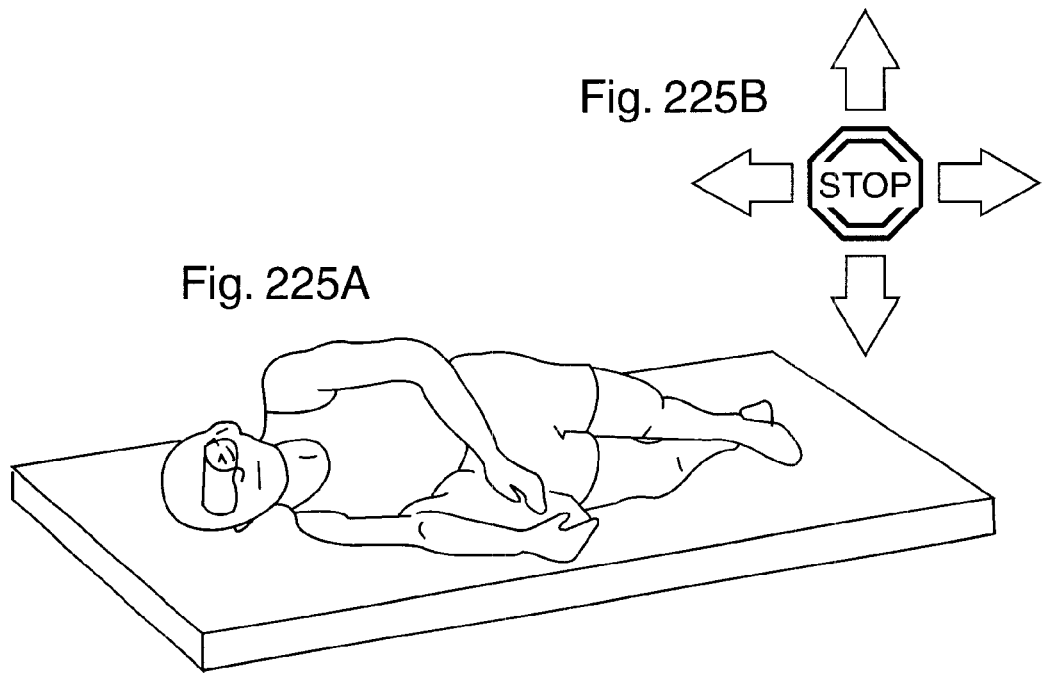
Fig. 225B
Fig. 225A
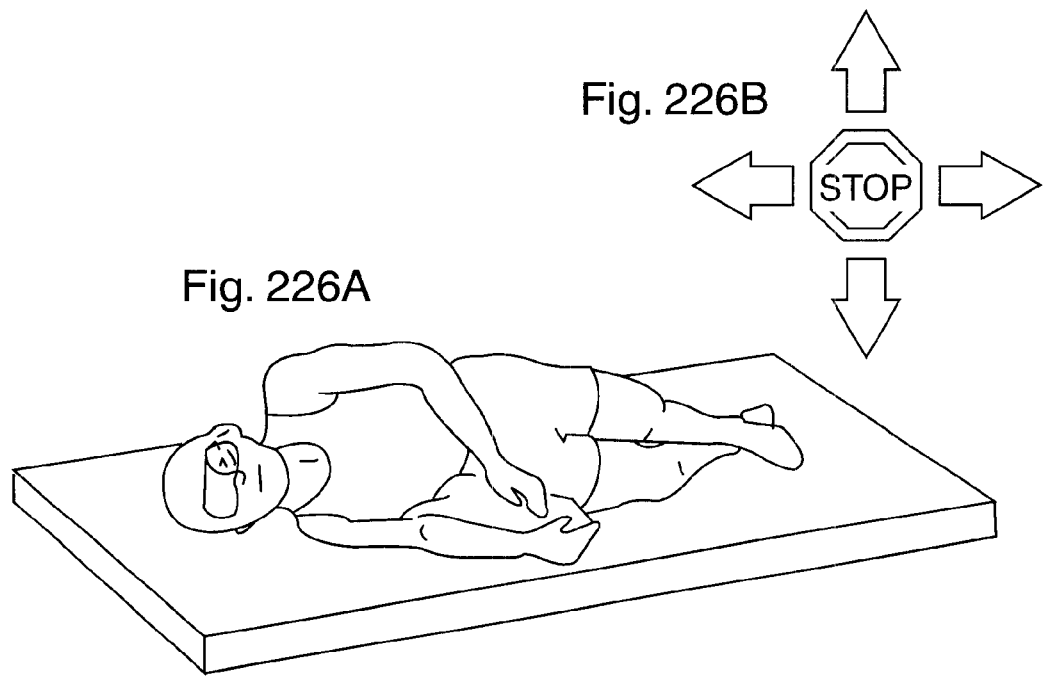
Fig. 226B
Fig. 226A

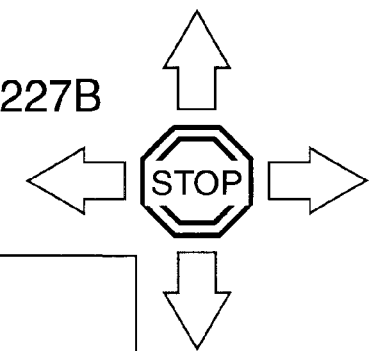
Fig. 227B
Fig. 227A
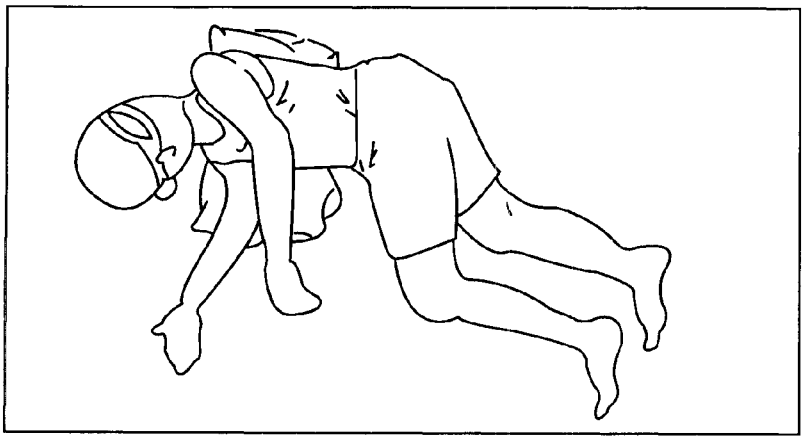
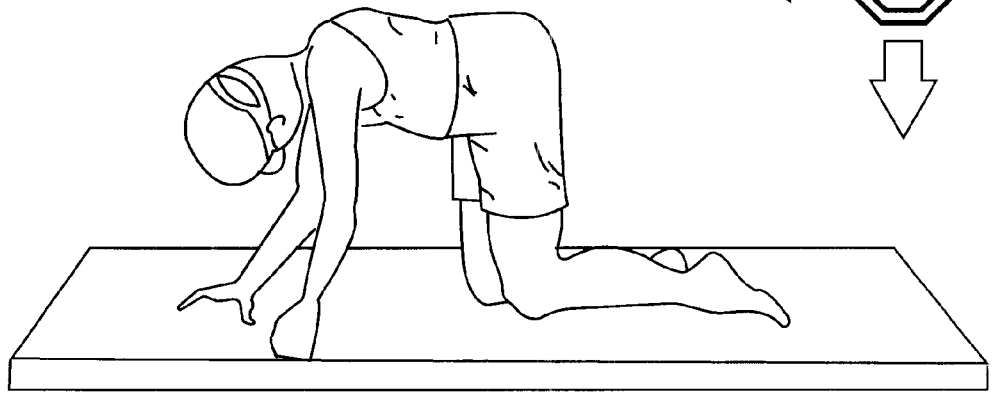
Fig. 228A
Fig. 228B

NINETY DEGREE CALIBRATION

Two Hundred Seventy ( Minus Ninety) Degree Calibration

Fig. 234A
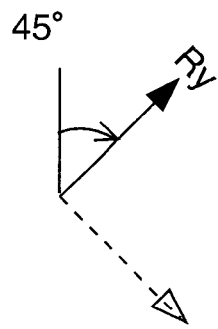
Forty Five Degree Calibration
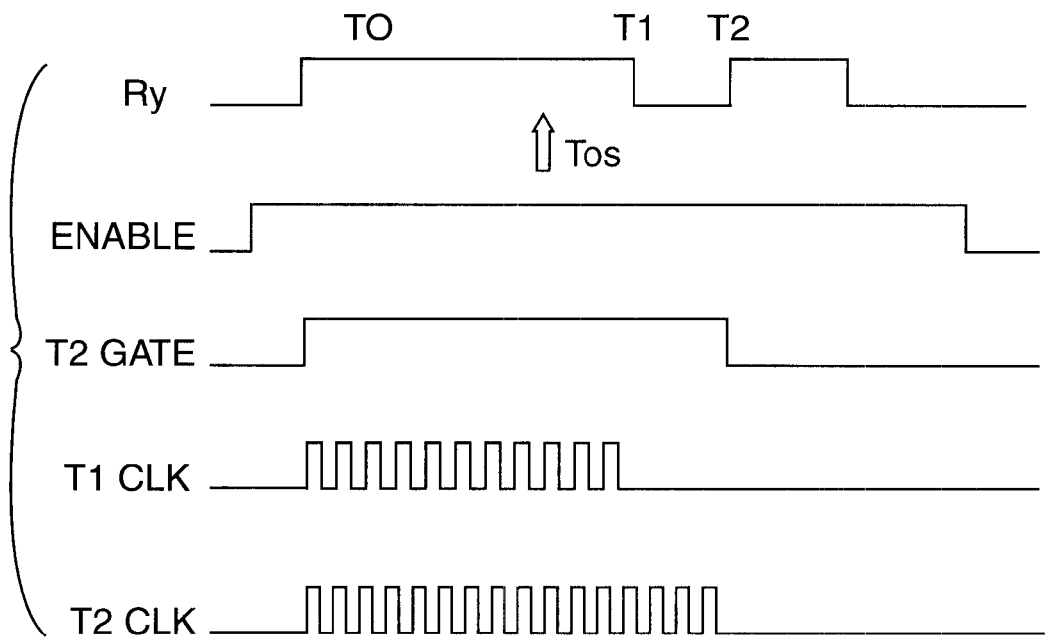
Fig. 234B

335 Degree Calculation

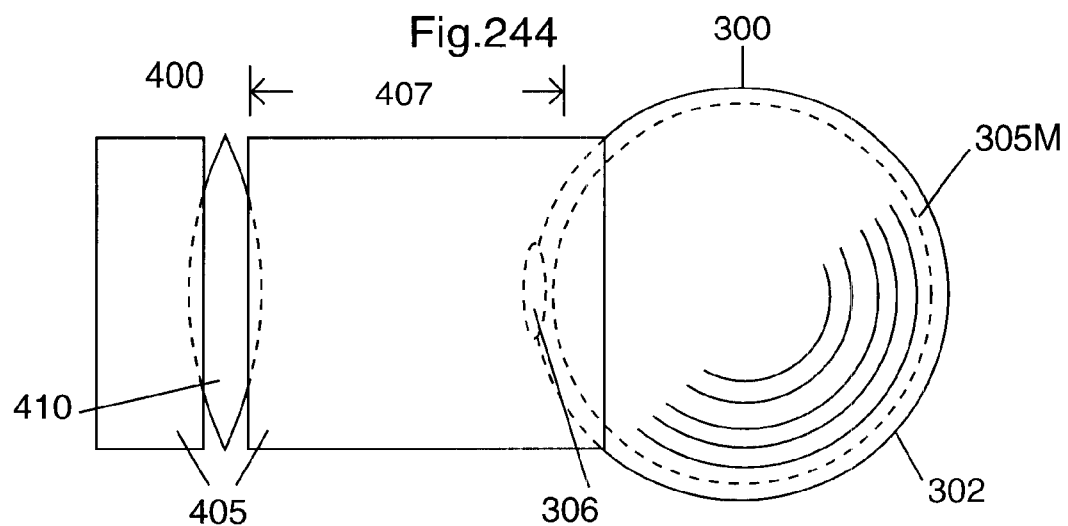
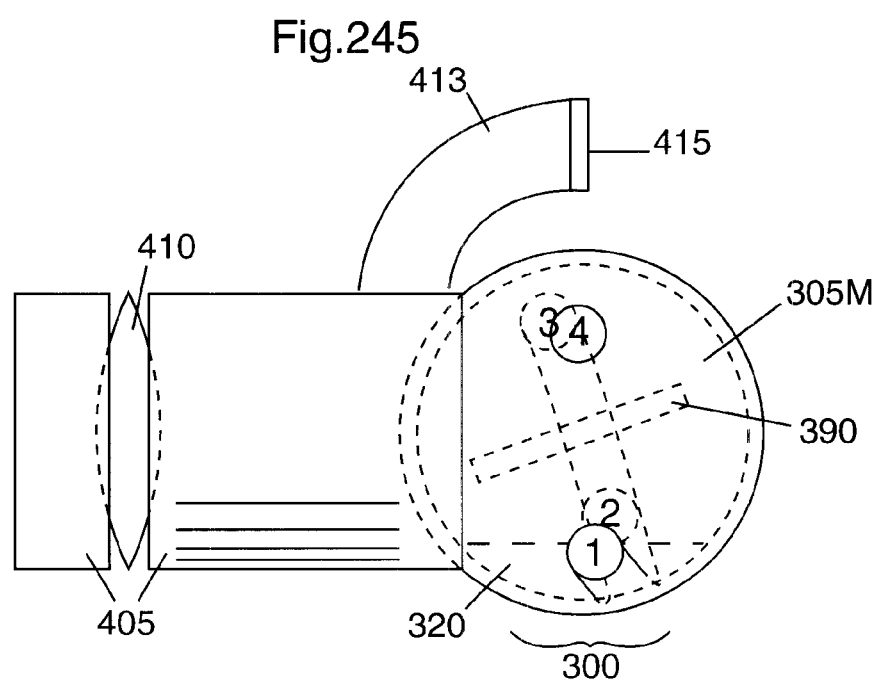

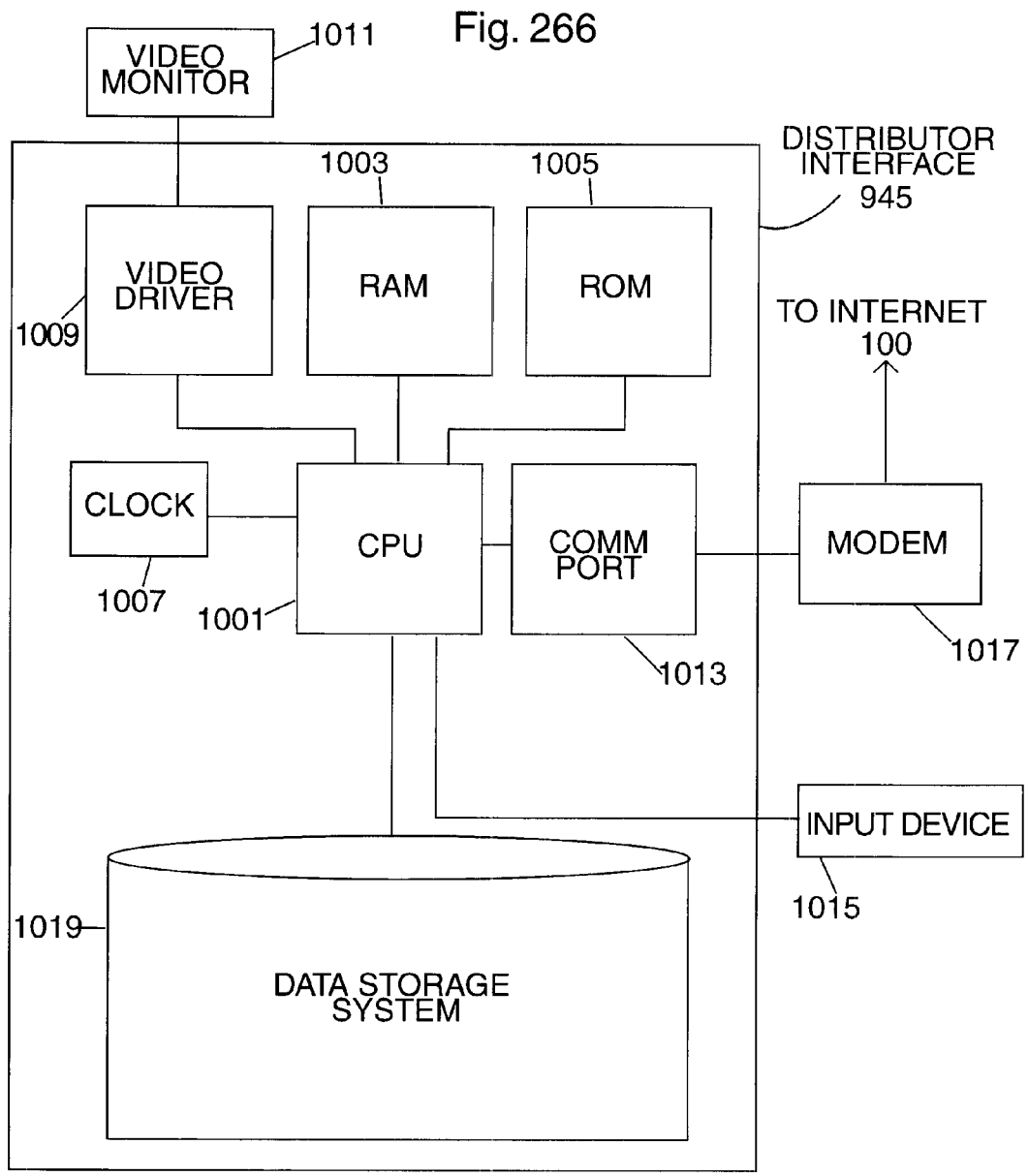

COMPUTER BASED BUSINESS MODEL FOR A STATISTICAL METHOD FOR THE DIAGNOSIS AND TREATMENT OF BPPV

This application is a continuation-in-part of U.S. application Ser. No. 09/570,002, entitled 3 Dimensional Head Apparatus, and Method For The Treatment Of BPPV, filed on May 12, 2000, now abandoned, and this application also claims the benefit of U.S. provisional application No. 60/175,554, filed Jan. 11, 2000 and entitled 3 Dimensional Head Apparatus For The Treatment Of BPPV, and of U.S. provisional application No. 60/161,426, filed Oct. 26, 1999, entitled 3 Dimensional Head Compass For The Treatment Of BPPV.

BACKGROUND OF THE INVENTION

1. Field of the Invention

The invention relates to a business based model for the diagnosis of BPPV and the sale of devices for the diagnosis and treatment of BPPV.

2. Background

BPPV

BPPV is classically used to refer to vertigo caused by loosened otoconia crystals in the posterior semicircular canal, the most common inner ear semicircular canal effected by loosened otoconia. To those trained in the art, given the current understanding of the pathophysiology of BPPV, the definition of BPPV is positional vertigo caused by loosened crystals in any of the membranous semicircular canals moving in response to gravity. This more generalized definition is the one used in this application. I will refer to classic posterior semicircular canal positional vertigo as posterior BPPV or PBPPV, horizontal BPPV as HBPPV and superior semicircular canal BPPV as SBPPV.

Pathophysiology of BPPV

BPPV is caused by 1) naturally occurring calcium carbonate crystals becoming dislodged and falling from their normally occurring position on the utricular macula and 2) a significant number of the crystals coming to be located in a membranous semicircular canal. When the patient places the head such that a particular semicircular canal is vertical, the loosened crystal(s) causes motion of the rotation sensor causing the patient to sense vertigo. These symptoms typically resolve when the loosened crystal dissolves in the surrounding endolymphatic fluid. If the loosened crystals can be moved out of the affected membranous SCC then the patient symptoms are markedly decreased or resolved.

Incidence of BPPV 90 million Americans (42% of the population) will experience vertigo some time in their life. Approximately three million people of the 250 million people in the US suffer some vertigo each year. Vertigo is the most common physician visit diagnosis in patients over 65 years of age. Seventeen percent of patients who have dizziness have benign paroxysmal positional vertigo (BPPV). According to Fife[1], 91% of the BPPV patients were thought to have involvement of the posterior semicircular canal, 6% involvement of the horizontal canal (7.8% according to Takegoshi[2]), and 3% involvement of the superior (or anterior) semicircular canal. This application is directed to a new method for the diagnosis and treatment of posterior BPPV and the treatment of benign paroxysmal positional vertigo in the horizontal and superior semicircular canals.

Types of BPPV

Posterior BPPV

PBBPV's hallmark is vertigo when the patient moves into the affected ear downward position. The patient may also have symptoms of dizziness with looking up, or looking down. The diagnosis is clinically confirmed by placing the patient in the affected ear down position and watching a characteristic rotary motion of the eyes. Although some cases of BPPV follow head trauma, most cases have spontaneous onset of unknown origin. The natural history of positional vertigo is one of spontaneous remission, typically over 6 weeks. Recurrence is common and can last from weeks to months.

One ear is usually involved but reports of up to 15% of bilateral ear involvement have been made.

PBPPV is caused when a significant number of the loosened crystals come to be located within the posterior semicircular canal.

PBPPV Treatments

In 1980 Brandt Daroff[3] described a sequence of maneuvers in which the patient sat on the edge of a bed/surface and laid down laterally with the head touching the surface. After the symptoms resolved, the patient sat up and laid down on the opposite side. This was done every three hours while awake and terminated after two symptom-free days. This maneuver was thought to free the otolithic debris which was attached to the cupula of the posterior semicircular canal ampulla.

Semont[4] described what he called a Liberatory maneuver in which the patient was rapidly moved from a sitting position to the provoking position and kept in that position for 2–3 minutes. The patient was then rapidly brought up through the sitting position to lie on the contralateral side with the head turned downward 45 degrees. The therapist maintained the alignment of the neck and head on the body. The patient stayed in this second position for 5 minutes. In this second position the vertigo reappears and resolves. After the vertigo resolved the patient was slowly returned to a seated position and remained vertical for 48 hours thereafter. This technique was thought to work by causing the debris within the posterior semicircular canal to fall out of the canal.

Norre[5,6,7] described the use of vestibular rehabilitation maneuvers for the treatment of BPPV. Some support for this compared to the liberatory and Epley canalith repositioning maneuvers (CRM) has been expressed.

Epley[8,9] studied and refined Semont's Liberatory maneuver[4]. Epley's maneuver is now thought to be the most effective technique for moving the crystals out of the posterior membranous SCC (posterior canalith repositioning maneuver).

This maneuver is defined by Epley[8,9] as being made up of 6 positions: Start, and Positions 1, 2, 3, 4, & 5. The start position is the patient seated upright in an examination chair or on a table looking forward with the operator behind the patient and a mastoid oscillator applied to the effected ear behind the ear (ipsilateral mastoid area). In position 1, the patient is lying supine with the neck extended 20 degrees and the head turned 45 degrees toward the effected ear downward position. While in position 1, with the neck continuing to be extended 20 degrees, the head is turned 90 degrees toward the unaffected ear i.e. 45 degrees from vertical in the direction of the unaffected ear into postion 2. To go from position 2 to position 3, the neck is kept extended 20 degrees, the patient rolls onto the unaffected ear side of his or her body and the head is rolled into position 3. In position three, the head (nose) is pointed 135 degrees downward, affected ear upward, from the supine position. Keeping the head (nose) in the 135 degrees downward position, the patient is brought up to a sitting position, position 4. In position 5, the head is turned forward and the chin downward 20 degrees. Each position is held until the induced nystagmus stops ("approaches termination").

Harvey[10] described a modification of Semont's Liberatory maneuver which is very similar in its positions to that of Epley's canalith repositioning maneuver.

Katsarkas[11] showed a modification of the Epley canalith repositioning maneuver which he developed. In his maneuver, after the Epley position 3, he extends the neck as far as is reasonably possible to allow (he believes) the otoconia to fall into and through the common crus portion of the posterior semicircular canal crystal removal route.

Best PBPPV Treatment Observations

One skilled in the art will recognize that the head maneuver to relieve PBPPV can be done in an large (theoretically infinite) number of positions. That is, this maneuver could be done using the same head movement sequence outlined by the six positions of the posterior CRP maneuver, but it could be done such that instead of Epley positions 1, 2 and 3 being 90 degrees from the previous positions, the maneuver could be divided into five positions each 45 degrees from the position that preceded it and 45 degree from the position that follows it. If resolution of clinical vertigo caused by each position was used as the indicator to proceed to the next position, this theoretical five position maneuver would be as effective in the resolution of BPPV as Epley described in his positions 1, 2, and 3.

In the same way, those skilled in the art will recognize that this rotation of the head could be broken up into many (theoretically an infinite number of) positions. To one skilled in the art, the clinical use of a complex multipositioned maneuver is not clinically possible because of the increased difficulty of correct and consistent positioning when a multipositional maneuver is done manually. This difficulty is increased further for the occasional performer, and markedly more for the less educated and therefore less physiologically understanding occasional performer.

Those skilled in the art recognize that the posterior CRP technique teaches that the Epley positions 1, and 2 are done with the patient's head extended 20 degrees, the patient's head is supine and rotated 45 degrees in the effected ear downward position (position one) and rotates toward the unaffected ear downward (into position two) and then into position three with the nose pointed 135 degrees downward from supine (position three).

Theoretically the best sequence of head positions for clearing crystals from the posterior SCC is the position sequence which would cause position two to have the top of the patient's head directly downward. Positions one and three could be approximately the same as Epley classically described. That is, those skilled in the art will recognize that the greater the patient's neck is extended (up to 90 degrees) in positions one and two but especially in position two, the greater the chances that the maneuver will effectively clear the symptom-causing crystals from the posterior SCC.

This technique of total patient rotation in the plane of the posterior semicircular canal has been done by Epley[8] using a specially build chair and rotation apparatus. Lempert[12] performed a similar procedure demonstrating the value of the Epley position one to the Epley position three through an Epely position two in which the patient's head was pointed directly downward.

Understanding that this head extension greater than 20 degrees and up to 90 degrees makes the maneuver more effective, the current process discloses devices which cause the head extension up to 110 degrees. Based on this teaching, this process includes not only the current configuration but devices which cause the neck to be extended greater than or equal to 10 degrees and up to 110 degrees in the Epley positions one and two.

A Clinical Perspective

The posterior canalith repositioning maneuver technique is currently used by medical and paramedical personnel worldwide for the relief of the symptoms of posterior semicircular canal BPPV. The technique, although easy to do and successful after it is learned, is difficult to successfully teach. The maneuver requires significant experience by the performer to be consistently successful. Attempts to teach the maneuver to patients have been unsuccessful. The devices described herein accurately, consistently and inexpensively provides the user visual feedback as to his head position at any given moment, and provides a path for the user to follow to move his head correctly through the series of positions to accomplish the canalith repositioning maneuver.

Horizontal BPPV

Horizontal BPPV (HBPPV) was first recognized by McClure[13] who reported 7 cases with brief episodes of positional vertigo associated with horizontal direction changing positional vertigo. Subsequent studies have reported several variation in the type of nystagmus produced by horizontal canal BPPV, including geotropic and ageotropic direction changing positional nystagmus.

The clinical characteristics are 1) brief episodes of positional vertigo and 2) paroxysmal bursts of horizontal positional nystagmus and 3) lack of any other identifiable central nervous system disorder.

Geotropic horizontal direction changing paroxysmal nystagmus has been found in HBPPV in 90% by Nuti[14], and 73% by Takegoshi[2] and 84% by Fife[1]. Takegoshi[2] and reported finding BPPV in both the posterior and horizontal semicircular canals. Nuti[14], McClure[13] and Herdman[15] reported finding horizontal canal BPPV after canalith repositioning maneuver for relief of PBPPV.

HBPPV Treatments

Fife[1] described three maneuver techniques for treating HBPPV.

The first maneuver was a three-quarter contralateral roll in which the patient's head was moved in 90 degree increments away from the side with the most intense nystagmus to achieve a 270 degree turn. This maneuver was largely unsuccessful in the small number of patient upon whom it was used.

The second maneuver was a single full contralateral roll. This second maneuver was similar to the first, except that the head was rotated the entire 360 degree turn from supine face up to supine face up, again turning toward the presumably unaffected ear.

The third maneuver was the iterative full contralateral roll. These exercises were performed once or twice in the clinic and the patient was encouraged to continue these at home for 7 days or until the symptoms subsided. The head was maintained in 30 degree flexion throughout the maneuver.

Epley[8] describes treating horizontal canal HBPPV with a 360 degree "barrel roll" away from the involved ear, keeping the horizontal canal in the earth vertical plane. To avoid dumping particles from the utricle back into the horizontal canal at the end of the procedure, the patient was returned to upright without first moving to the straight supine position. Epley notes that in the less agile patients, success can still be obtained by turning the head only 135 degrees from supine, opposite the involved ear.

Superior BPPV Treatments

Treatment maneuver to remove loosened otoconia from the superior (or anterior) semicircular canal has only been described by one author. Epley[8] notes "the anterior canals can usually be cleared of canaliths by using the same positioning sequence as contralateral posterior canaliths".

BPPV Diagnostic

The classic clinical description of PBPPV includes rotary nystagmus in the effected ear down Dix-Hallpike position. Because head placement is difficult to describe in a manner that a non medical person could accurately and consistently perform, and because the accuracy of which posterior semicircular canal is not detected perfectly by the questionnaire, there will be described a device which will guide the user's head into the right Dix-Hallpike and the left Dix-Hallpike positions. While in these positions the user can detect and understand which ear down causes the greatest amount of vertigo symptoms and hence which (right or left) post SCC is effected by the loosened otoconia. The ear which is effected is the ear which is initially placed downward in the treatment maneuver. That is, the treatment maneuver is effected-side-specific.

Based on this information and the fact that the studies of BPPV, response to head maneuvers all start from the knowledge of which ear is effected. A device to guide the user's head into each of the two Dix Hallpike positions is described herein.

There are no prior art devices to this applicant's knowledge which guide the user's head into the Dix Hallpike positions for diagnostic purposes.

Historical Diagnosis and Treatment Systems

The historical method for diagnosing and treating BPPV is for the patient to visit his physician, be recognized as having vertigo and after some hopeful observation for spontaneous clearing and symptomatic treatment, be referred to an otolaryngologist (ear nose and throat specialist). This specialist would normally perform an involved history and a physical exam, a balance test (electronystagmogram), arrive at the diagnosis of BPPV, and manually perform a posterior canalith-repositioning maneuver (PCRP) for the patient. This PCRP will typically resolve 85–100% of the patients symptoms. This scenario presumes good efficiency on the part of each of the physicians and any technicians involved.

Background Statistics

Questionnaire

BPPV has characteristic clinical findings that a patient can recognize. Because the clinical findings are easy to recognize, they can be successfully elicited by questionnaire. The results of these question answers can be statistically examined to determine the chance that Epley maneuver responsive BPPV is the origin of the patient's vertigo, dizziness, or imbalance.

An original set of questions (DxQ) have been developed and the predictive value of each of the questions and question sets has been quantified such that the answers to the questions can be used to give a % chance that the user has BPPV.

Dizziness Handicap Inventory (DHI)[16] is a series of 25 questions that have been written, tested and established as a method of measuring the physical, functional, and emotional effects of vertigo, dizziness or imbalance. This question series has been used to measure the severity of the user's dizziness symptoms.

Patient responses to the DHI and DxQ questions were collected and correlated with the patient responsiveness to the Epley maneuvers. This correlation yielded proprietary information about the correlation of the DHI and DxQ question answers and Epley maneuver responsiveness and 2) proprietary information about the correlation of the DHI and DxQ question answers and posterior SCC crystal moving device success.

Computer Diagnostic History

Traditional medicine uses a medical personnel question system to elicit the patient's history of symptoms combined with physical examination, laboratory findings and x-ray examinations to determine a diagnosis. Diagnoses are:related to treatments of varying success, and side effects.

With the advent of computer technology many attempts have been made to query patients (users) and/or medical personnel for combination of patient history, physical examination, laboratory findings, and x-ray findings to determine a diagnosis(DX) and to arrive at an appropriate treatment.

No computer system which will query a patient and render a diagnosis based on these questions have been successfully implemented. These have been unsuccessful because 1) the patient responses have not been satisfactorily systematized, 2) patient are either not careful or trained observers, 3) patient are not able to input the diagnostically necessary PE, lab or x-ray data, and 4) if responses can be obtained properly from the patient/user such that a diagnosis is established, treatment modalities typically require clearance by medical personnel. Based on these characteristics, medical diagnostic expert computer systems have been directed primarily for medical personnel use.

These medical diagnostic expert systems have not found a significant following among medical personnel. The lack of success is based on the time benefit ratio i.e. the value of the users time vs. the value to the medical personnel of the systems output. Also the users are able to work through the clinical problem without the computer dx (diagnostic) assistance.

There are multiple successful expert medical systems which address small areas within medicine. This invention addresses one such area in medical diagnosis, the diagnosis of BPPV. This invention identifies patients with classic BPPV within the group of patients who have vertigo/dizziness/imbalance.

Questionnaires in the Medical Literature

Many questionnaires have been used to either collect information from a patient efficiently for human mental analysis and use, or to analyze the public health conditions or the perspective of a community or to even screen those using the questionnaire for a certain condition which will then make the human treatment of those individuals more efficient or will detect those individuals in need of treatment by doctors such that they can be treated by doctors before their condition worsens i.e. make the ultimately necessary treatment more efficient[17-25].

In 1965 Busis[24] published a guide to dizziness/vertigo diagnosis. A section of that publication was devoted to disease characteristics and the differential diagnosis of vertigo. As a portion of his history of the vertigo patient, Busis pointed out that he could increase the clarity of his identifying patients with ear origin dizziness by broadening his questions to include symptoms that if present, automatically excluded the labyrinth as the sole problem. With this in mind he outlined a 4-section questionnaire. In the four sections of the questionnaire were 11, 12, 5, and 8 questions, respectively.

In 1967 Sheehy[25] modified Busis' questionnaire. Sheehy's questionnaire was a 4-part questionnaire of 11, 14, 5, and 8 questions.

Both of these questionnaires were designed with the notion that the questionnaire "facilitated the matter of history taking in the case of the dizzy patient". The Busis and Sheehy questionnaires, although related directed to collecting information, were not directed to collecting that information for computational/diagnosis reasons, but rather to collecting information for making the physician's history data collection more efficient. These 2 questionnaires do not directly impact on the current invention.

Vertigo Diagnostic Software in the Medical Literature

There have been 3 significant vertigo diagnostic computer software development efforts described in the medical literature. Each of these systems use patient history as an information source and each attempt to diagnose the origin of vertigo.

The first software effort is a program called Vertigo[26-29]. The effort to build this vertigo/dizziness/imbalance diagnostic system was begun in 1984 and is described in articles in 1987, 1988, and 1990. In the 1987 article, 150 patients are described; in the 1990 article 200 patients are described. The goal of this software was to provide an expert software system with which otolaryngology residents could hone their vertigo diagnostic skills and to serve as a resource for non-expert M.D.'s in the diagnosis of vertigo. The software is not intended for consumer use. The Vertigo system uses only patient history. It is based on Rutger's University Expert system shell using Bayesian analysis techniques combined with a knowledge database.

The Vertigo software system uses a computer generated questionnaire, deals only with differentiating diseases of the inner ear, uses patient history only for diagnosis, and classifies diseases identified by the software as being inner ear in origin or being "other" in origin, it does not focus significantly on BPPV. The criteria for the classification of these abnormalities is physician diagnosis based and not Epley procedure response based. The system does not use a device whatsoever to guide the patient through the canalith repositioning maneuver. The interface for this system is a complex interface of lists, yes/no answers, and multiple choices. From an output point of view the systems provides multiple differential diagnoses with a statistical probability of the patient having each differential diagnostic possibility.

The second vertigo diagnostic system is called ONE[30-32]. ONE was described in 1993, 1995, and 1996. Although the 1993 article describes the testing/developing of the ONE system with 173 patients, by 1996 the authors have tested and honed their system on 564 patients. The ONE system is specifically designed to be an intellectual assistant to the neurotologist (inner ear dizziness expert). ONE uses patient history, clinical examination findings, as well as test findings to predict the diagnosis for the patient's dizziness or vertigo. The technique of determining the correct diagnosis has to do with what the authors call "a new technique which outputs diagnosis probabilities." It is specifically designed to minimize wrong answers rather than specifically identify a correct answer. In this technique each question is weighted. Of the 142 patients clinical diagnoses analyzed by this system, 68 had acoustic neuromas and 63 had Meniere's disease. The number of BPPV patients in the 142 patient samples was 3. This system is clearly not optimized for BPPV identification. The normal incidence of BPPV in 142 patients is 17%, or 44 patients.

The ONE system differs from the current invention in that it is directed to neurotologists and not patients. The questions have a complex number of options, yes/no, and multiple answers. The questions are not BPPV oriented as demonstrated by the limited number of cases of BPPV in the series. They do not use the Epley maneuver response as a definitive answer for the determination of the diagnosis of BPPV, but rather clinician diagnostic opinion. Finally, there is no device for guiding the patient's head through a sequence of positions for accomplishing the Epley maneuver. This computer system has never been used in a commercially successful manner.

The third diagnostic program described in the medical literature is called Carrusel[33]. Carrousel had its start in 1987 and was originally described in 1990. This system's stated goal is to be a "powerful educational tool for students and non-expert physicians". The Carrousel system is a rule based diagnostic system which queries the patient.

Carrousel and the current invention both have computer-generated questions. They are dissimilar in that after the patient history is taken, the Carrousel system queries for lab test results as if the system were coaching an otolaryngology (ear nose and throat) resident (trainee) in an educational environment or as if it were coaching a non-expert physician in how to continue the work up of the patient. The authors state that most end organ vestibular problems are deduced and have no objective clinical confirmation. It would be my observation that BPPV has clear Dix Hallpike position induced rotary nystagmus and an Epley response is a clear clinical confirmation mechanism. Further dissimilarities are that Carrousel is not BPPV directed. They do not use an Epley maneuver as a definitive confirmation of their positional vertigo. There is no device for guiding the patient's head through the maneuver either patient monitored or healthcare provider monitored. The Carrousel system is now 10 years old and has not been used commercially successfully.

2. Prior Art Patents

Several patents were found which describe systems which are significantly different from those described in this invention.

U.S. Pat. Nos. 5,471,382 and 5,764,923.

These patents describe a computer system in medical managed care in which a patient calls a medical management staff person. The patient relates his symptoms to the computer operator. The computer operator uses computer software utilizing "branch chain algorithm utilizing Bayes theorem" to assign a risk category without diagnosis to the patient's problem and to determine whether the patient needs to see a medical staff person and to what level of medical staff person the patient should be directed. The patient always has the computer operator between him and the computer questions. The system assigns risks and to what human healthcare resource the user is to be assigned. The system only directs the patient to one of several different human medical staff persons. There is no device central to the method of the patent. The patents make no mention of vertigo or positional vertigo.

U.S. Pat. No. 5,660,176

This patient describes a computer system which can be accessed by phone or by computer modem. The patent background makes clear that the most frequently seen 100 diagnoses are targeted. The user answers questions verbally or by tone phone keyboard. This system provides medical advice based on question answer determined common diagnosis. BPPV is not in the top 100 diagnoses. The user is not referred for head movement treatment. There is no device offered for sale in this patented system.

Prior Art Devices

A device for sale by Medical Surgical Innovations 1 Ocean Drive, Jupiter, Fla. consists of a combination of head band and skull vibrator.

The headband is worn around the head like a tennis sweat band. It is made from colorful neoprene and is of adjustable tension by varying the tightness of the attaching VELCRO® strip. Attached to the VELCRO® head band at the lateral side of the forehead on both sides in a plane parallel to the posterior semicircular canal on the same side is a small clear tube filled with water and containing a small amount of sand. This tube is intended to give the medical/paramedical person performing the maneuver for the patient, a visual feedback technique to see that the position sequence into which they are positioning the patient will cause the sand suspended in water to move around the tube of water in the same way that the loosened crystalline otoconia are being moved around and out of the posterior membranous semicircular canal. This device is intended for use by medical/paramedical personnel to judge the success of the positioning sequence that they are performing for the user.

The head band is used to hold a vibrator against the skull behind the effected ear for several minutes before and during the PCRP.

The skull vibrator is a small hand held, battery operated vibrator within a smooth plastic case. This vibrator was held against the mastoid surface behind the ear which was thought to be causing the BPPV symptoms.

Two authors (Epley[8], Lempert[12]) have reported seating the patient in a device and completely rotating the patient in the plane of the posterior semicircular canal (with the capability to rotate the patient in the plane of any of the semicircular canals). These large devices represent the most accurate method of CRP for any of the canals. Ownership and self operation of these devices is certainly not feasible for the vast majority of patient suffering from BPPV.

SUMMARY OF INVENTION

The current invention provides a new process and system for the diagnosis and sale of devices for the treatment of BPPV. The current invention is directed to a medical diagnosis and treatment system in which in one embodiment the patient goes to a computer and answers a series of questions or is walked through the questions by another person. If the question answers indicate that the user has BPPV of one of the SCC's, he is offered for sale or provided devices which 1) help in the diagnosis of which SCC is involved by the loosened crystals and 2) allows him to perform a head maneuver to move the loosened crystals out of the involved SCC. The user could be instructed to go to a provider of care for treatment of his BPPV. The two devices which perform diagnosis and treatment could be sold or used separately.

In another embodiment, the user could use the diagnostic questions to purchase the diagnostic portion of the device. With the diagnostic device findings entered into the question answer information, the statistical recommendation as to whether to purchase the treatment device would be more accurate.

In the preferred embodiment the user uses an electronic network (internet) to communicate with a central computer. The user answers a series of computer presented BPPV screening questions (DHI and DxQ). These questions are combined with the predictive value of each question answer and question set answer. Rule based decision making can be used or added to the statistical question analysis. The calculated chance that the user has Epley maneuver responsive BPPV is shared with the user.

BRIEF DESCRIPTION OF DRAWINGS

Device

Treatment

PBPPV

FIGS. 11–17 depict the inner sphere surface location of the three position bull's eye markings which when put within the outer sphere target marking will indicate that the user's head is correctly positioned through the sequence of positions necessary to cause loosened crystalline otoconia debris to fall out of the posterior semicircular canal and into the utricle.

HBPPV

FIGS. 18–24 depict the inner sphere surface location of the four position bull's eye markings which when put within the outer sphere target marking will indicate that the user's head is correctly positioned through the sequence of positions necessary to cause loosened crystalline otoconia debris to fall out of the horizontal semicircular canal and into the utricle.

SBPPV

The inner sphere position bull's eye locations are the same for the treatment of posterior SCC BPPV and superior SCC BPPV. In left superior SCC BPPV treatment, the right posterior SCC BPPV first component and treatment sequence is used. For the right superior SCC BPPV treatment, the left posterior SCC BPPV first component and treatment sequence is used. There is no different position bull's eye configuration for superior SCC BPPV treatment.

Diagnostic

Figure 25:
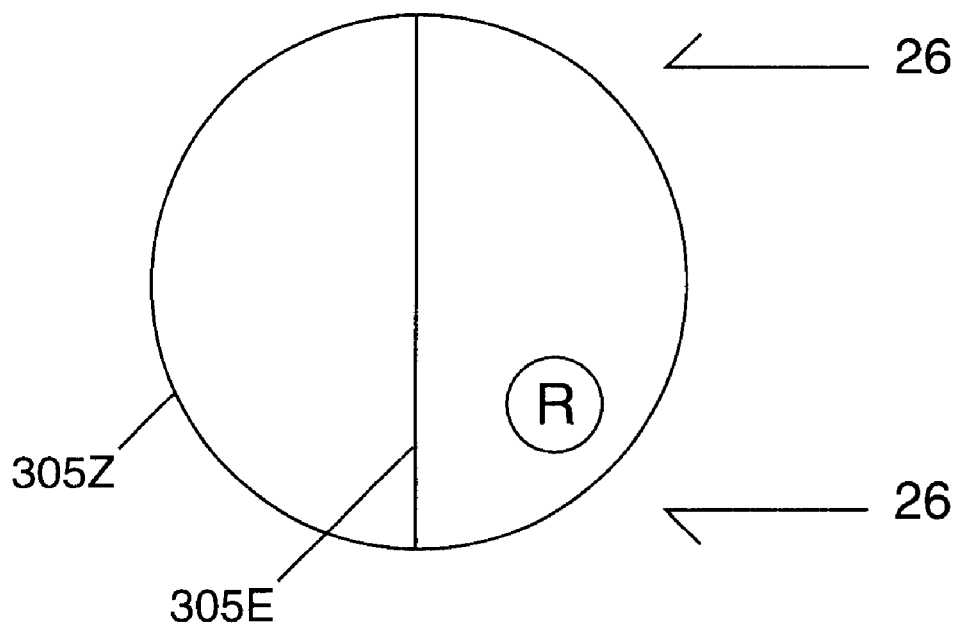
Figure 26:
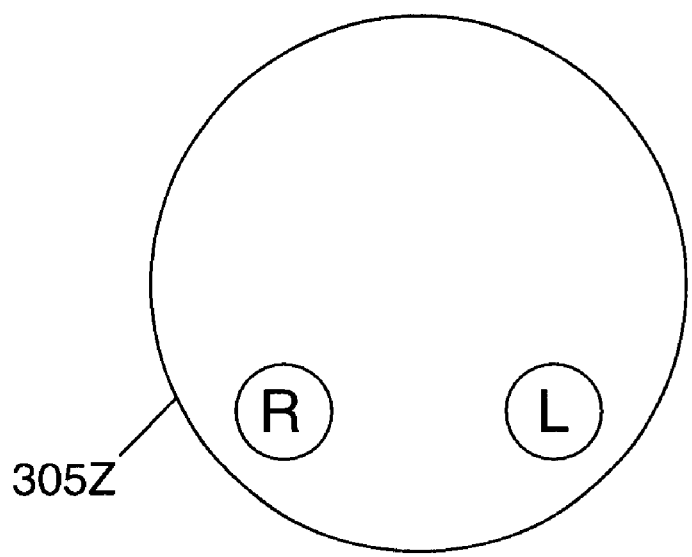

FIGS. 25 and 26 depict the positioning of the two position bull's eye markings which when put within the outer sphere target marking will indicate that the user's head is in the right or left Dix Hallpike positions used in the diagnosis of PBPPV.

Specific Descriptions of FIGS. 1–26.

Figure 1:
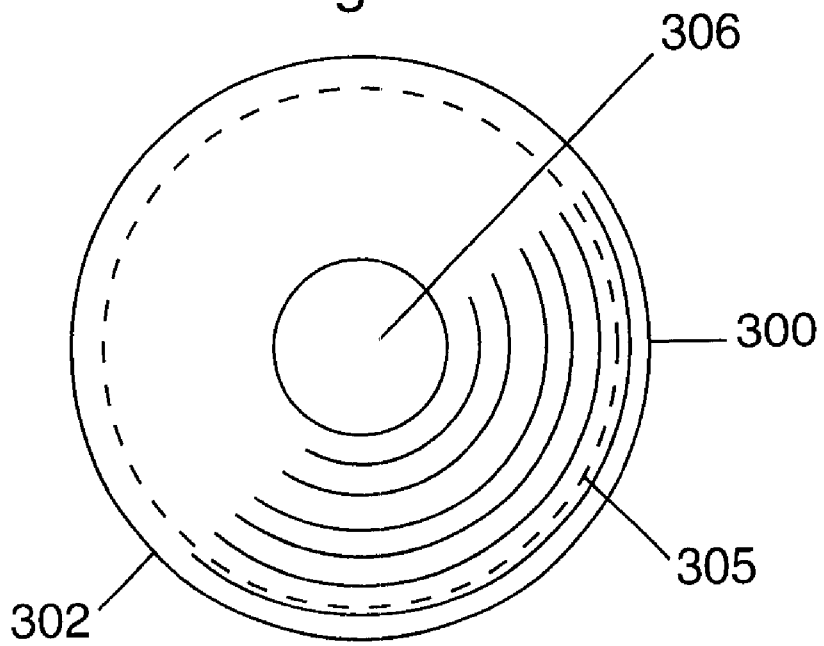
FIGS. 1, 2, 3, 4, and 5 depict a vertically and horizontally oriented, buoyancy neutral inner sphere upon which has been printed a series of position bull's eyes. Each position bull's eye is connected to the next by a path printed upon the sphere. An outer clear plastic sphere has a sighting marking upon it.

FIG. 1 illustrates an outer sphere of the preferred embodiment of the device with a sighting marking on its exterior.

Figure 2:
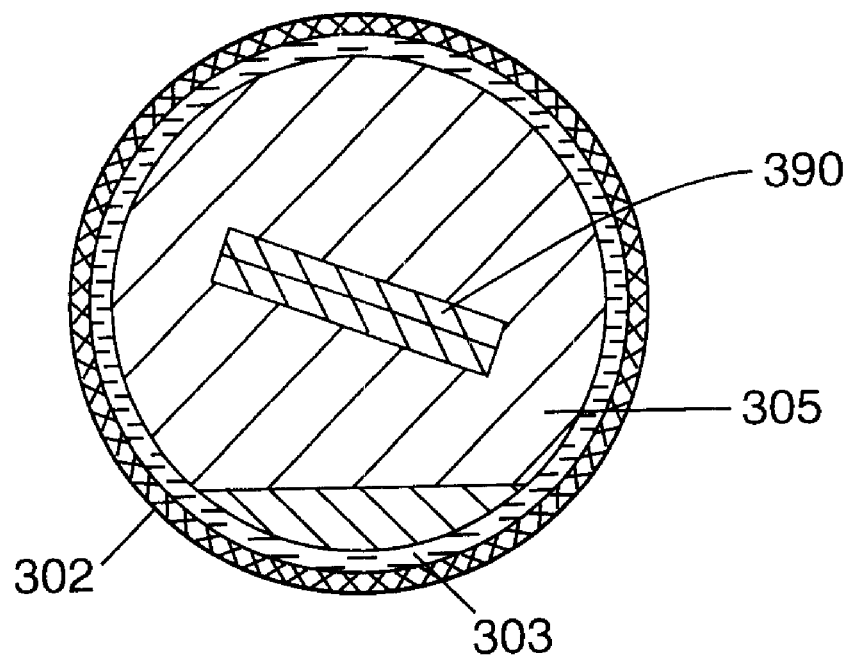

FIG. 2 is a cross-section of the device of FIG. 1 showing an inner sphere supported in a liquid.

Figure 3:
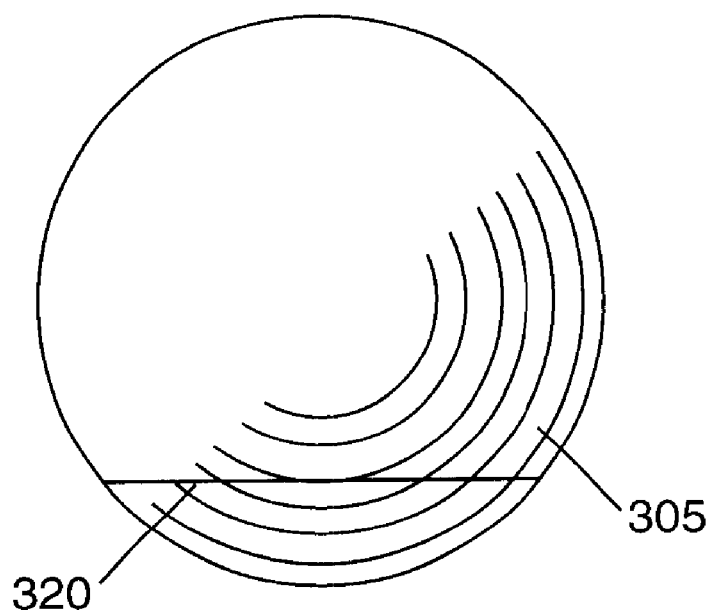

FIG. 3 illustrates a weight secured to one end of the inner sphere.

Figure 4:
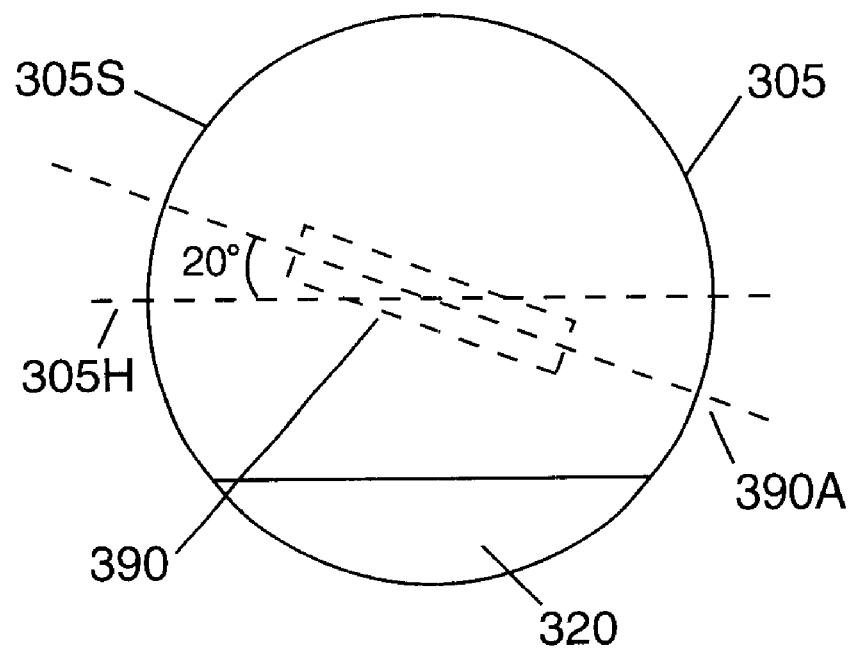

FIG. 4 illustrates a permanent magnet secured to the inside of the inner sphere.

Figure 5:
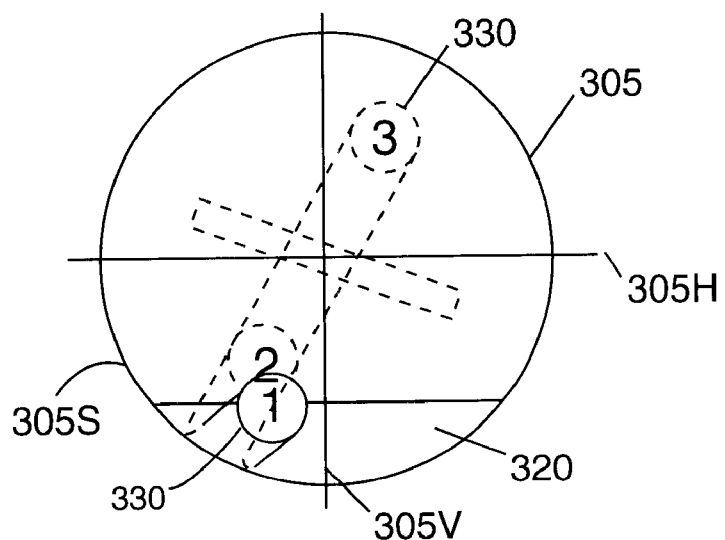

FIG. 5 illustrates position bull's eyes located on the outside of the inner sphere connected by path lines.

Figure 6:
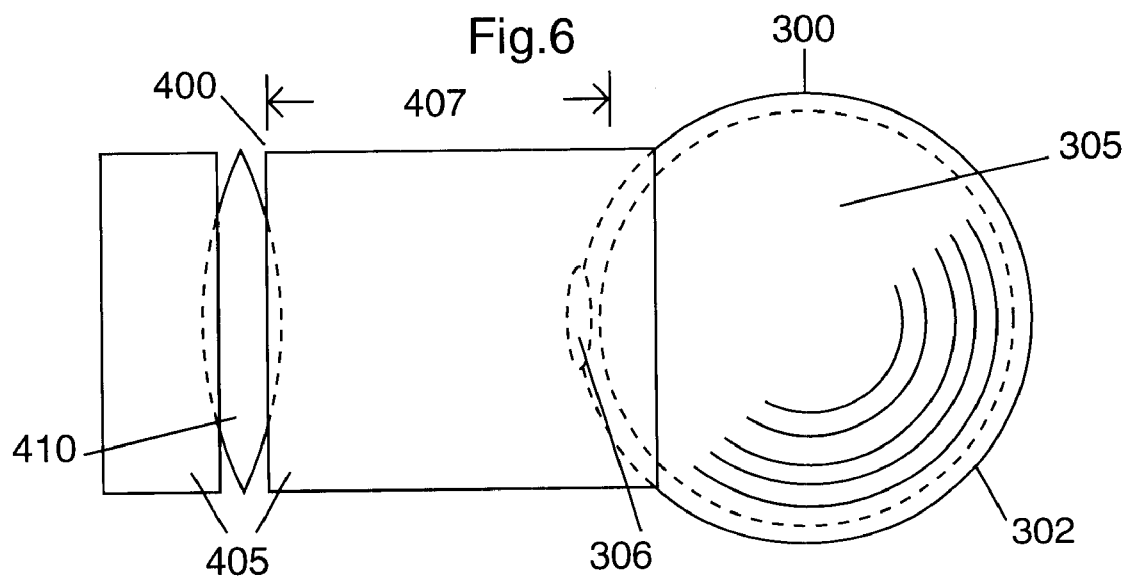
FIGS. 6, 7, and 8 depict a tube like device to hold the first component shown in FIGS. 1, 2, 3, 4, and 5 such that the first component is held at the focal length of the lens shown in FIGS. 6, 7, and 8.

FIG. 6 is a side view of a cylindrical tube supporting the device of FIGS. 1–5 at one end and a lens at the other end.

Figure 7:
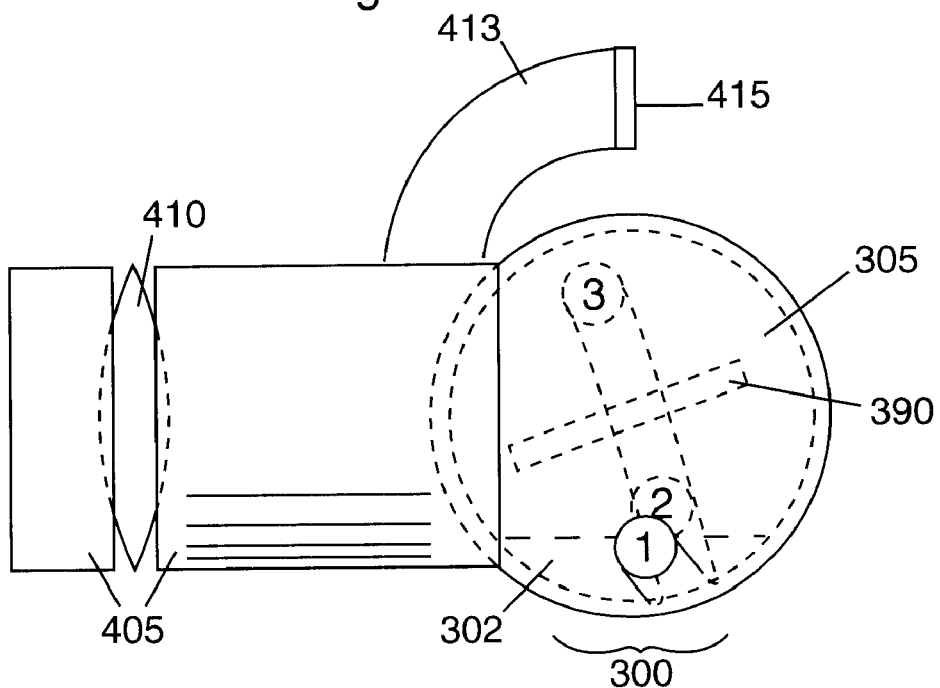

FIG. 7 illustrates an outer permanent magnet attached to the cylindrical tube of FIG. 6.

Figure 8:
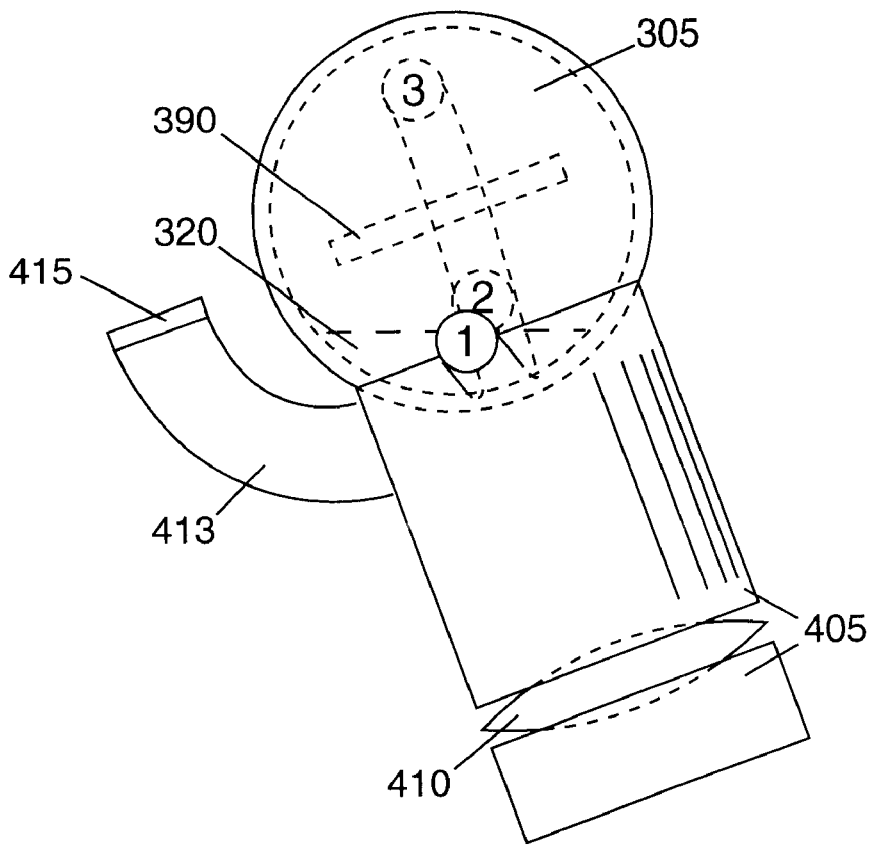

FIG. 8 illustrates the device of FIG. 7 in a different angular position.

Figure 9:
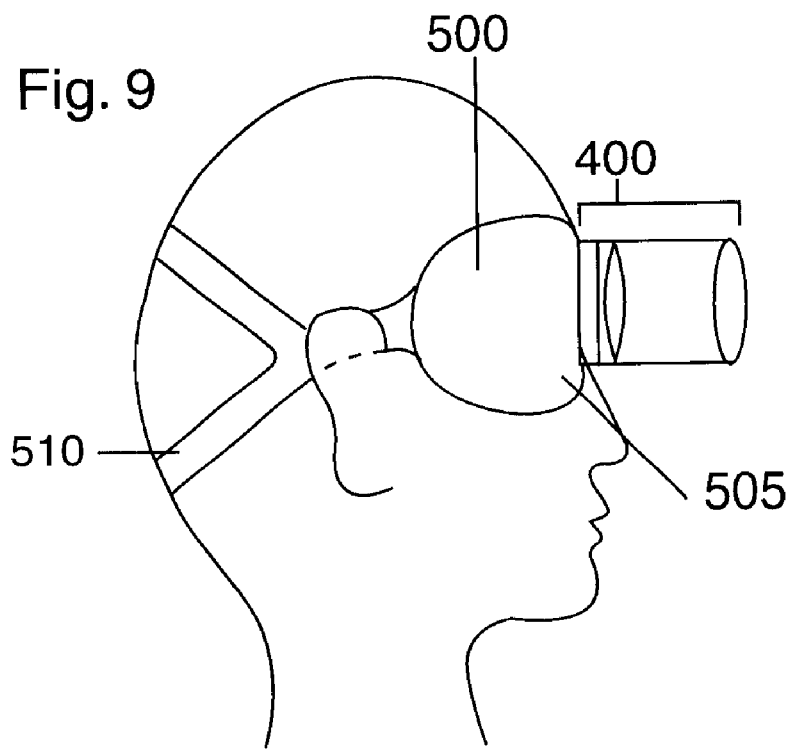
FIGS. 9 and 10 depict the combination of the first component (FIGS. 1–5), and the second component (FIGS. 6–8) and a device, the third component for securing the first and second components over the eye of the user.
Figure 10:
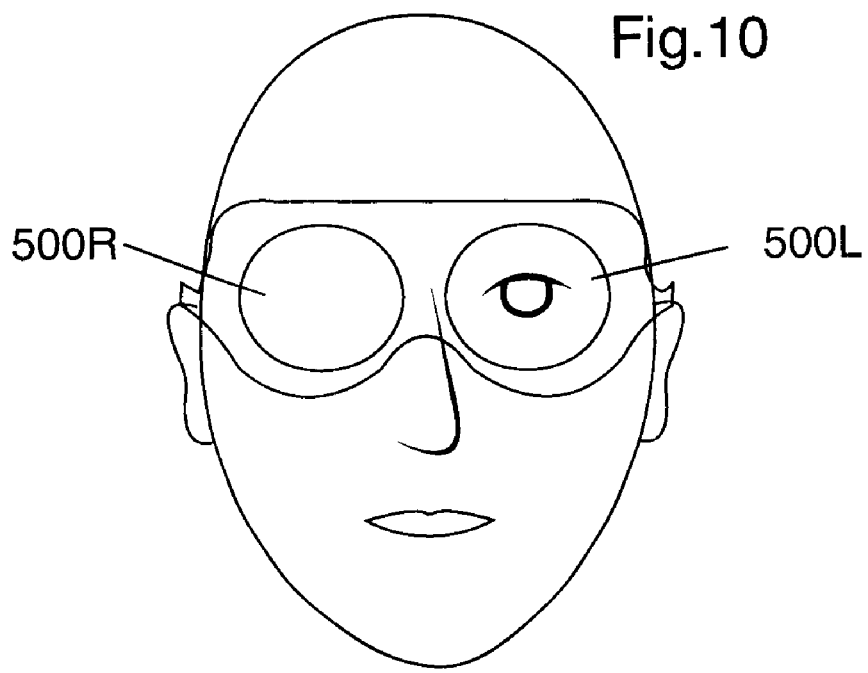

FIGS. 9 and 10 illustrate goggles for supporting the device of FIGS. 7 and 8.

Figure 11:
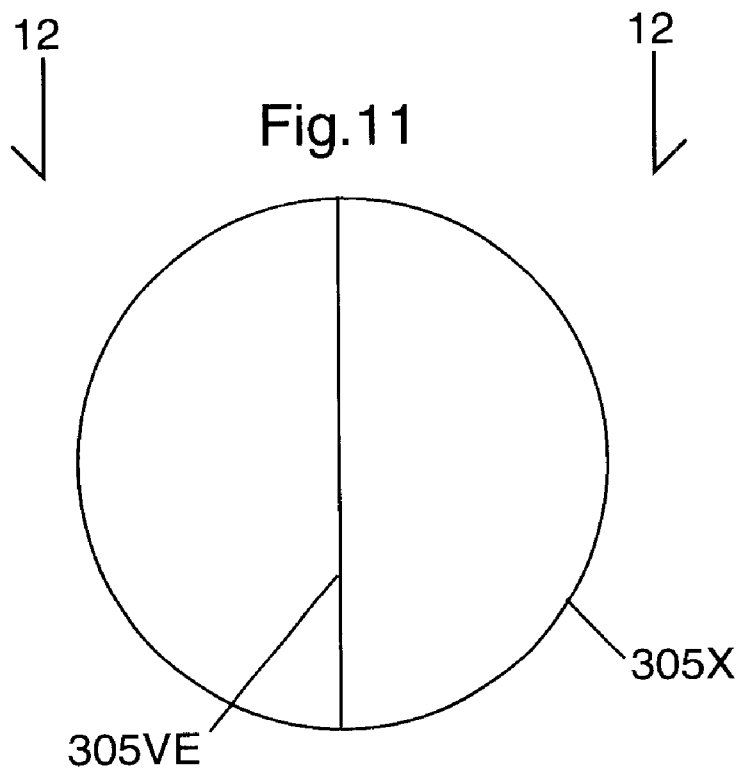

FIG. 11 illustrates an inner sphere with its vertical equator.

Figure 12:
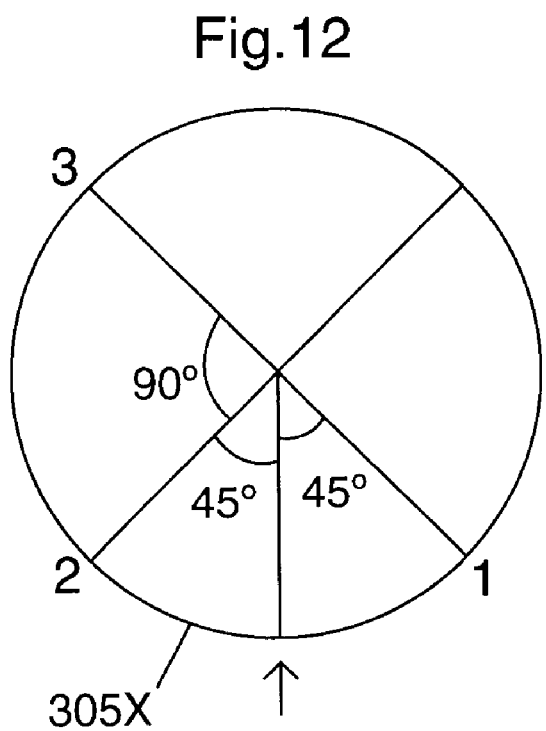

FIG. 12 is a view of FIG. 11 as seen along the lines 12—12 thereof and illustrating the angular relationship of the three position bull's eyes.

Figure 13:
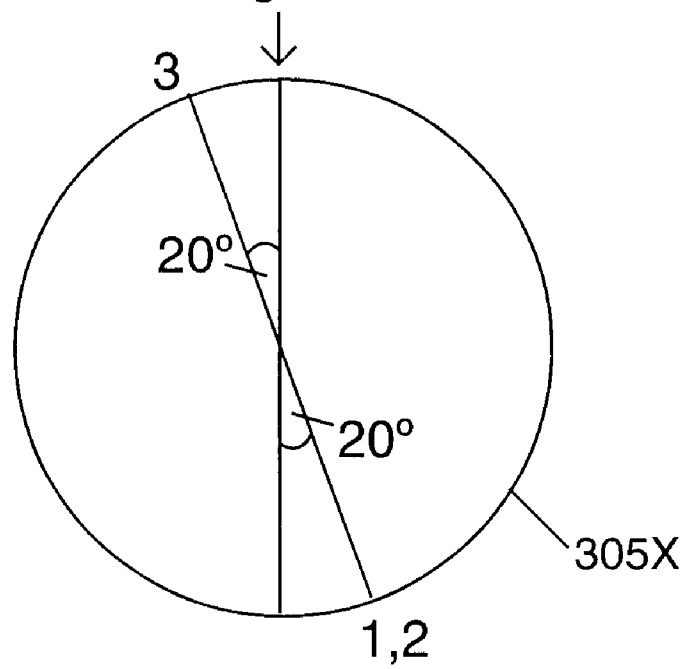

FIG. 13 is a view similar to that of FIG. 11 illustrating the angular positions of the three bull's eyes relative to the vertical equator.

Figure 14:
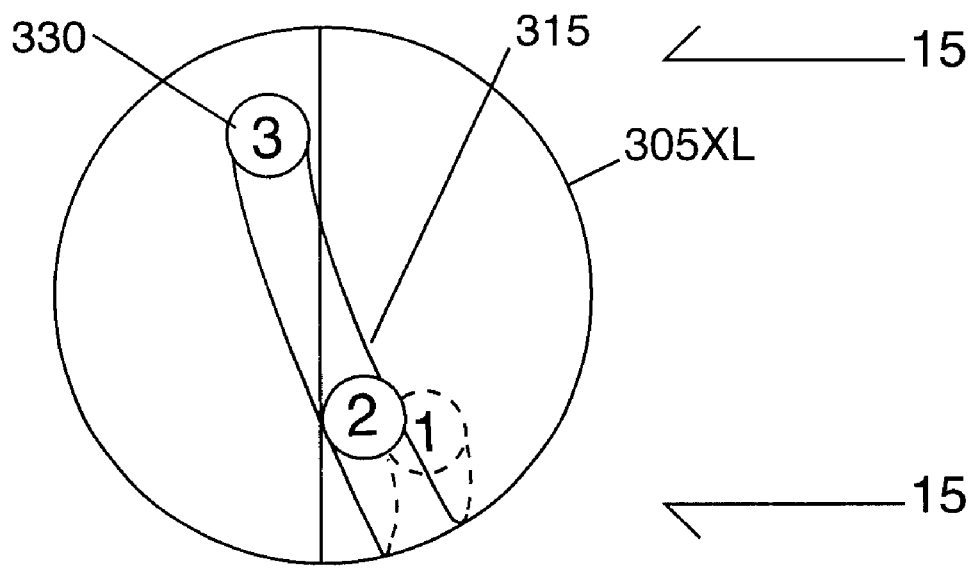

FIG. 14 illustrates the three position bull's eyes relative to the vertical equator for the left posterior SCC BPPV treatment.

Figure 15:
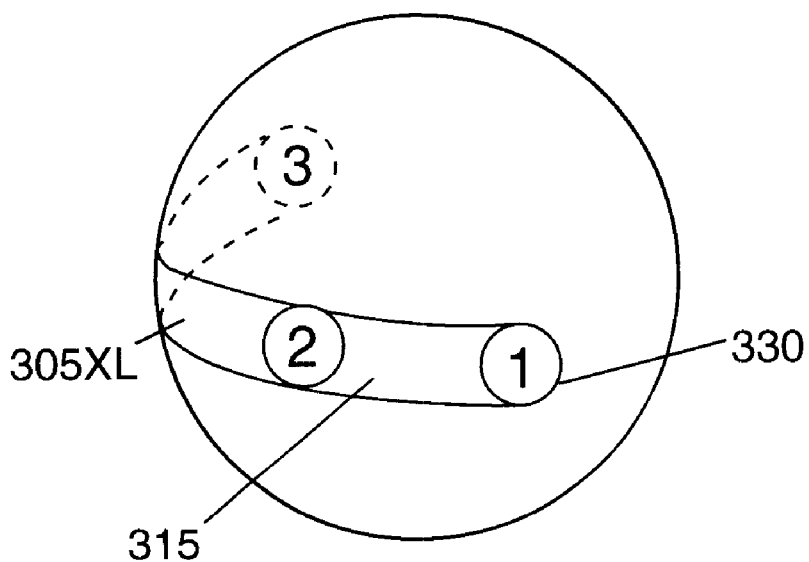

FIG. 15 is a.view of FIG. 9 as seen from lines 15—15 thereof.

Figure 16:
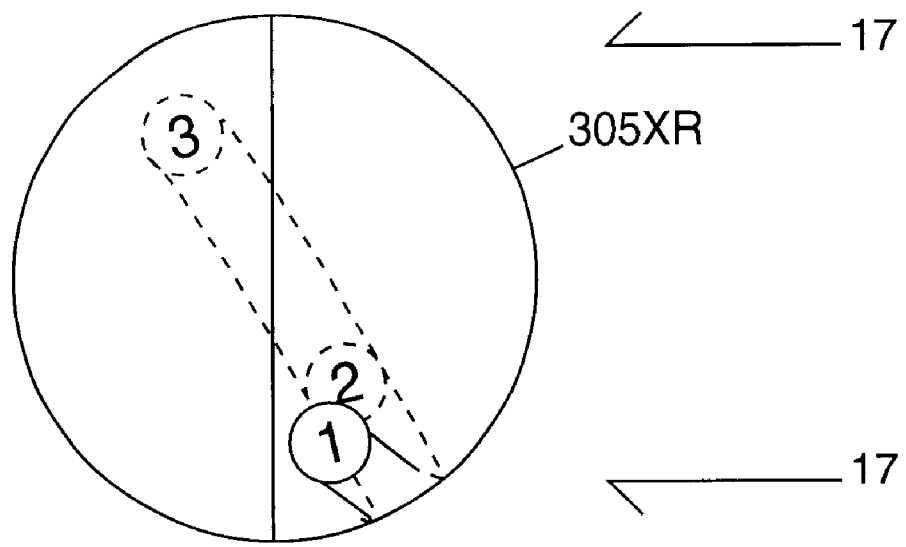

FIG. 16 shows the locations of the three position bull's eyes for the right posterior SCC BPPV.

Figure 17:
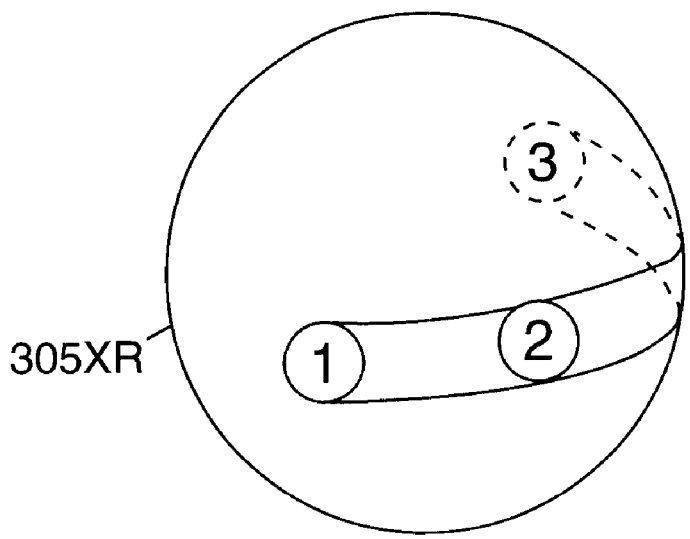

FIG. 17 is a view of FIGS. 16 as seen along lines 17—17 thereof.

Figure 18:
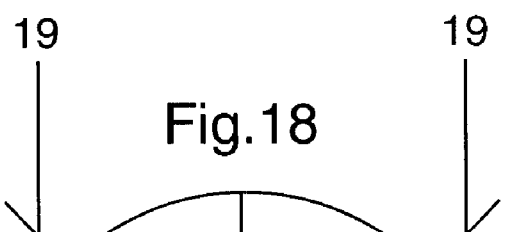

FIG. 18 illustrates an inner sphere with its vertical equator.

Figure 19:
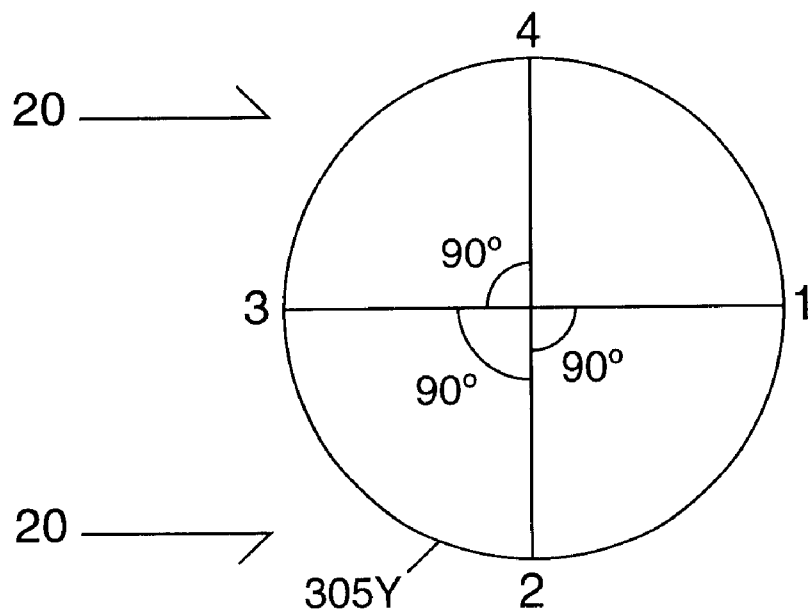

FIG. 19 is a view of FIG. 18 as seen along the lines 19—19 thereof and illustrating the angular relationship of four position bull's eyes.

Figure 20:
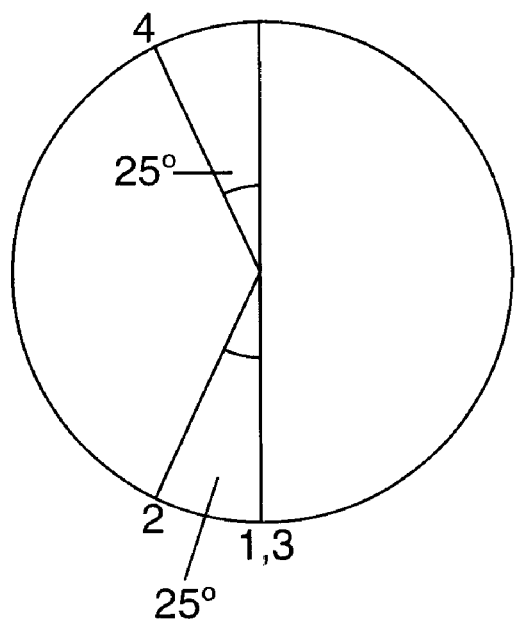

FIG. 20 is a view similar to that of FIG. 18 illustrating the angular positions of four position bull's eyes relative to the vertical equator.

Figure 21:
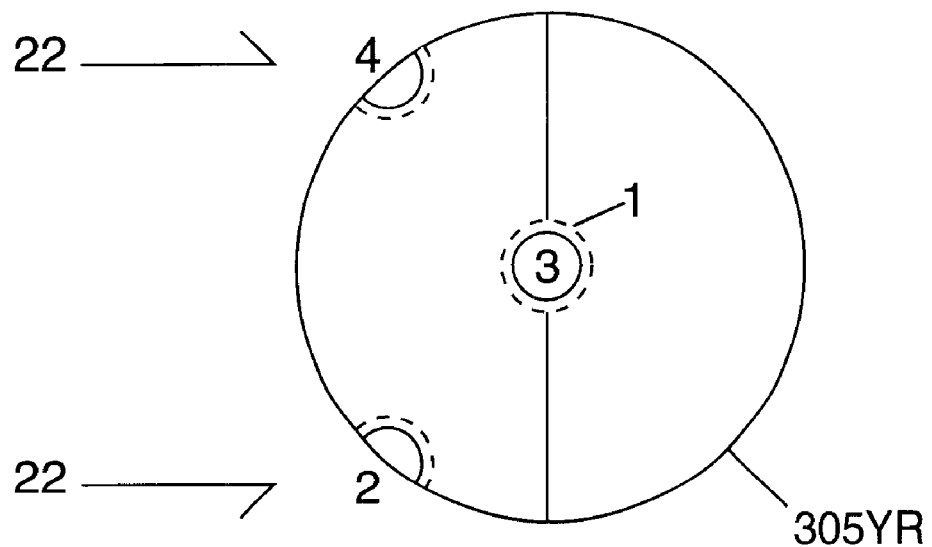

FIG. 21 shows the location of the four position bull's eyes for treatment of right horizontal BPPV.

Figure 22:
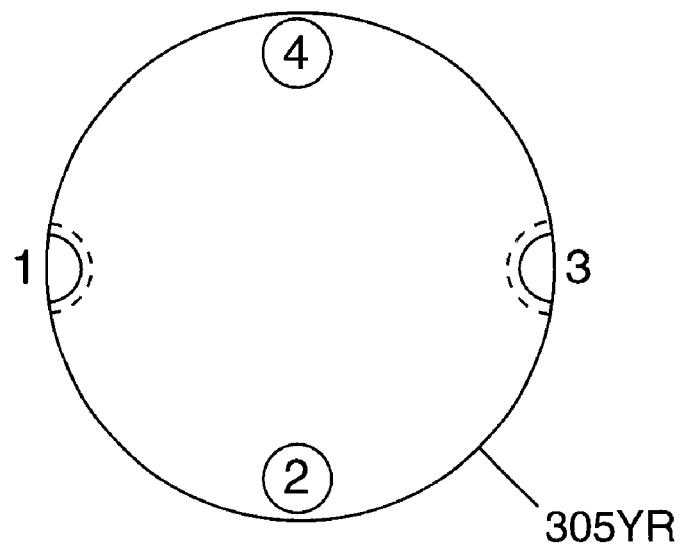

FIG. 22 is a view of FIG. 21 as seen along lines 22—22 thereof.

Figure 23:
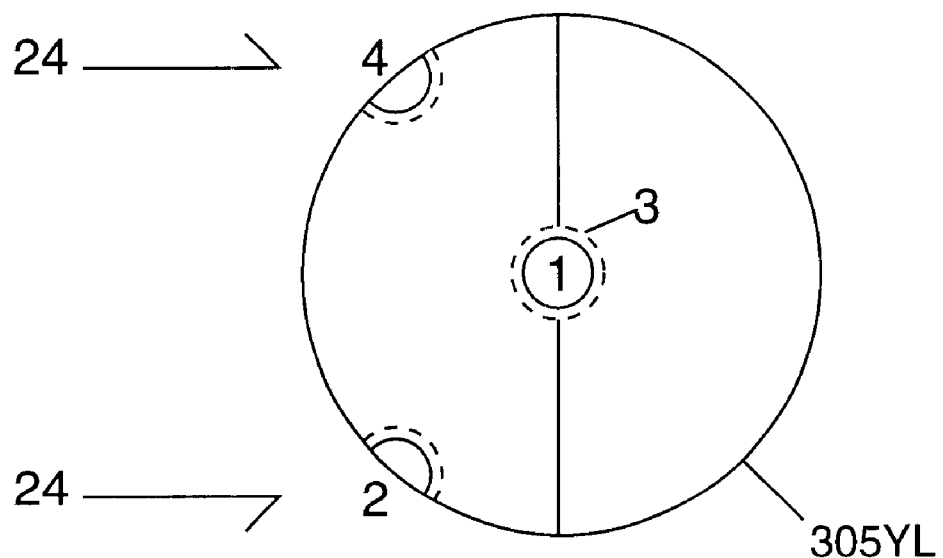

FIG. 23 shows the location of the four position bull's eyes for the treatment of left horizontal BPPV.

Figure 24:
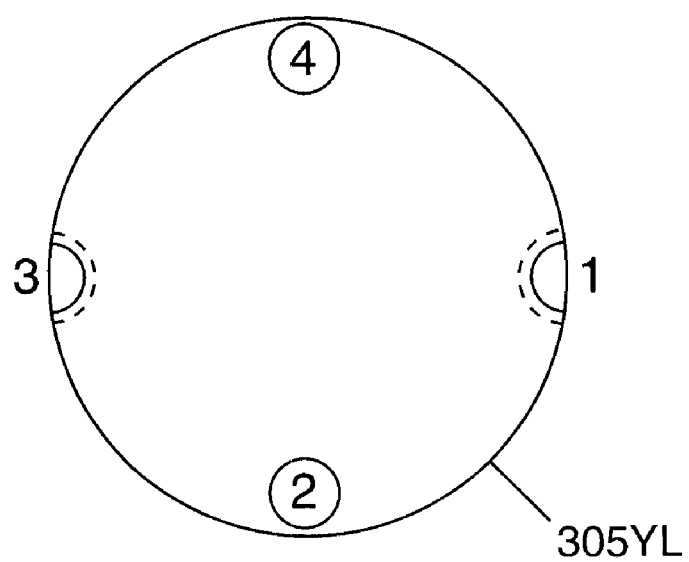

FIG. 24 is a view of FIG. 23 as seen along lines 24—24 thereof.

FIG. 25 is a side view of the inner sphere showing a vertical equator and R marking.

FIG. 26 is a view of FIG. 25 as seen along lines 26—26 thereof.

Method

BPPV Diagnostic

Figure 27:
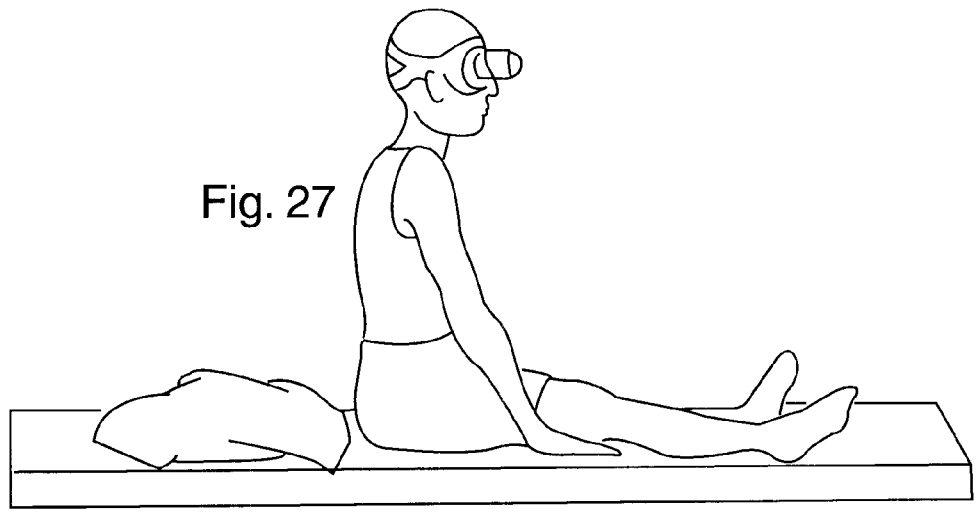
Figure 28:
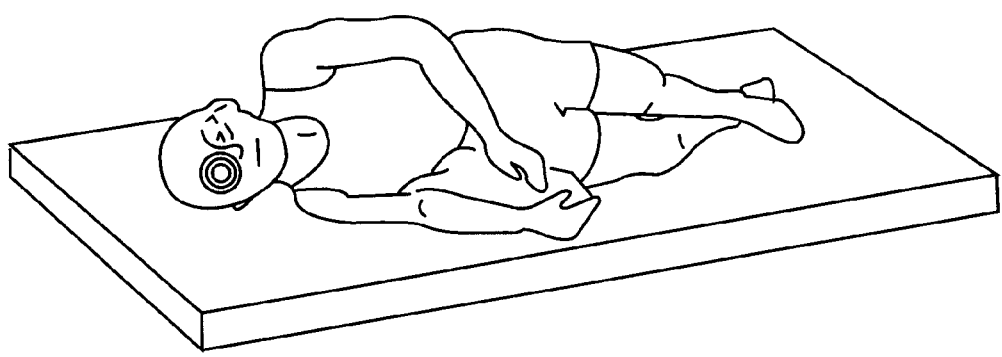
Figure 29:
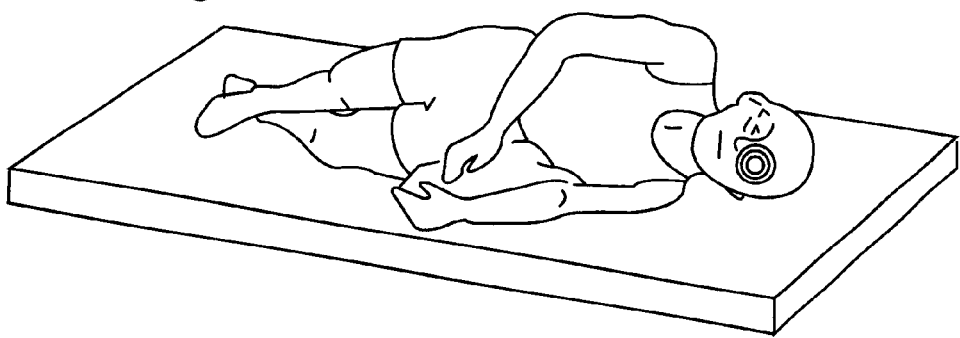

FIGS. 27–29 depicts the goggle guided BPPV diagnostic body positions sequence.

FIGS. 27 depicts the starting position in the device use instructions. The user is sitting on a mat with pillow behind him and goggles over his eyes. He has the diagnostic first component in place.

FIG. 28 depicts the position "R" (right) in the diagnostic method instructions. The user's head is turned to the right 45 degrees and the neck is extended 20 degrees. The user can see the "R" (right) completely within the outer sphere sighting mark.

FIG. 29 depicts the position "L" (left) in the diagnostic method instructions. The user's head is turned to the left 45 degrees and the neck is extended 20 degrees. The user can see the "L" (left) completely within the outer sphere sighting mark.

BPPV Treatment

PBPPV

The following figures depict the goggle guided posterior SCC BPPV treatment body positions sequence.

Figure 30:
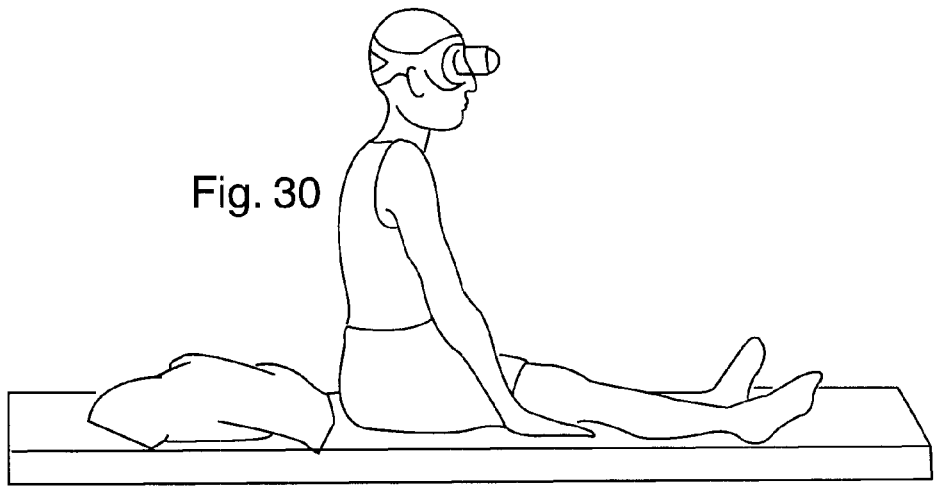

FIG. 30 depicts the starting position in the device use instructions. The user is sitting on a mat with pillow behind him and goggles over his eyes. He has the right posterior SCC BPPV treatment first component in place.

Figure 31:
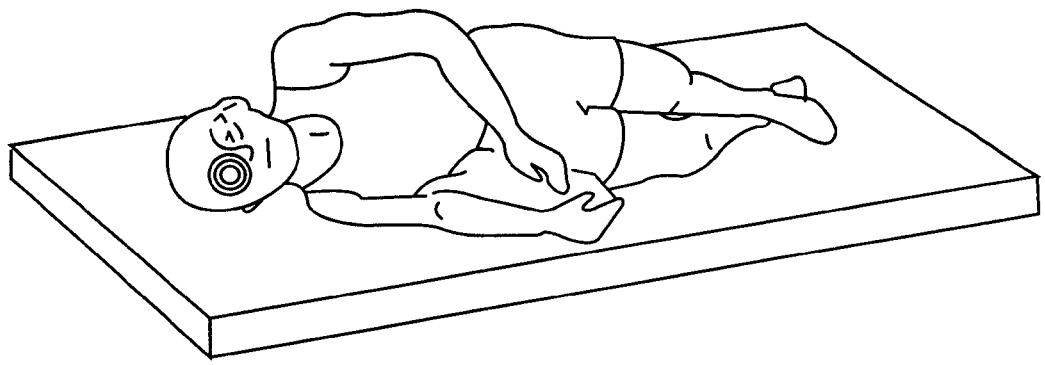

FIG. 31 depicts the position No. 1 in the right posterior BPPV treatment device method instructions. The user's head is turned to the right 45 degrees and the neck is extended 20 degrees. The user can see the No. 1 completely within the outer sphere sighting mark.

Figure 32:
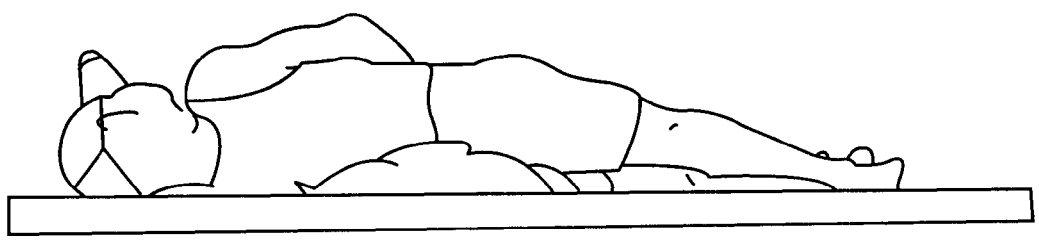

FIG. 32 depicts the position No. 2 in the right posterior BPPV treatment device method instructions. The user's head is turned to the left 45 degrees and the neck.is extended 20 degrees. The user can see the No. 2 completely within the outer sphere sighting mark.

Figure 33:
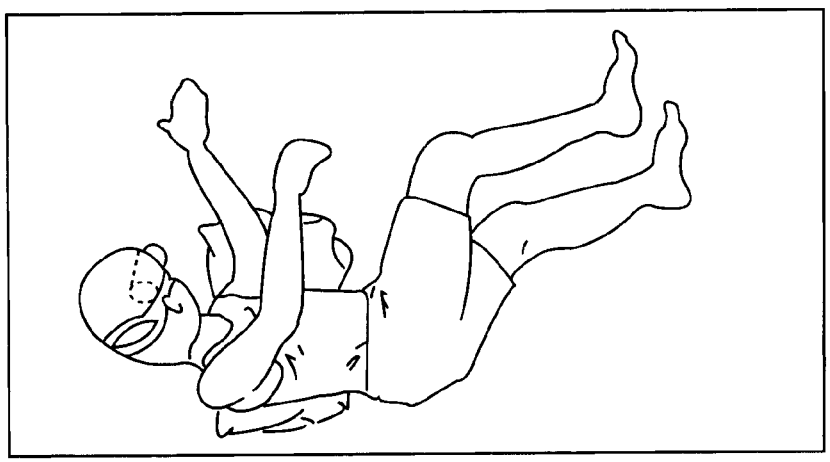

FIG. 33 depicts the position No. 3 in the right posterior BPPV treatment device method instructions. The user's head is turned to the left 135 degrees and the neck is flexed 20 degrees. The flexure of the neck may be less than 20 degrees, for example 10 degrees in some cases. The user is on his left side.

Figure 34:
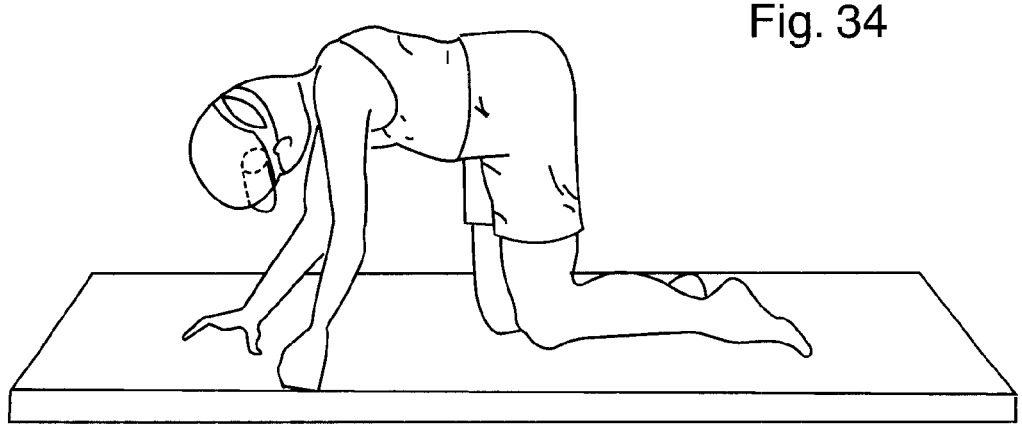

FIG. 34 depicts the user in position No. 4 in the right posterior BPPV treatment device method instructions. The user's head is turned to the left 135 degrees and the neck is flexed 20 degrees. This flexure of the neck may be less than 20 degrees, for example, 10 degrees in some cases. The user is in the crawl position.

Figure 35:
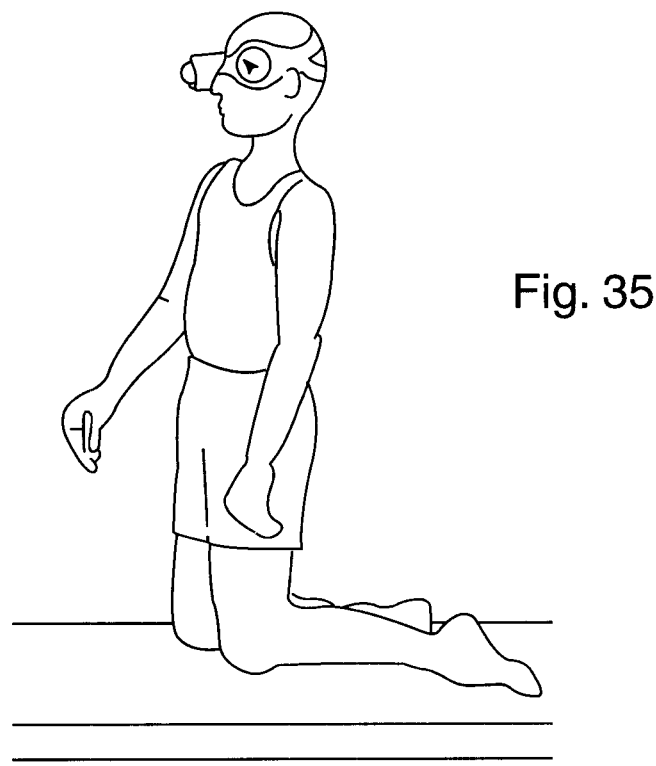

FIG. 35 depicts the user in position No. 5 in the right posterior BPPV treatment device method instructions. The user is in the kneeling position looking straight ahead.

Figure 36:
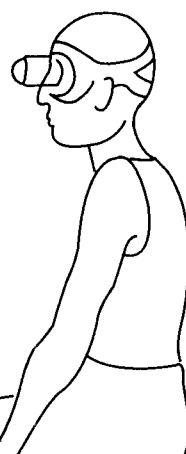

FIG. 36 depicts the starting position in the device use instructions. The user is sitting on a mat with pillow behind him and goggles over his eyes. He has the left posterior SCC BPPV treatment first component in place.

Figure 37:
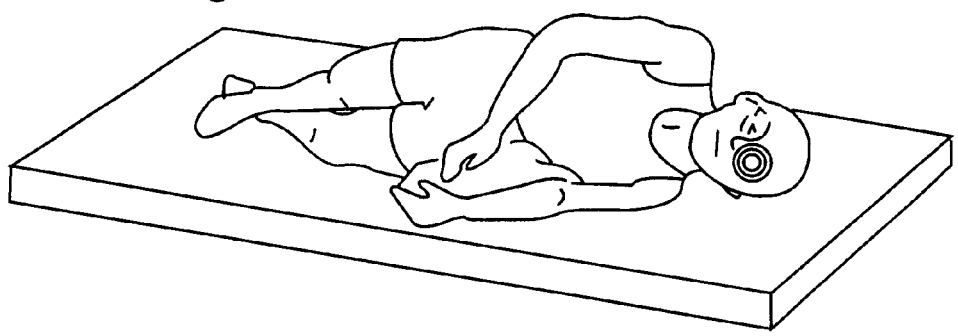

FIG. 37 depicts the position No. 1 in the left posterior BPPV treatment device method instructions. The user's head is turned to the left 45 degrees and the neck is extended 20 degrees. The user can see the No. 1 completely within the outer sphere sighting mark.

Figure 38:
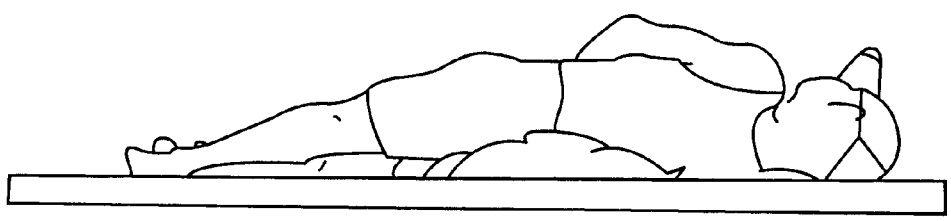

FIG. 38 depicts the position No. 2 in the left posterior BPPV treatment device method instructions. The user's head is turned to the right 45 degrees and the neck is extended 20 degrees. The user can see the No. 2 completely within the outer sphere sighting mark.

Figure 39:
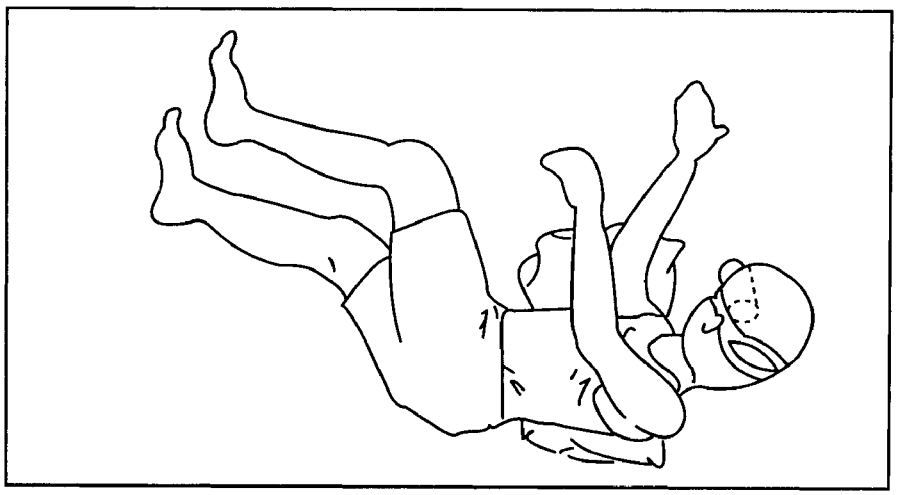

FIG. 39 depicts the position No. 3 in the left posterior BPPV treatment device method instructions. The user's head is turned to the right 135 degrees and the neck is flexed 20 degrees. This flexure of the neck may be less than 20 degrees, for example, 10 degrees in some cases. The user is on his left side.

Figure 40:
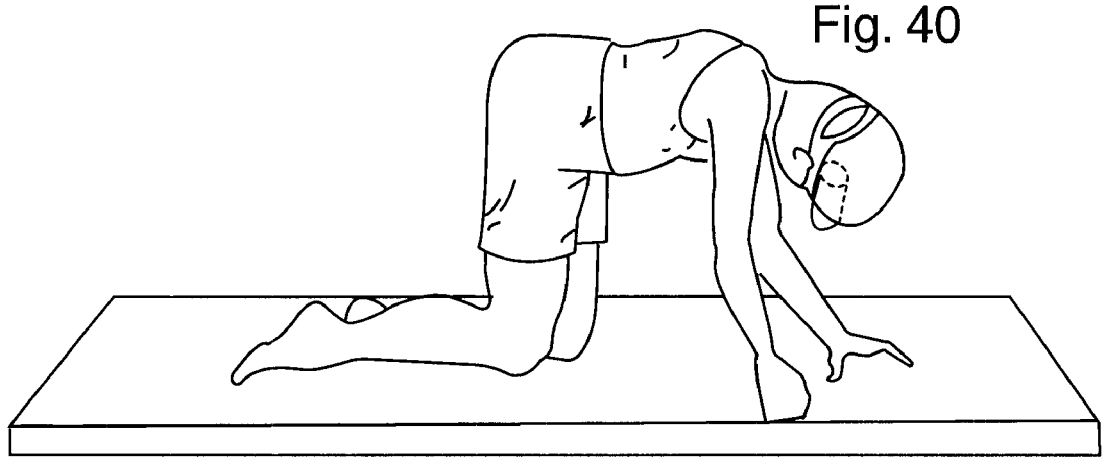

FIG. 40 depicts the user in position No. 4 in the left posterior BPPV treatment device method instructions. The user's head is turned to the right 135 degrees and the neck is flexed 20 degrees. This flexure of the neck may be less than 20 degrees, for example, 10 degrees in some cases. The user is in the crawl position.

Figure 41:
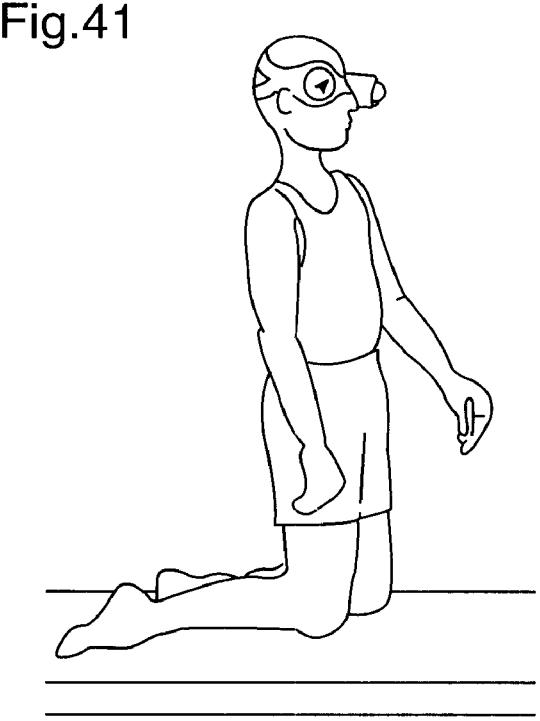

FIG. 41 depicts the user in position No. 5 in the left posterior BPPV treatment device method instructions. The user is in the kneeling position looking straight ahead.

HPBBV

The following Figures depict the goggle guided right horizontal SCC BPPV treatment body positions sequence.

Figure 42:
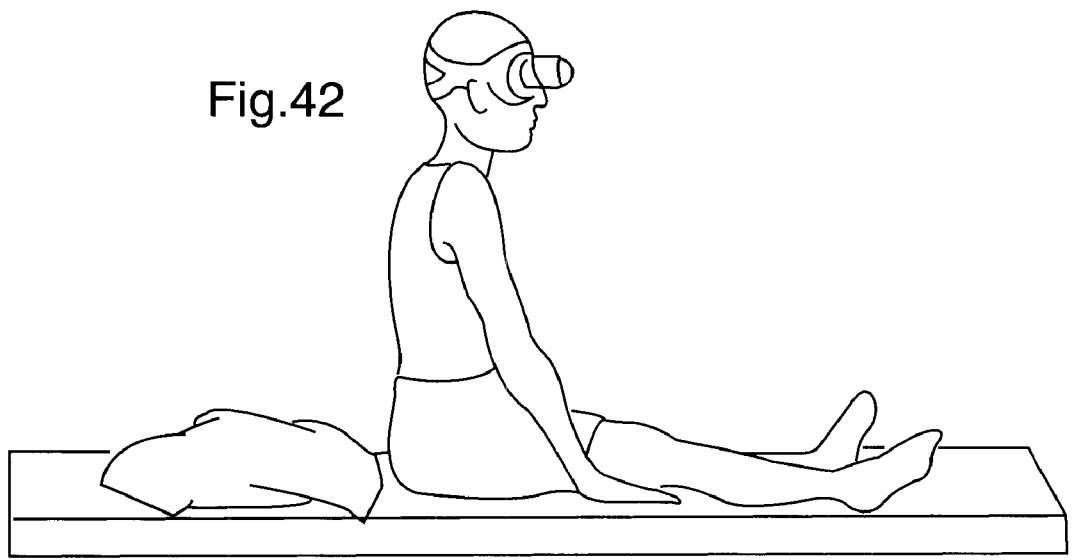

FIG. 42 depicts the starting position in the device use instructions. The user is sitting on a mat with pillow behind him and goggles over his eyes.

Figure 43:
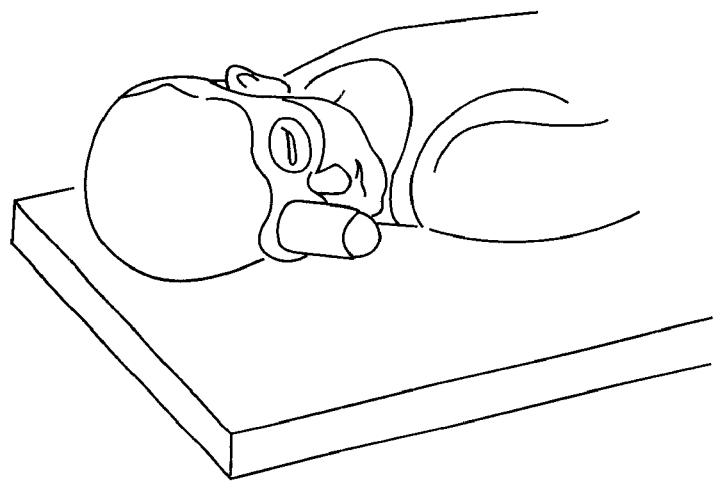

FIG. 43 depicts the user lying supine with his head turned 90 degrees to the right. He stays in this position for 30 seconds or until the vertigo stops.

Figure 44:
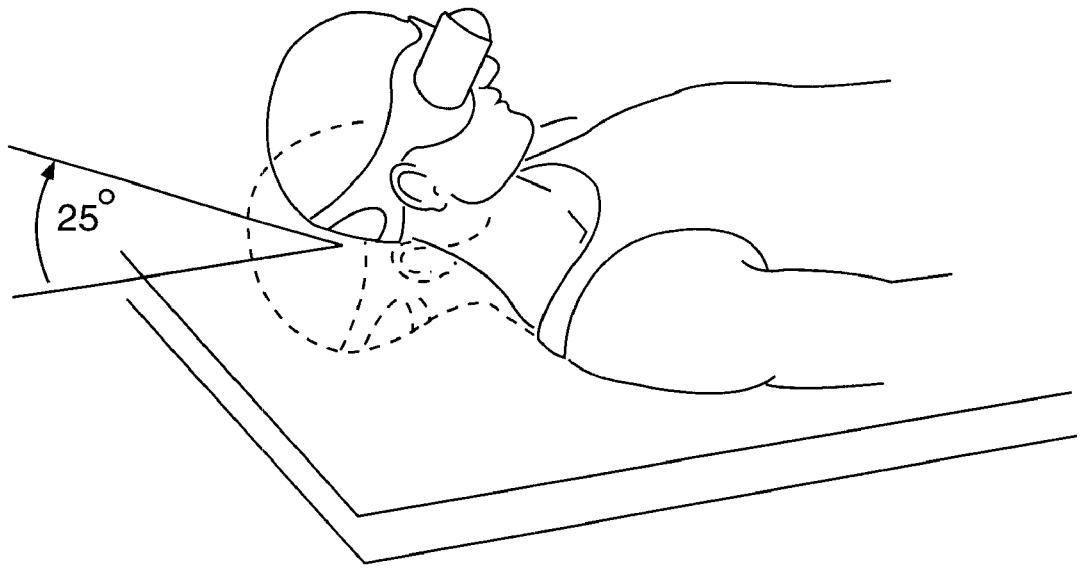

FIG. 44 depicts the user in a classic supine position with his neck flexed 25 degrees. He stays in this position for 30 seconds or until the vertigo stops.

Figure 45:
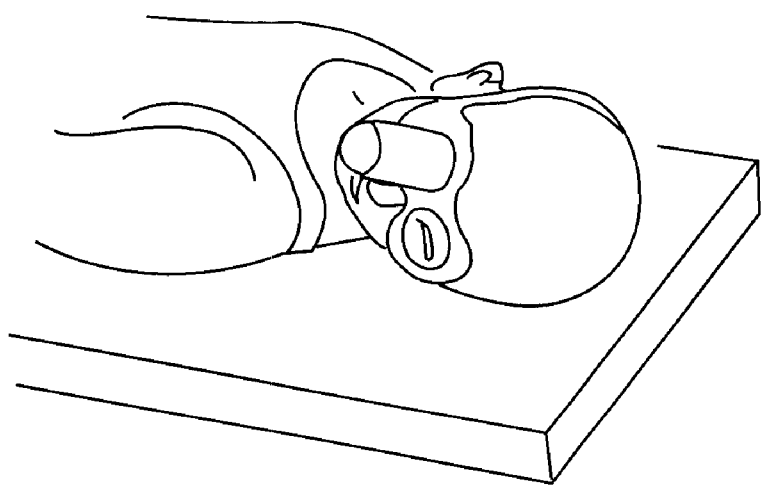

FIG. 45 depicts the user turning his head 90 degrees to the left and no longer flexing his neck. He stays in this position for 30 seconds or until the vertigo stops.

Figure 46:
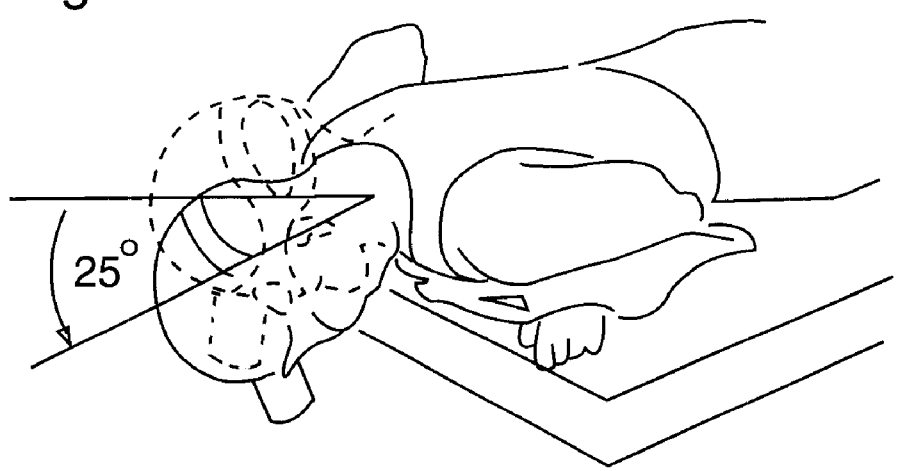

FIG. 46 depicts the user keeping his head in position shown in FIG. 45, while turning his body from supine to prone. He then turns his head such that his nose in directly downward and again flexes his neck 25 degrees. He stays in this position for 30 seconds or until the vertigo stops.

Figure 47:
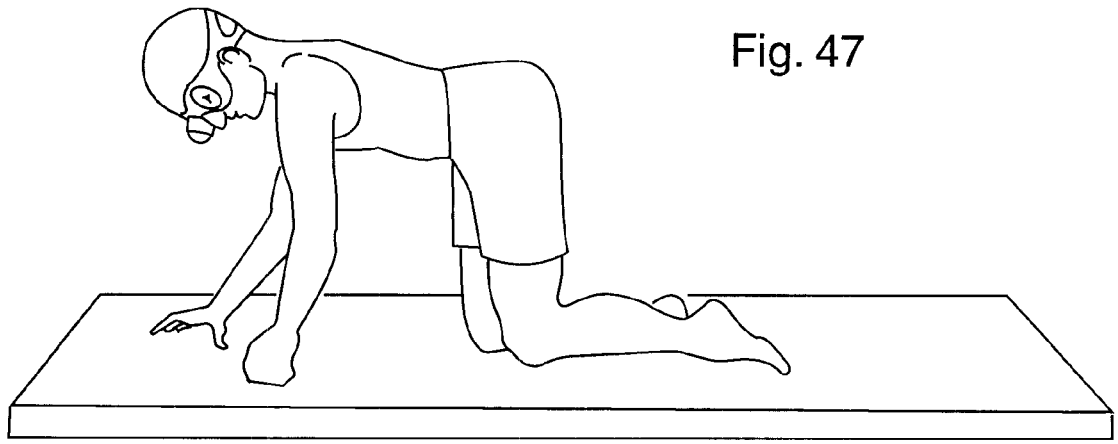

FIG. 47 depicts the user staying in a prone position and moving into the crawl position. He stays in this position for 30 seconds or until the vertigo stops.

Figure 48:
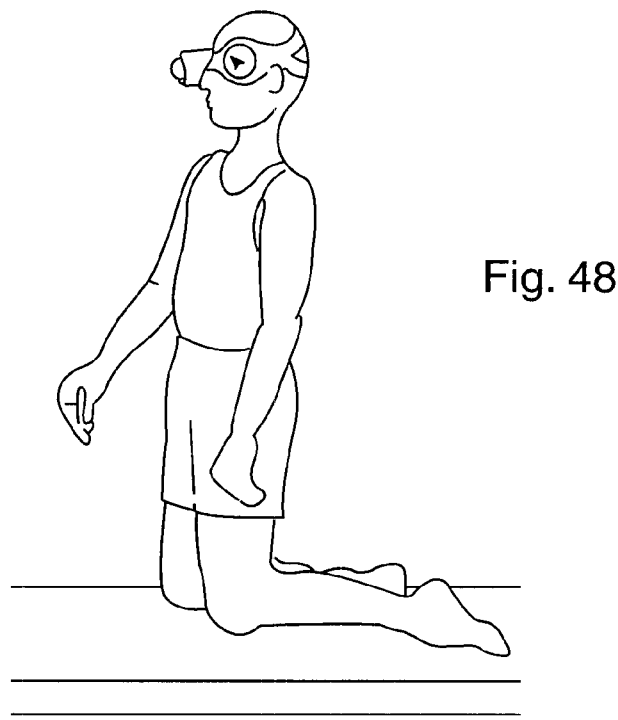

FIG. 48 depicts the user rising from the crawl position into a kneeling position. He stays in this position for 30 seconds or until the vertigo resolves.

The following Figures depict the goggle guided left horizontal SCC BPPV treatment body positions sequence.

Figure 49:
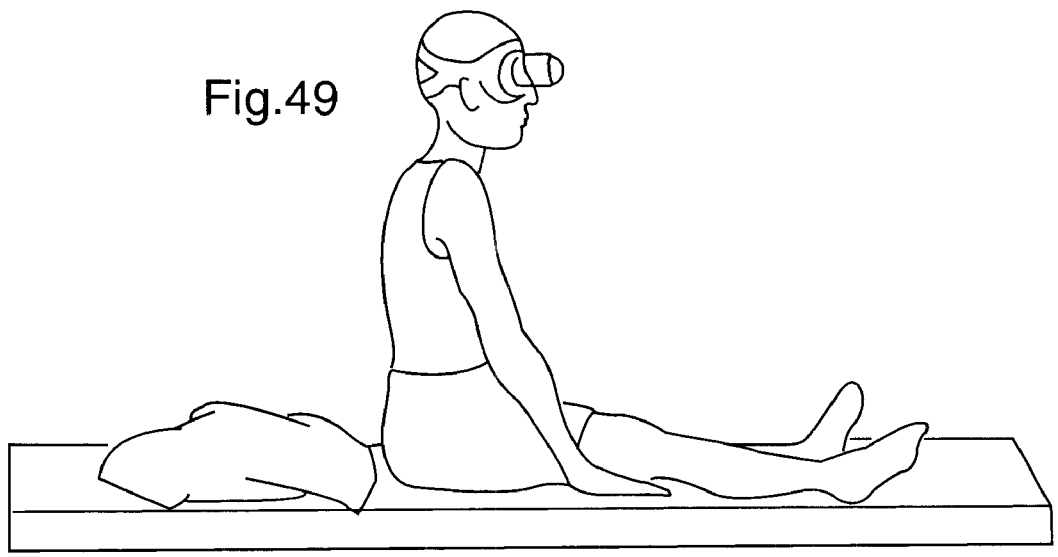

FIG. 49 depicts the starting position in the device use instructions. The user is sitting on a mat with pillow behind him and goggles over his eyes.

Figure 50:
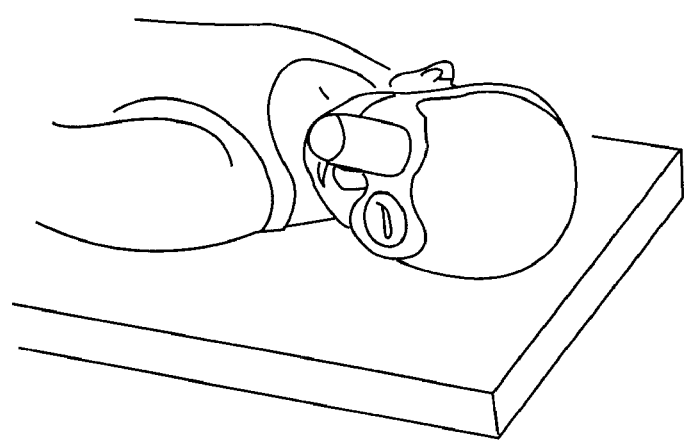

FIG. 50 depicts the user lying supine with his head turned 90 degrees to the left. He stays in this position for 30 seconds or until the vertigo stops.

Figure 51:
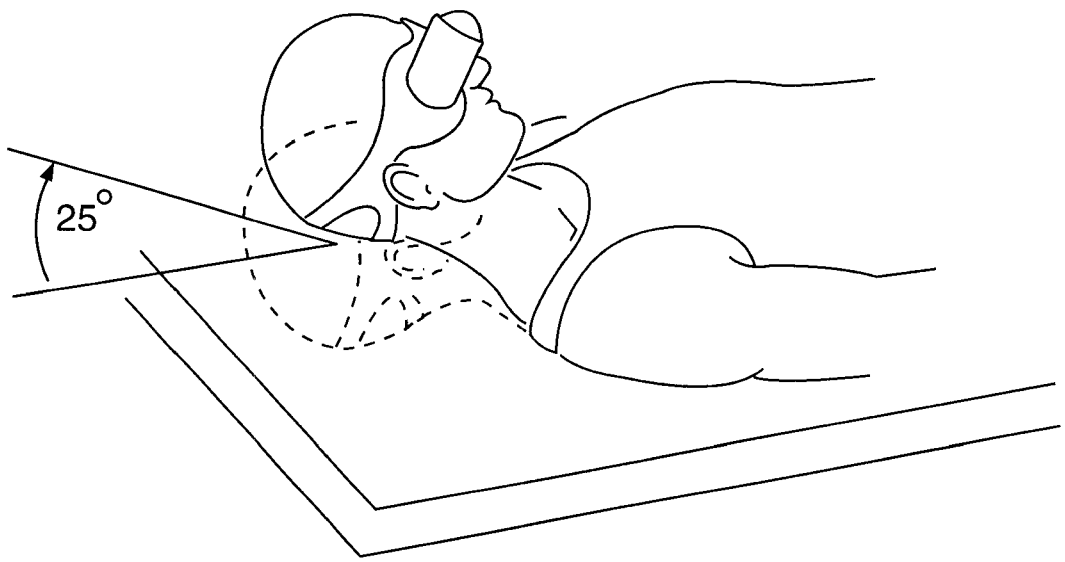

FIG. 51 depicts the user in a classic supine position with his neck flexed 25 degrees. He stays in this position for 30 seconds or until the vertigo stops.

Figure 52:
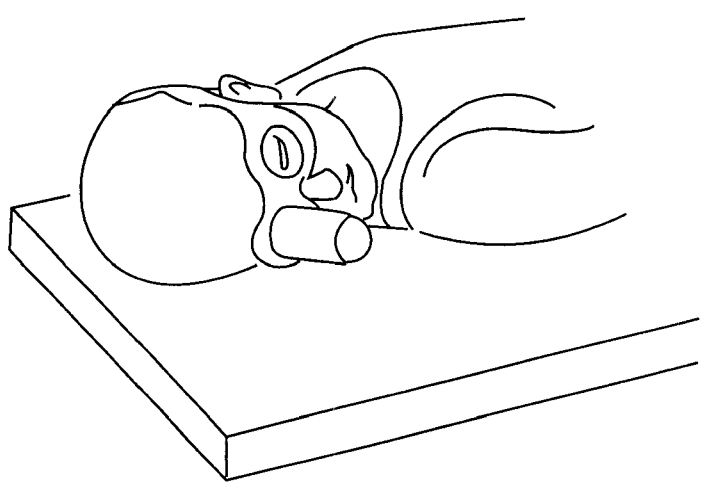

FIG. 52 depicts the user turning his head 90 degrees to the right and no longer flexing his neck. He stays in this position for 30 seconds or until the vertigo stops.

FIG. 53 depicts the user keeping his head in position shown in FIG. 52, while turning his body from supine to prone. He then turns his head such that his nose is directly downward and again flexes his neck 25 degrees. He stays in this position for 30 seconds or until the vertigo stops.

FIG. 54 depicts the user staying in a prone position and moving into the crawl position. He stays in this position for 30 seconds or until the vertigo stops.

Figure 55:
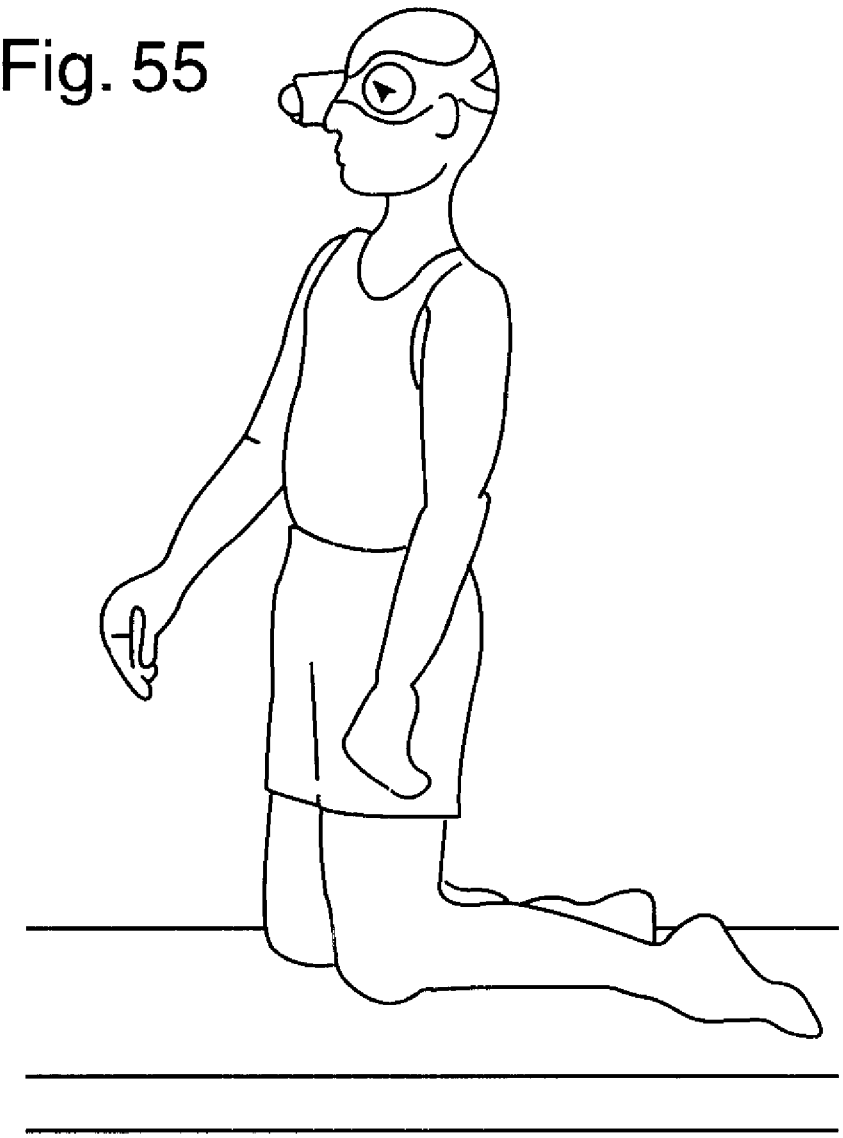

FIG. 55 depicts the user rising from the crawl position into a kneeling position. He stays in this position for 30 seconds or until the vertigo resolves.

FIGS. 56–87 illustrate more details of the embodiment of FIGS. 1–26 employing a magnet in the inner sphere and an exterior magnet attached to the device.

Figure 56:
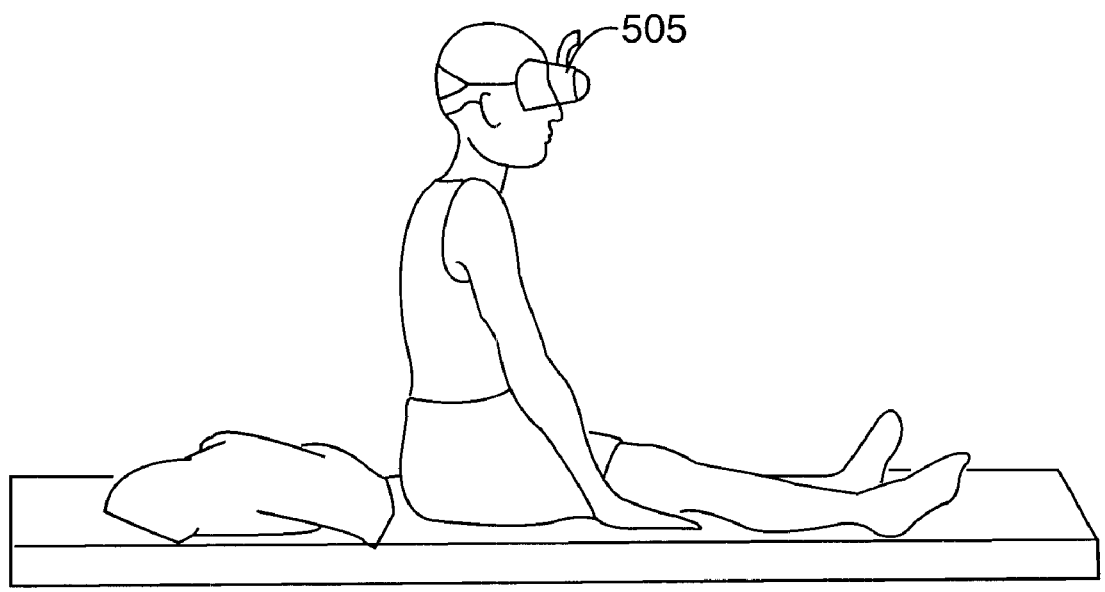

FIG. 56 illustrates the user in a setting position with the apparatus of FIG. 7 attached in place to the users head.

Figure 57:
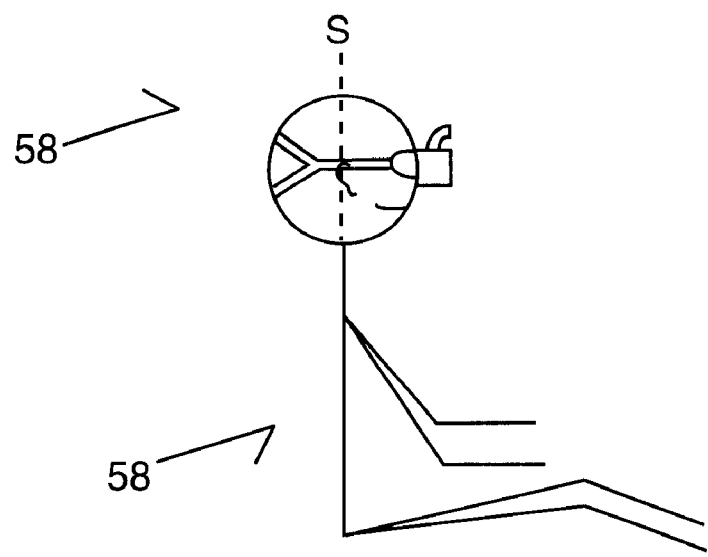

FIG. 57 is a simplified view of FIG. 56.

Figure 58:
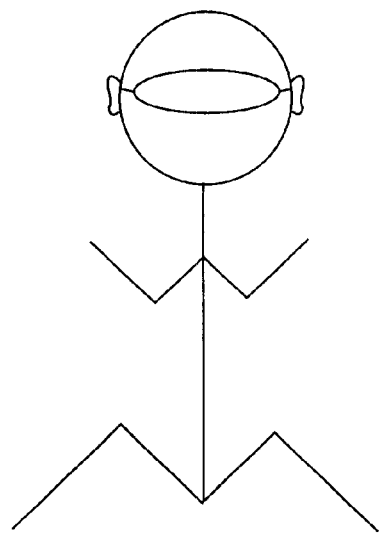

FIG. 58 is a rear view of the user as seen along lines 58—58 of FIG. 57.

Figure 59:
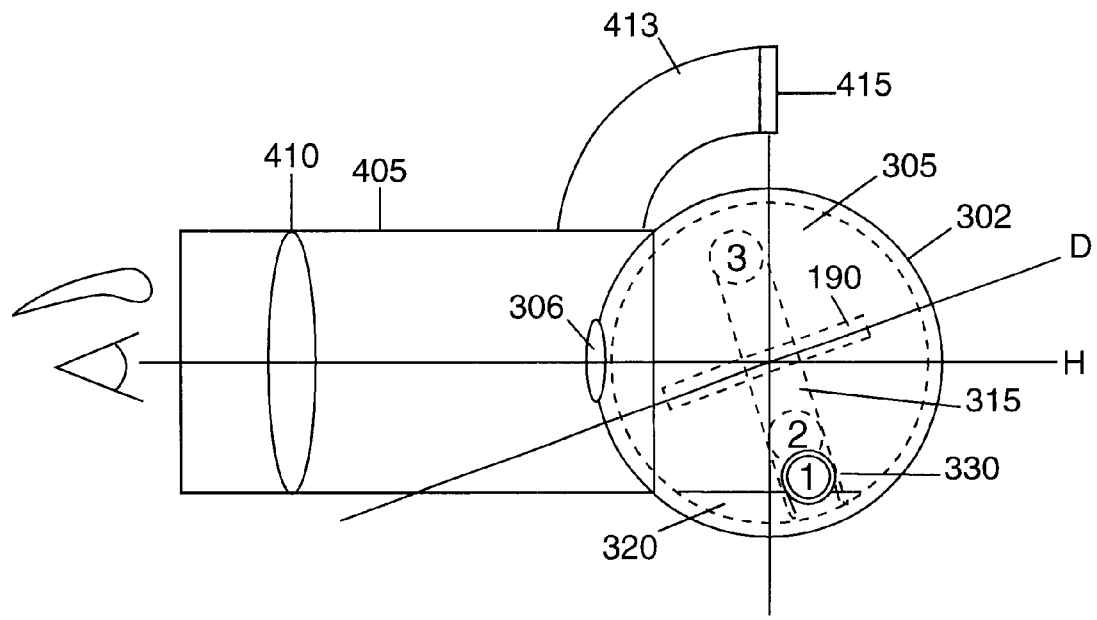

FIG. 59 is a view of the apparatus similar to that of FIG. 7.

Figure 60:
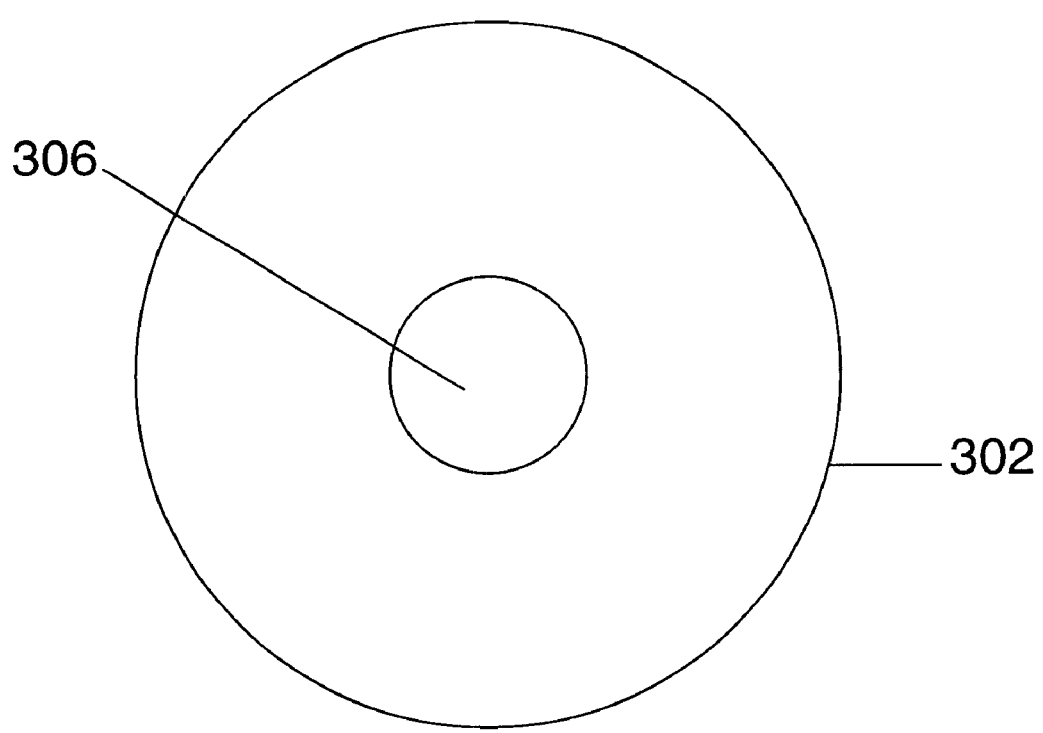

FIG. 60 illustrates the sighting mark on the inner sphere of the device of FIG. 59.

Figure 61:
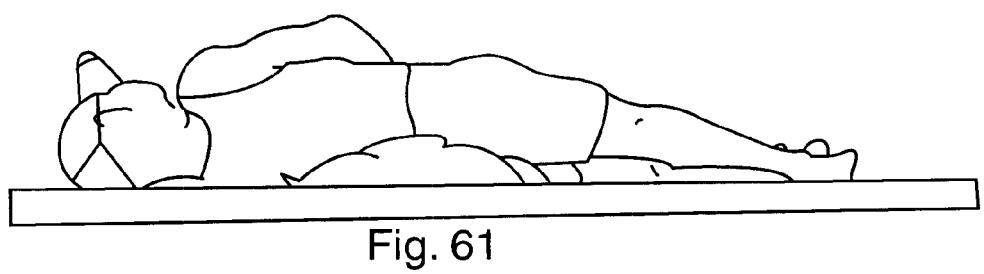

FIG. 61 illustrates the user with his or her head inclined downward at an angle of 20 degrees relative to the horizontal with the left side of the head located 45 degrees relative to the vertical.

Figure 62:
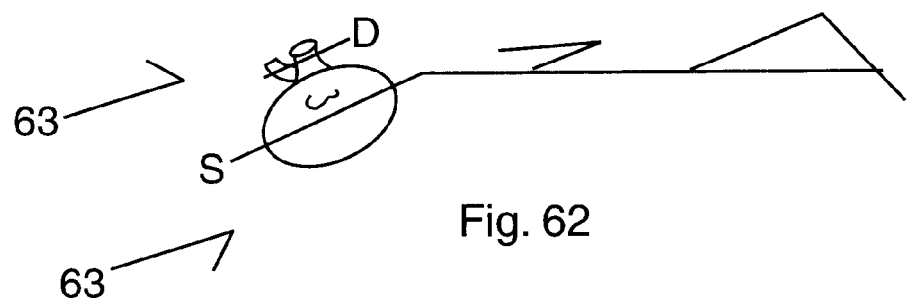

FIG. 62 is a simplified view of FIG. 61.

Figure 63:
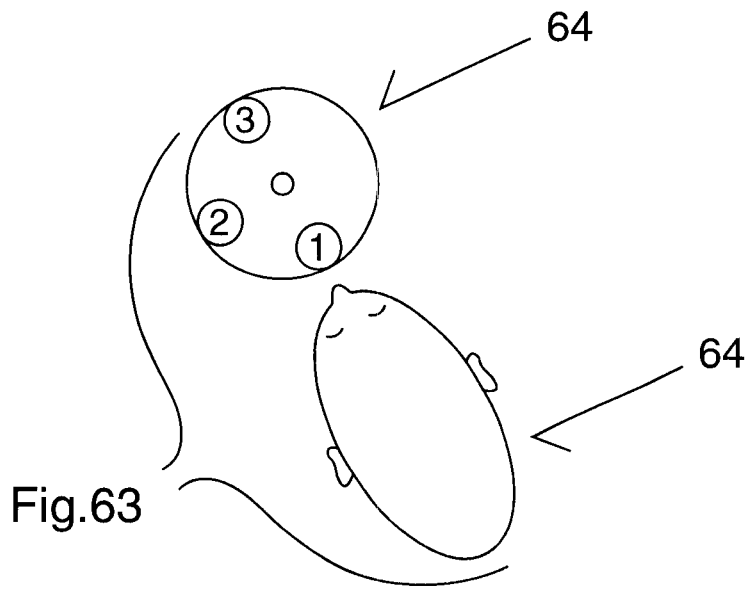

FIG. 63 is a view of FIG. 62 as seen along lines 63—63 thereof with the No. 1 position of the inner sphere within the sighting mark.

Figure 64:
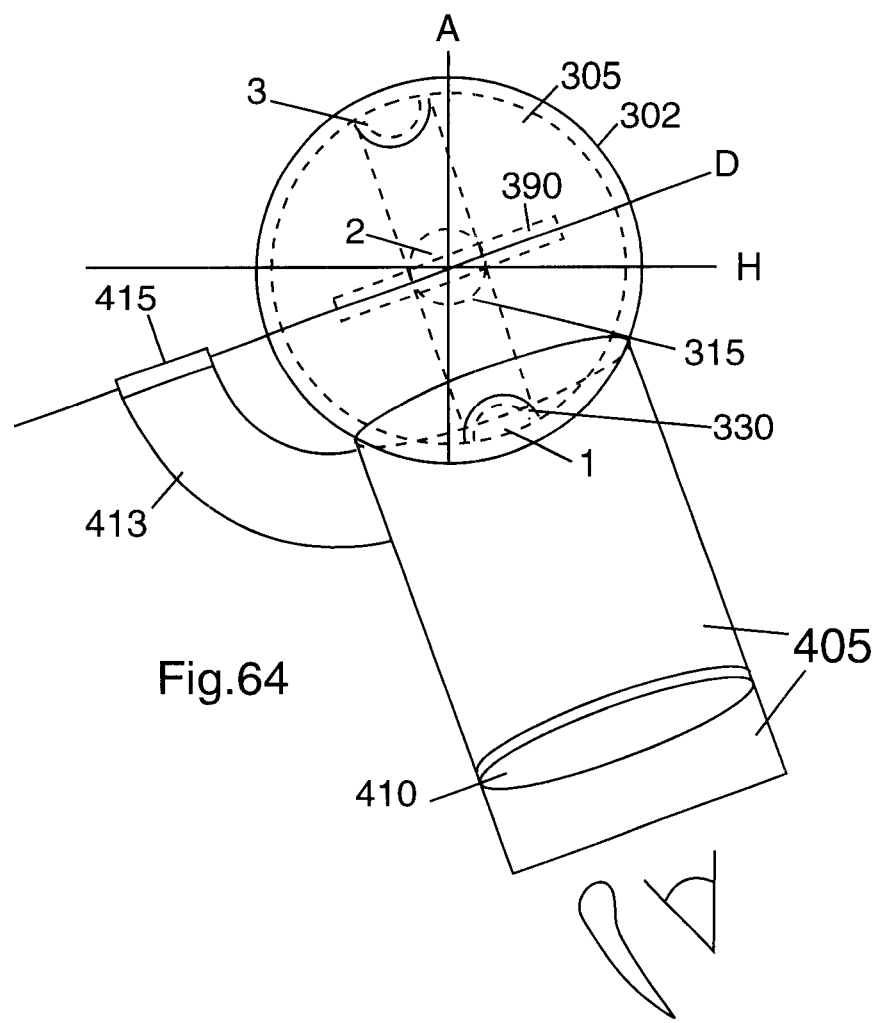

FIG. 64 is a view of the apparatus of FIG. 59 when the user is in the position of FIGS. 61–63.

Figure 65:
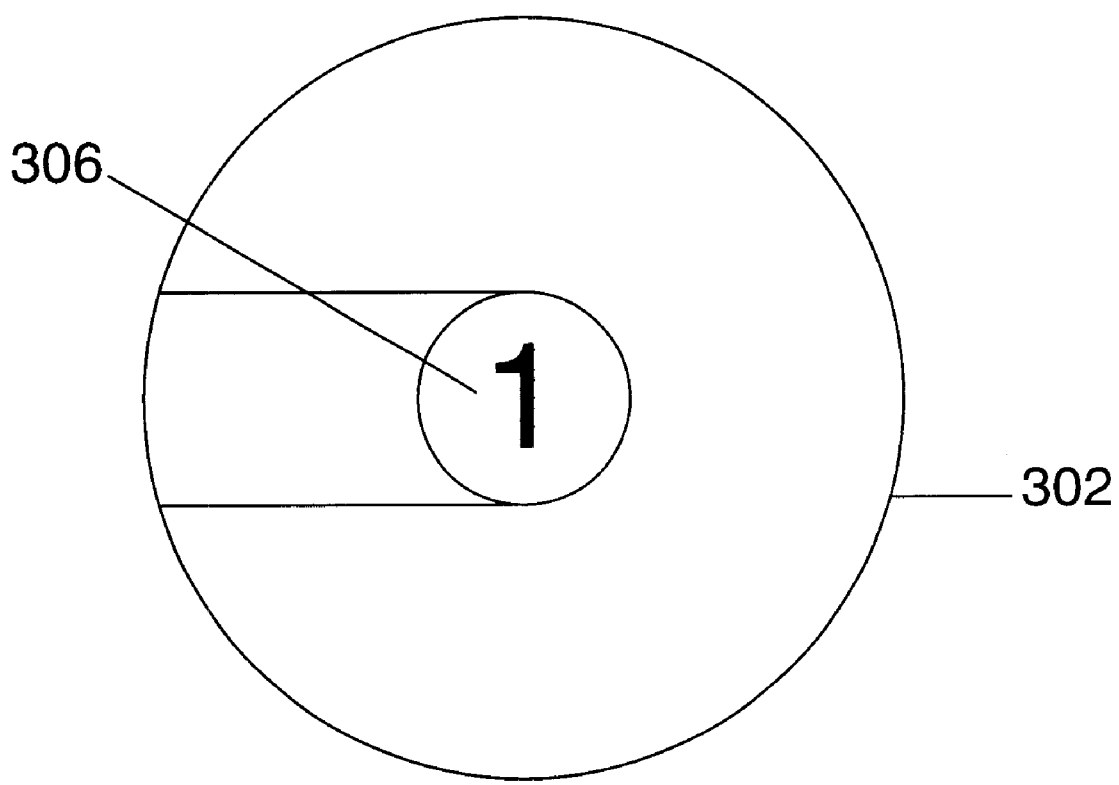

FIG. 65 illustrates the No. 1 position of the inner sphere within the sighting mark.

FIG. 66 illustrates the user with his or her head inclined downward at an angle of 20 degrees relative to the horizontal with the left side of the head located 45 degrees relative to the vertical.

FIG. 67 is a simplified view of FIG. 66.

Figure 68:
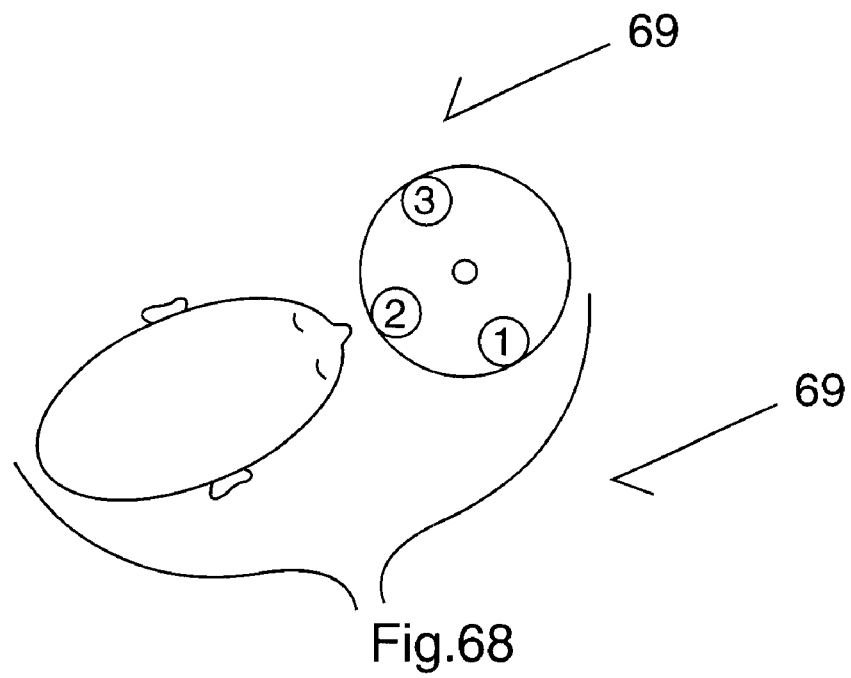

FIG. 68 is a view of FIG. 67 as seen along the lines 68—68 with the No. 2 position of the inner sphere within the sighting mark.

Figure 69:
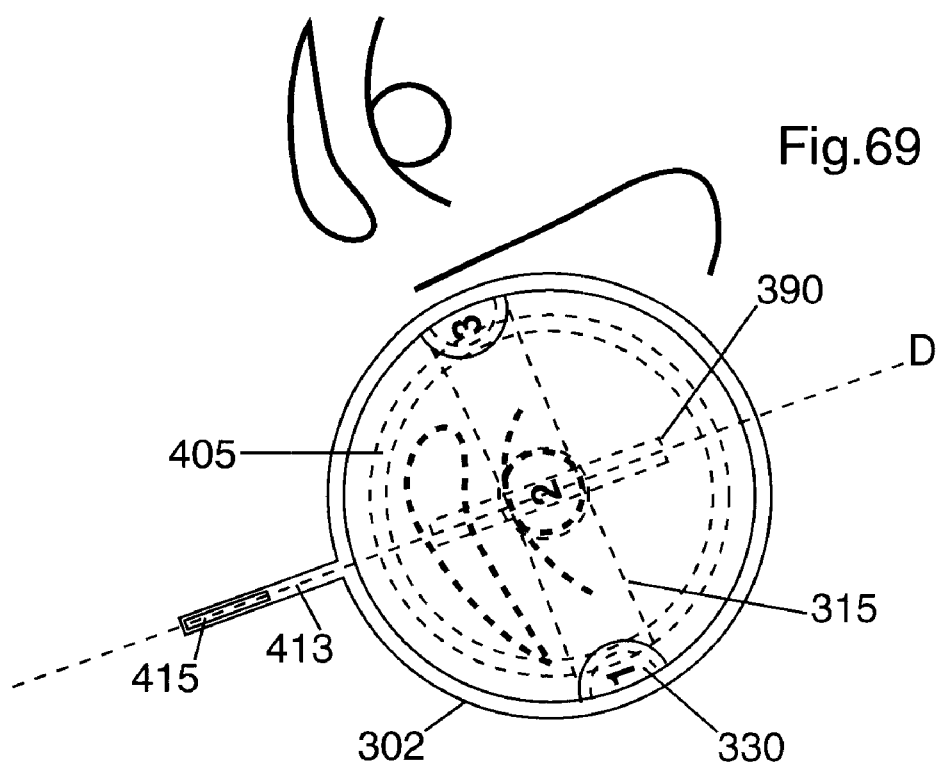

FIG. 69 is a view of the apparatus of FIG. 59 when the user is in the position of FIGS. 66–68.

Figure 70:
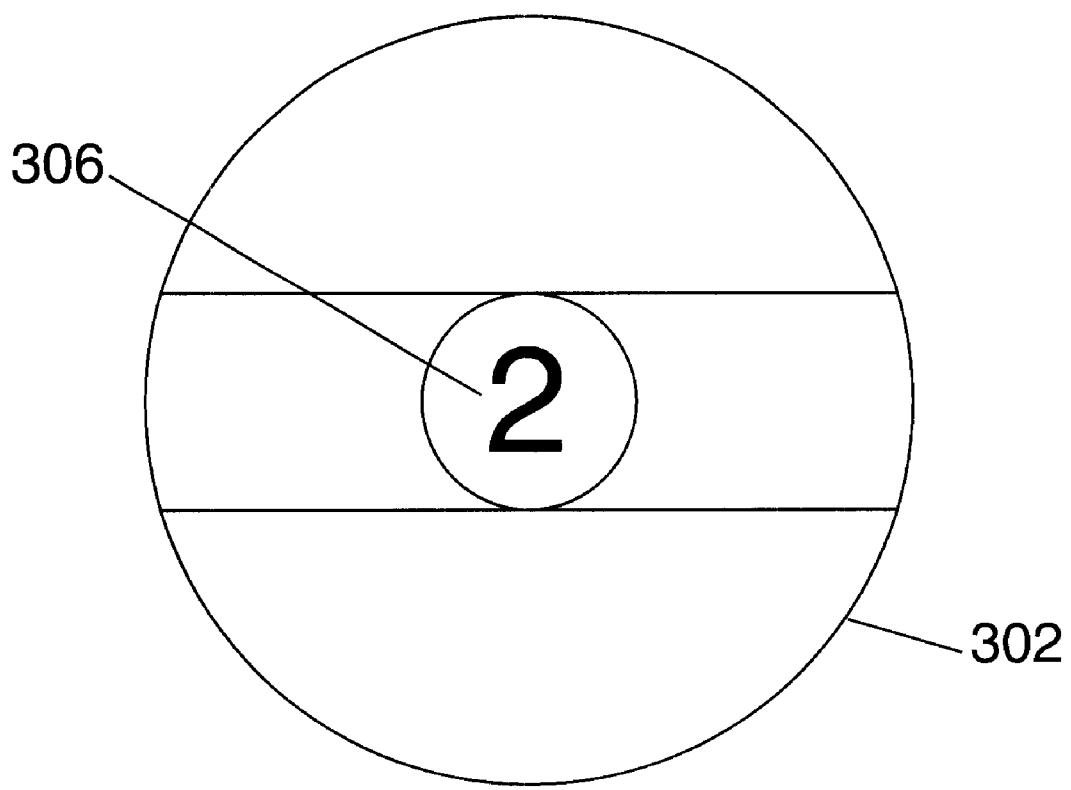

FIG. 70 illustrates the No. 2 position of the inner sphere within the sighting mark.

Figure 71:
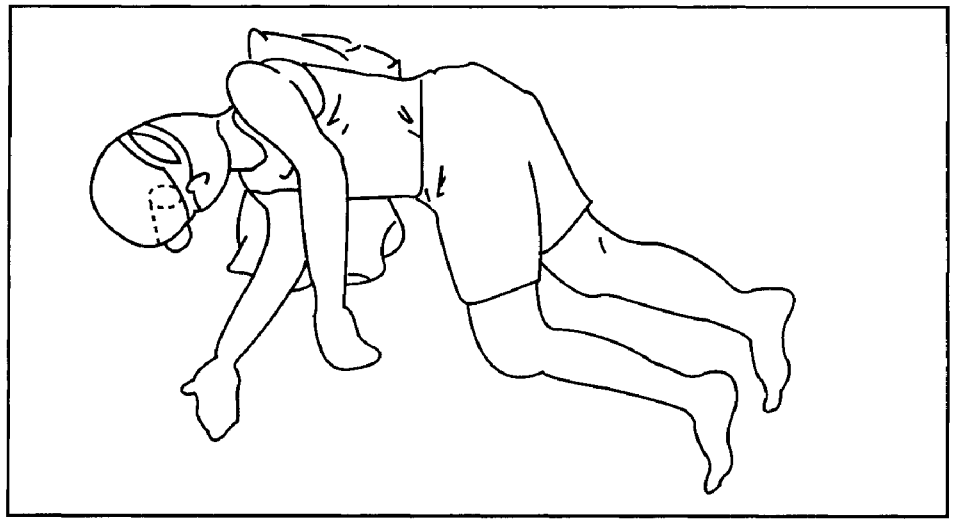

FIG. 71 illustrates the user with his or her head inclined downward 20 degrees relative to the horizontal with the head rotated clockwise 135 degrees form the position of FIGS. 66–68.

Figure 72:
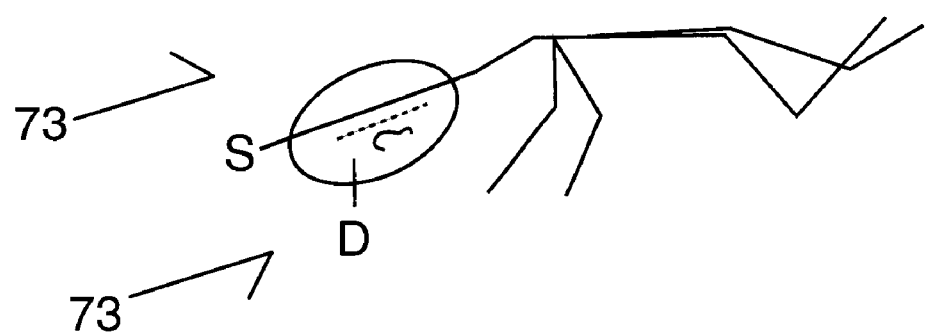

FIG. 72 is a simplified view of FIG. 71.

Figure 73:
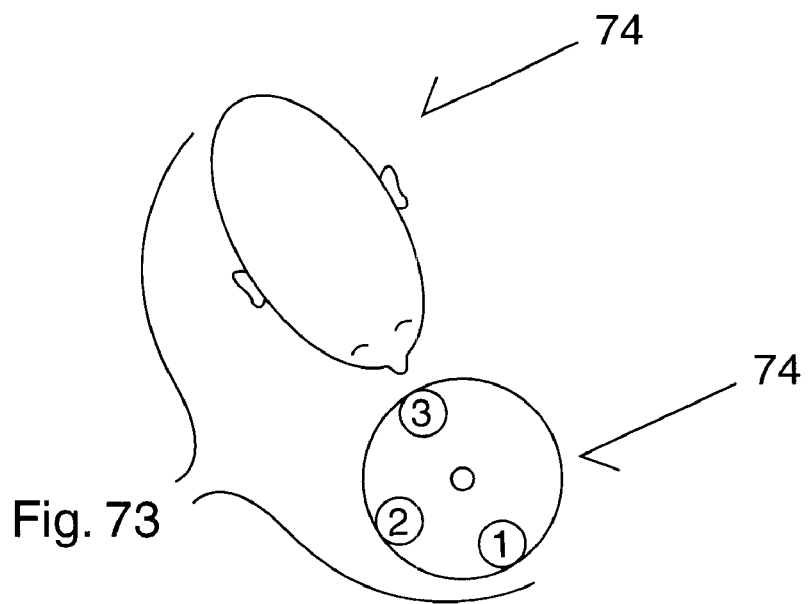

FIG. 73 is a view of FIG. 72 as seen along the lines 73—73 thereof with the No. 3 position of the inner sphere within the sighting mark.

Figure 74:
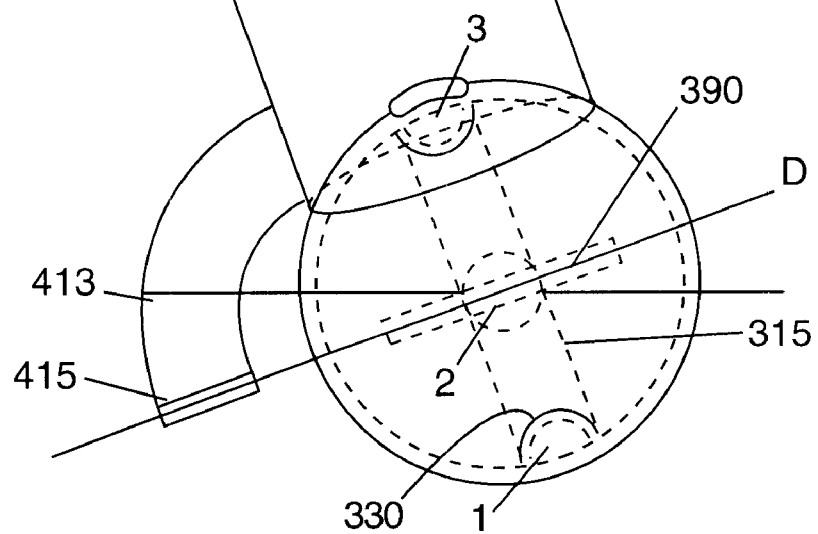

FIG. 74 is a view of the apparatus of FIG. 59 when the user is in the position of FIGS. 71–73.

Figure 75:
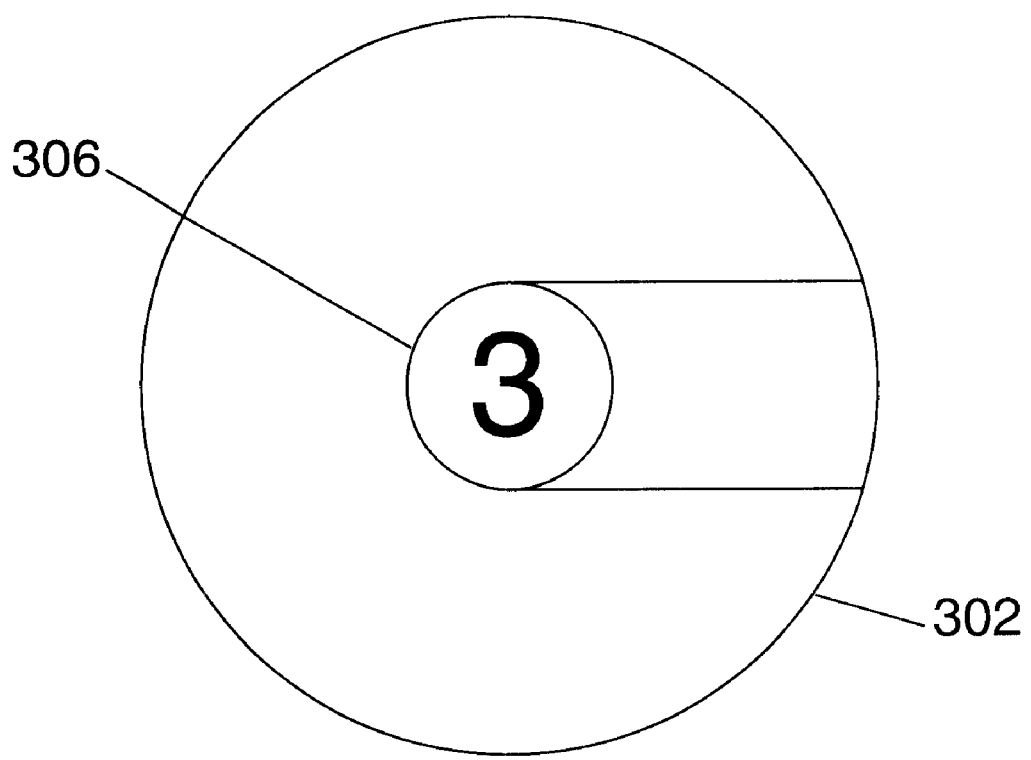

FIG. 75 illustrates the No. 3 position of the inner sphere within the sighting mark.

Figure 76:
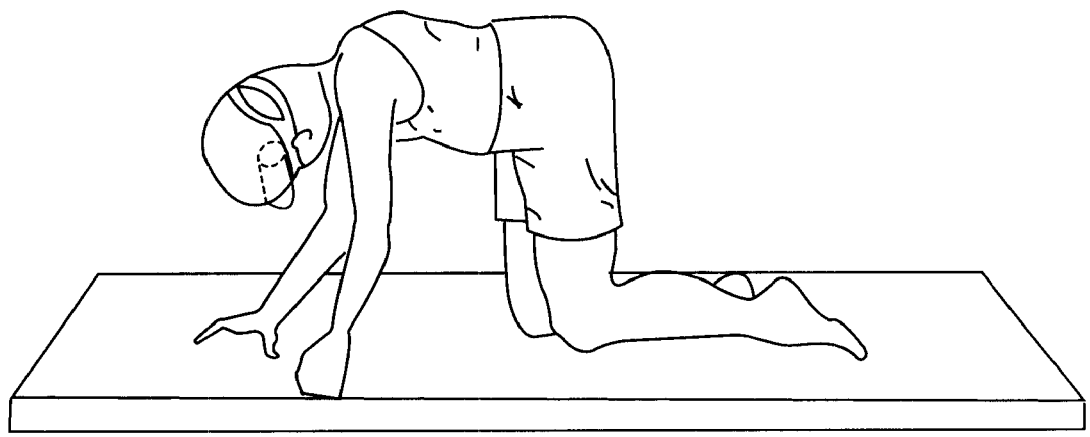
Figure 77:
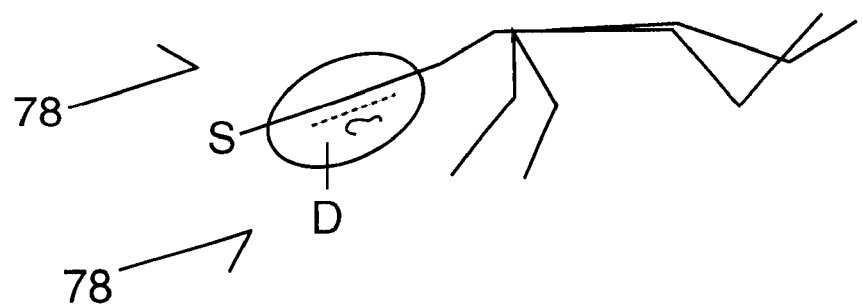

FIGS. 76 and 77 illustrate the user in the kneeling position with his or her hands on the mat and with the head still in the position of FIGS. 71–73.

Figure 78:
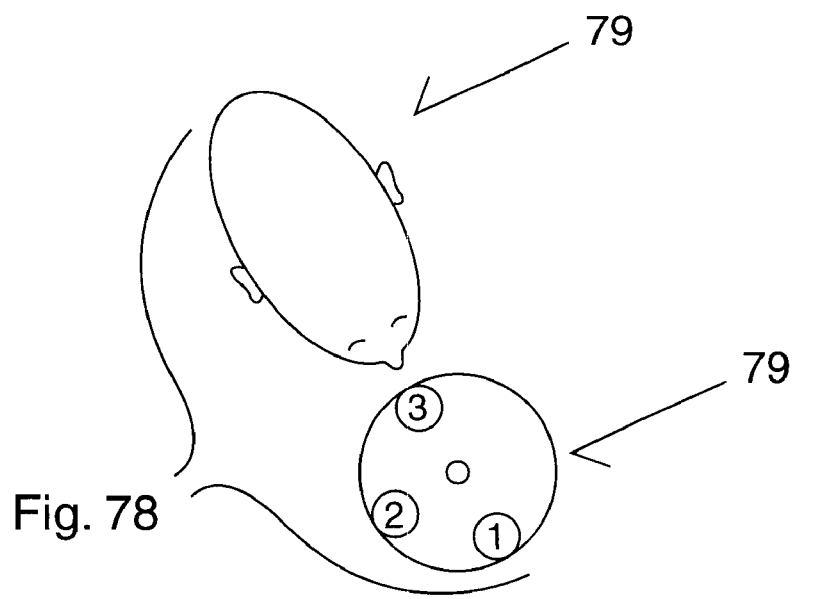

FIG. 78 is a view of FIG. 77 as seen along lines 78—78 thereof with the No. 3 position of the inner sphere within the sighting mark.

Figure 79:
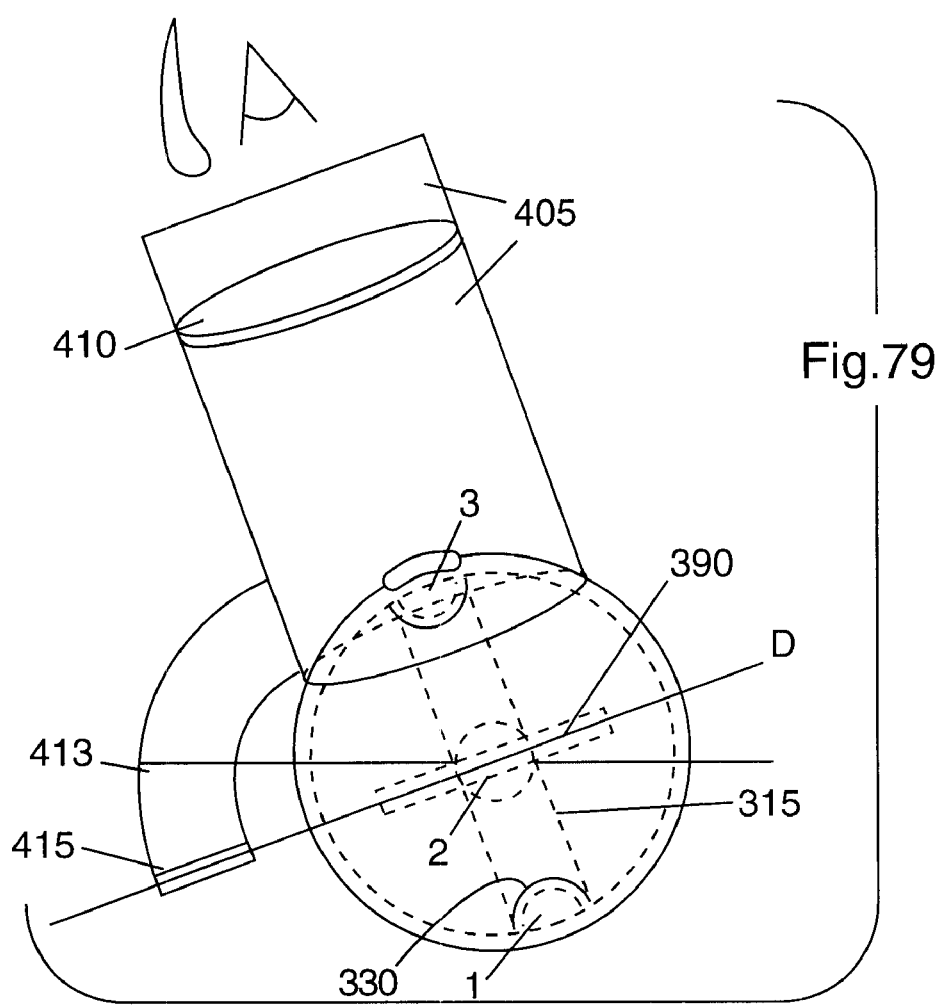

FIG. 79 is a view of the apparatus of FIG. 59 when the user is in the position of FIGS. 76–78.

Figure 80:
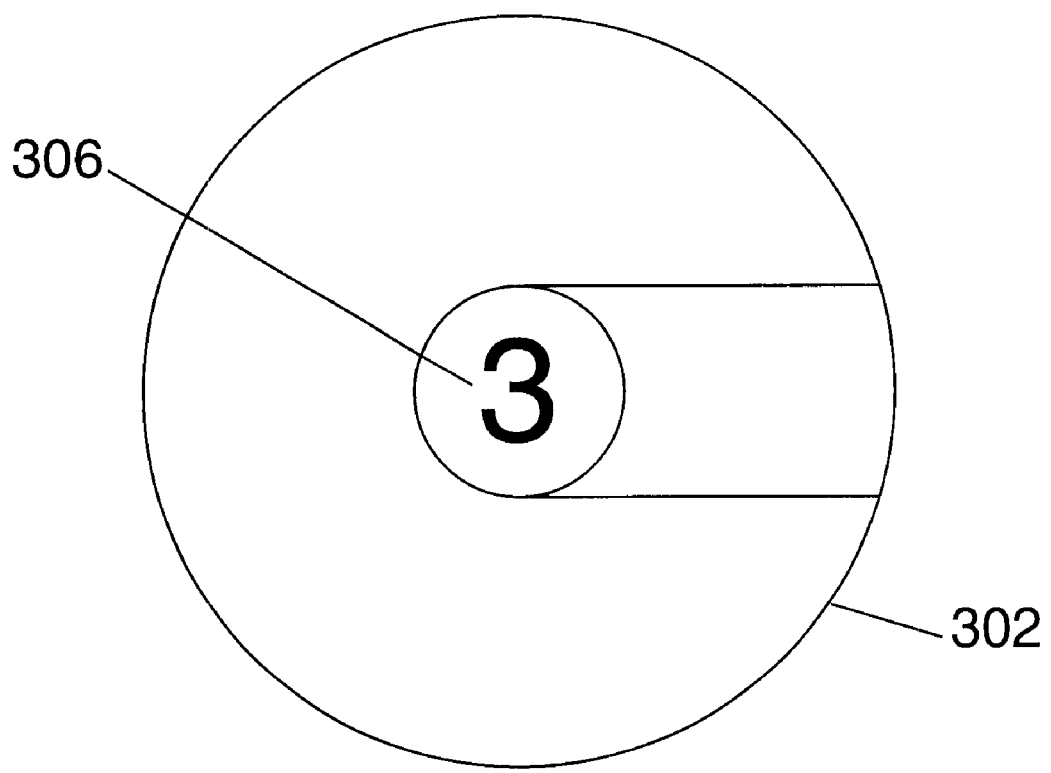

FIG. 80 illustrates the No. 3 position of the inner sphere within the sighting mark.

Figure 81:
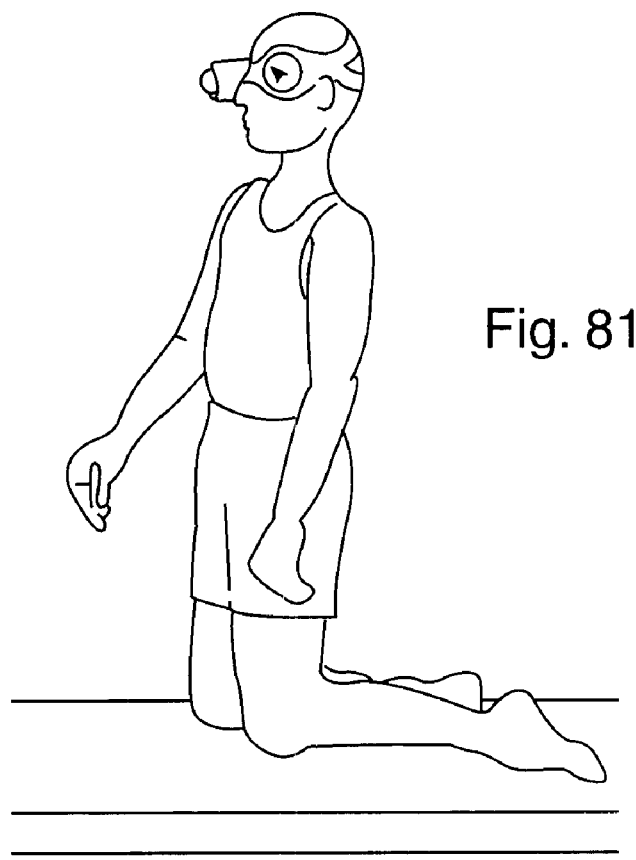

FIG. 81 illustrates the user in a kneeling position with his or her head in an upright position.

Figure 82:
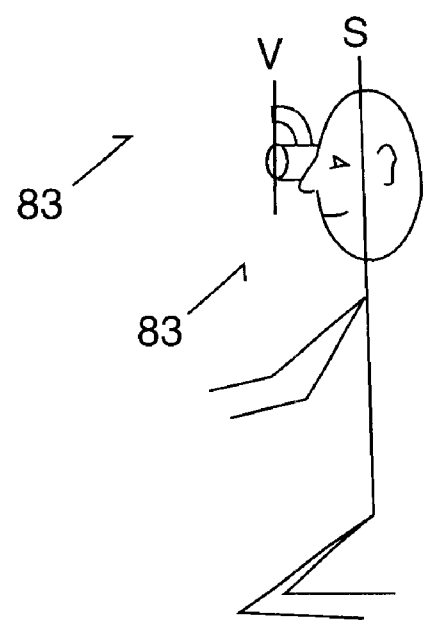

FIG. 82 is a simplified view of FIG. 81.

Figure 83:
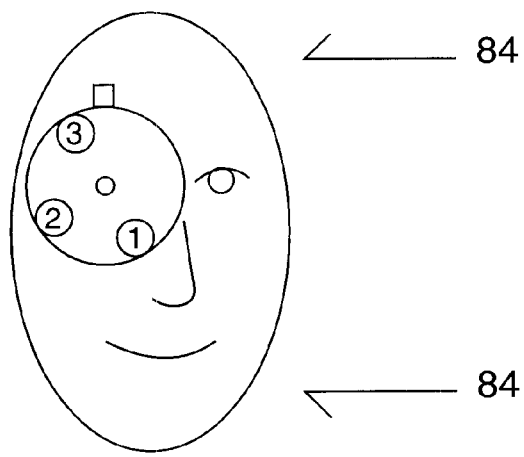

FIG. 83 illustrates the Nos. 1–3 positions of the inner sphere when the user is in the position of FIGS. 81 and 82.

Figure 84:
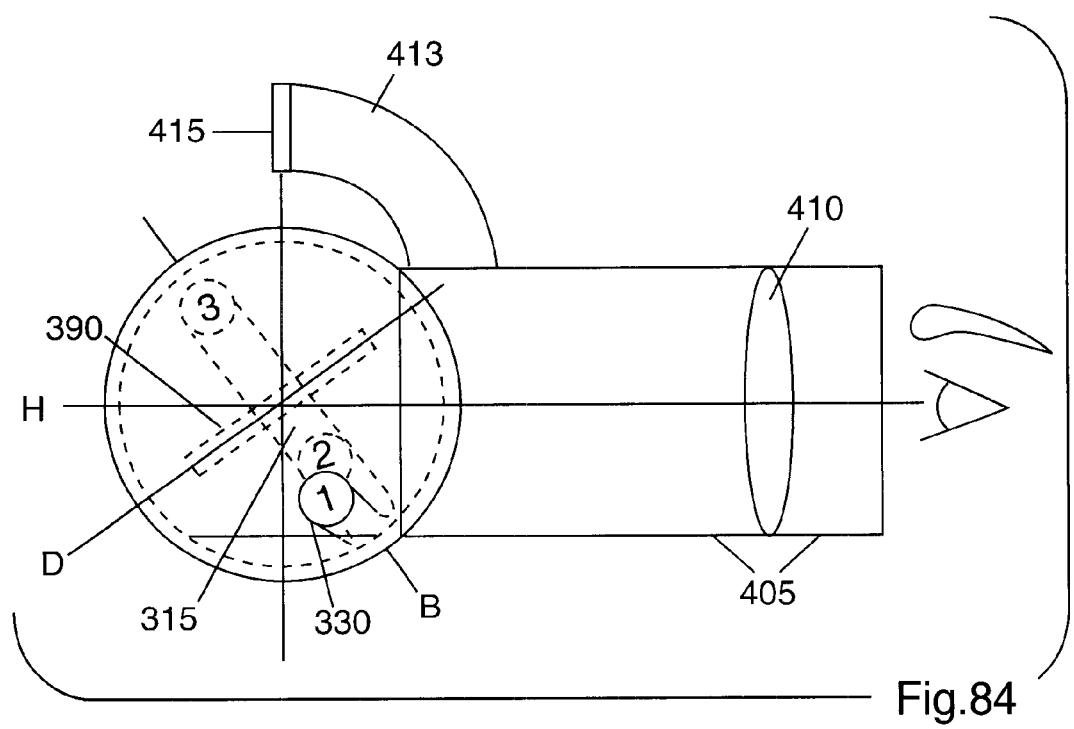

FIG. 84 is a view of the apparatus of FIG. 59 when the user is in the position of FIGS. 81 and 82.

Figure 85:
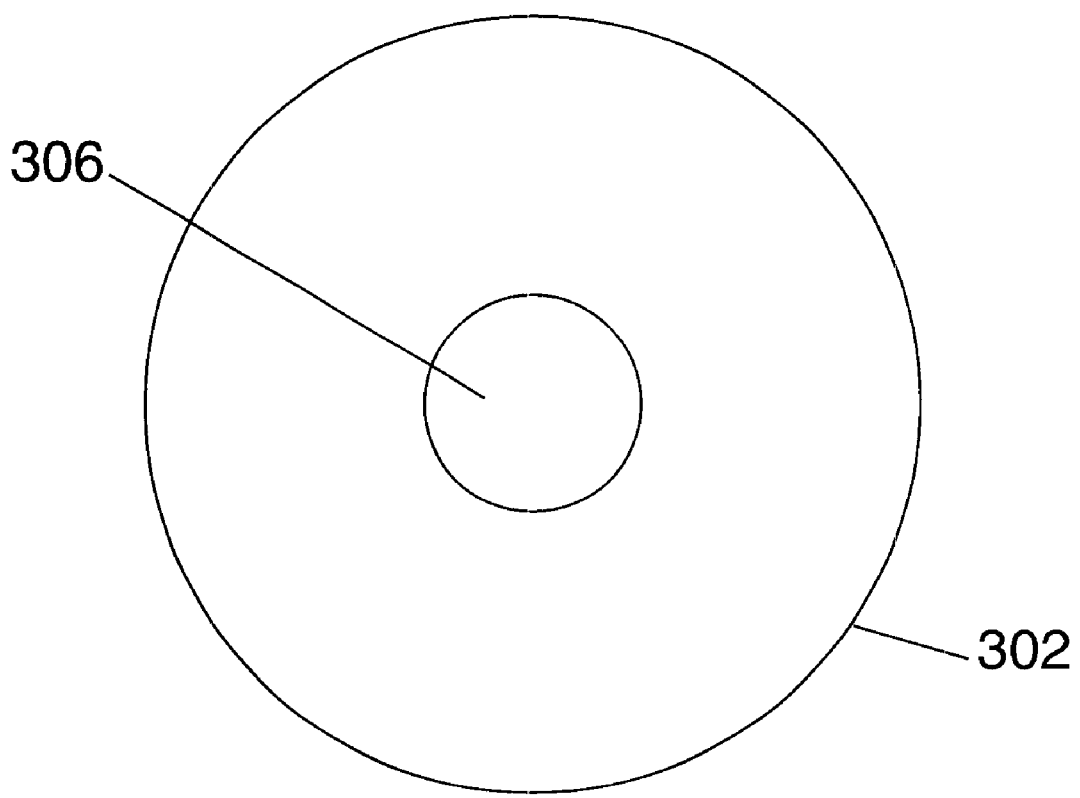

FIG. 85 illustrates that the user does not see the path or the Nos. 1–3 positions of the inner sphere when the user is in the position of FIGS. 81 and 82.

Figures 86, 87:
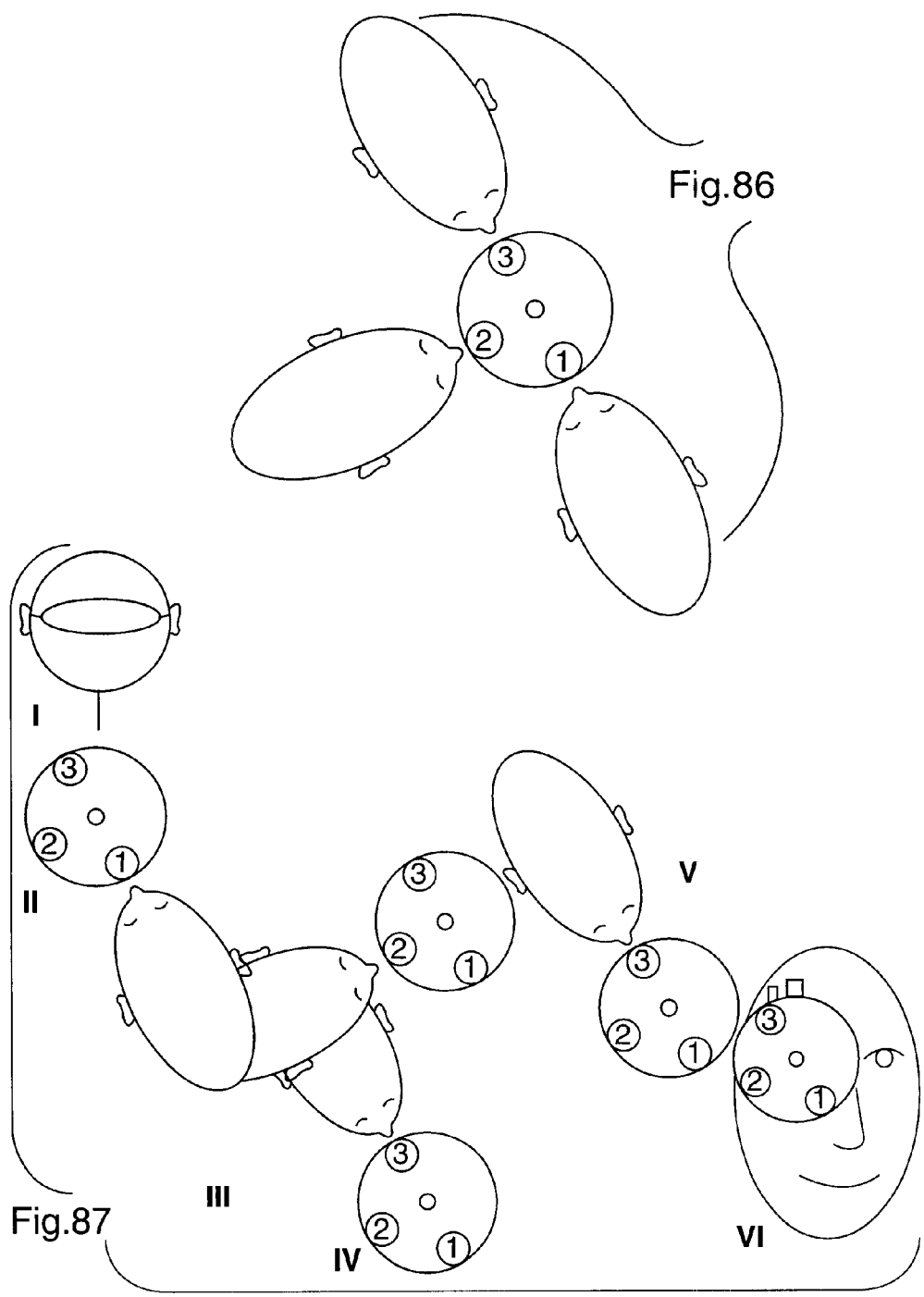

FIG. 86 illustrates the 180 degree rotation of the user head around the inner sphere for treatment of left posterior SCC BPPV.

FIG. 87 shows the complete sequence of head positions for left posterior SCC BPPV treatment using the apparatus of FIG. 59.

FIGS. 88–93 illustrate modifications of the holding tube with the use of additional magnets and of the inner sphere magnet orientation.

FIG. 88 illustrates the device of FIG. 7 with additional external magnets secured to the tubular body with the axis of the tubular body located in a horizontal position.

FIG. 89 shows the position of the device of FIG. 88 rotated 110 degrees counter clockwise from that of FIG. 88.

Figure 90:
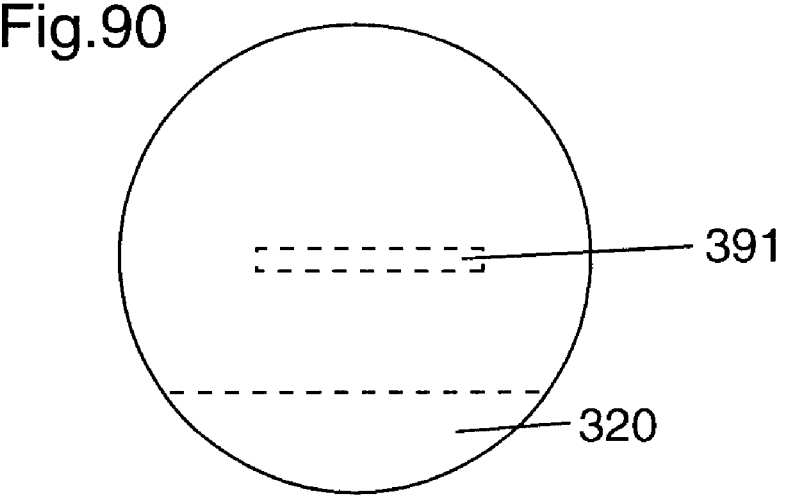

FIG. 90 shows the internal magnet of the internal sphere located parallel to the top plane of the weight.

Figure 91:
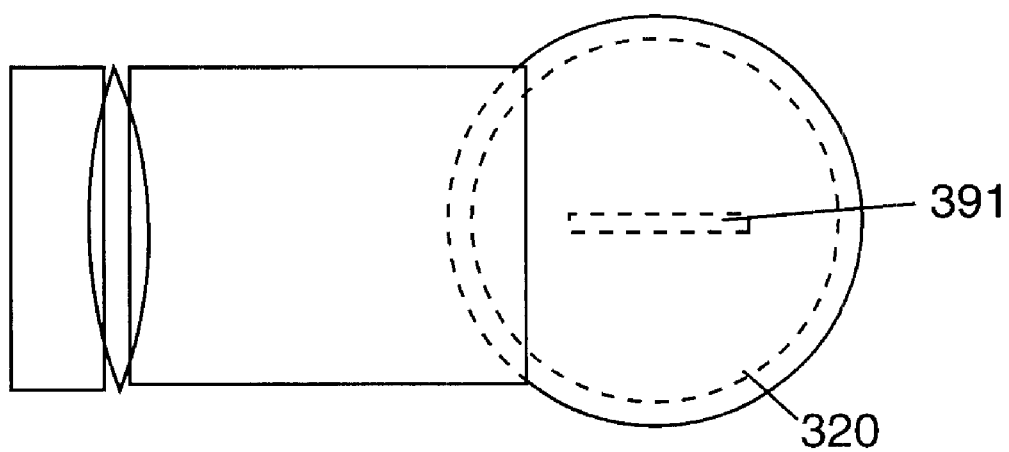

FIG. 91 shows the device using the internal sphere of FIG. 90 with the axis of the tubular body in a horizontal plane.

Figure 92:
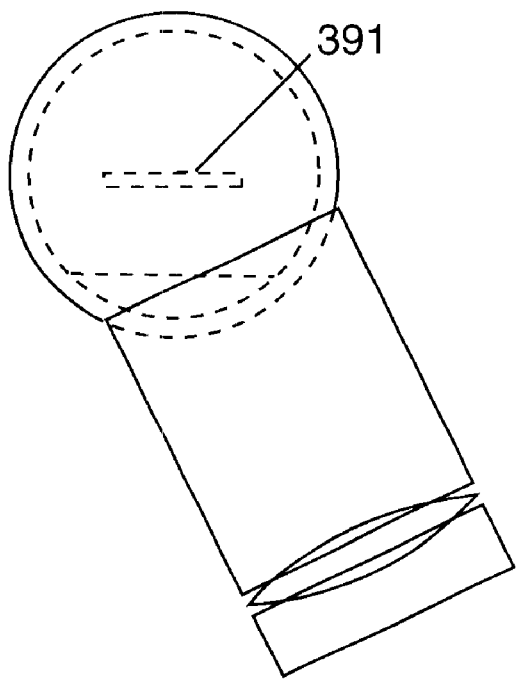

FIG. 92 shows the position of the device of FIG. 90 rotated 110 degrees counter clockwise from that of FIG. 91.

Figure 93:
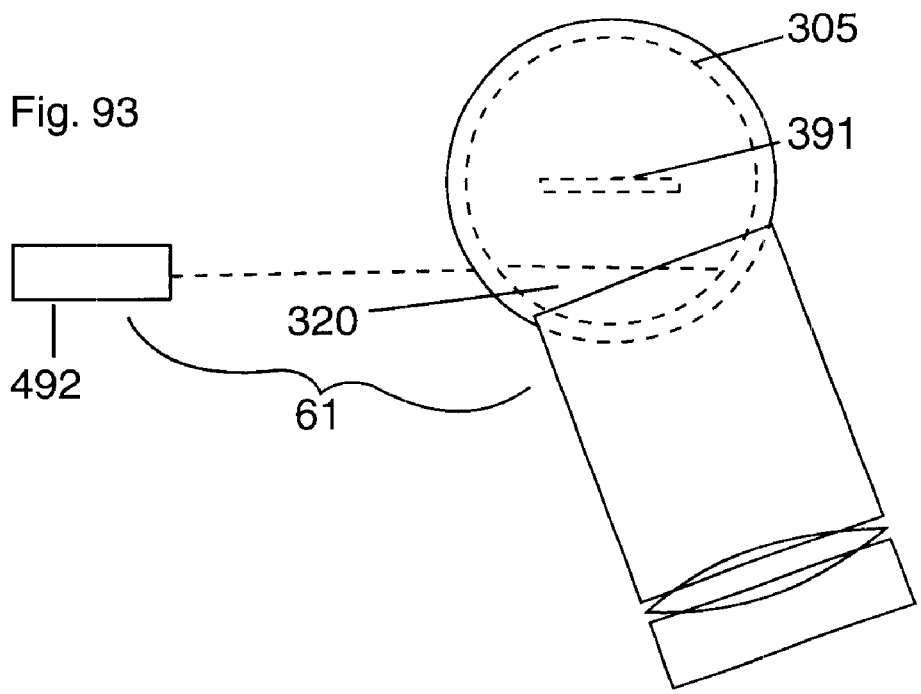

FIG. 93 is a view similar to the FIG. 92 but employing an exterior magnet located spaced from but close to the device.

FIGS. 94–142 illustrates an entrapment device for controlling the horizontal axis of the inner sphere.

Figure 94:
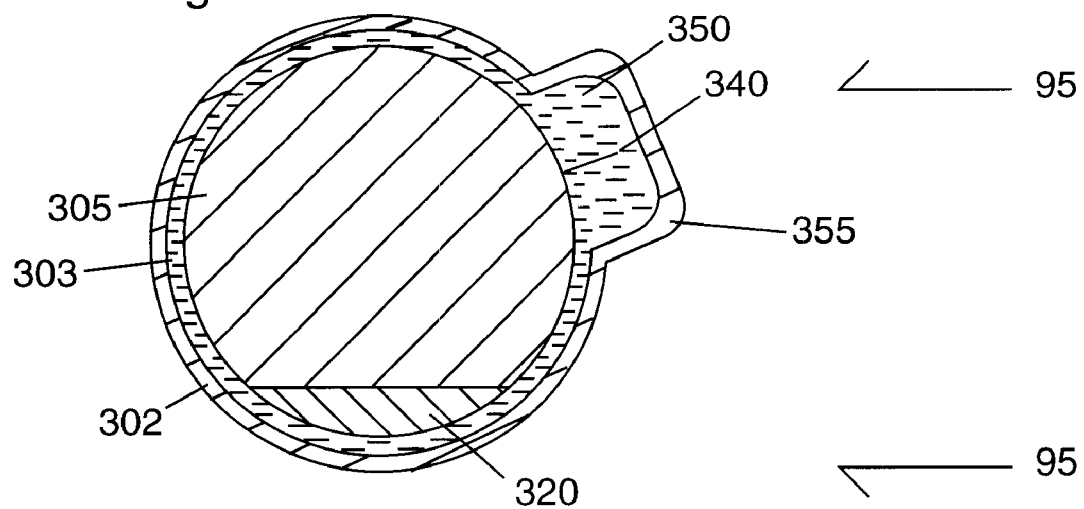

FIG. 94 is a cross-section of the entrapment device for controlling the horizontal axes of the inner sphere.

Figure 95:
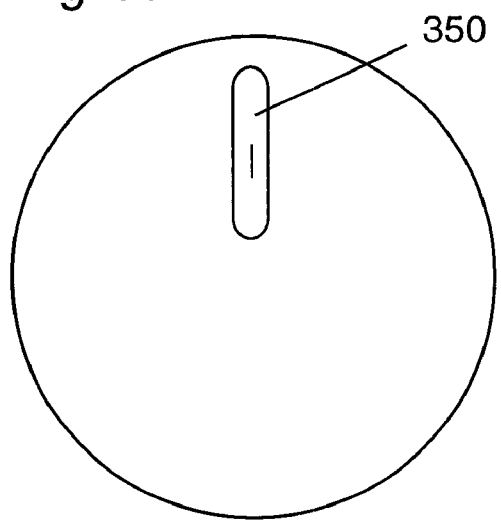

FIG. 95 is a view of the exterior of the device of FIG. 94 (with the entrapment cover removed) as seen from lines 95—95 thereof.

FIGS. 96–101 illustrates different entrapment slot shapes.

FIG. 102 illustrates the orientation of the entrapment protrusion of FIG. 94.

Figure 103:
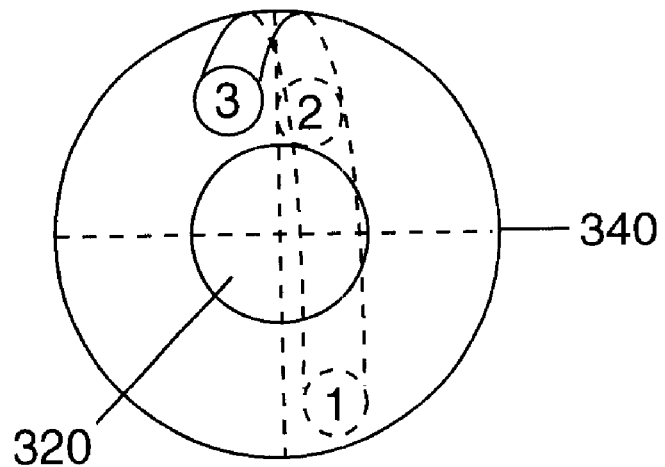

FIG. 103 is a view of FIG. 102 as seen along lines 103—103 thereof.

Figure 104:
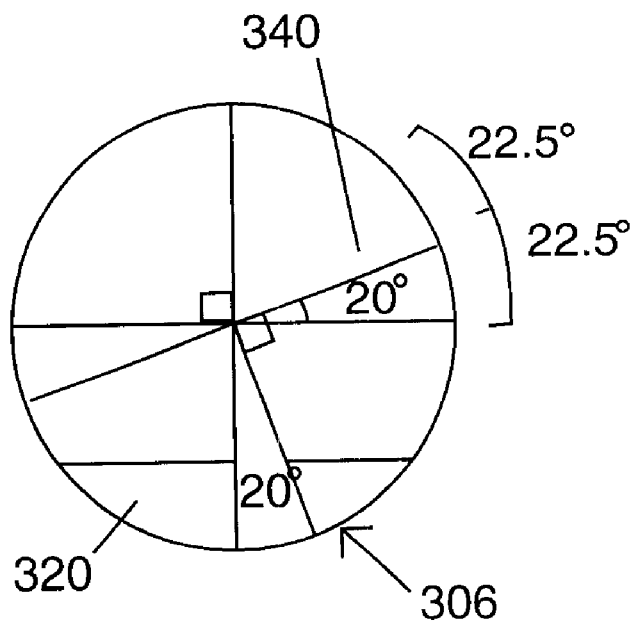
Figure 105:
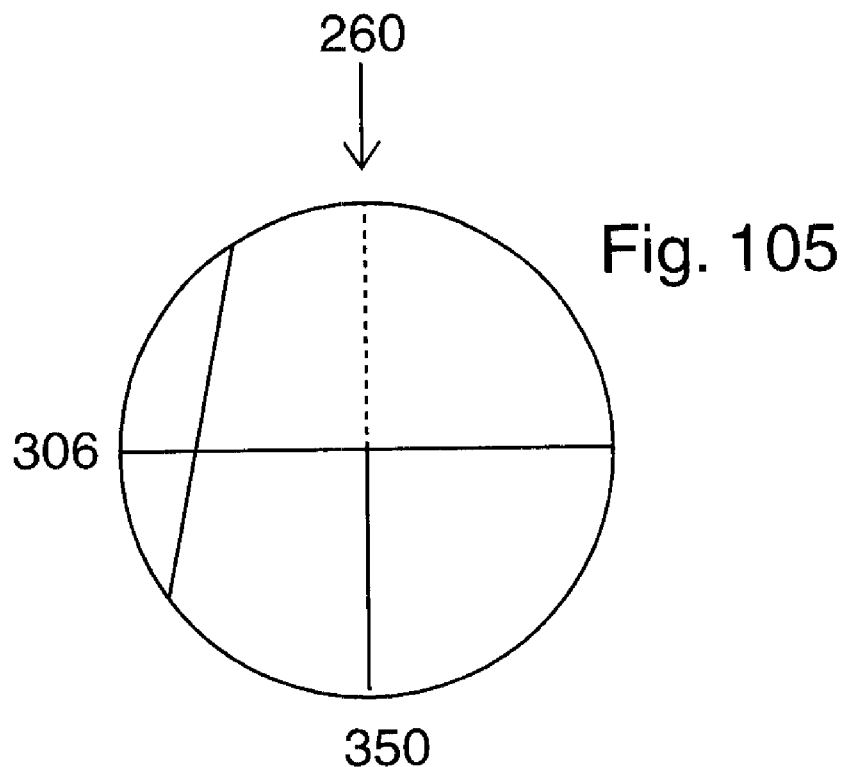

FIGS. 104 and 105 illustrate the angular relationship between the sighting mark and the entrapment slot of the device of FIG. 94.

Figure 106:
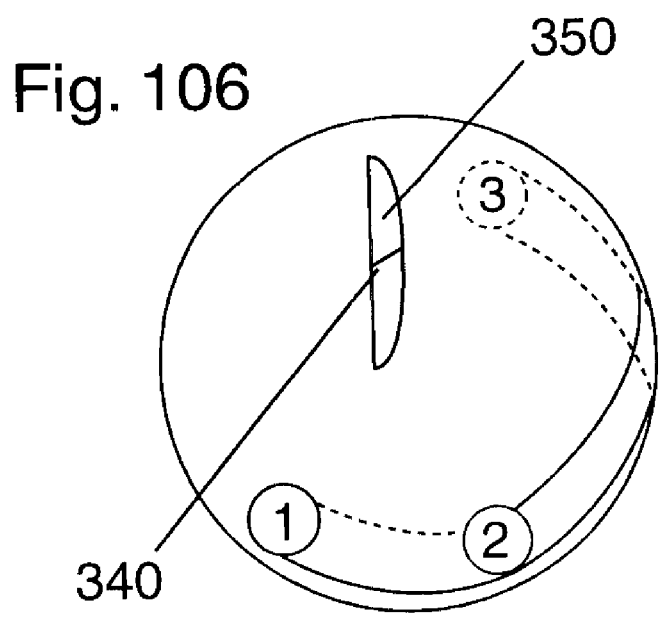

FIG. 106 is an exterior view of outer sphere the device without a cover showing the inner sphere protrusion extending through the entrapment slot from the perspective of FIG. 95.

Figure 107:
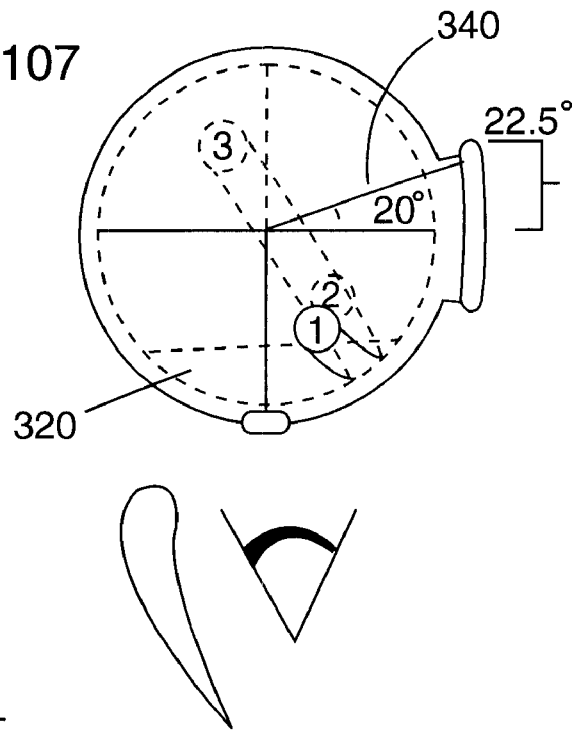

FIG. 107 illustrates the positions of the entrapment protrusion and inner sphere when the user rises from supine with 20 degrees neck extension to a classic supine position.

Figure 108:
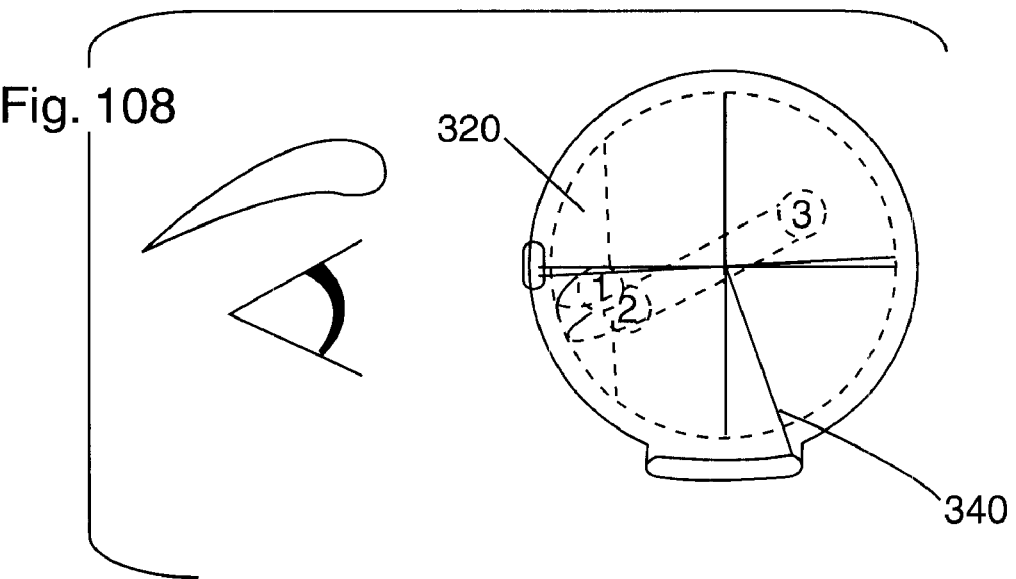

FIG. 108 illustrates the rotational position of the inner sphere when the user rises from a classic supine position to a sitting position.

Figure 109:
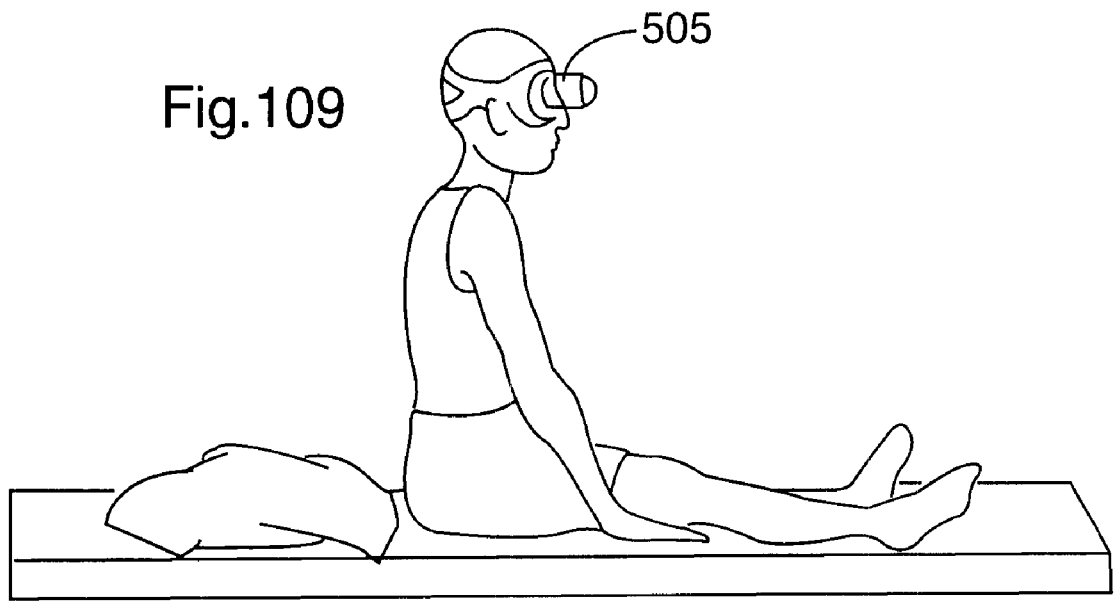

FIG. 109 illustrates the user in a sitting position with the apparatus of FIGS. 94–108 attached in place to the users head.

Figure 110:
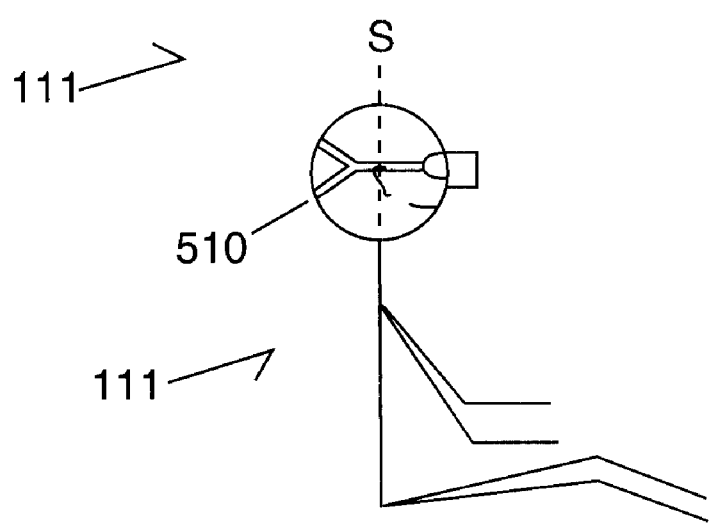

FIG. 110 is a simplified view of FIG. 109.

Figure 111:
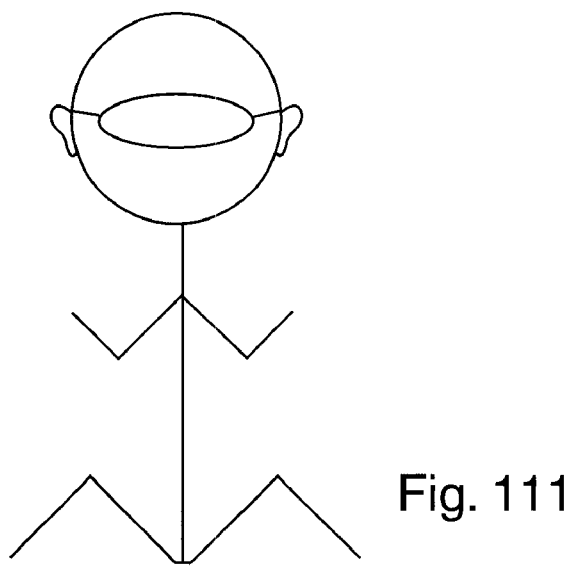

FIG. 111 is a rear view of the user as seen along lines 111—111 of FIG. 110.

Figure 112:
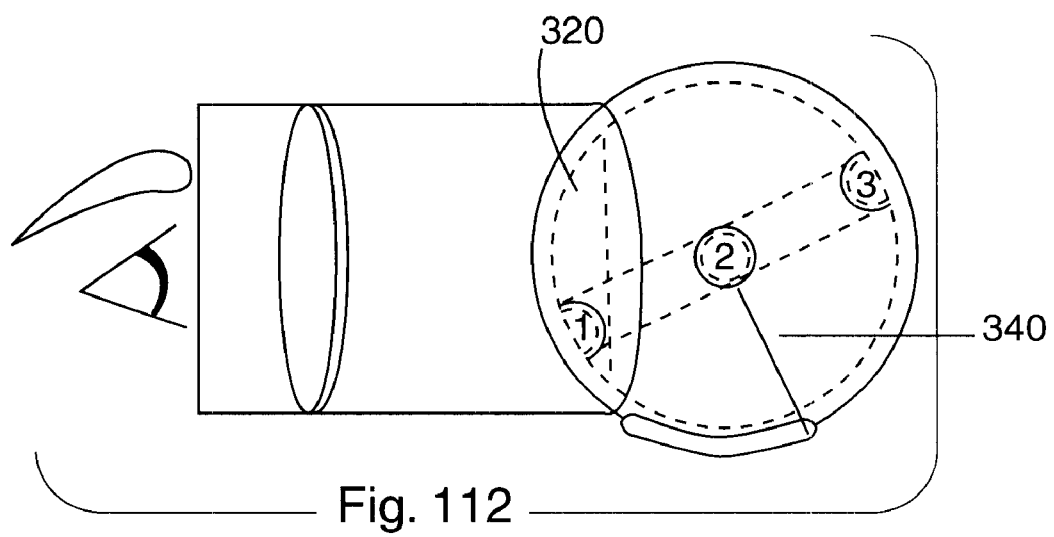

FIG. 112 is a view of the apparatus similar to that of FIGS. 94–108.

Figure 113:
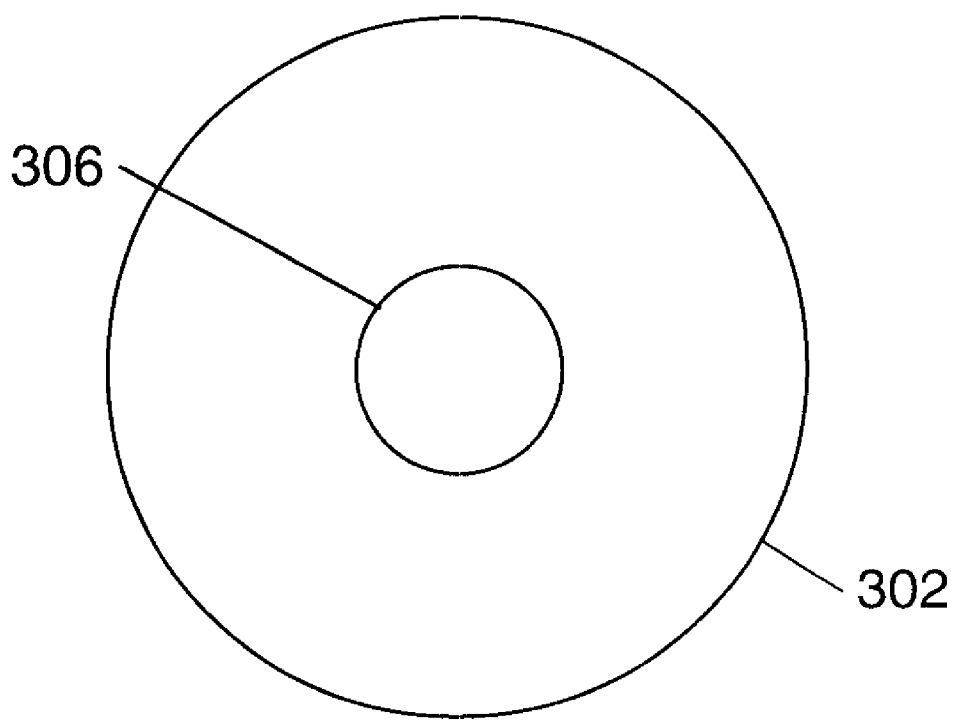

FIG. 113 illustrates the sighting mark on the inner sphere of the device of FIGS. 94–108.

Figure 114:
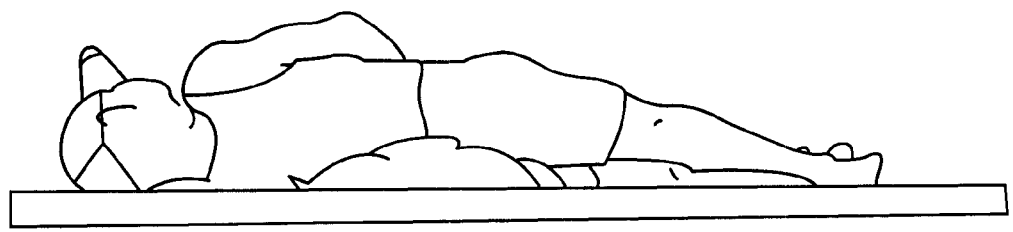

FIG. 114 illustrates the user with his or her head inclined downward at an angle of 20 degrees relative to the horizontal with the left side of the head located 45 degrees relative to the vertical.

Figure 115:
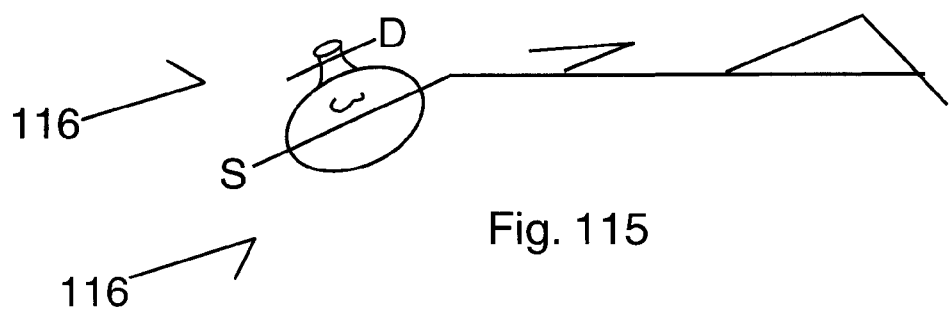

FIG. 115 is a simplified view of FIG. 114.

Figure 116:
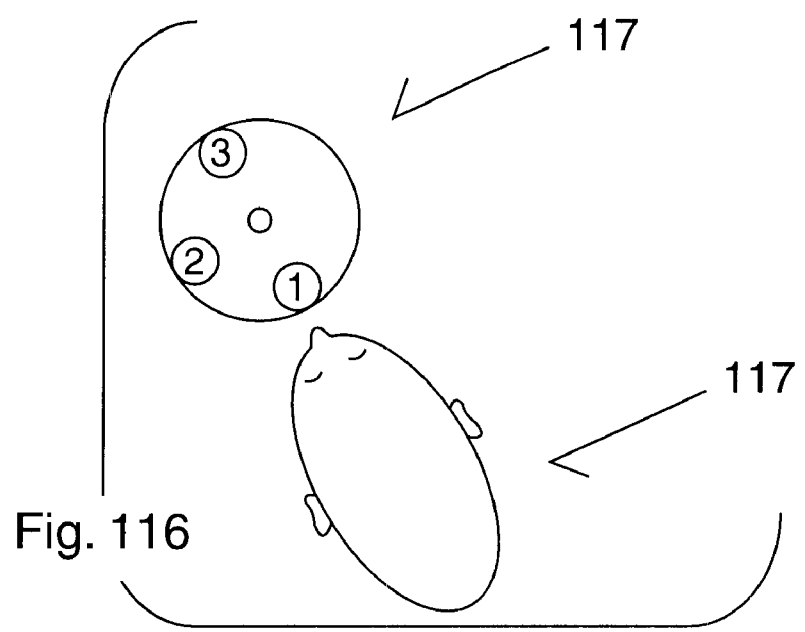

FIG. 116 is a view of FIG. 115 seen along lines 116—116 thereof with the No. 1 position of the inner sphere within the sighting mark.

Figure 117:
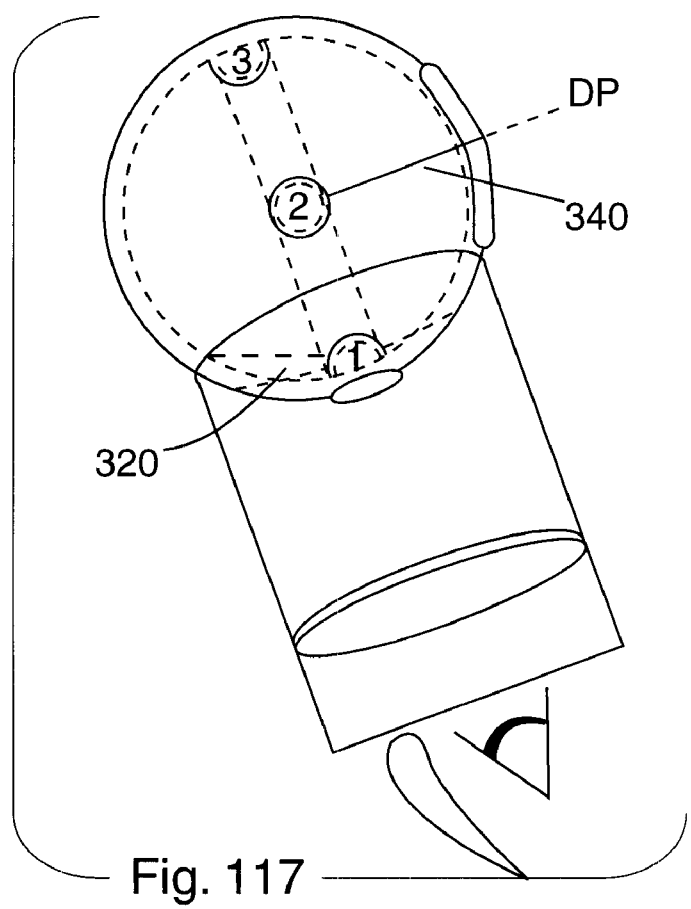

FIG. 117 is a view of the apparatus of FIGS. 94–108 when the user is in the position of FIGS. 114–116.

Figure 118:
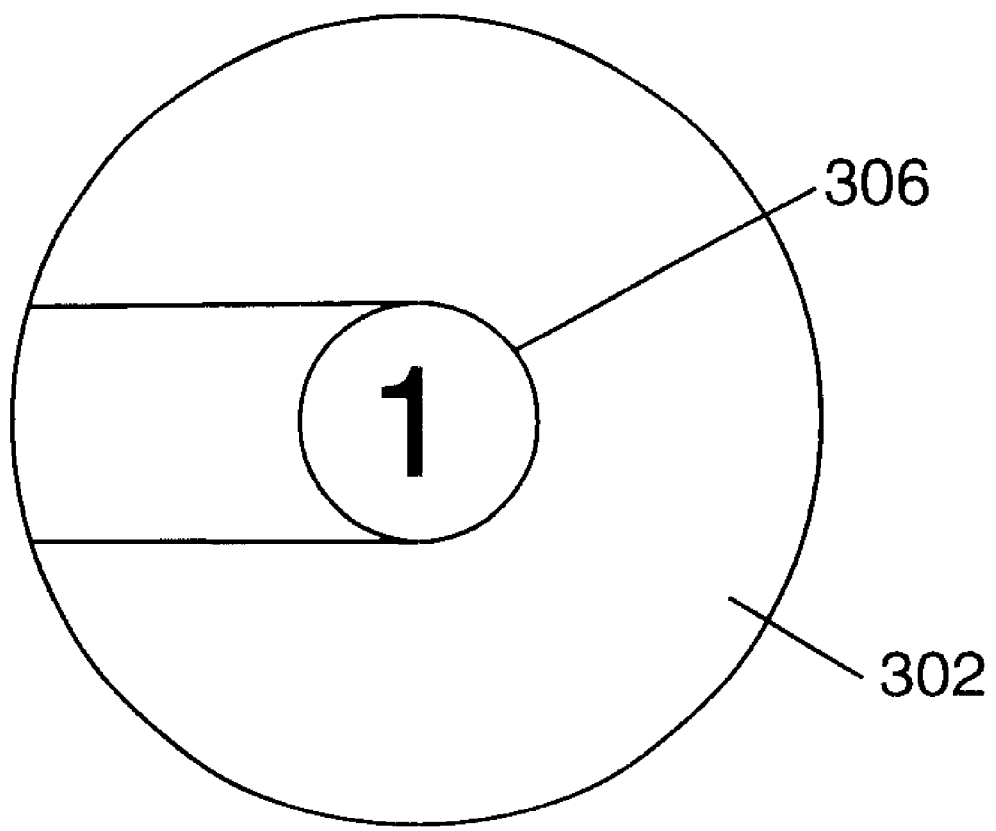

FIG. 118 illustrates the No. 1 position of the inner sphere within the sighting mark.

Figure 119:
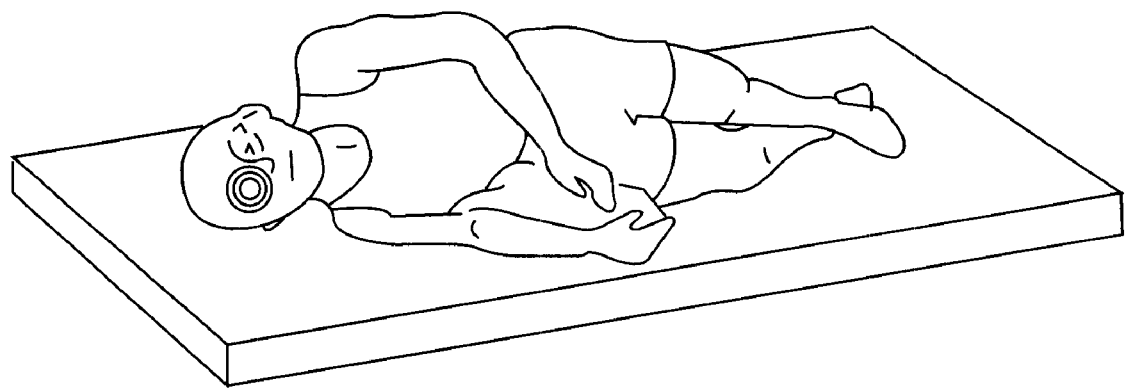

FIG. 119 illustrates the user with his or her head inclined downward at an angle of 20 degrees relative to the horizontal with the left side of the head located 45 degrees relative to the vertical.

Figure 120:
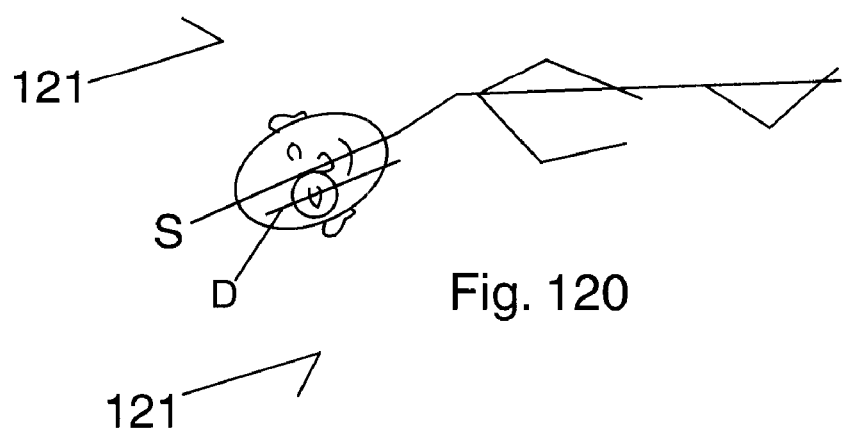

FIG. 120 is a simplified view of FIG. 119.

Figure 121:
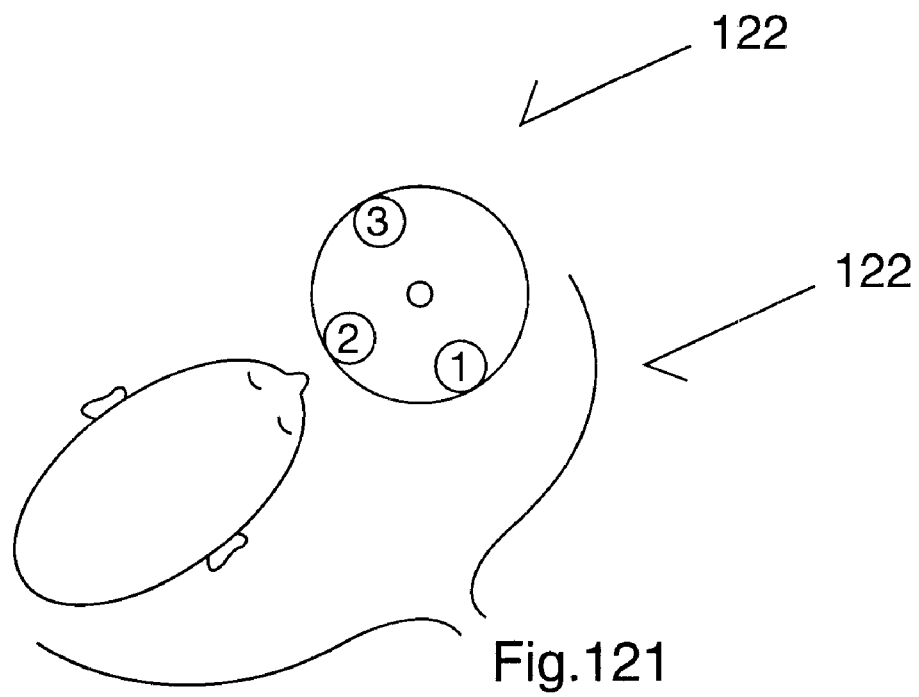

FIG. 121 is a view of FIGS. 120 as seen along the lines 121—121 with the No. 2 position of the inner sphere within the sighting mark.

Figure 122:
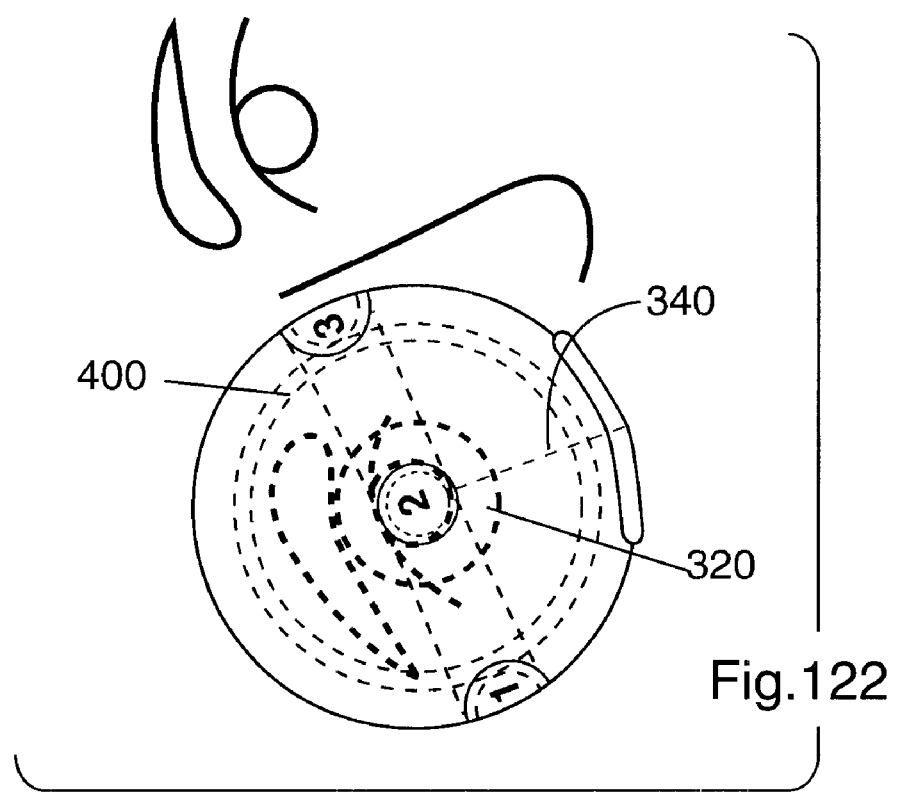

FIG. 122 is a view of the apparatus of FIGS. 94–108 when the user is in the position of FIGS. 119–120.

Figure 123:
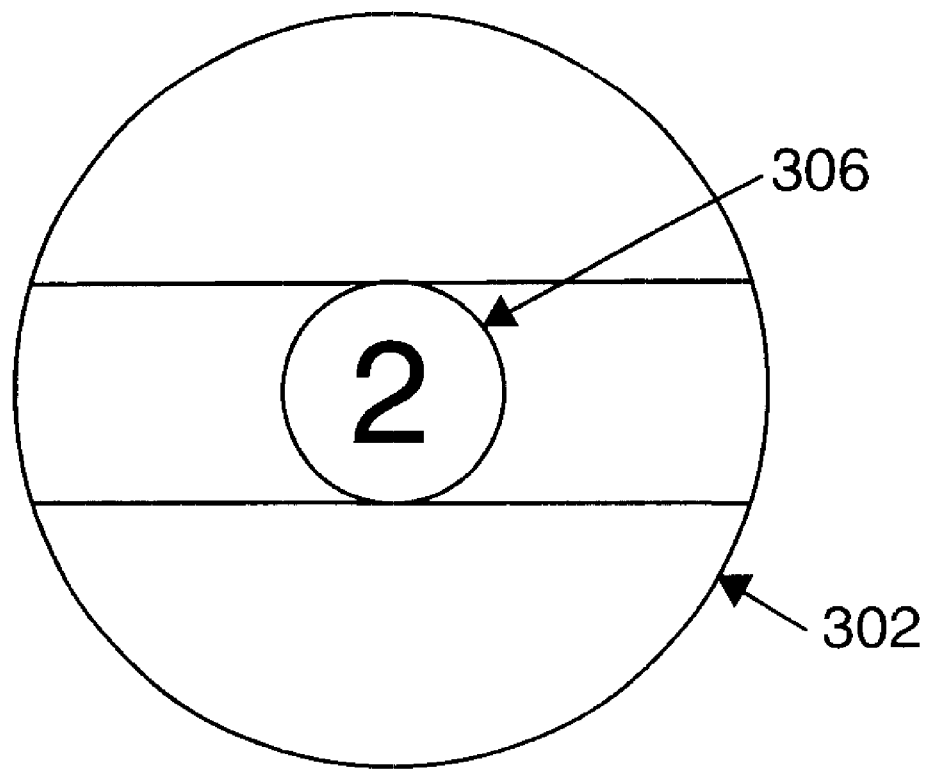

FIG. 123 illustrates the No. 2 position of the inner sphere in the sighting mark.

Figure 124:
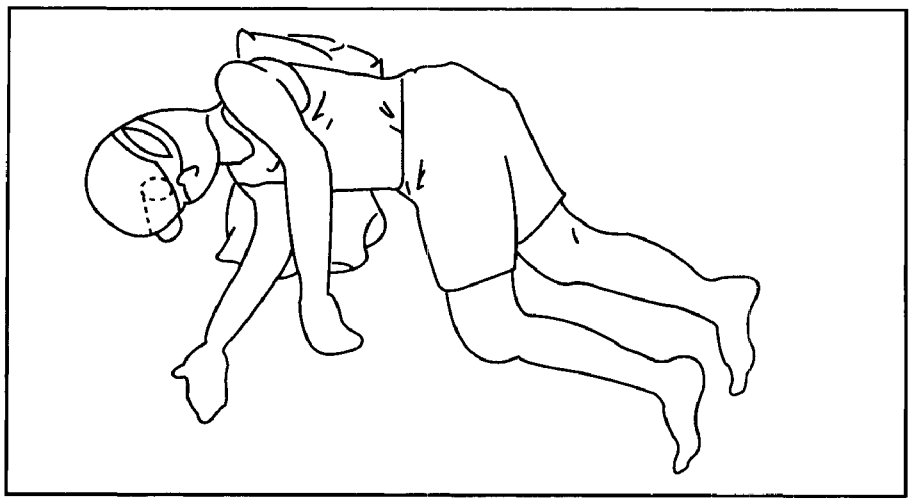

FIG. 124 illustrates the user with his or her head flexed downward 20 degrees relative to the horizontal with the head rotated clockwise 135 degrees from the position of FIGS. 119–121.

Figure 125:
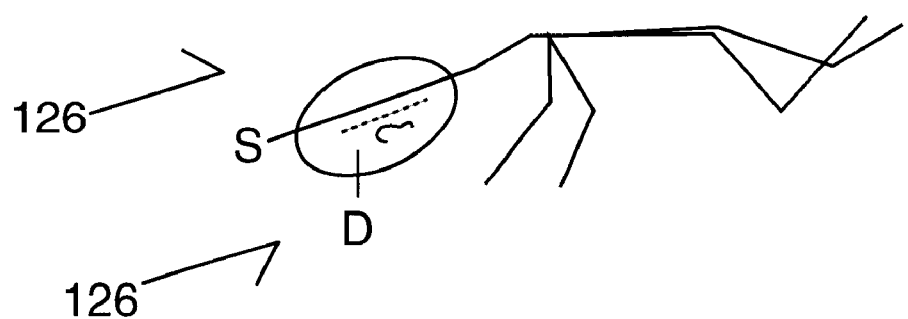

FIG. 125 is a simplified view of FIG. 124.

Figure 126:
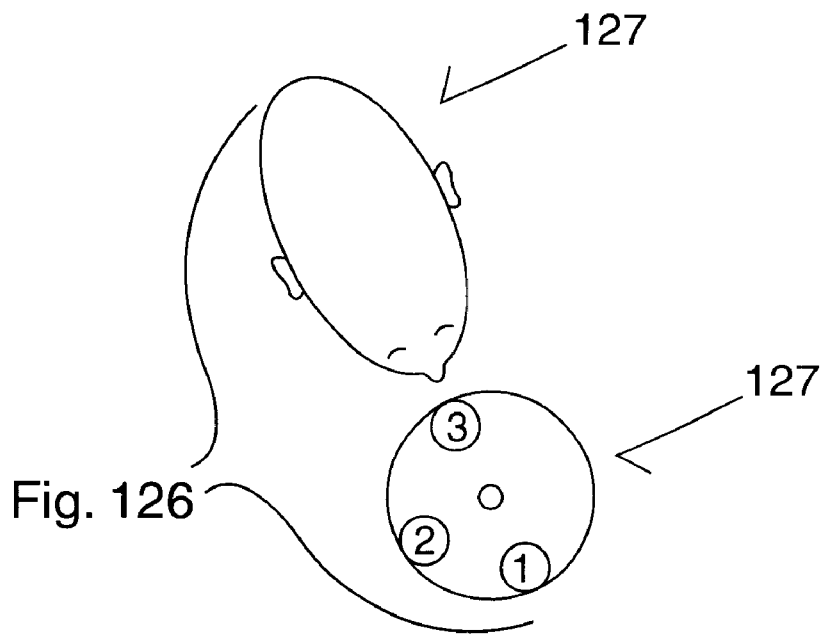

FIG. 126 is a view of FIG. 125 as seen along lines 126—126 thereof with the No. 3 position of the inner sphere within the sighting mark.

Figure 127:
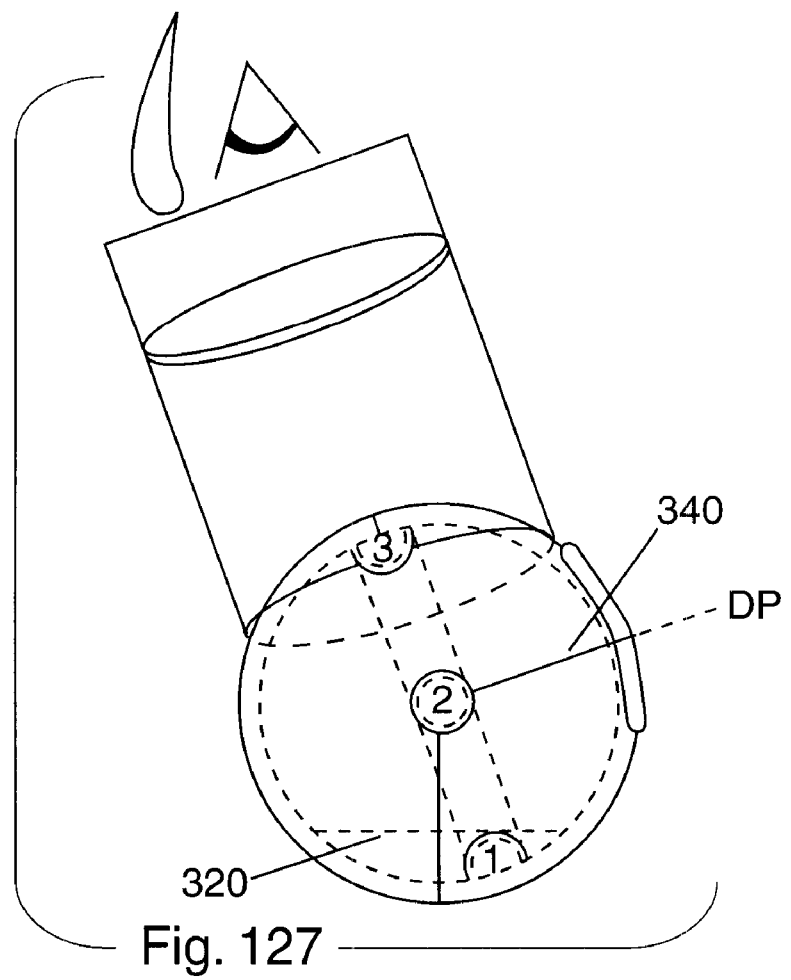

FIG. 127 is a view of the apparatus of FIGS. 94–108 when the user is in the position of FIGS. 124–126.

Figure 128:
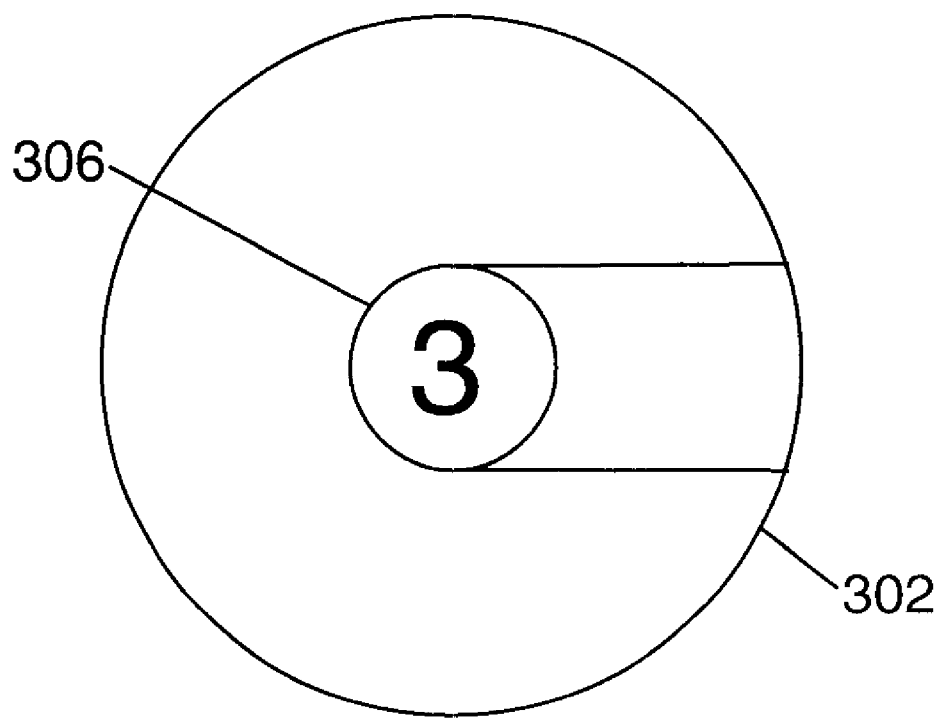

FIG. 128 illustrates the No. 3 position of the inner sphere within the sighting mark.

Figure 129:
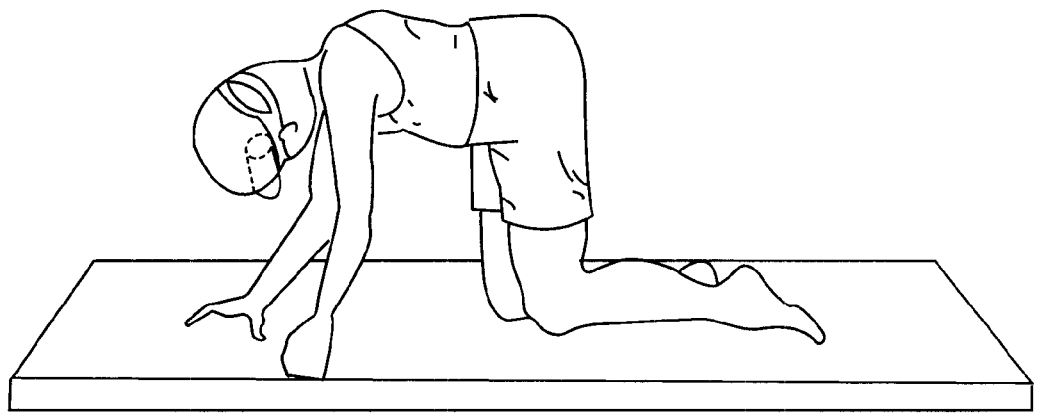
Figure 130:
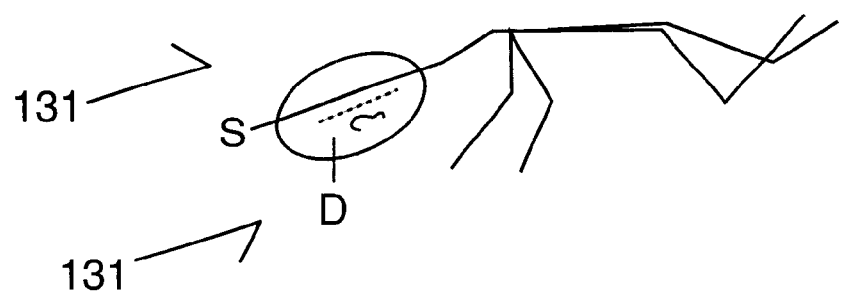

FIGS. 129 and 130 illustrate the user in the kneeling position with his or her hands on the mat and with the head still in the position of FIGS. 124–126.

Figure 131:
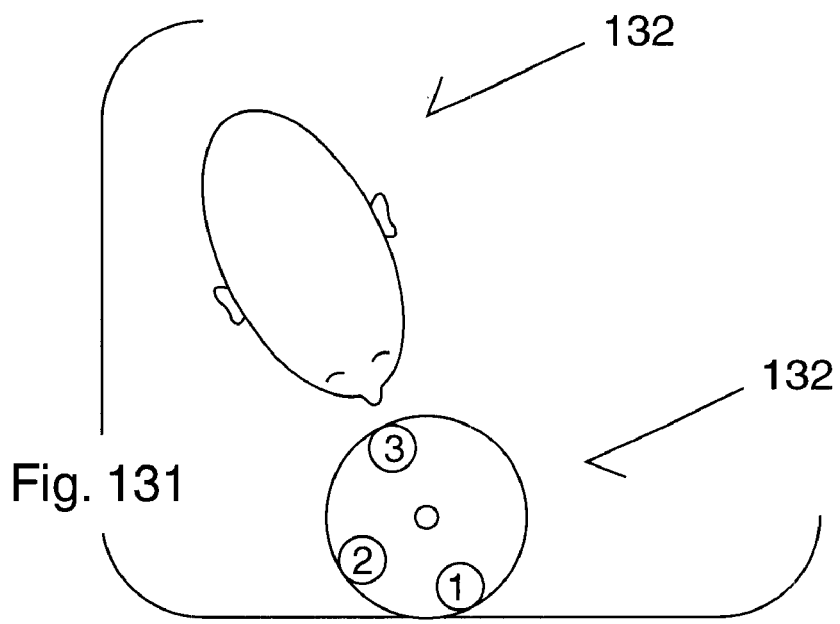

FIG. 131 is a view of FIG. 130 as seen along the lines 131—131 thereof with the No. 3 position of the inner sphere within the sighting mark.

Figure 132:
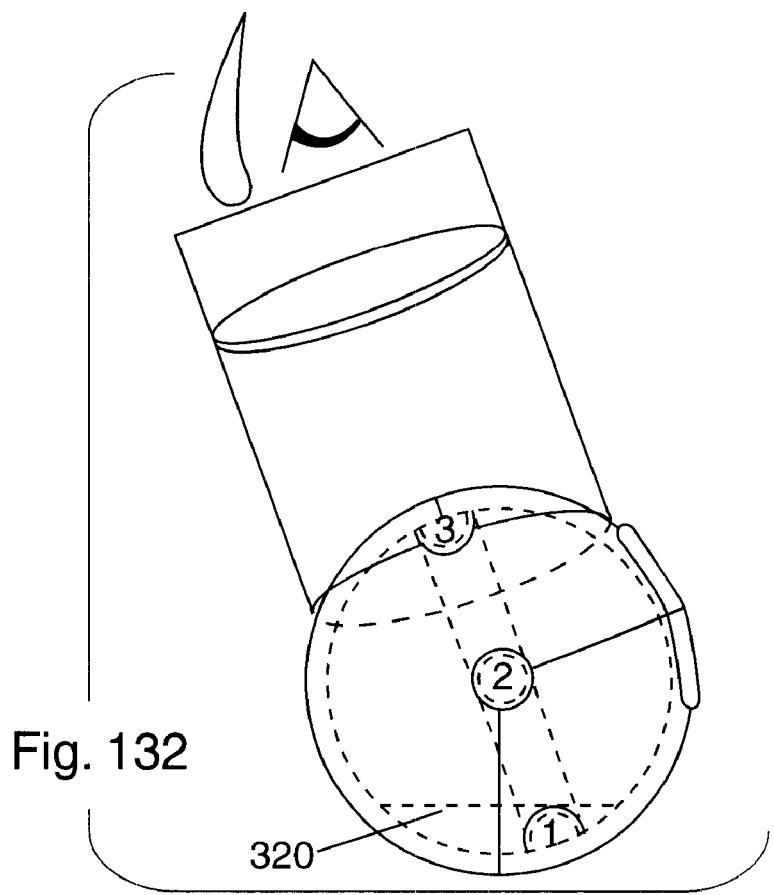

FIG. 132 is a view of the apparatus of 94–108 when the user is in the position of FIGS. 129–130.

Figure 133:
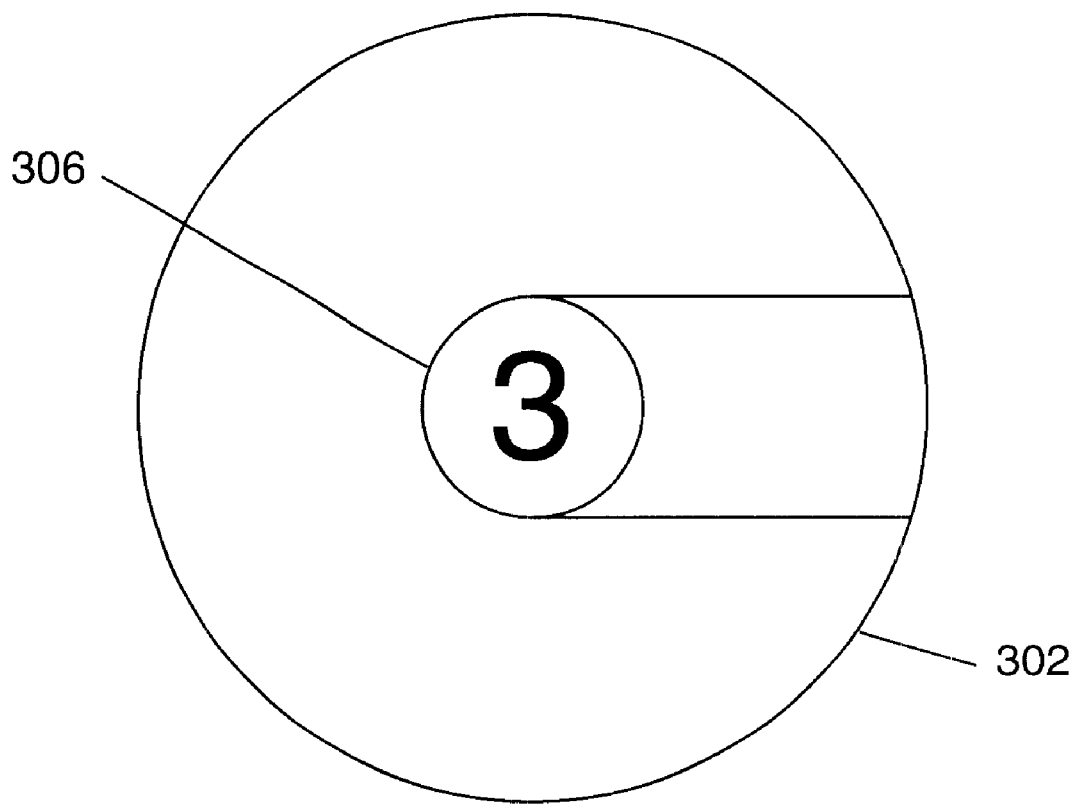

FIG. 133 illustrates the No. 3 position of the inner sphere within the sighting mark.

Figure 134:
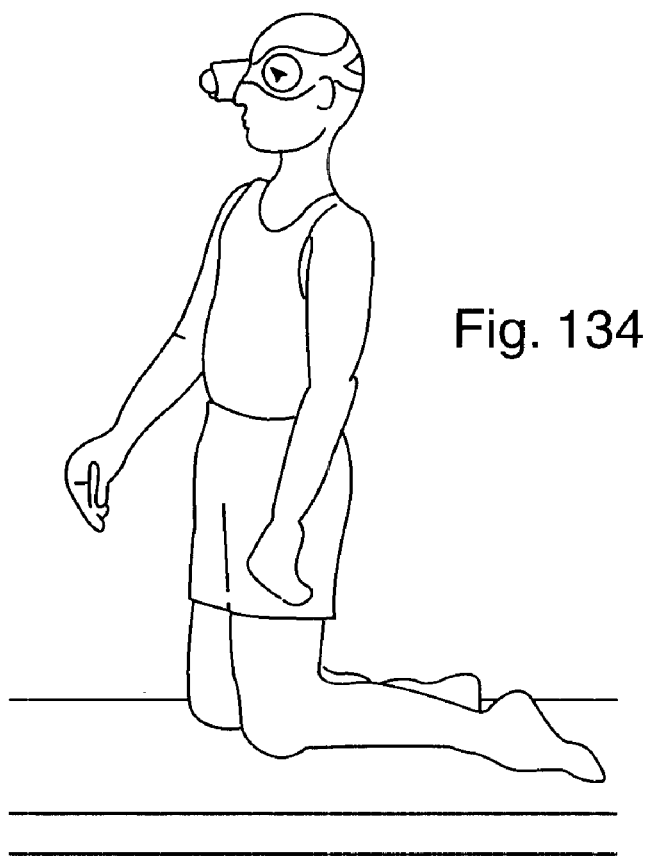

FIG. 134 illustrates the user in a kneeling position with his or her head in an upright position.

Figure 135:
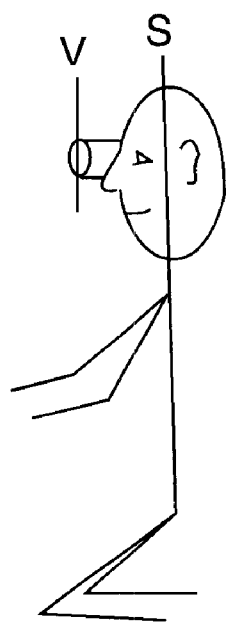

FIG. 135 is a simplified view of FIG. 134.

Figure 136:
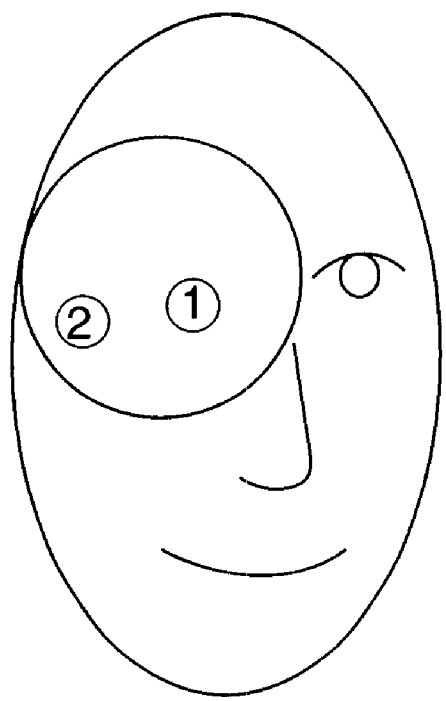
Figure 137:
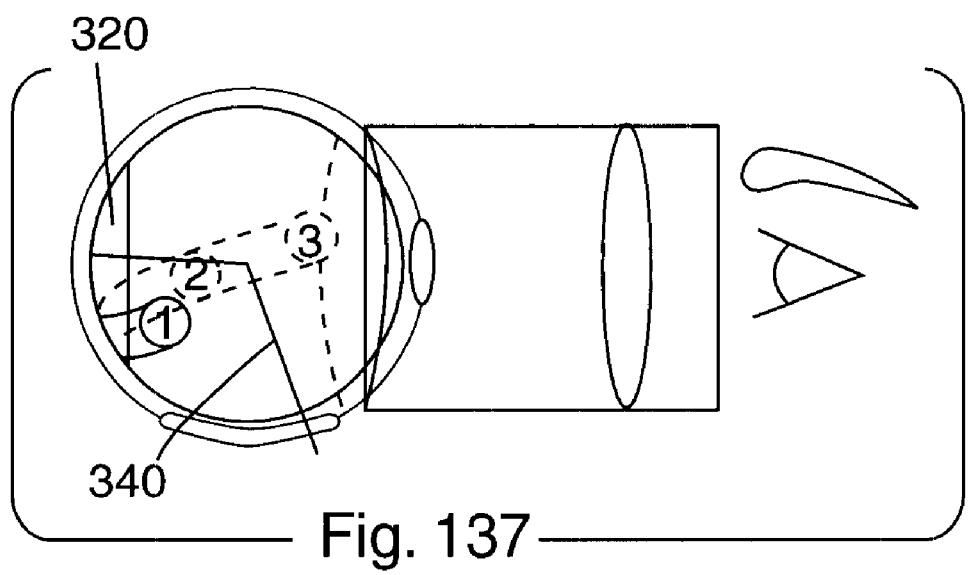

FIGS. 136 and 137 illustrate inner sphere component orientation as the user approaches upright in FIGS. 134 and 135.

FIGS. 138 and 139 illustrate inner sphere component orientation as the user assumes the upright position in FIGS. 134 and 135.

Figure 140:
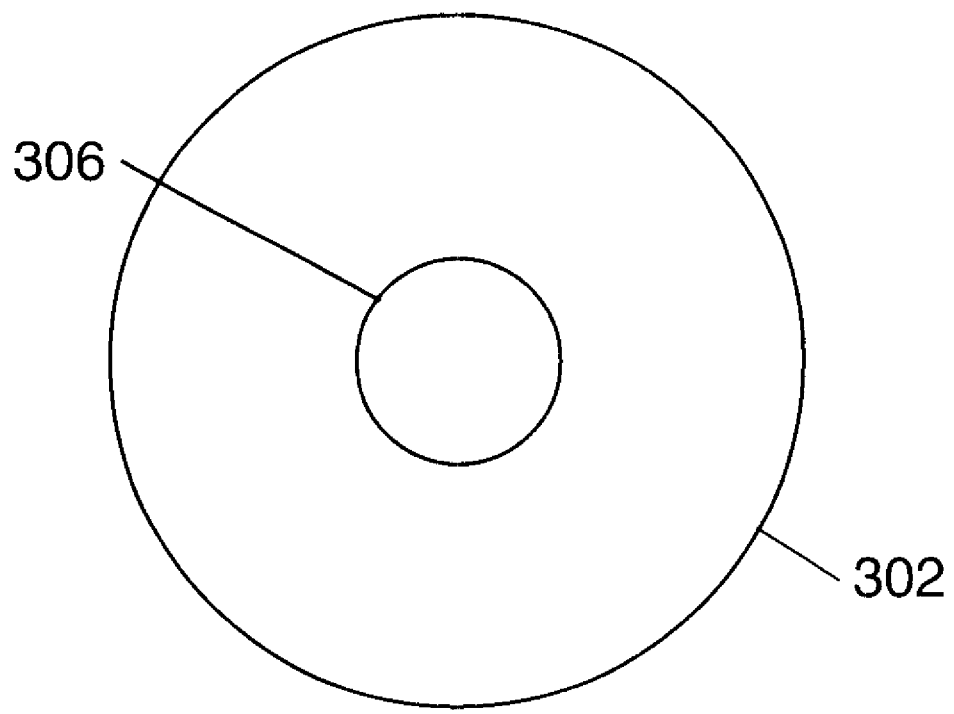

FIGS. 139 and 140 illustrate that the user does not see the path or the Nos. 1–3 positions of the inner sphere when the user is in the position of FIGS. 134 and 135.

Figure 141:
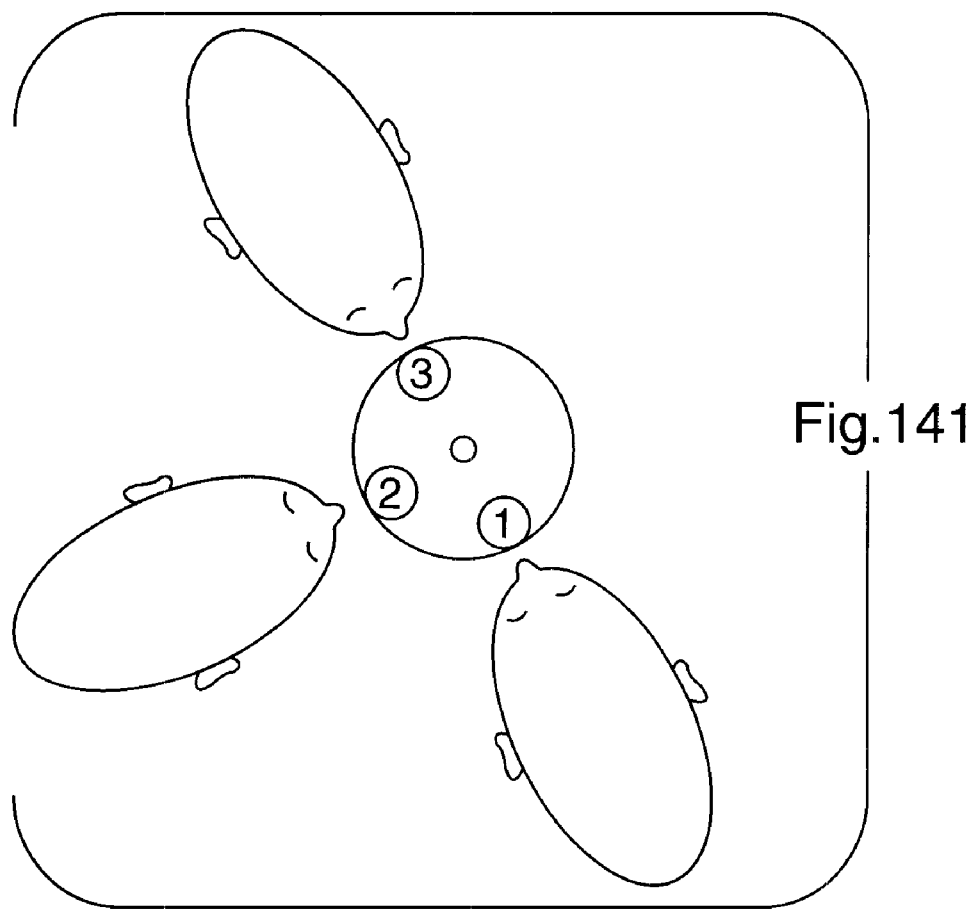

FIG. 141 illustrates the 180 degree rotation of the users head around the inner sphere axis perpendicular to the plane defined by the position bull's eyes for treatment of left posterior SCC BPPV.

Figure 142:
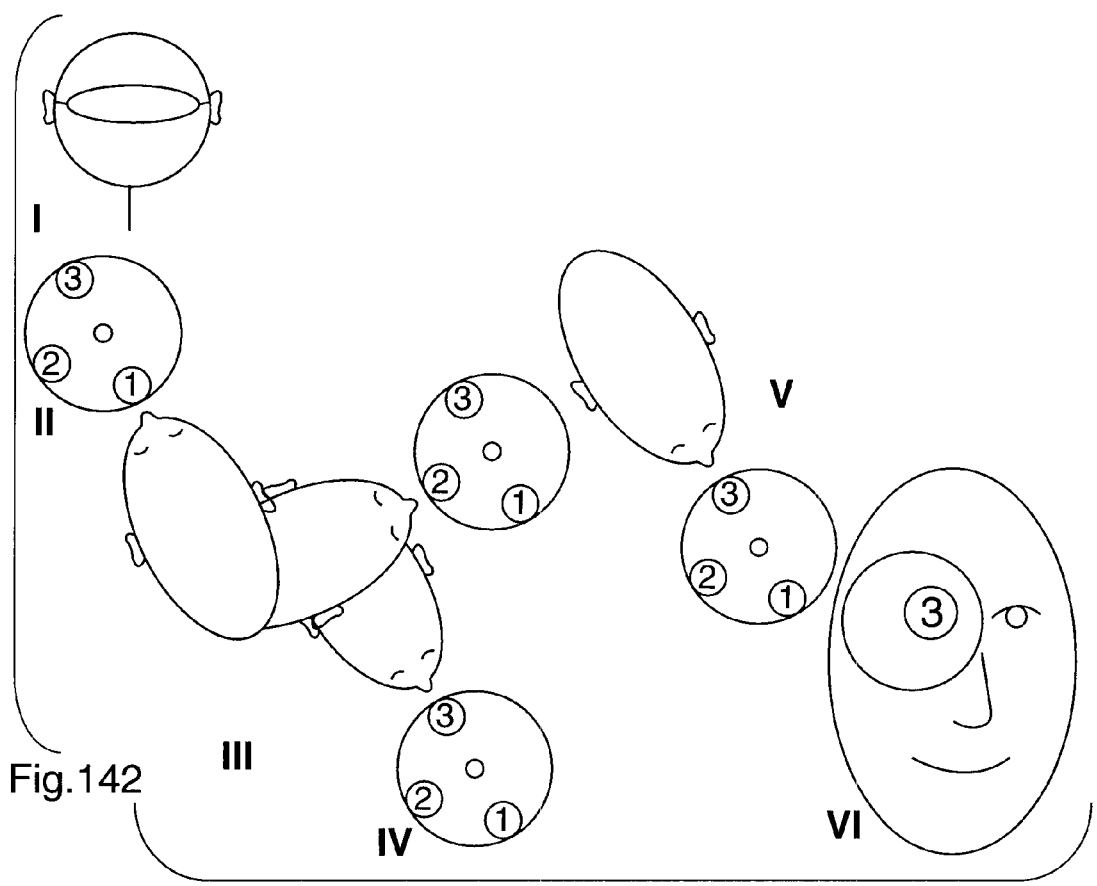

FIG. 142 illustrates the 180 degree rotation about the axis perpendicular to the plane defined by the position bull's eye and illustrates that although the axis moves during the rotation maneuver, its orientation is unchanged in II–V.

FIG. 142 shows the compete sequence of head positions for left posterior SCC BPPV treatment using the apparatus of FIG. 94–108.

Figure 143:
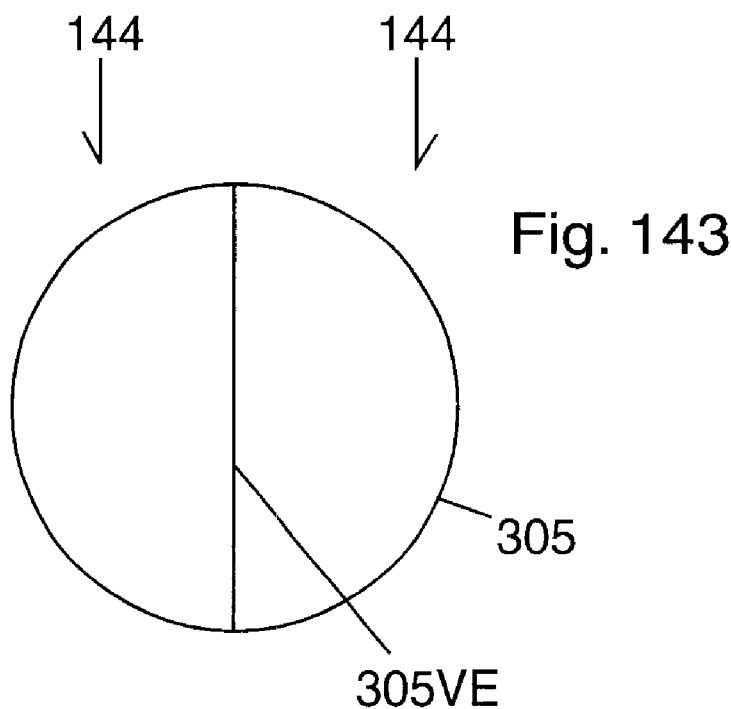
Figure 144:
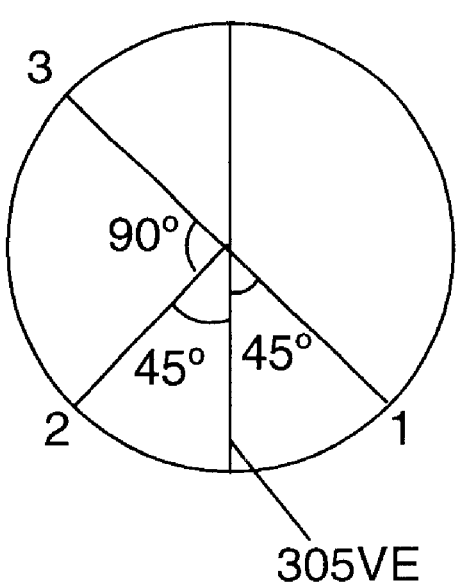

FIGS. 143 and 144 are views of the internal sphere similar to that of FIGS. 11 and 12.

FIGS. 145–149 illustrate other sphere markings.

FIGS. 145–149 are views of the internal sphere similar to that of FIGS. 13–17 but with the second position bull's eye located 30 degrees from the plane of the vertical equator.

FIGS. 150–165 illustrate a hanging device for use for BPPV treatment.

FIG. 150 illustrates an embodiment employing a sphere which has a hanging object.

Figure 151:
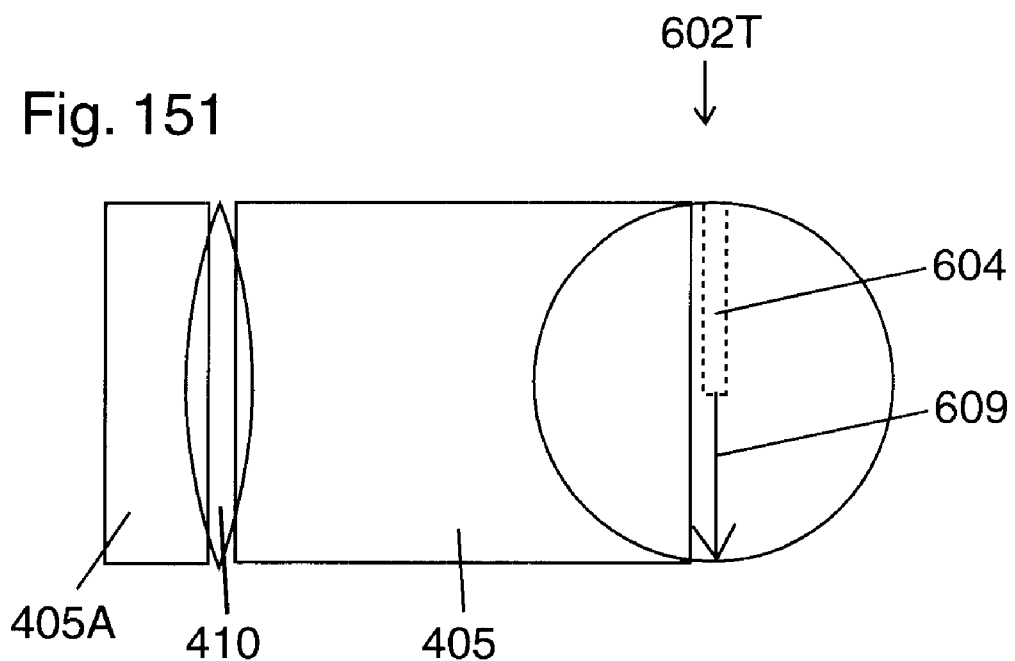

FIG. 151 illustrates the sphere of FIG. 150 coupled to the tubular member of FIG. 6.

Figure 152:
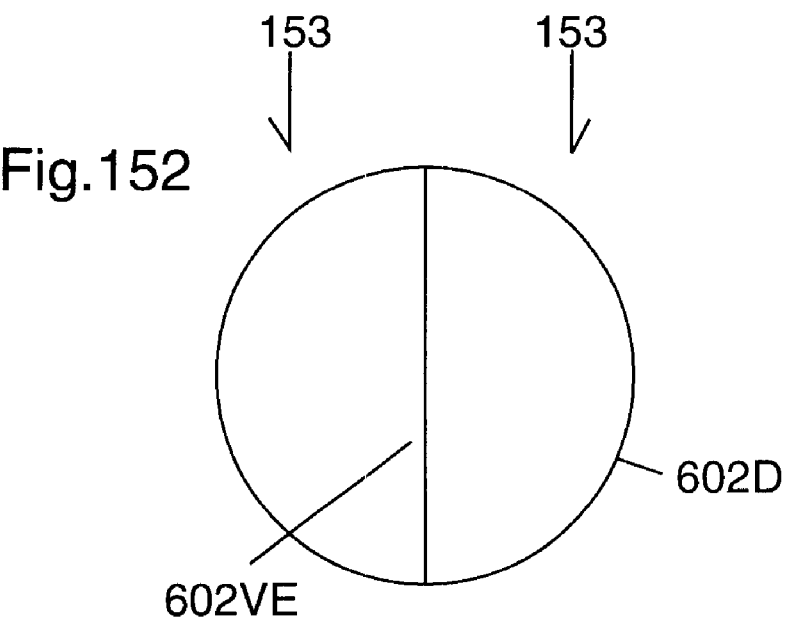

FIG. 152 is a side view of a diagnostic sphere having an inside hanging object.

Figure 153:
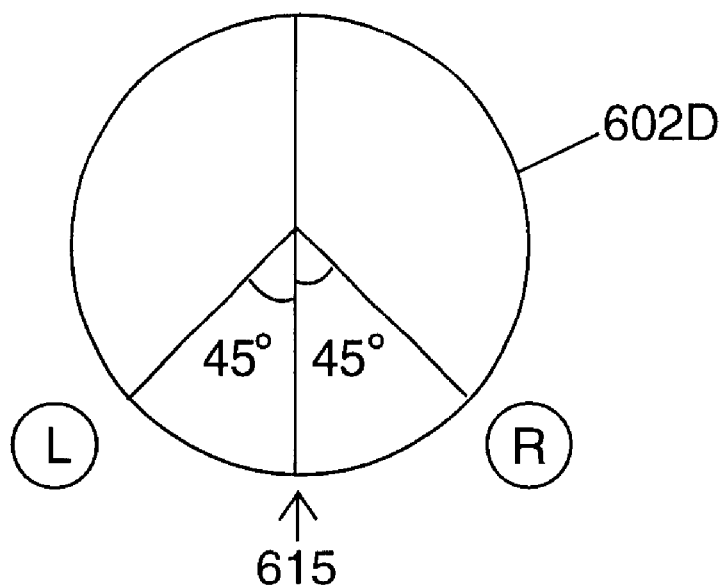

FIG. 153 is a view of FIG. 152 as seen along lines 153—153 thereof.

Figure 154:
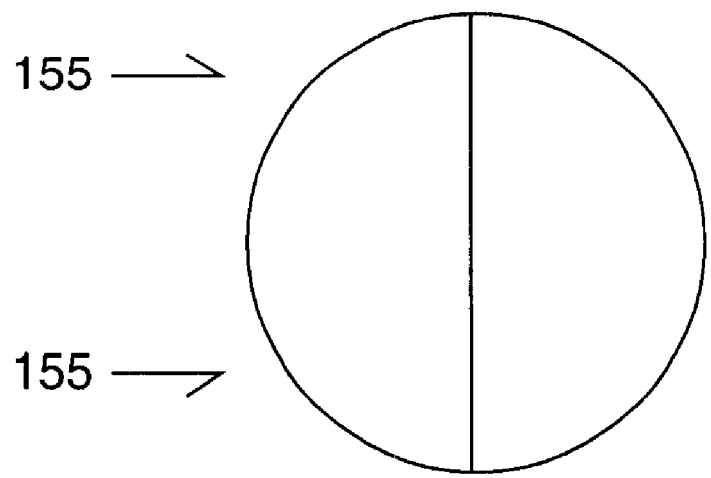

FIG. 154 is a similar view of the sphere of FIG. 152.

Figure 155:
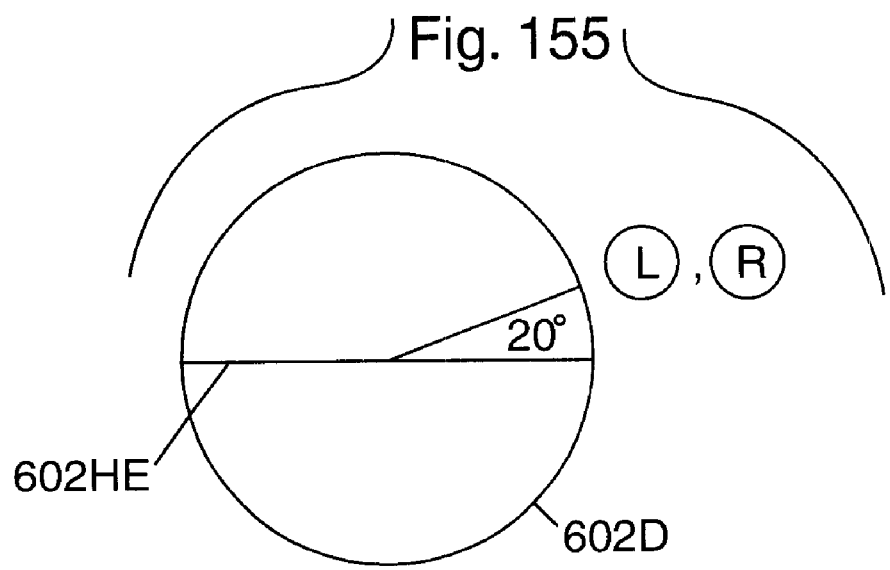

FIG. 155 is a view of FIG. 154 as seen along lines 155—155 thereof.

Figure 156:
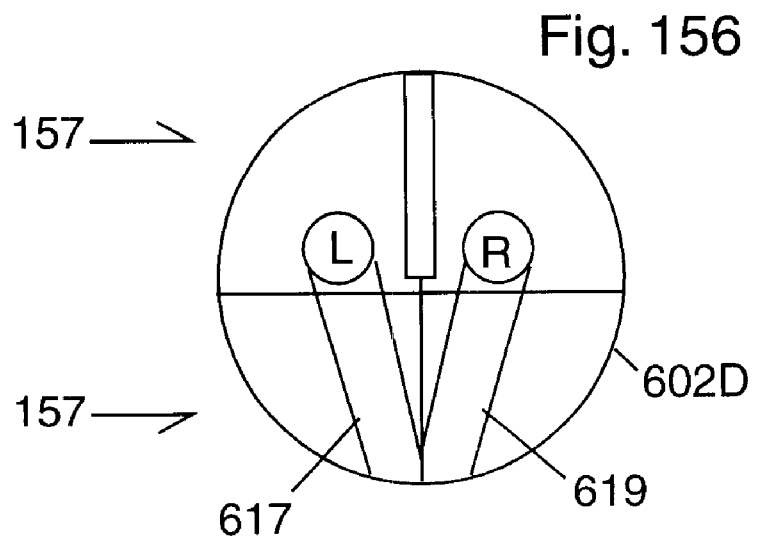

FIG. 156 shows the L and R markings of the sphere of FIGS. 152–155.

FIG. 157 is a view of FIG. 156 as seen along lines 157—157 thereof.

FIG. 158 is a view of a treatment sphere having an inside hanging object.

Figure 159:
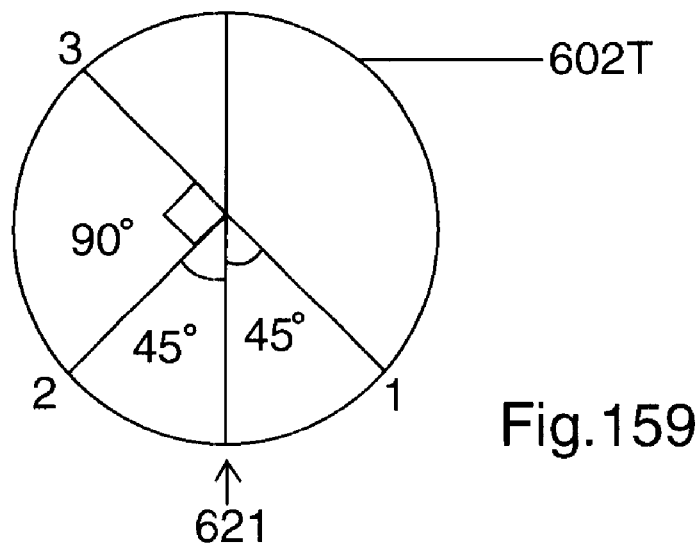

FIG. 159 is a view of FIG. 158 as seen along lines 159—159 thereof.

Figure 160:
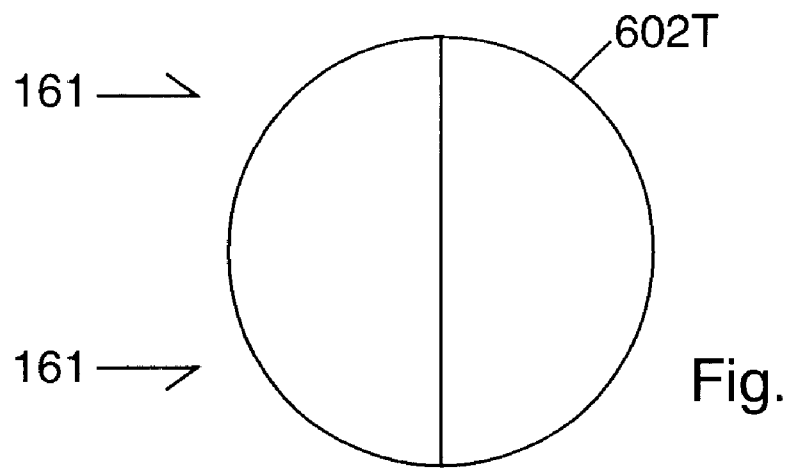

FIG. 160 is a view of the sphere similar to that of FIG. 158.

Figure 161:
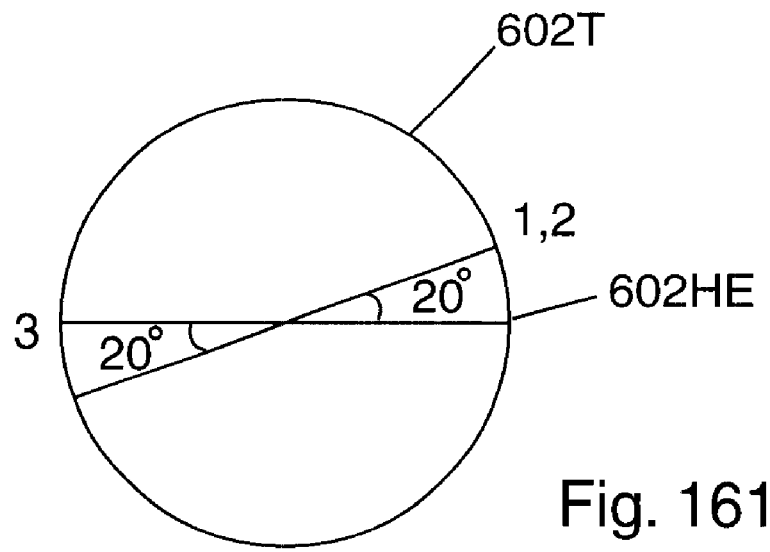

FIG. 161 is a view of FIG. 160 a seen along the lines 161—161.

Figure 162:
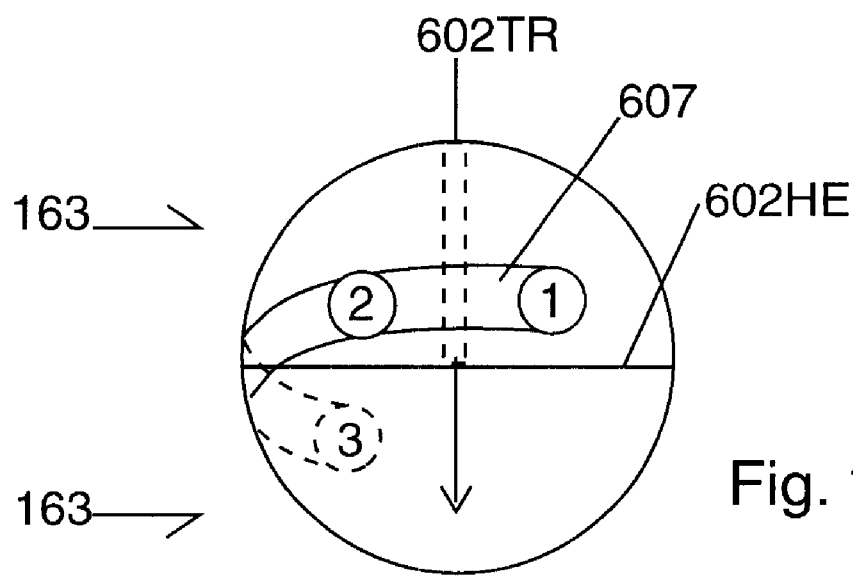

FIG. 162 is a side view of the right post SCC BPPV treatment sphere (having an interior hanging object) showing the marking Nos. 1, 2, and 3.

Figure 163:
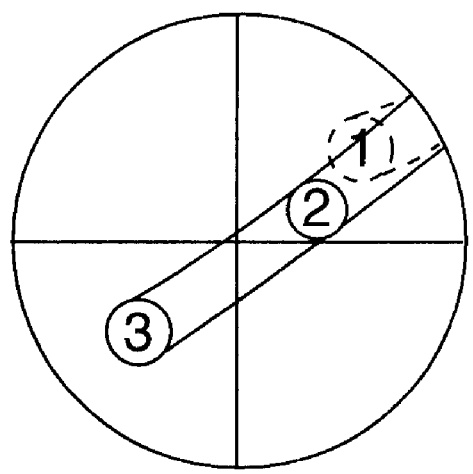

FIG. 163 is a view of FIG. 162 as seen along lines 163—163 thereof.

Figure 164:
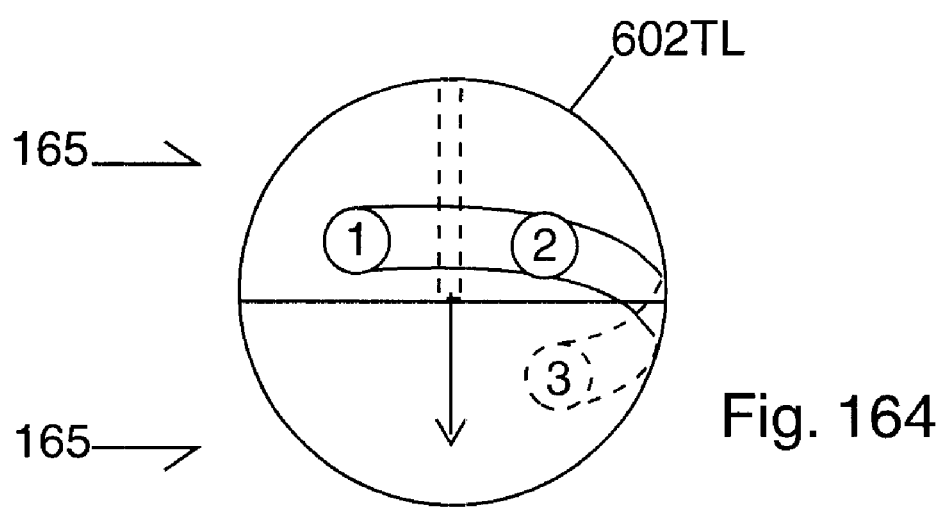

FIG. 164 is a side view of the left posterior SCC BPPV treatment sphere (having an interior hanging object) showing the marking Nos. 1, 2, and 3.

Figure 165:
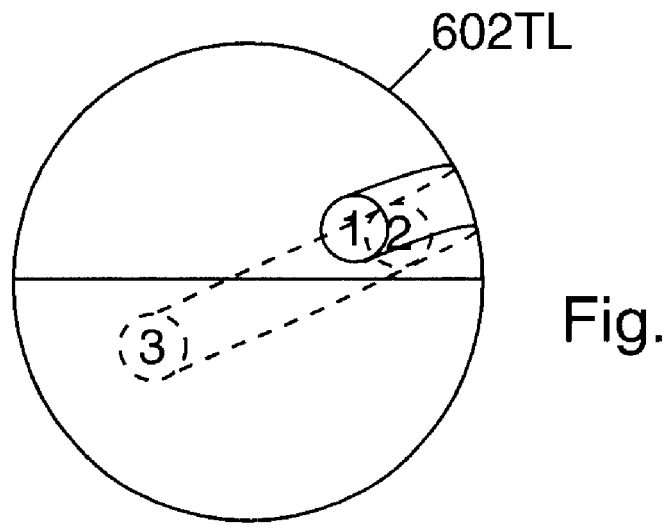

FIG. 165 is a view of FIG. 164 as seen along lines 165—165 thereof.

FIGS. 166–170 illustrate a device employing sand in a liquid contained in a toroidal shaped tube for use for BPPV treatment.

Figure 166:
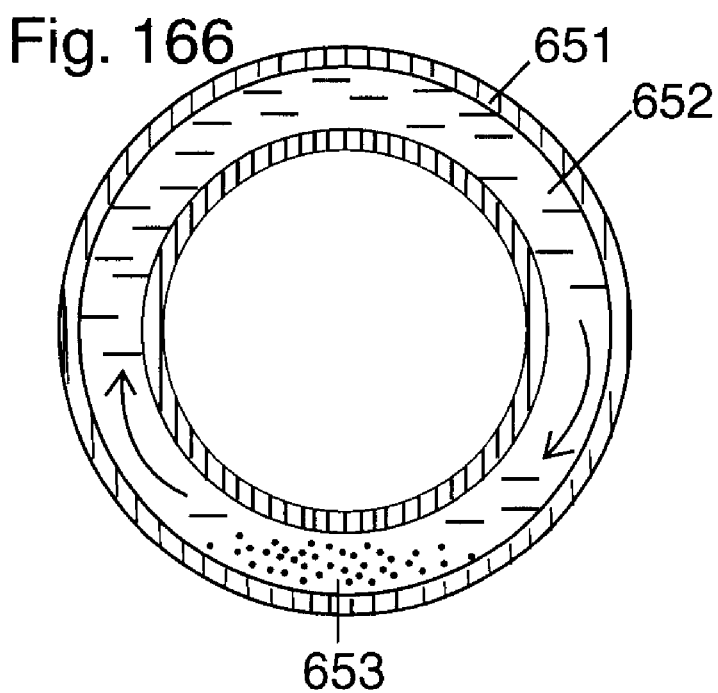

FIG. 166 illustrates a toroidal tube used in another embodiment of the invention.

Figure 167:
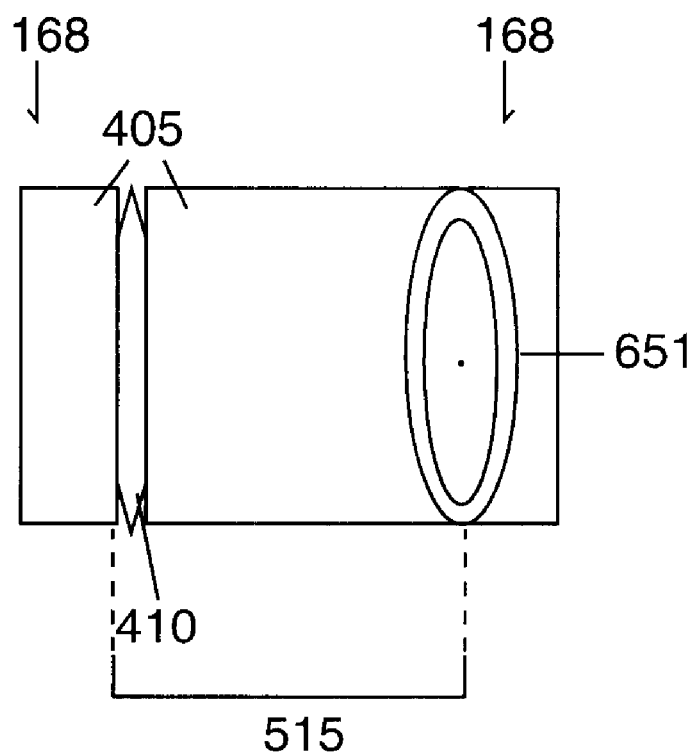

FIG. 167 is a side view of a cylindrical tube with the toroidal tube of FIG. 166 located therein.

Figure 168:
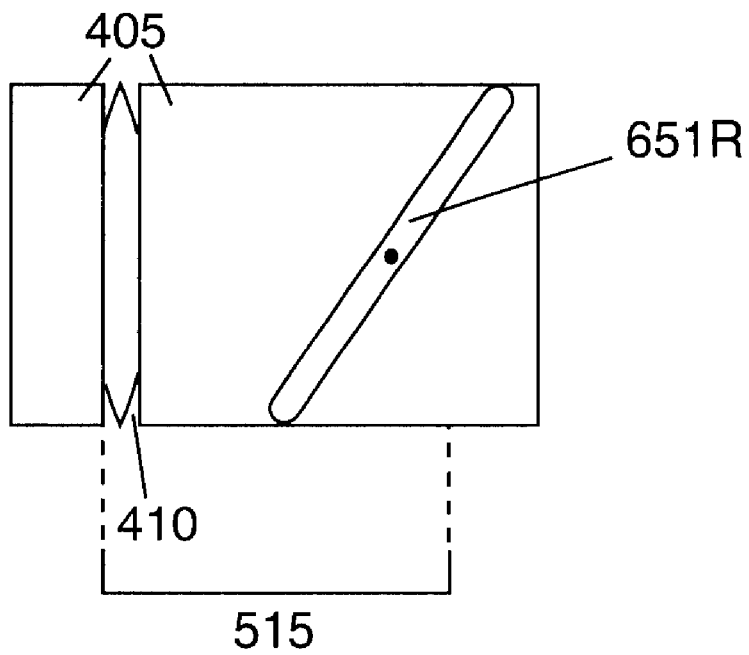

FIG. 168 is a top view of FIG. 167 as seen along lines 168—168 with the toroidal tube located in a first position for use for right posterior SCC BPPV treatment.

Figure 169:
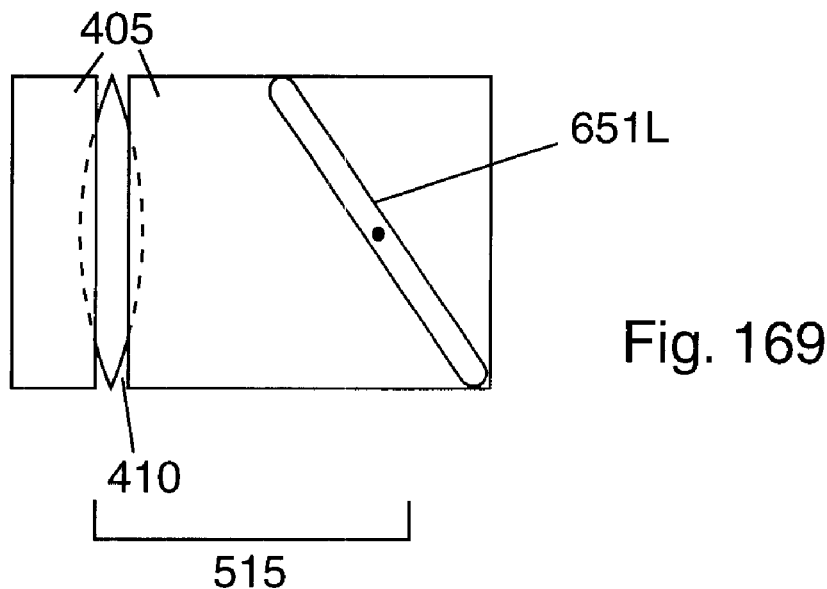

FIG. 169 is a top view of FIG. 167 as seen along lines 168—168 with the toroidal located at a second position for use for left posterior SCC BPPV treatment.

Figure 170:
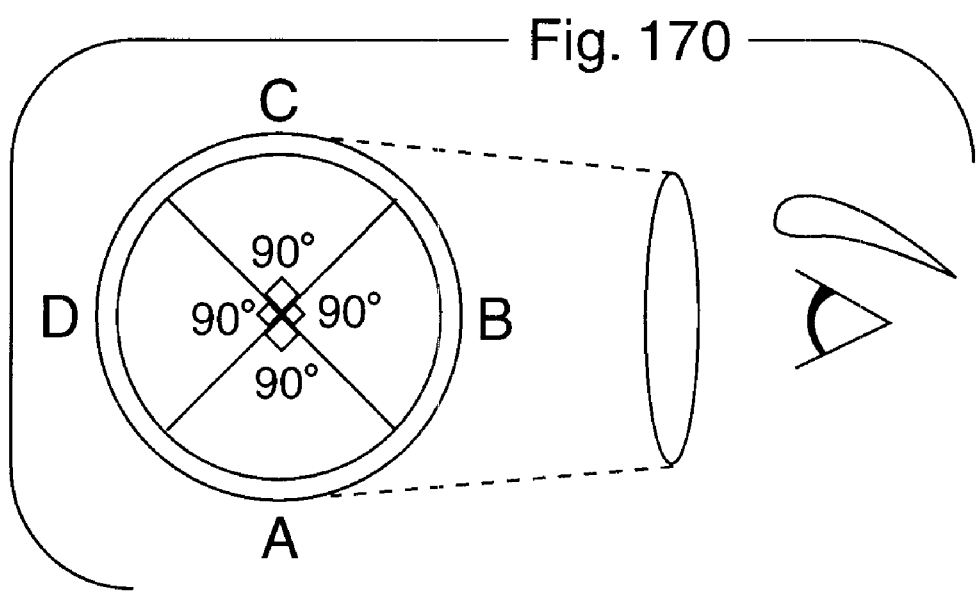

FIG. 170 illustrates four quadrants of the toroidal tube of FIGS. 166–169.

FIGS. 171–188 illustrate a rolling ball device for use for the treatment of BPPV.

Figure 171:
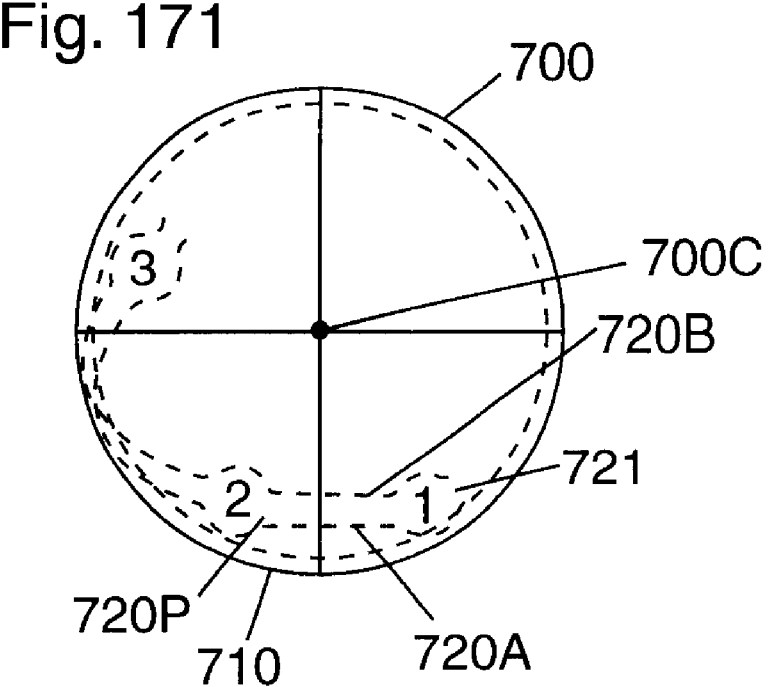
Figure 172:
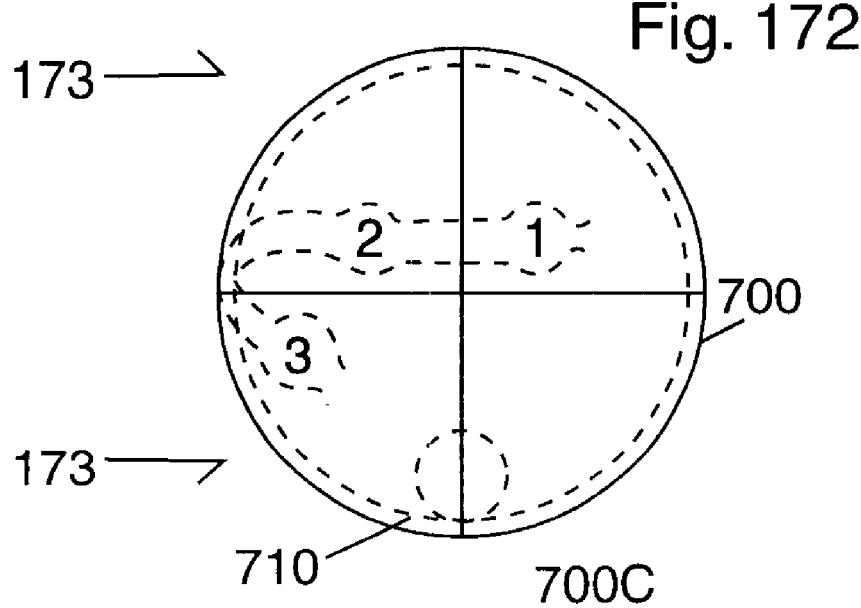
Figure 172:
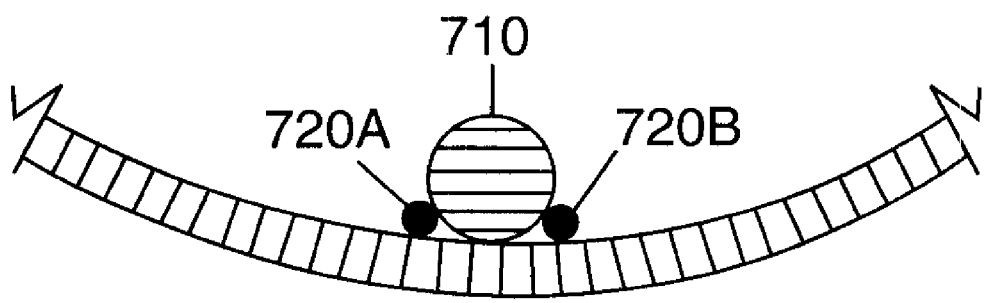
Figure 173:
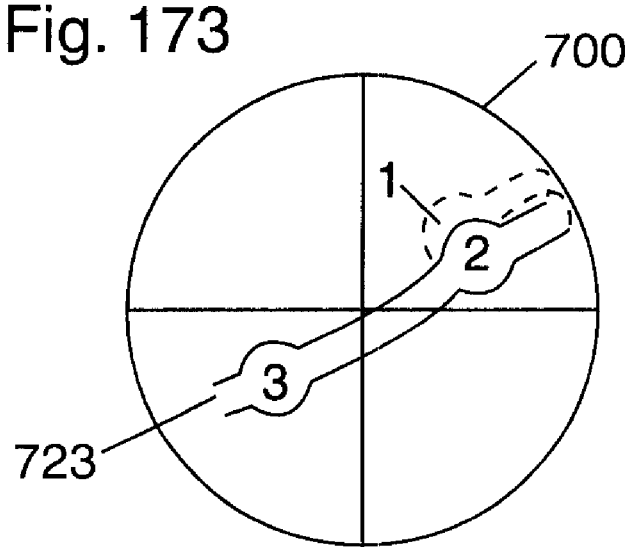

FIGS. 171, 172, and 173 illustrate the top and sides of the outer sphere of a rolling ball embodiment of the invention.

FIG. 172A is a partial cross-section of FIG. 171 showing the side walls of the path with a ball on the path.

Figure 174:
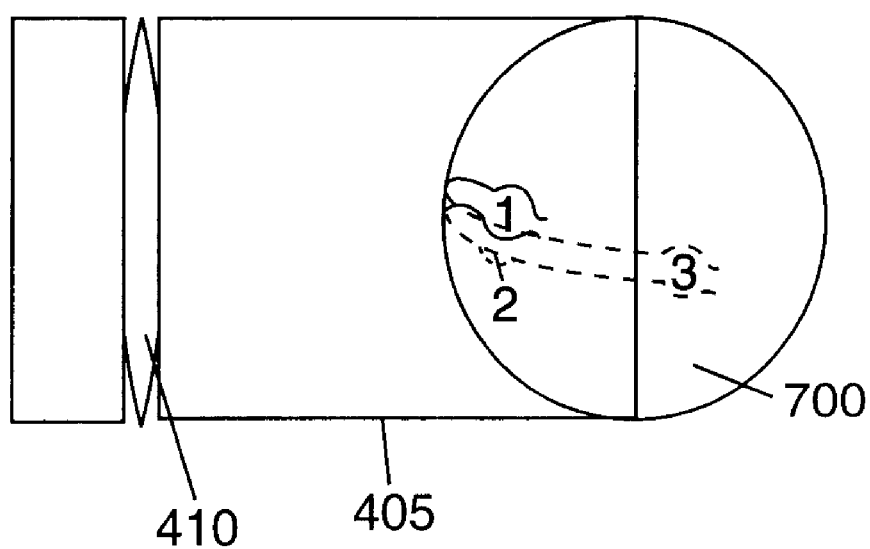

FIG. 174 illustrates the outer sphere of FIGS. 171, 172, and 173 in the cylindrical member of the device.

Figure 175:
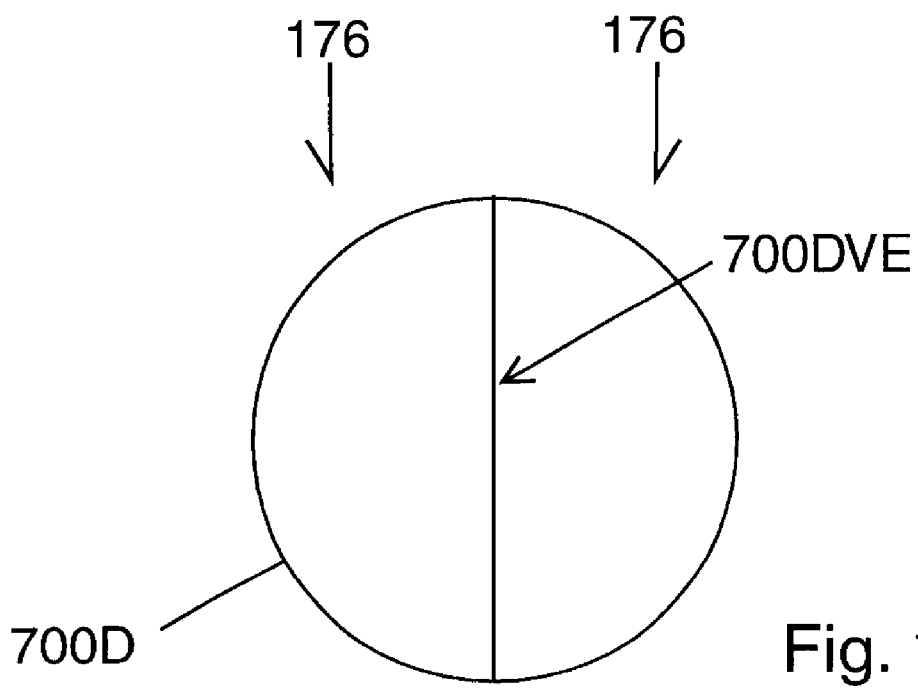

FIG. 175 is a side view of the diagnostic outer sphere of the rolling ball embodiment.

Figure 176:
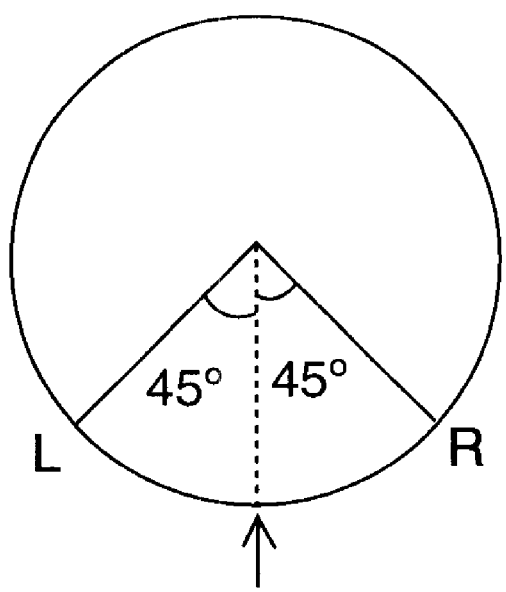

FIG. 176 is a view of FIG. 175 as seen along lines 176—176 thereof.

Figure 177:
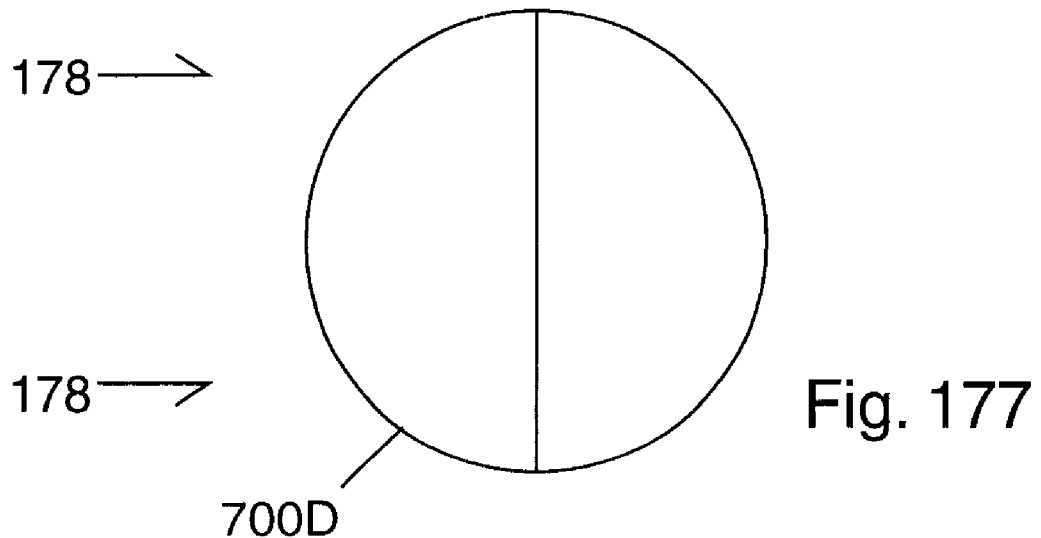

FIG. 177 is a view of the diagnostic outer sphere similar to that of FIG. 175.

Figure 178:
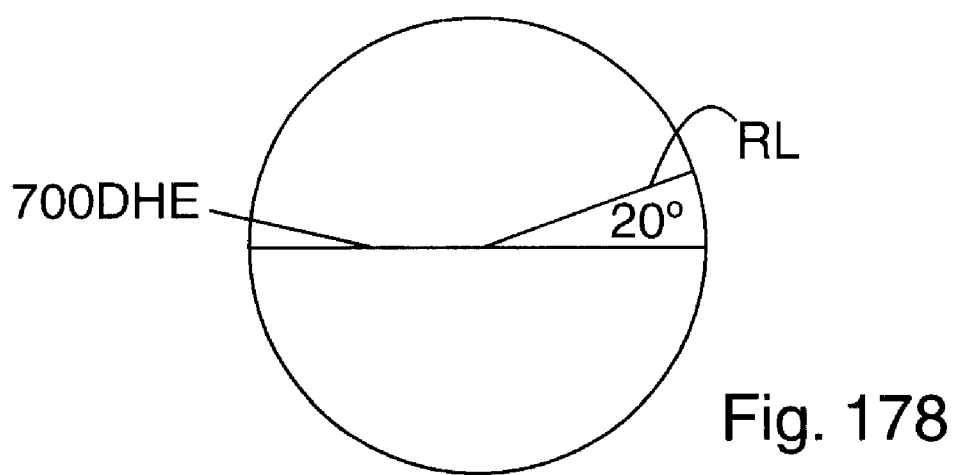

FIG. 178 is a view of FIG. 177 as seen along lines 178—178 thereof.

Figure 179:
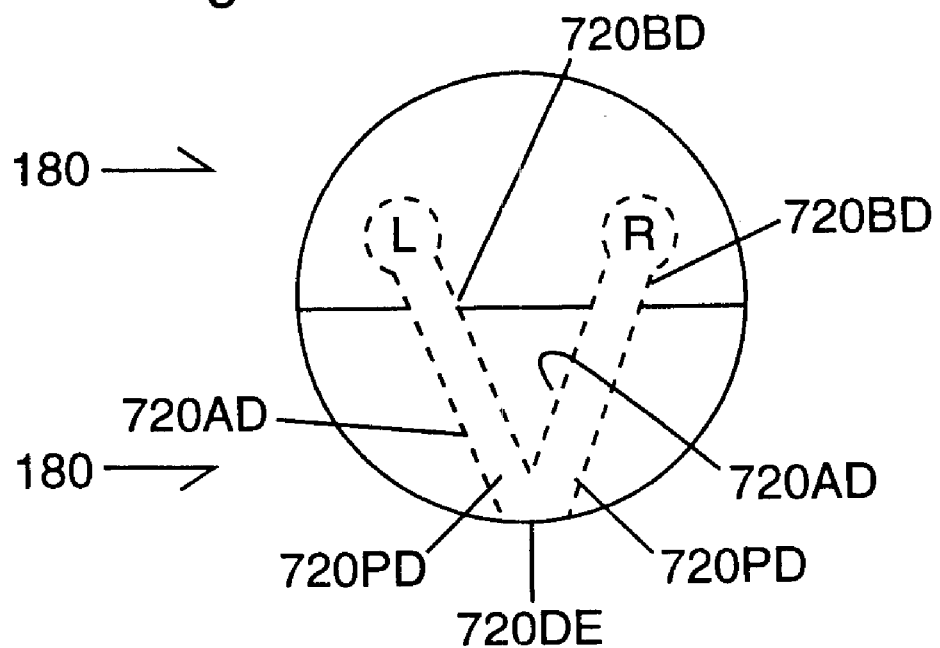

FIG. 179 illustrate the R and L markings of the sphere of FIGS. 175–178.

Figure 180:
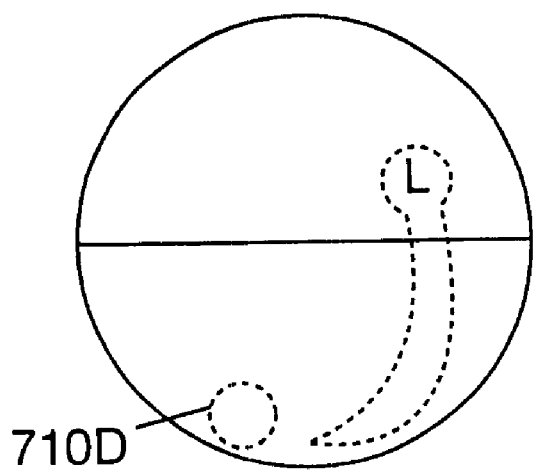

FIG. 180 is a view of FIG. 179 as seen along the lines 180—180 thereof.

Figure 181:
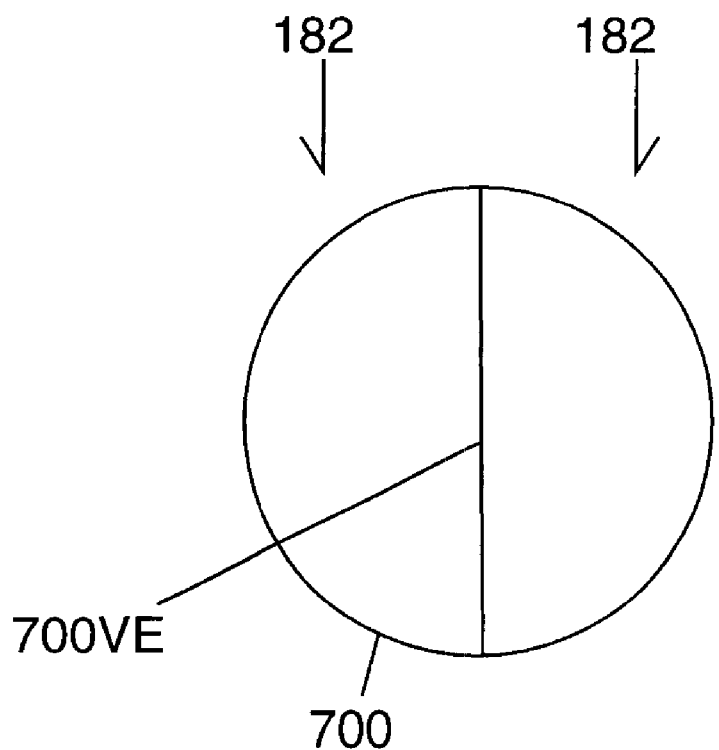

FIG. 181 is a side view of the treatment outer sphere of the rolling ball embodiment.

Figure 182:
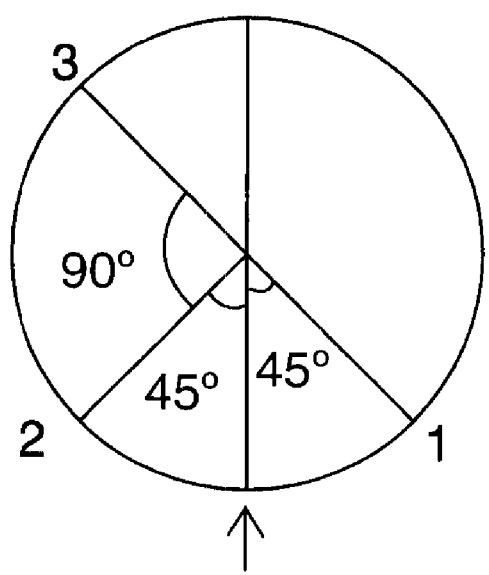

FIG. 182 is a view of FIG. 181 as seen along the lines 182—182 thereof.

Figure 183:
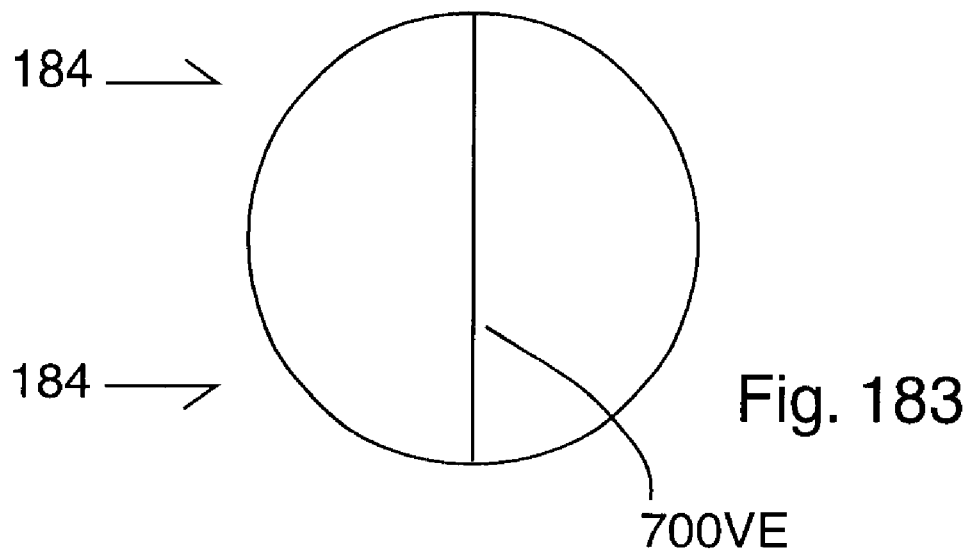

FIG. 183 is a view of the treatment sphere similar to that of FIG. 181.

Figure 184:
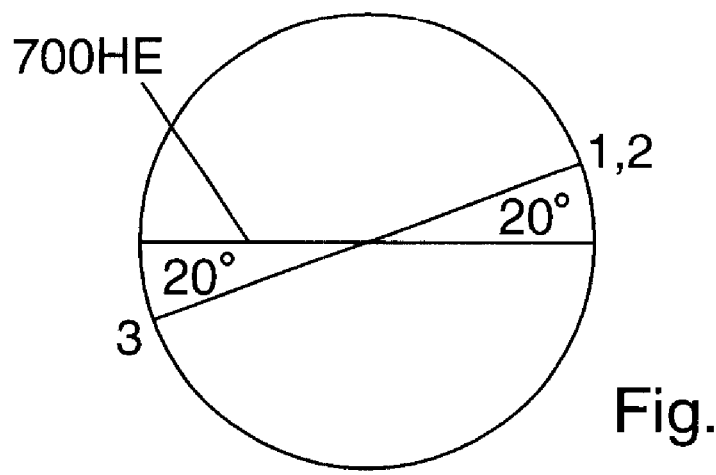

FIG. 184 is a view of FIG. 183 as seen along lines 184—184 thereof.

Figure 185:
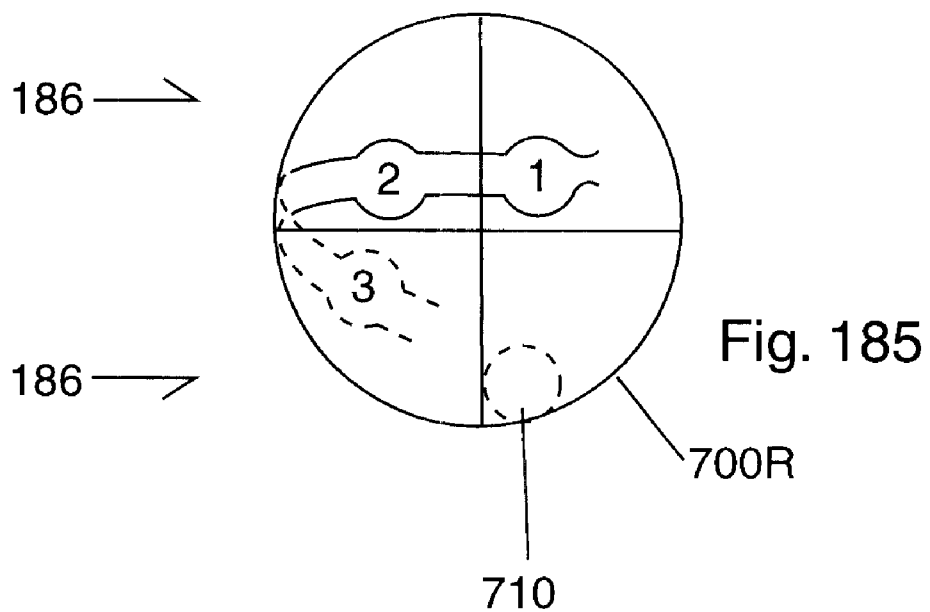

FIG. 185 is a side view of the right posterior SCC BPPV treatment outer sphere of the rolling ball embodiment showing the marks Nos. 1, 2, and 3.

Figure 186:
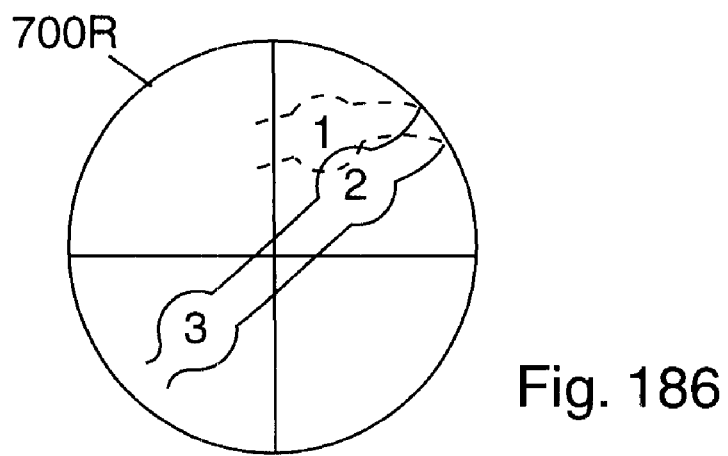

FIG. 186 is a view of FIG. 185 as seen along lines 186—186 thereof.

Figure 187:
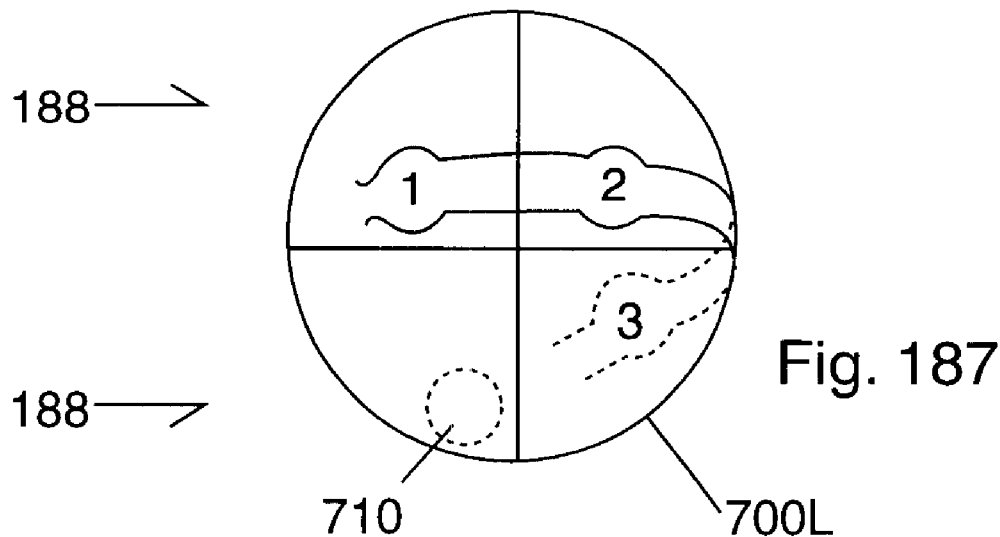

FIG. 187 is a side view of the left posterior SCC BPPV treatment outer sphere of the rolling ball embodiment showing the marks Nos. 1, 2, and 3.

Figure 188:
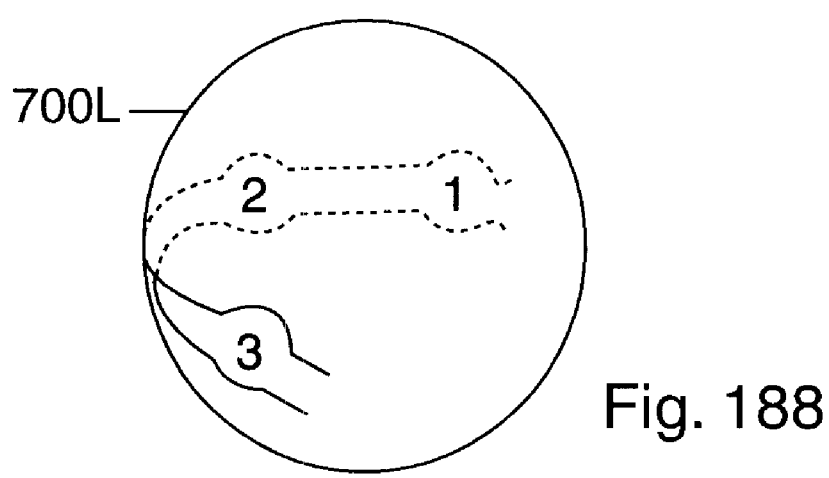

FIG. 188 is a view of FIG. 187 as seen along lines 188—188 thereof.

In the above Figures, the bull's eyes 1, 2, 3, 4, R, L, are shown in circular form on the exterior of the inner spheres in all lines of sight for purposes of clarity although in a true perspective, depending upon the line of sight, they may not be seen as circular.

In the above Figures, many of the various planes and axes are illustrated as solid lines.

FIGS. 189–204 illustrate the hardware and software configuration of an electronic device for use in BPPV treatment.

FIGS. 189A–189D diagram the electronic circuits for obtaining measurements which are a function of gravity and for operating Light Emitting Diodes for directing the patient's head movement for treating BPPV.

Figure 189A:
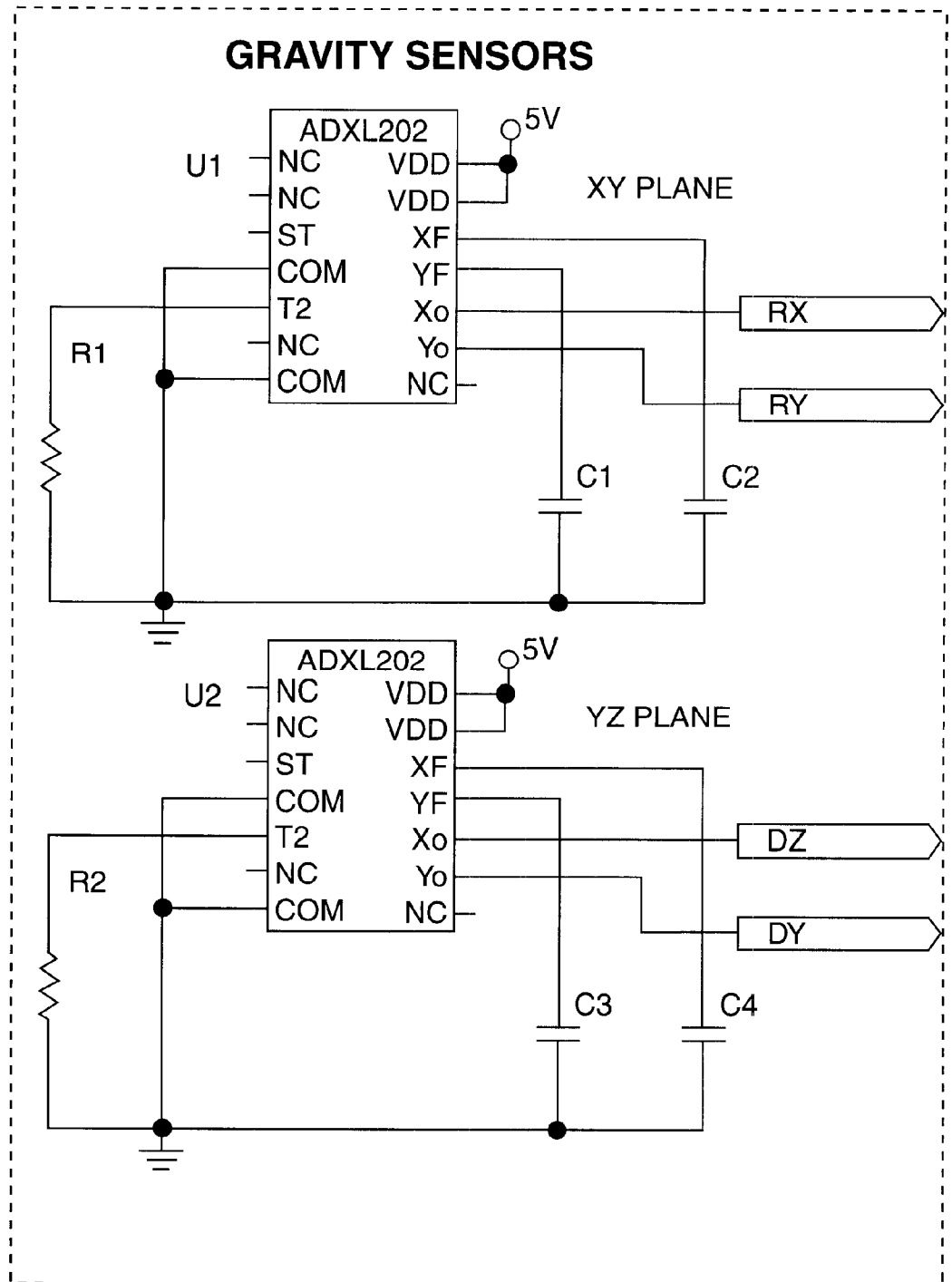
Figure 189B:
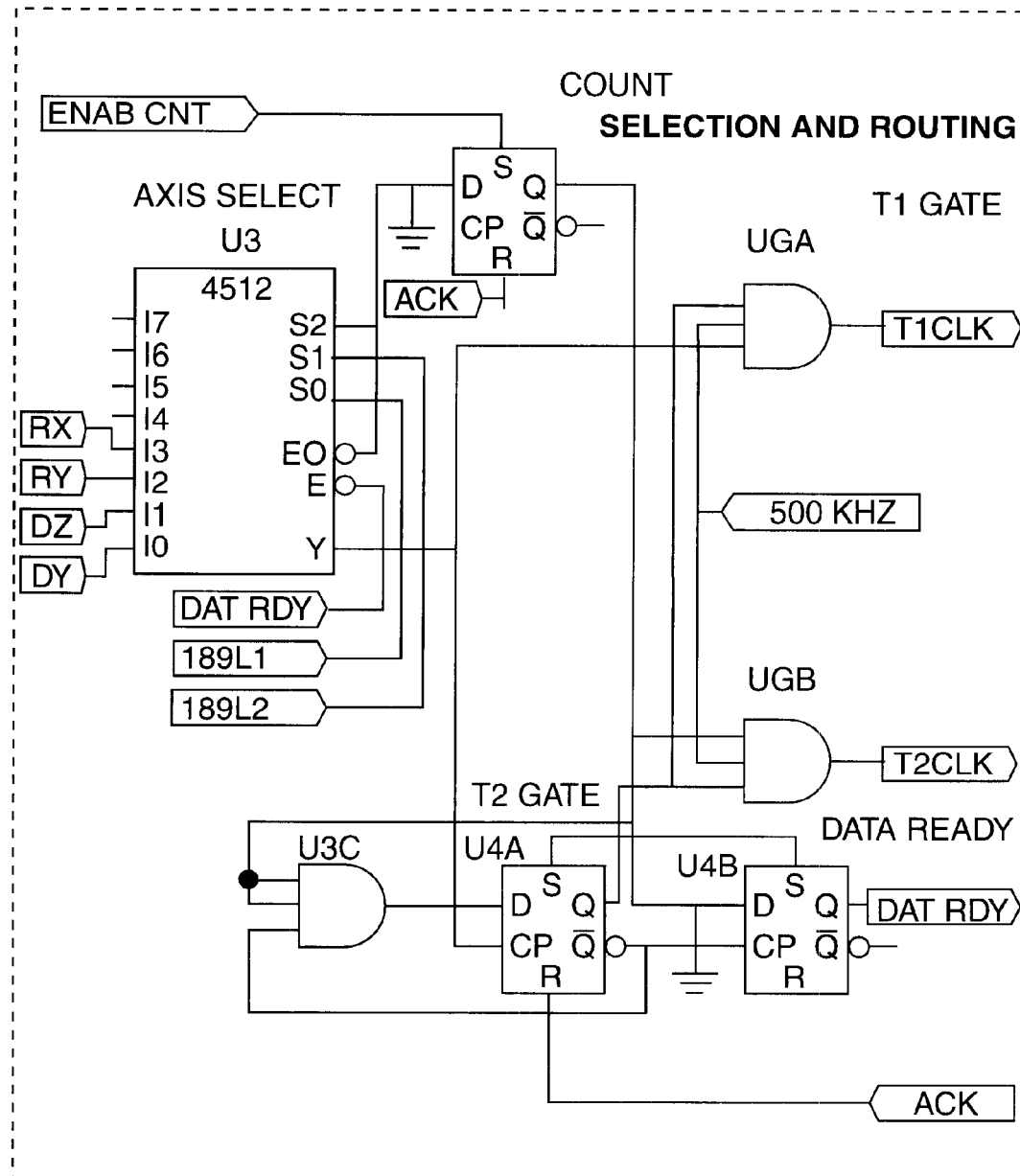
Figure 189C:
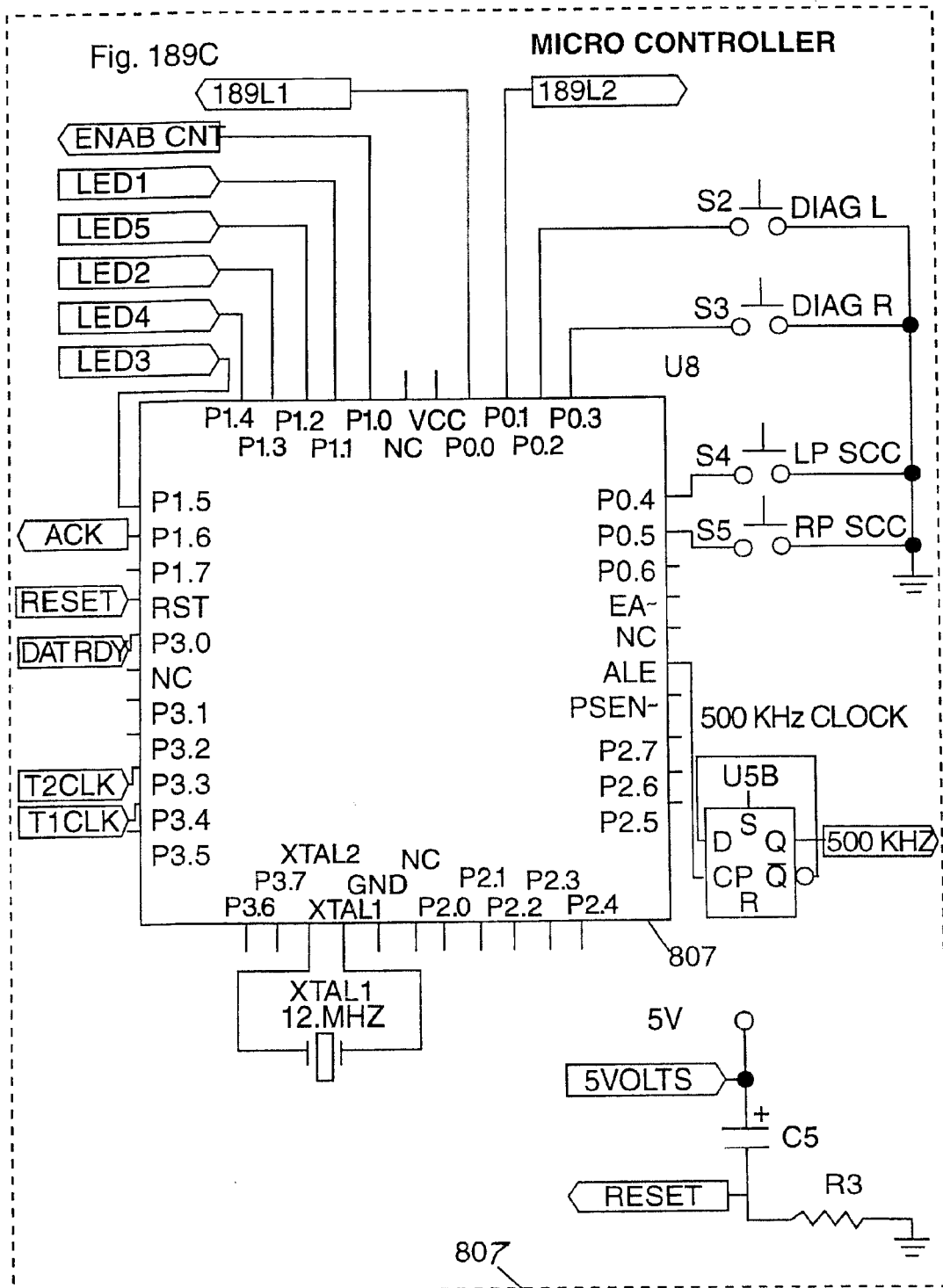
Figure 189D:
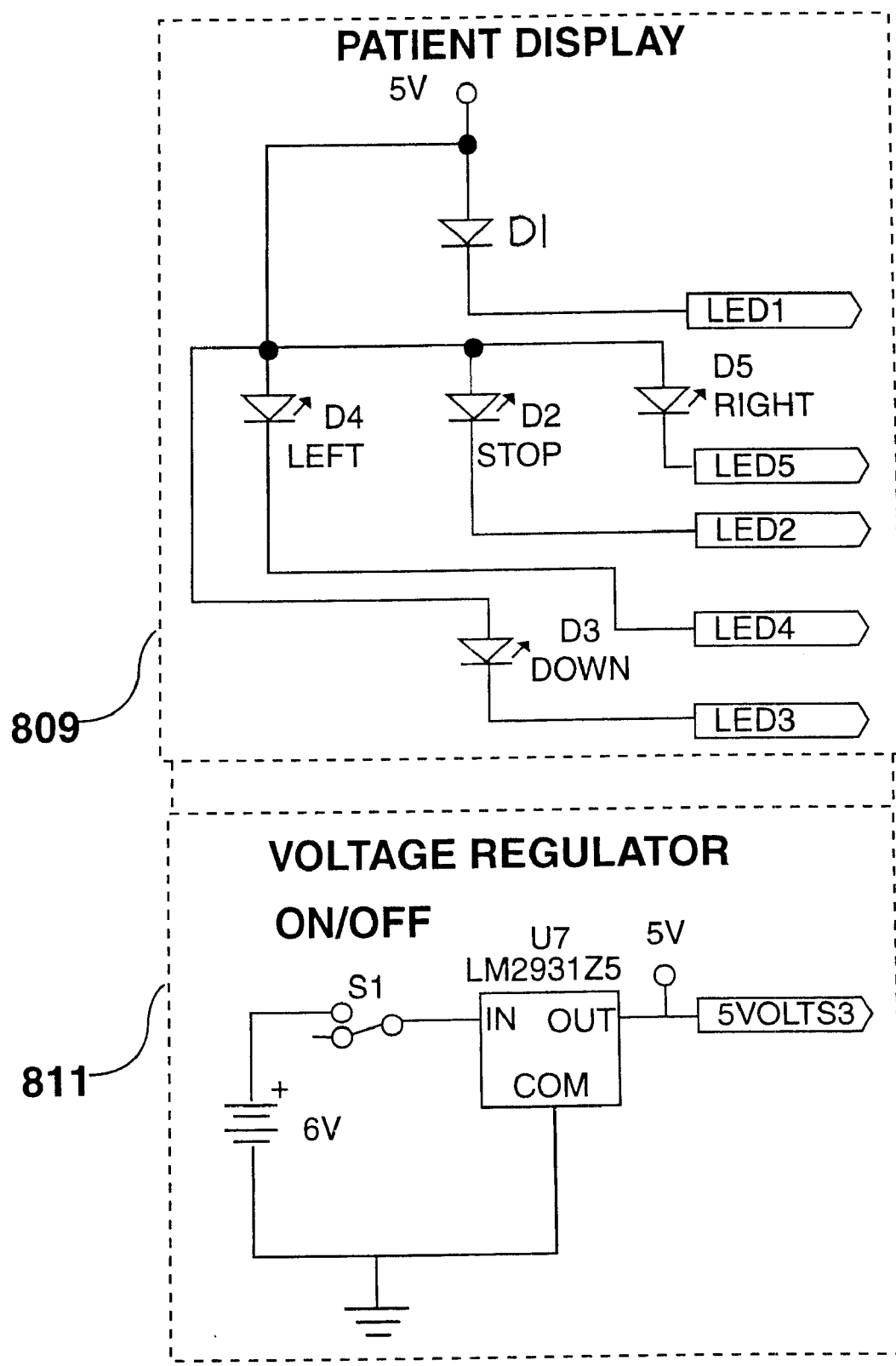
Figure 190:
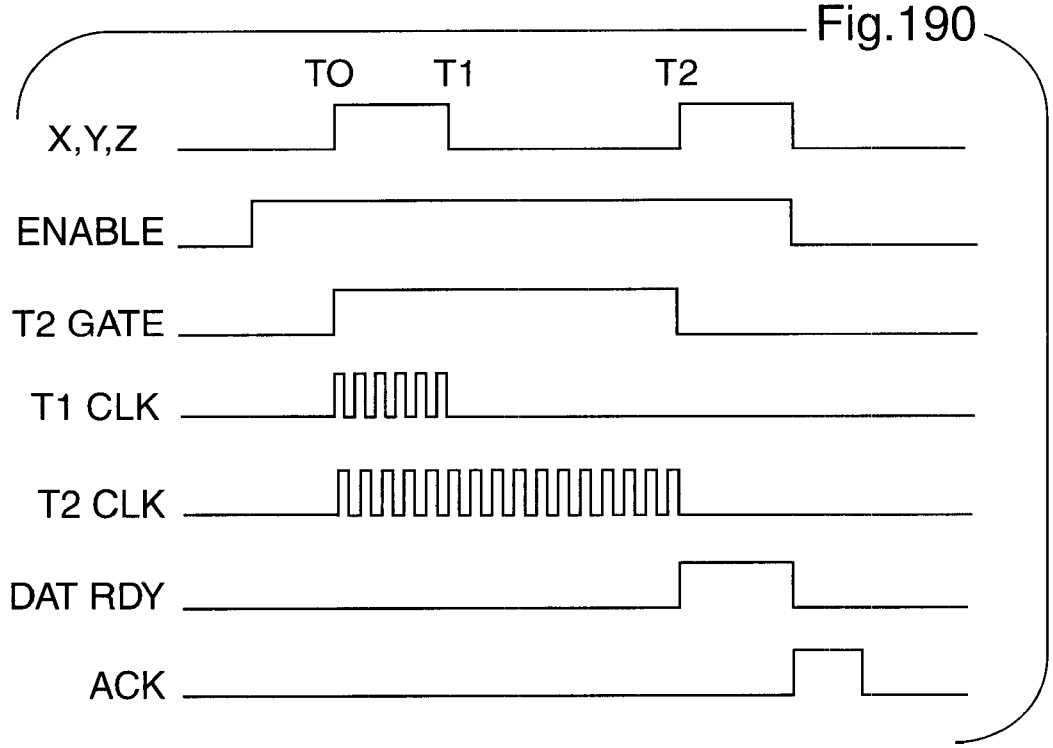

FIG. 190 are electrical time traces showing the event sequence of the system of FIG. 189.

Figure 191:
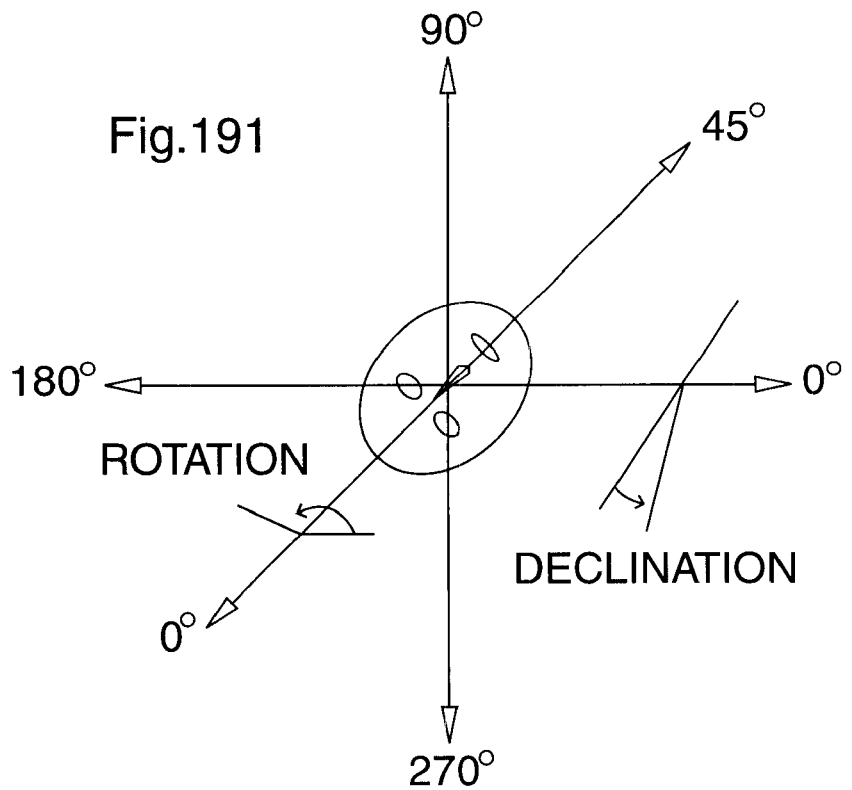

FIG. 191 illustrates how the rotational and declination angles are defined.

Figure 192:
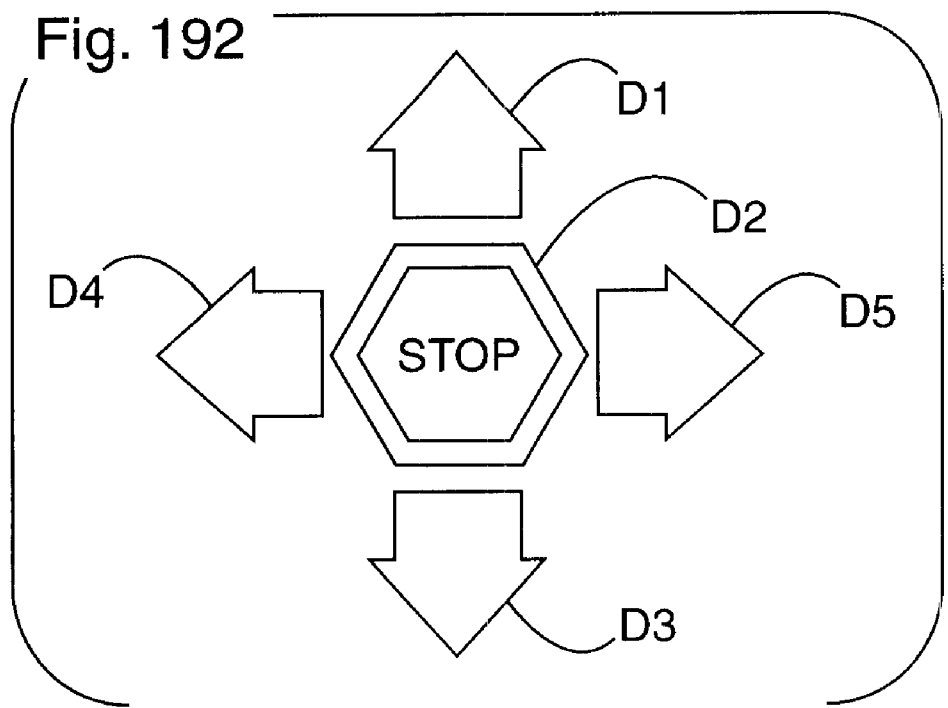

FIG. 192 illustrates the light indicators of the five light emitting diodes of the system of FIG. 189.

Figure 193A:
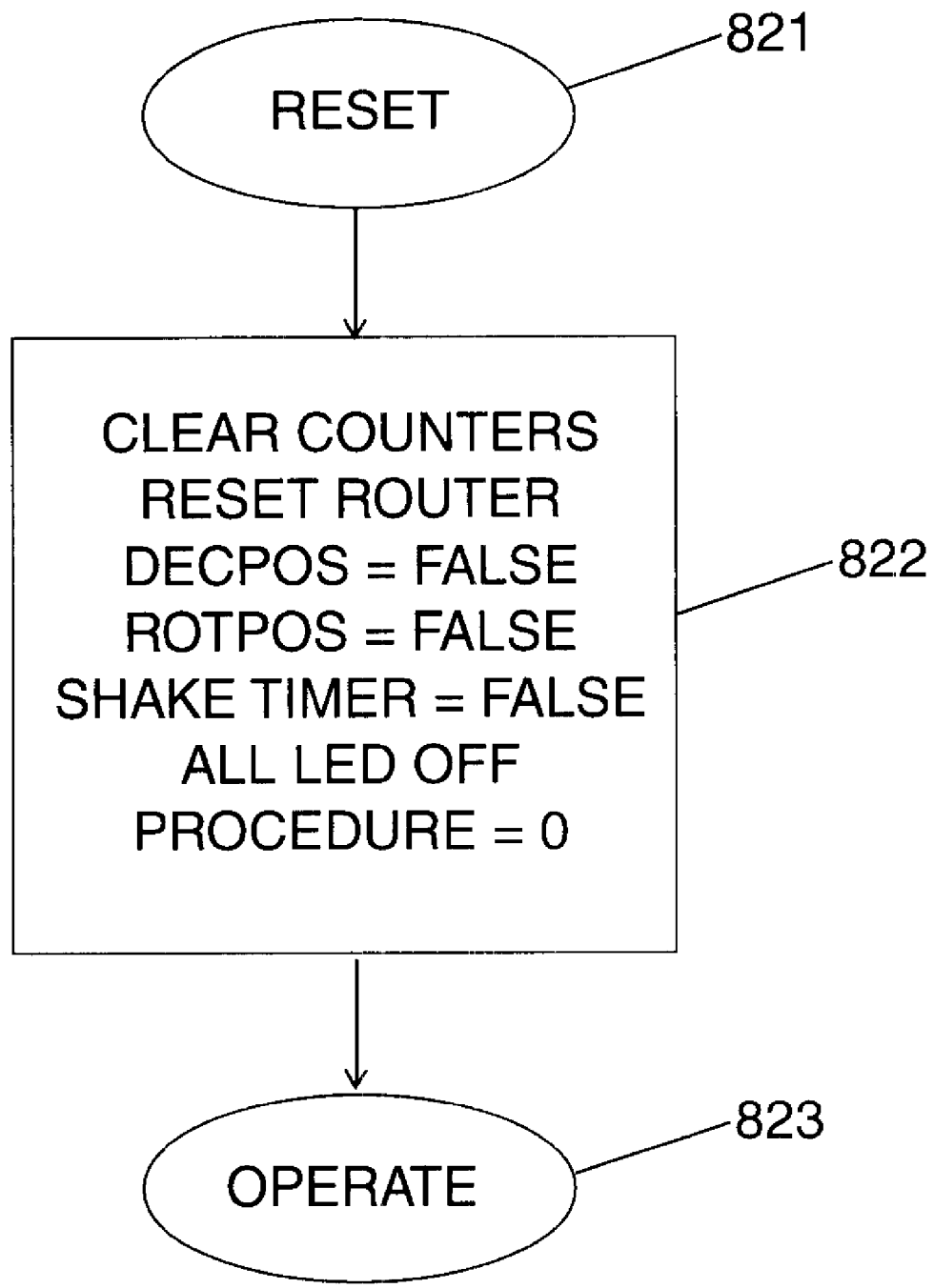
Figure 193B:
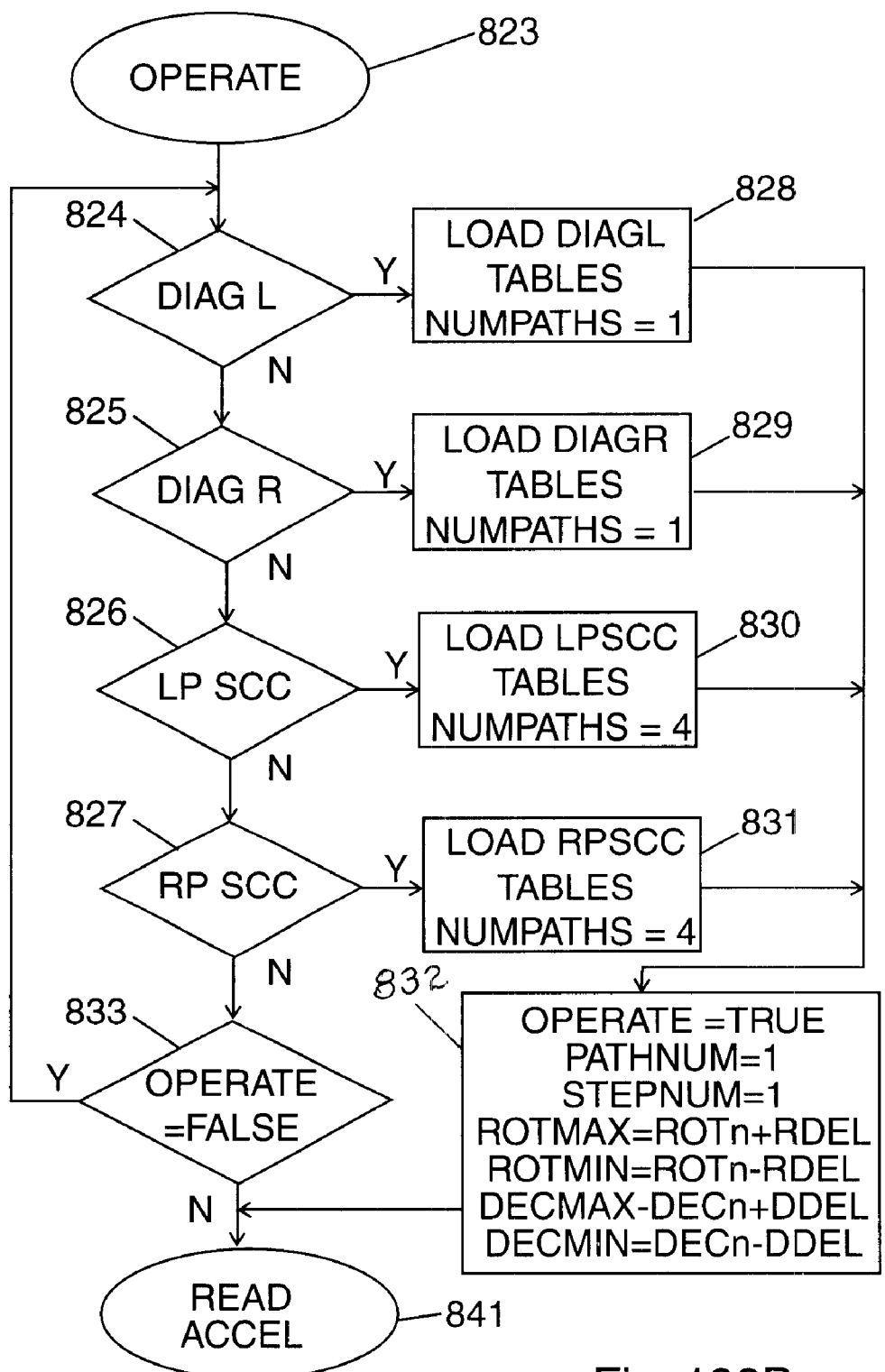

FIGS. 193A & 193B is a flow diagram of the operation segment.

Figure 194:
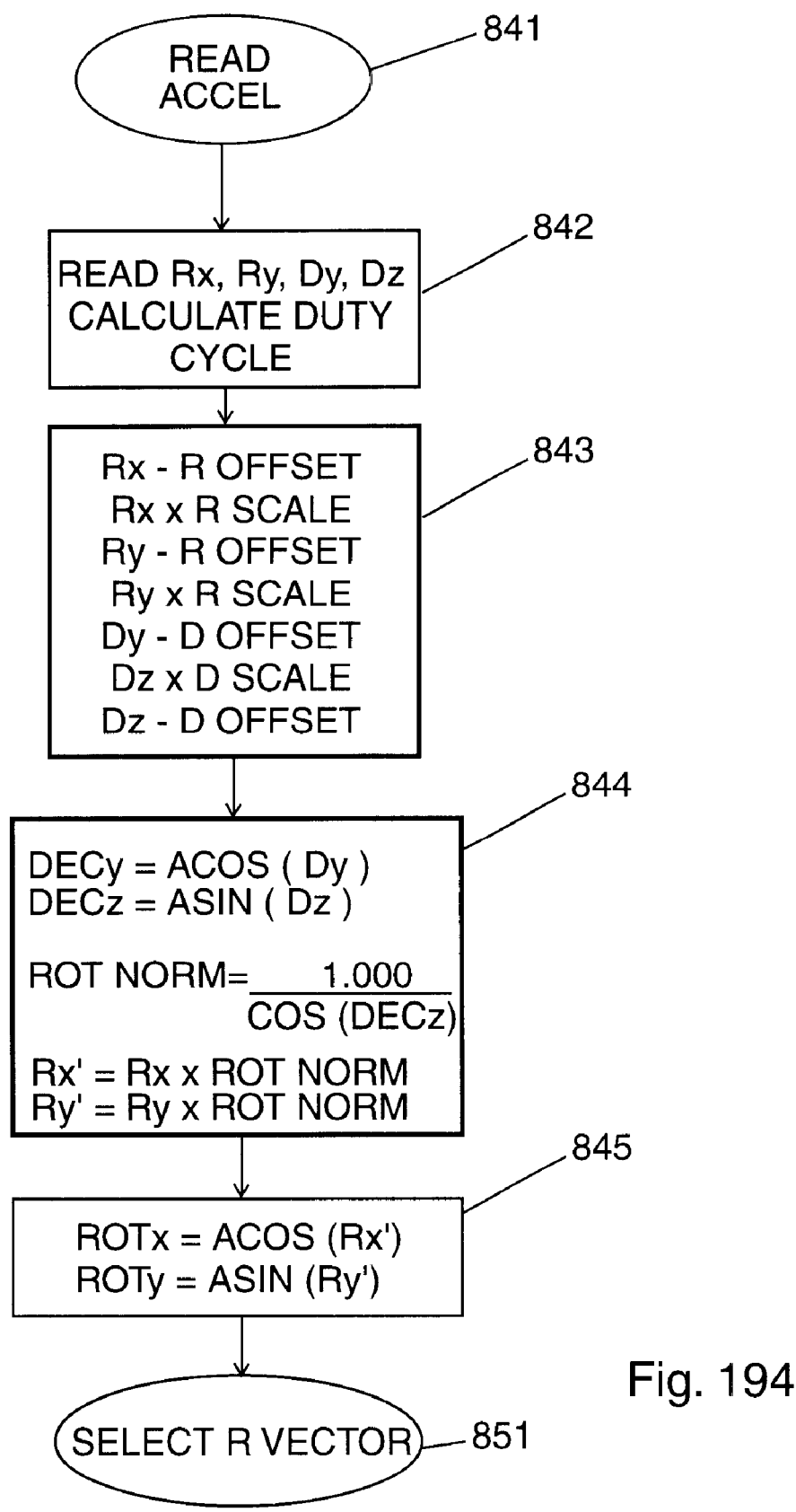

FIG. 194 is a flow diagram of the computation segment.

Figures 195, 196:
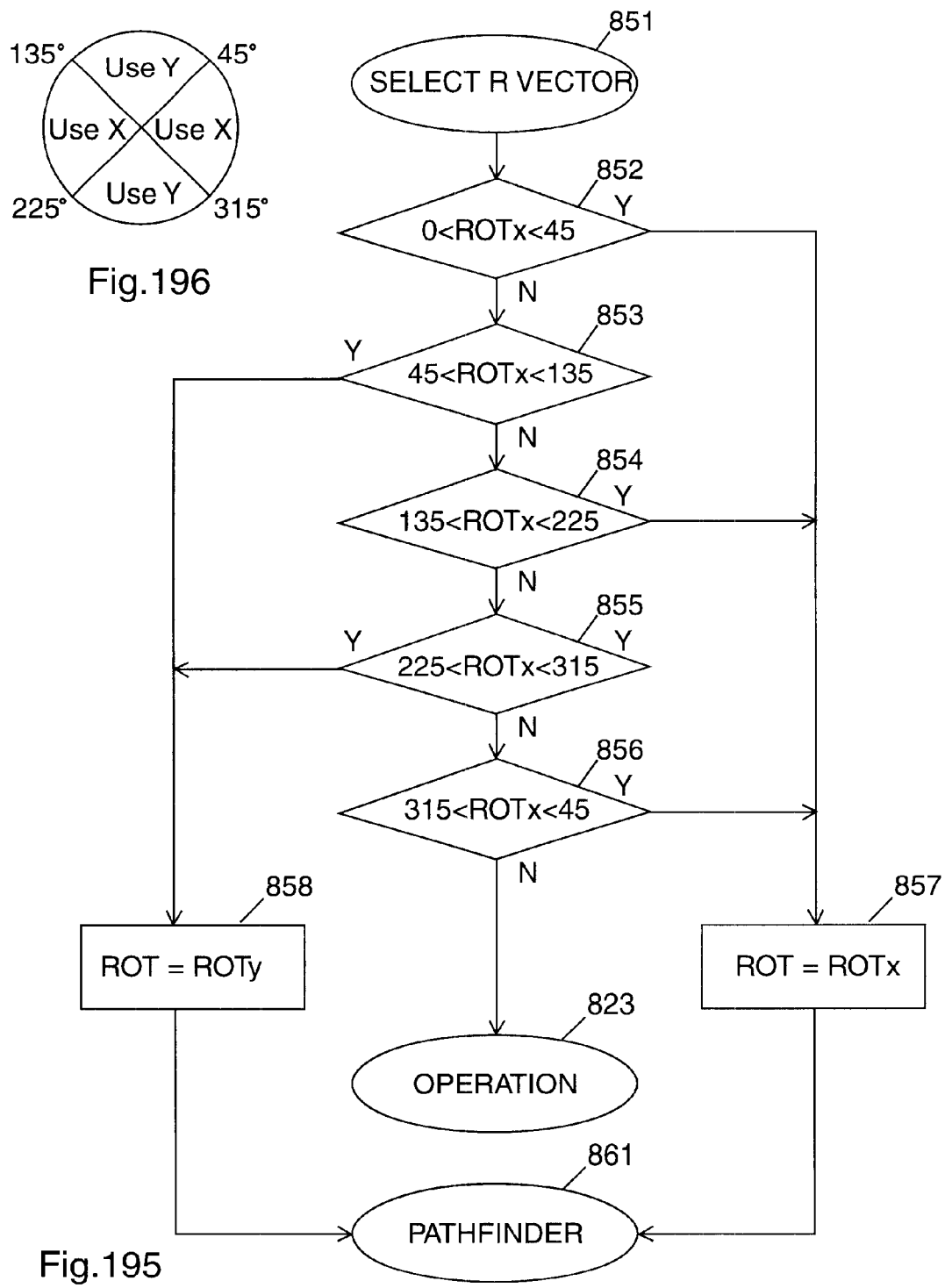

FIG. 195 is a flow diagram of a vector selection segment.

FIG. 196 illustrates a decision model.

The RX, RY, DY, DZ connectors of FIG. 189A are connected to the RX, RY, DY, DZ connectors of FIG. 189B respectively. The 189L1 and 189L2 connectors of FIG. 189B are connected to the 189L1 and 189L2 connectors of FIGS. 189C respectively. The LED1, LED2, LED3, LED4, LED5 connectors of FIG. 189C are connected to the LED1, LED2, LED3, LED4 connectors of FIG. 189D respectively.

Figure 197A:
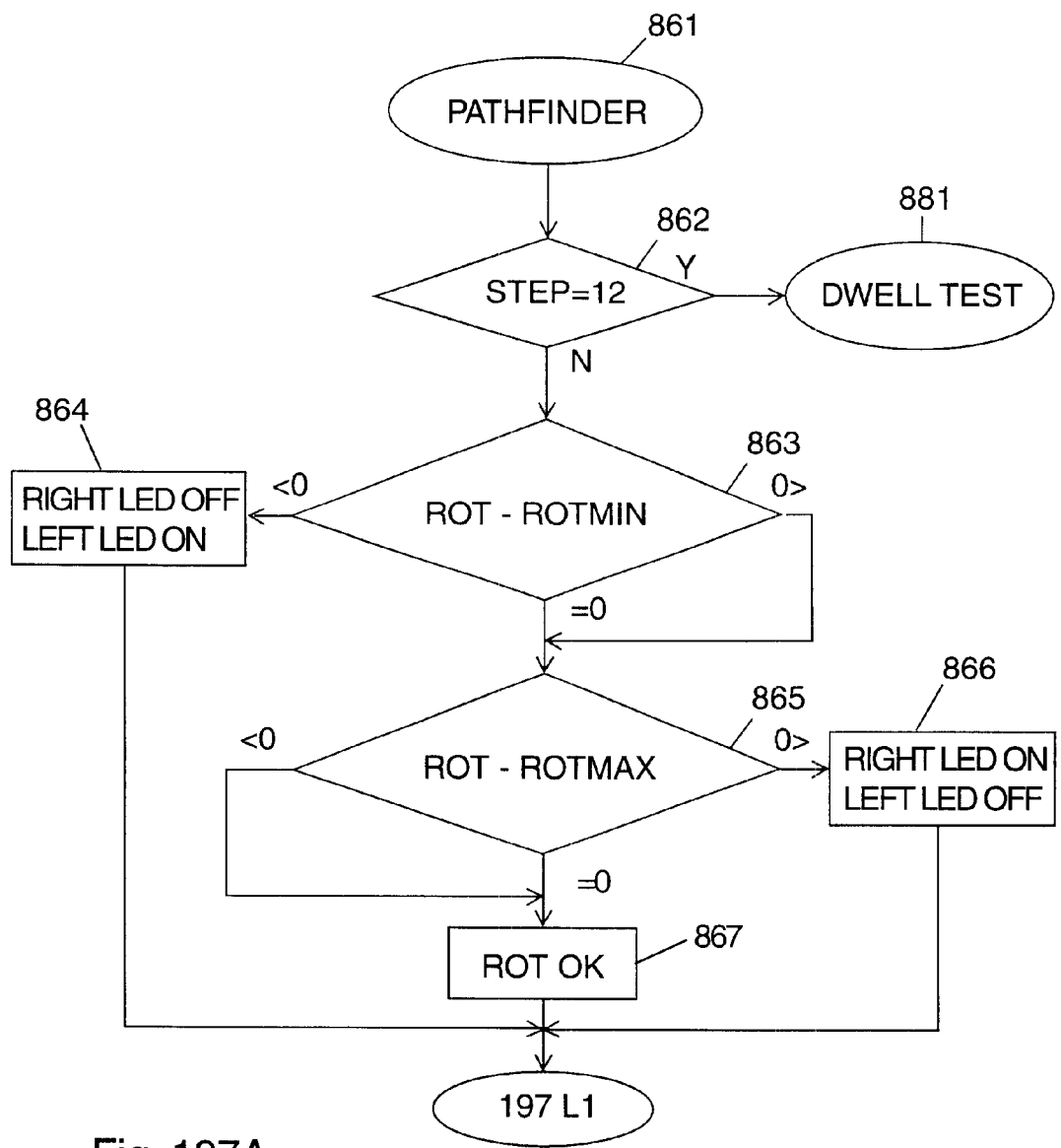
Figure 197B:
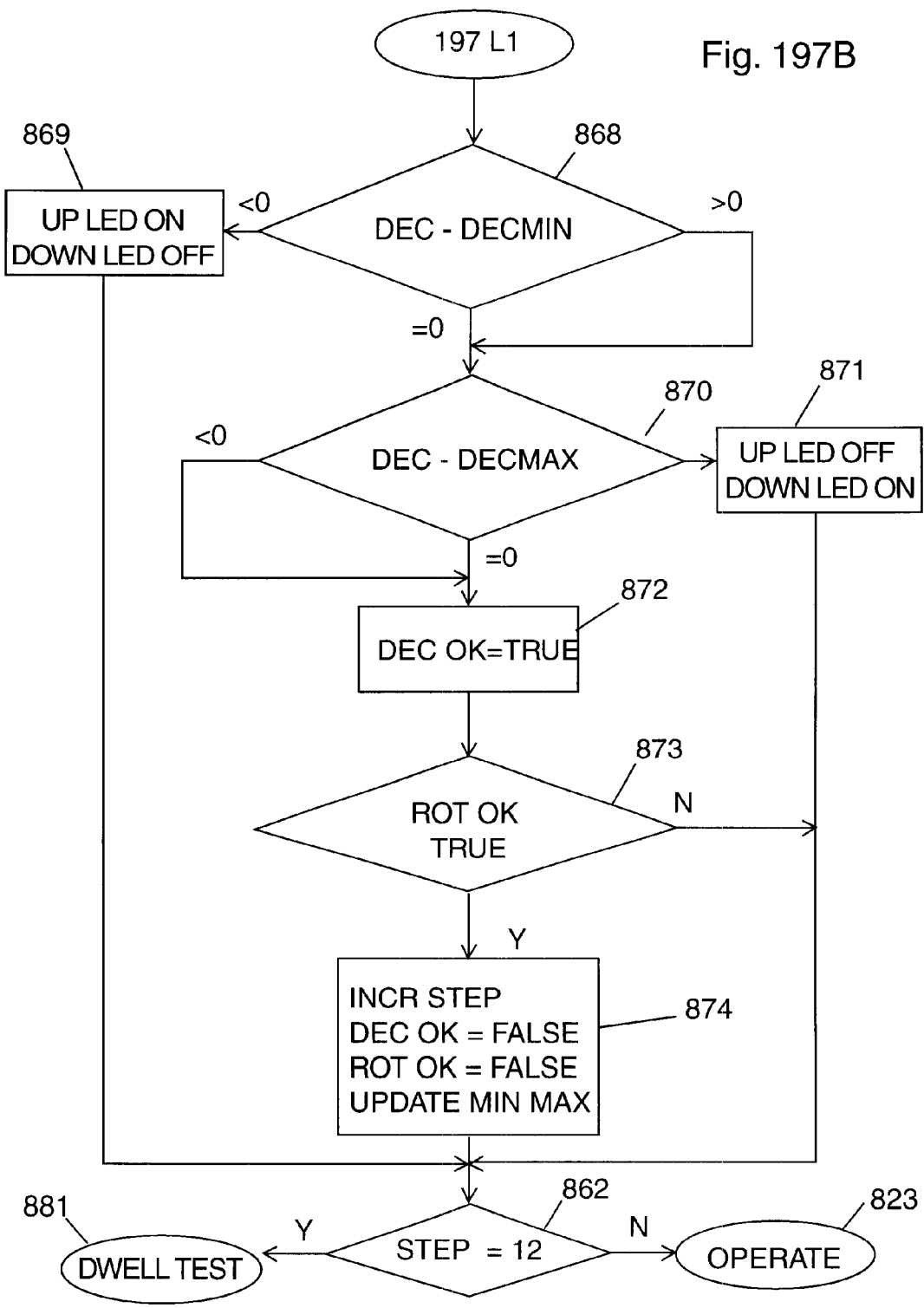

FIGS. 197A and 197B is a flow diagram of a pathfinder segment.

Figure 198:
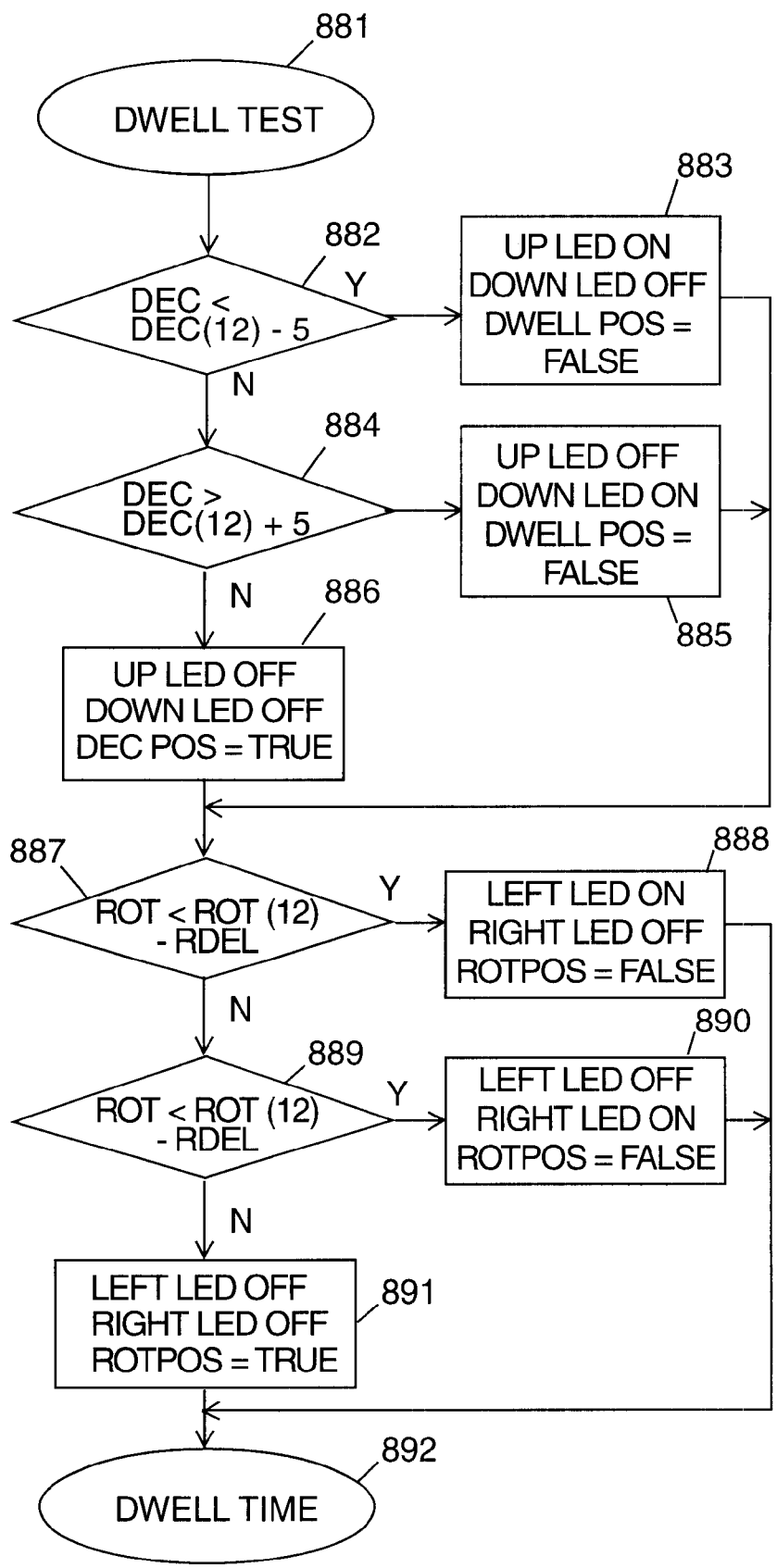

FIG. 198 is a flow diagram of a Dwell Test Segment.

Figure 199A:
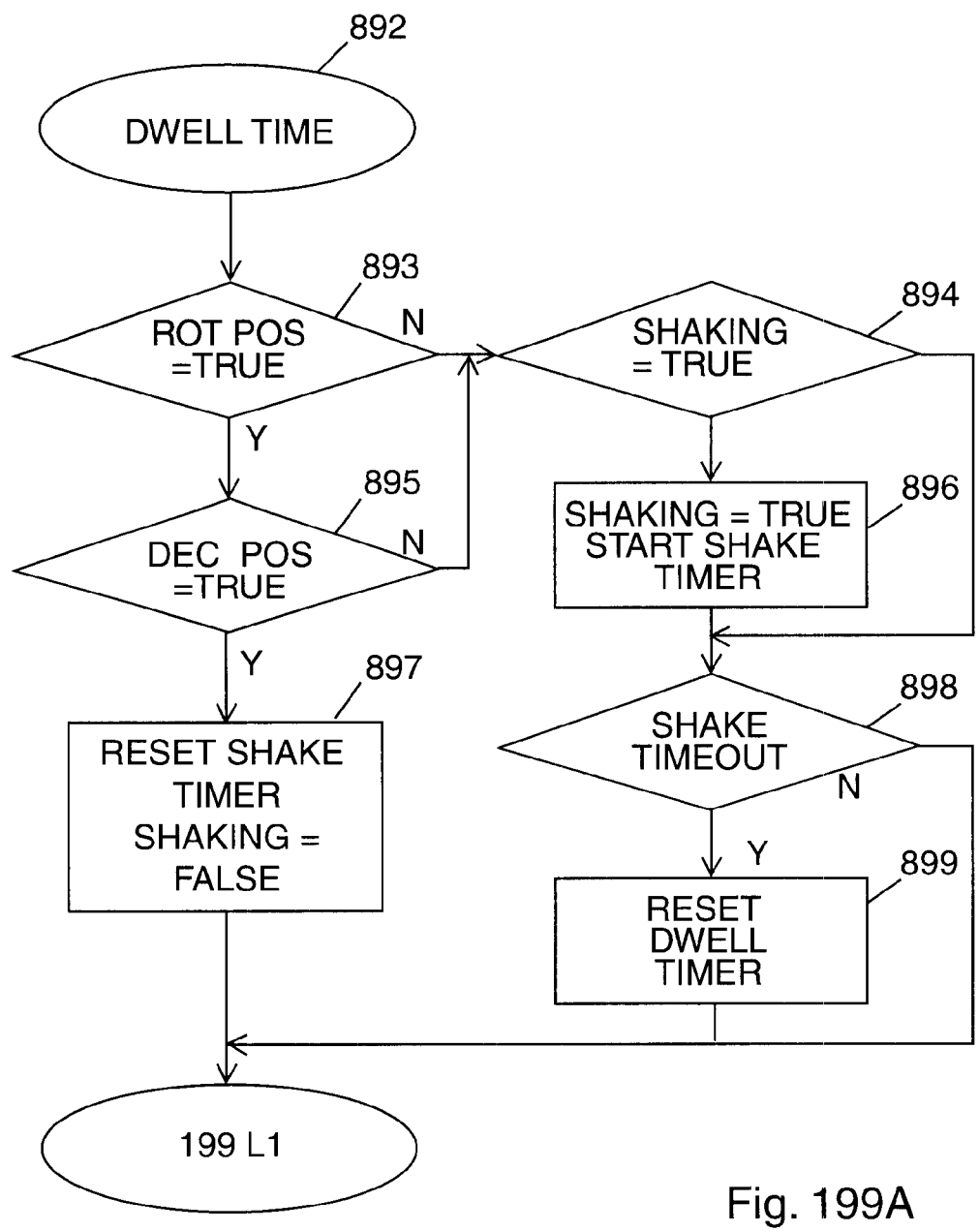
Figure 199B:
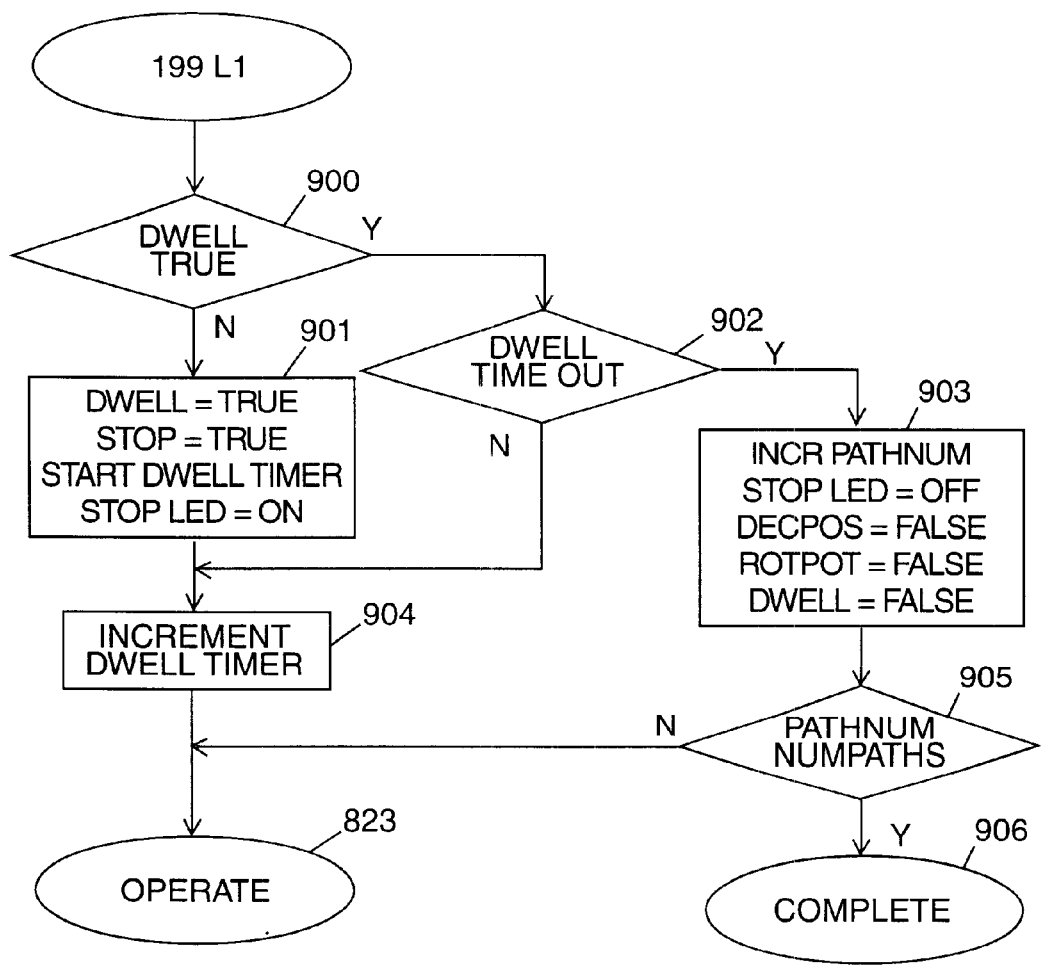

FIGS. 199A and 199B is a flow diagram of the Dwell Time Segment.

Figure 200:
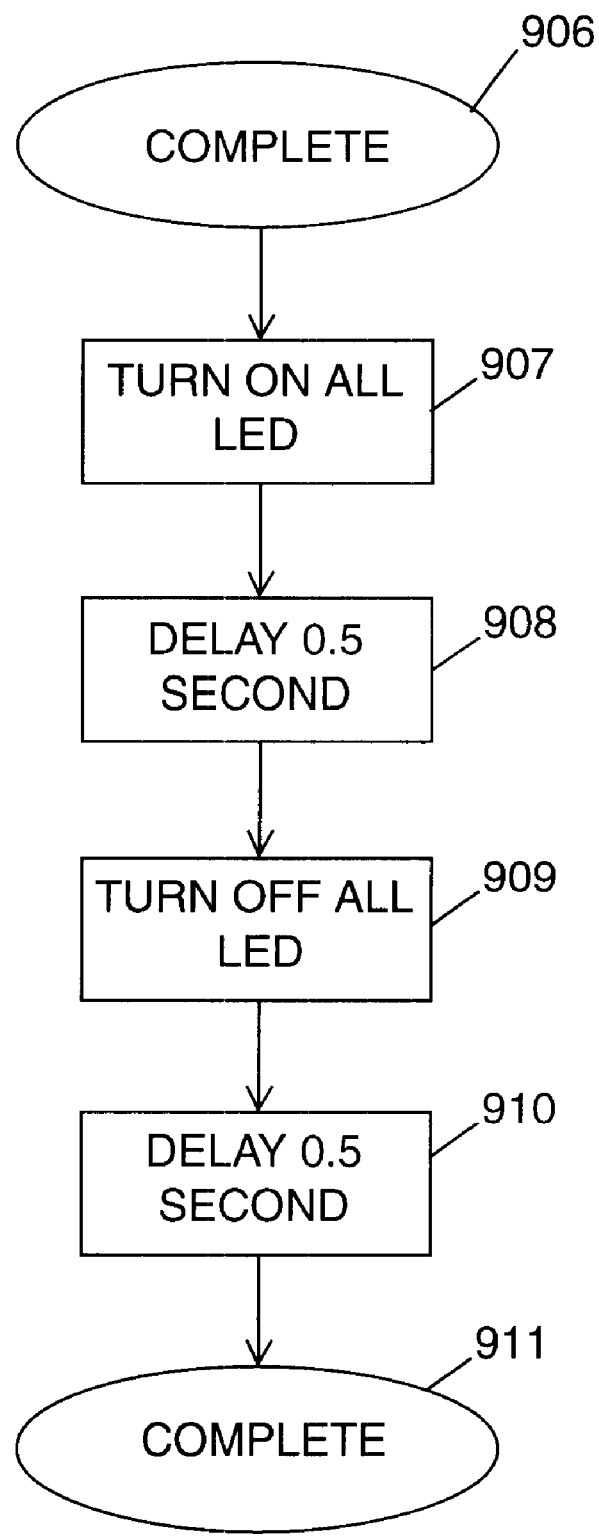

FIG. 200 is a flow diagram of the completion segment.

Figure 201:
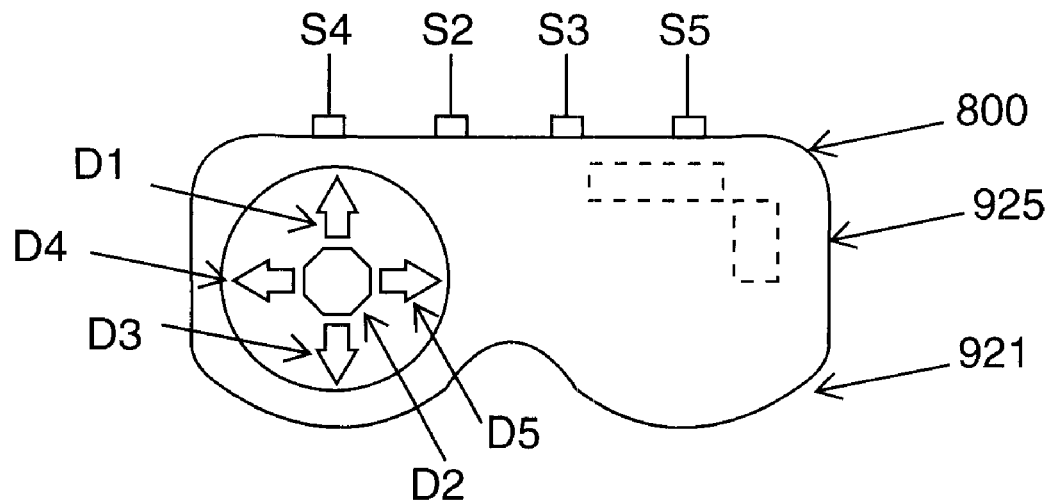

FIG. 201 illustrates the goggles for the electronic embodiment.

Figure 202:
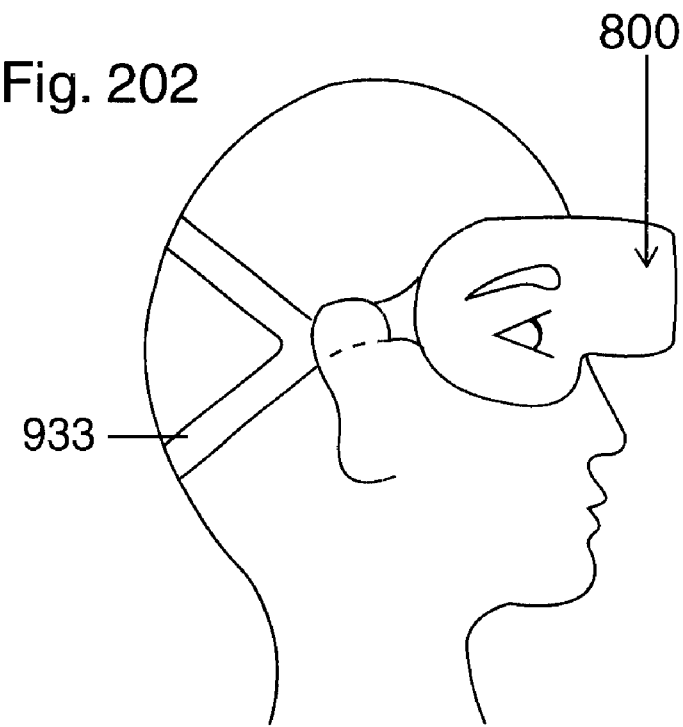

FIG. 202 is a side view of the goggles of FIG. 201 on the head of a person.

Figure 203:
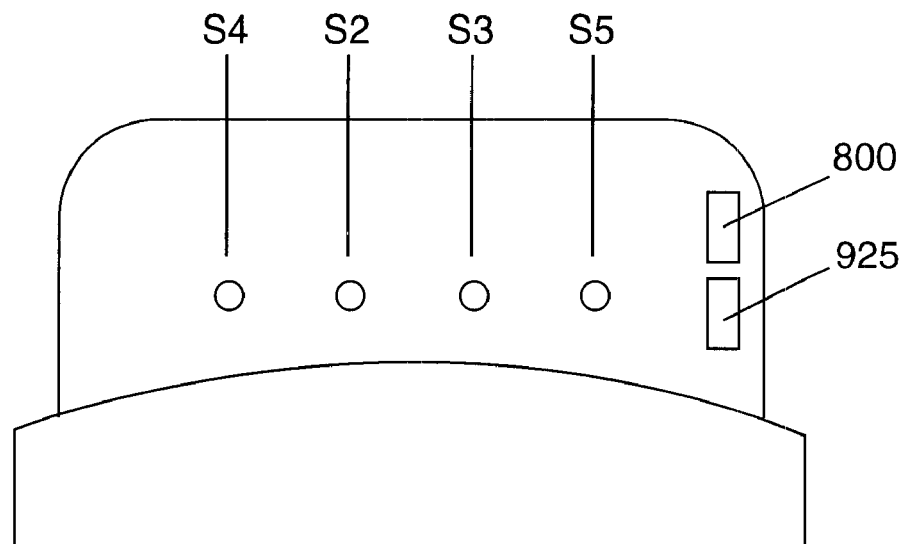

FIG. 203 is a top view of the goggles of FIG. 201.

Figure 204:
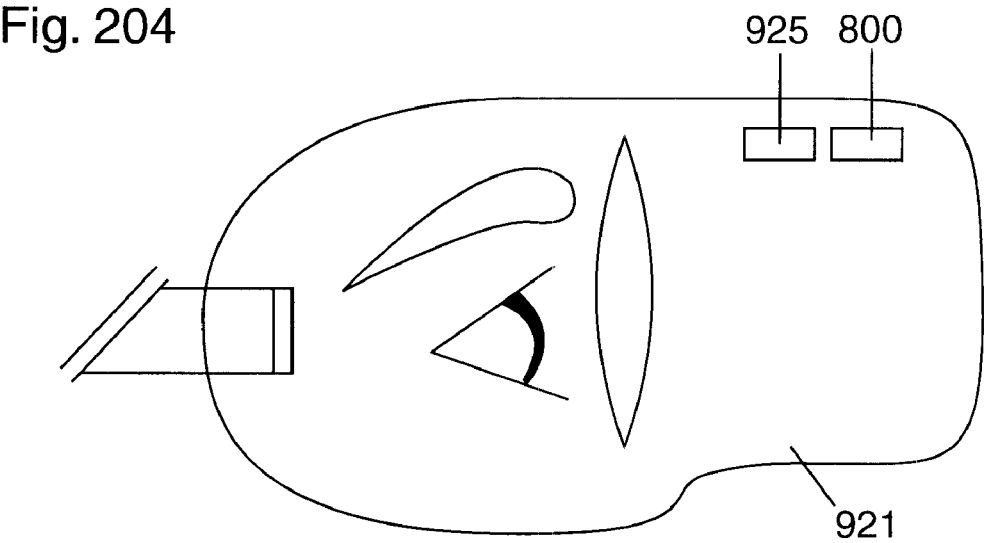

FIG. 204 is a side view of the goggles illustrating more detail.

FIGS. 205A–212A illustrate the positions taken by a user to diagnose right or left posterior semicircular canal (SCC) BPPV.

FIGS. 205B–212B indicate the LEDs that are lit up in each position of FIGS. 205A–212A respectively.

FIGS. 213A–222A illustrate the positions taken by a user in treating right posterior SCC BPPV.

FIGS. 213B–222B indicate the LEDs that are lit up in each position of FIGS. 213A–222A respectively.

FIGS. 223A–230A illustrate the positions taken by a user in treating left SCC BPPV.

FIGS. 223B–230B indicate the LEDs that are lit up in each position of FIGS. 223A–230A respectively.

In FIGS. 205B–230B the dark outlines of the arrows and of the octagons indicate the LEDs that are lit up.

Figure 231A:
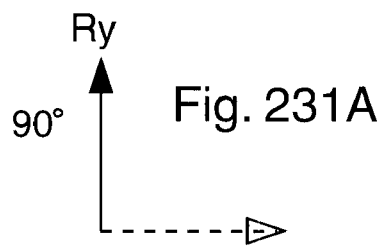
Figure 231B:
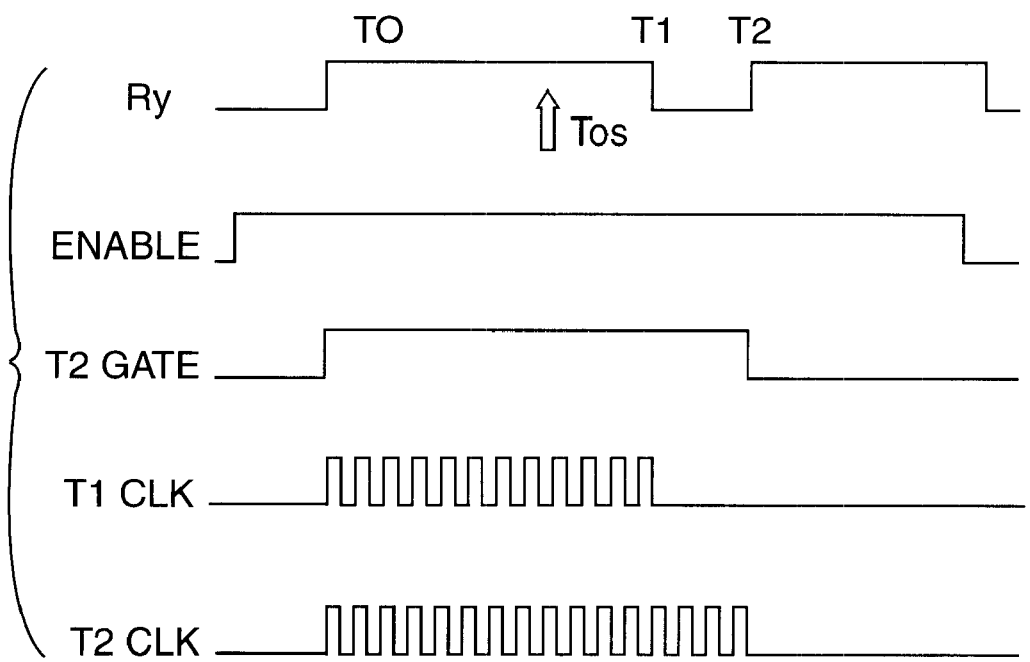

FIGS. 231A and 231B illustrate the 90 degrees acceleration vector Ry for a sensor and timing diagrams for the 90 degrees calibration of the sensor.

Figure 232A:
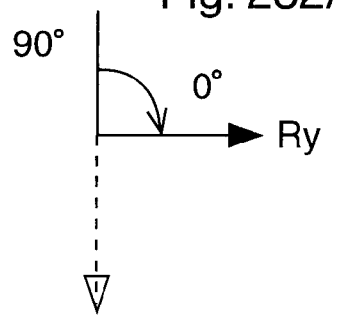
Figure 232B:
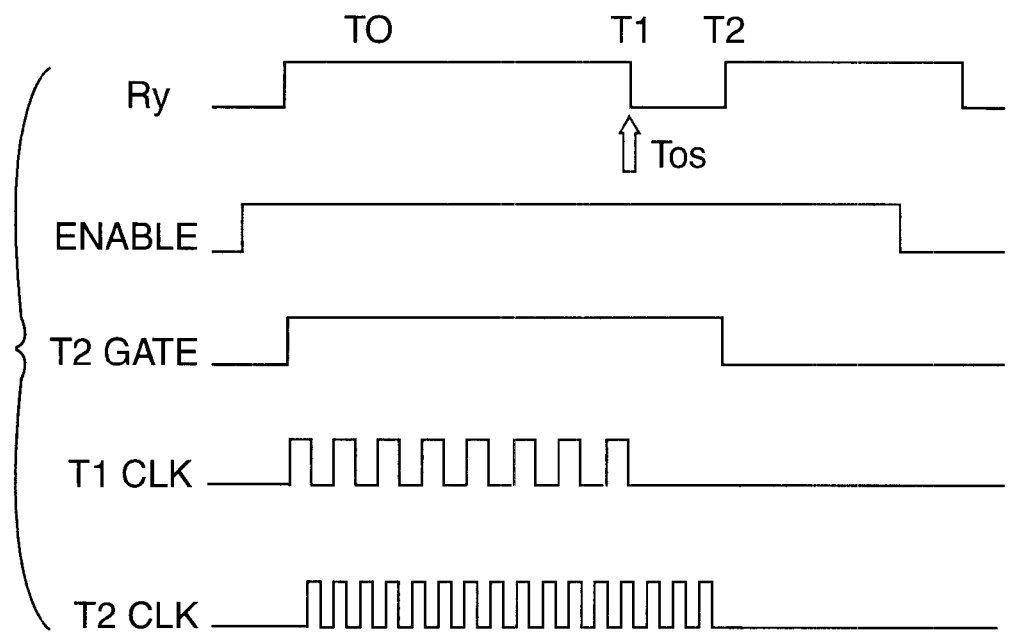

FIGS. 232A and 232B illustrate the 0 degrees acceleration vector Ry for a sensor and timing diagrams for the 0 degrees calibration of the sensor.

Figure 233A:
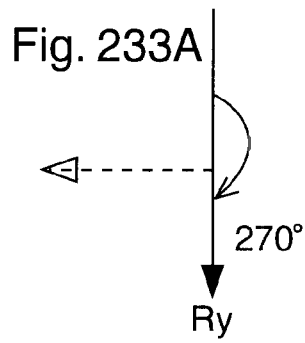
Figure 233B:
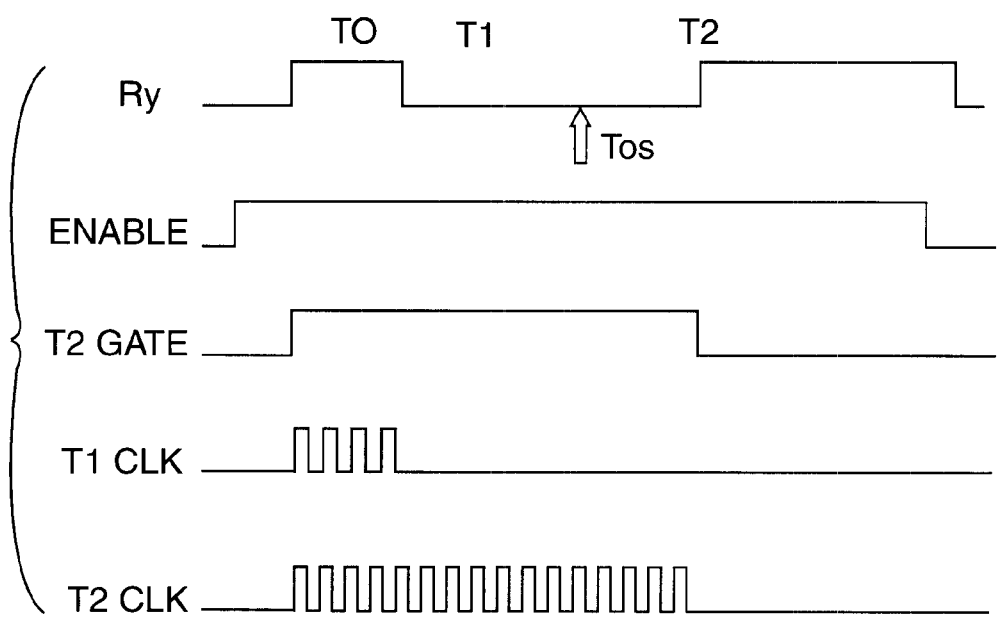

FIGS. 233A and 233B illustrate the 270 degrees (minus ninety) acceleration vector Ry for a sensor and timing diagrams for the 270 degrees calibration.

FIGS. 234A and 234B illustrate a sensor output at 45 degrees orientation for the Ry vector.

Figure 235A:
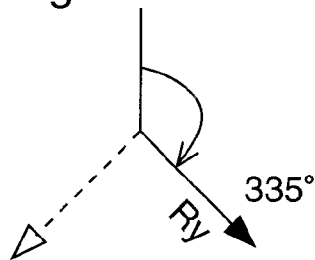
Figure 235B:
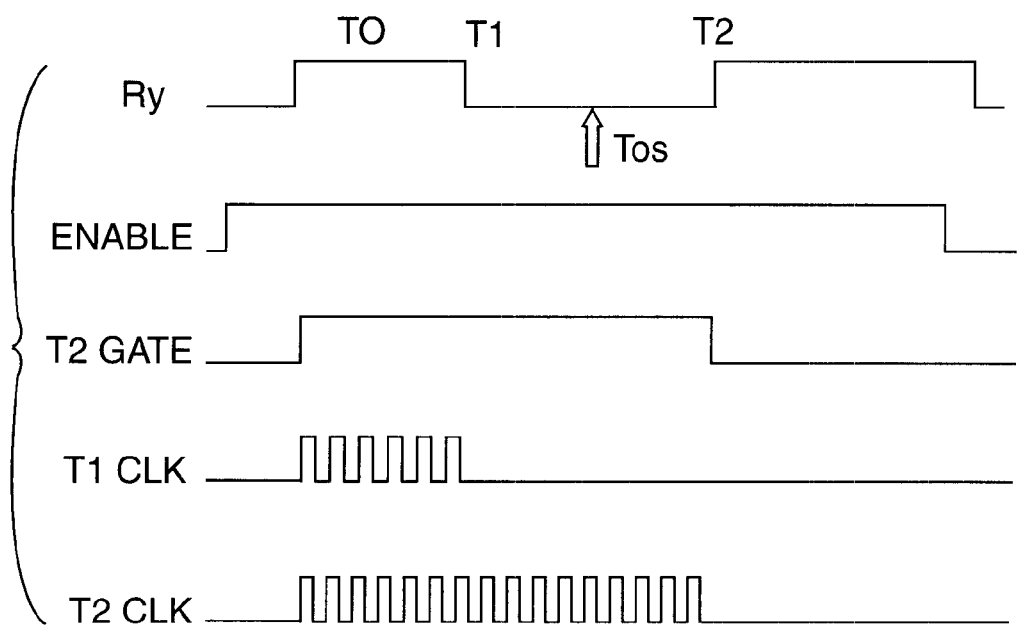

FIGS. 235A and 235B illustrate a sensor output at 335 degrees orientation for the Ry vector.

FIGS. 236–258 are directed to another embodiment of diagnostic and treatment devices similar to that of the devices of FIGS. 1–26 but with a marking on the inner housing or sphere and sighting marks on the outer housing or sphere to allow an observer to monitor the user's head movement.

Figure 236:
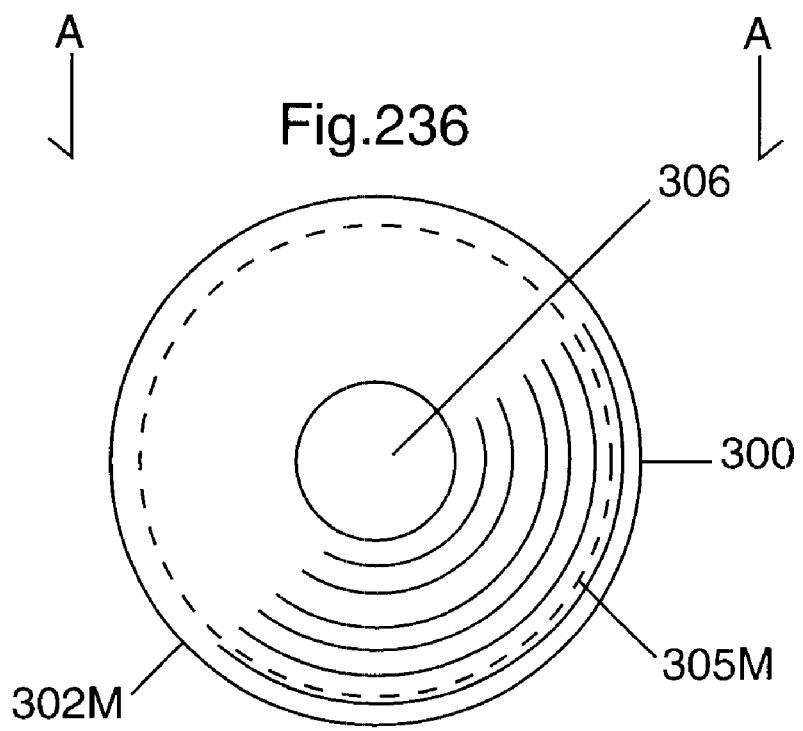

FIG. 236 illustrates an outer sphere similar to that of FIG. 1 but with the sphere of FIG. 236 having observer sighting markers thereon (but not shown in this Figure).

Figure 237:
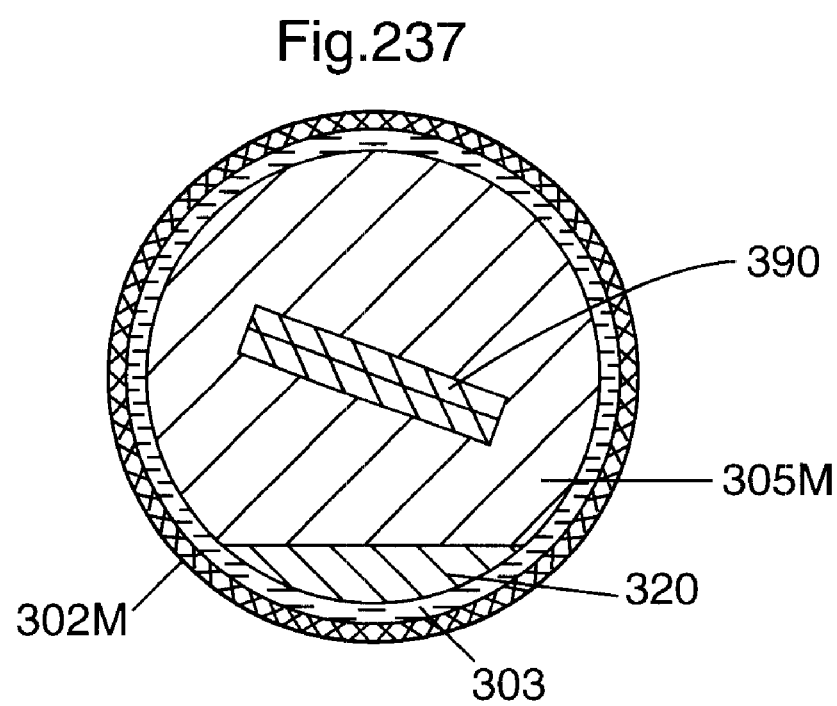

FIG. 237 is a cross section of the device of FIG. 236 showing an inner sphere in a liquid.

Figure 238:
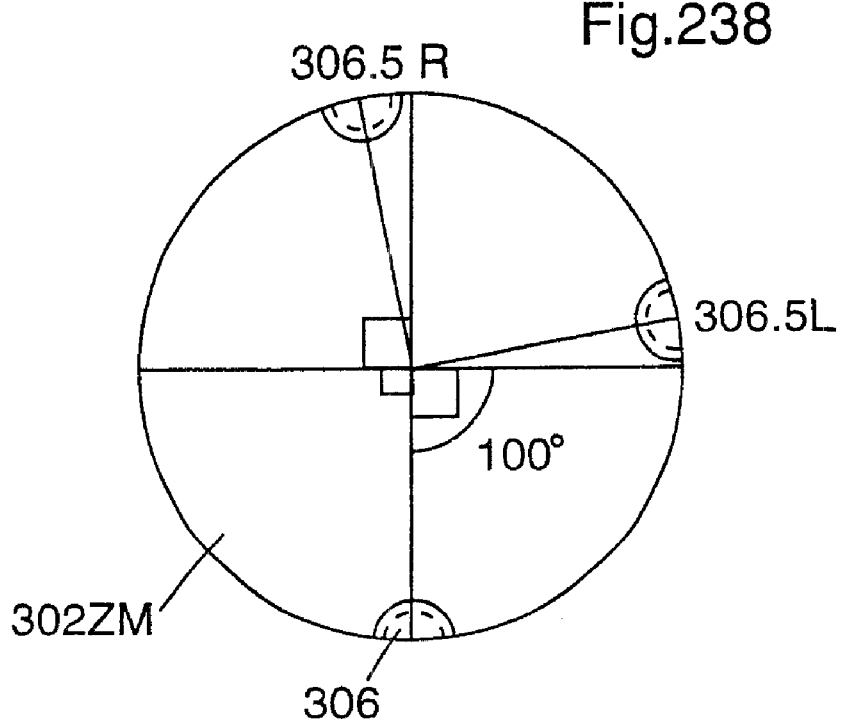

FIG. 238 illustrates sighing markers of the outer sphere of FIG. 236 as used for Posterior BPPV diagnostic purposes and as seen from lines A—A of FIG. 236.

Figure 239:
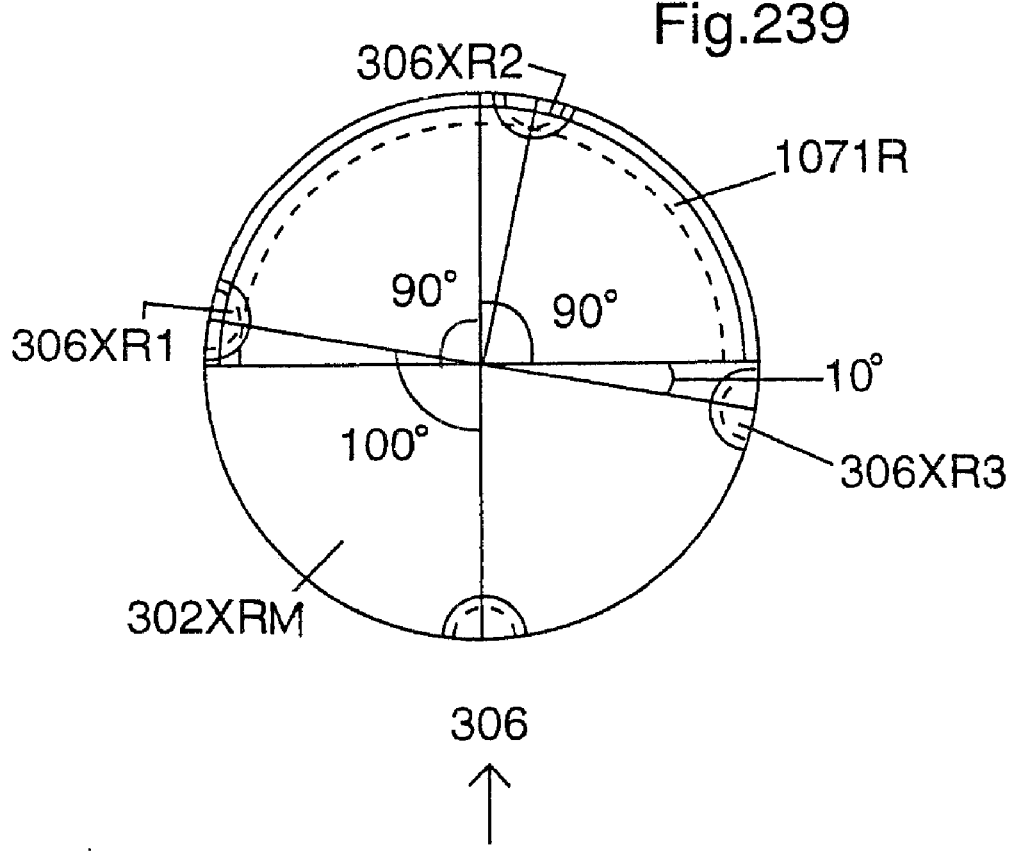

FIG. 239 is a view similar to that of FIG. 238 but illustrating sighting markers of the outer sphere of FIG. 236 as used for right posterior BPPV treatment.

Figure 240:
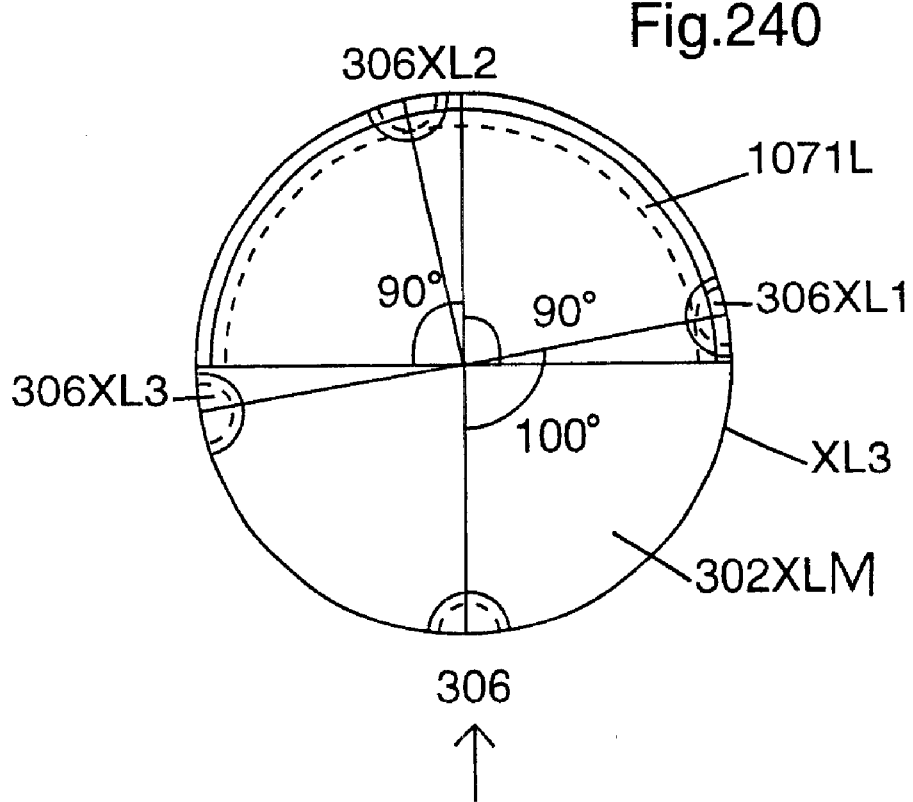

FIG. 240 is a view similar to that of FIG. 238 but illustrating sighting markers of the outer sphere of FIG. 236 as used for left posterior BPPV treatment.

Figure 241:
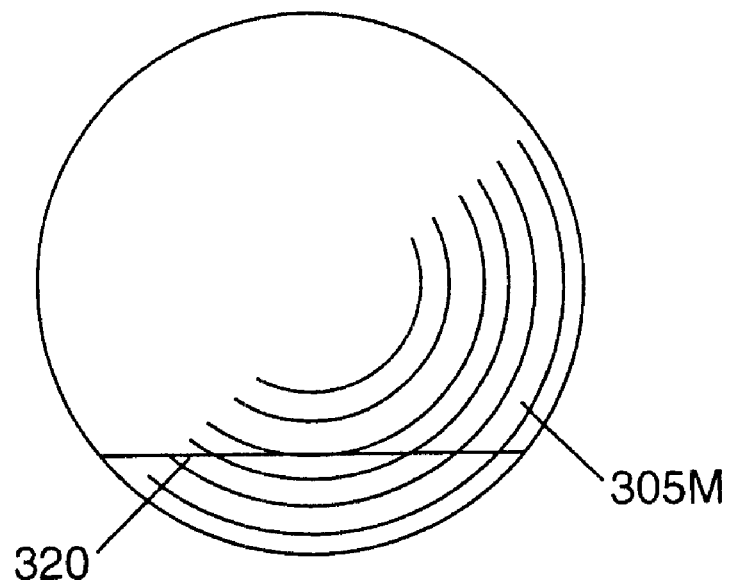

FIG. 241 illustrates a weight secured to one end of the inner sphere.

Figure 242:
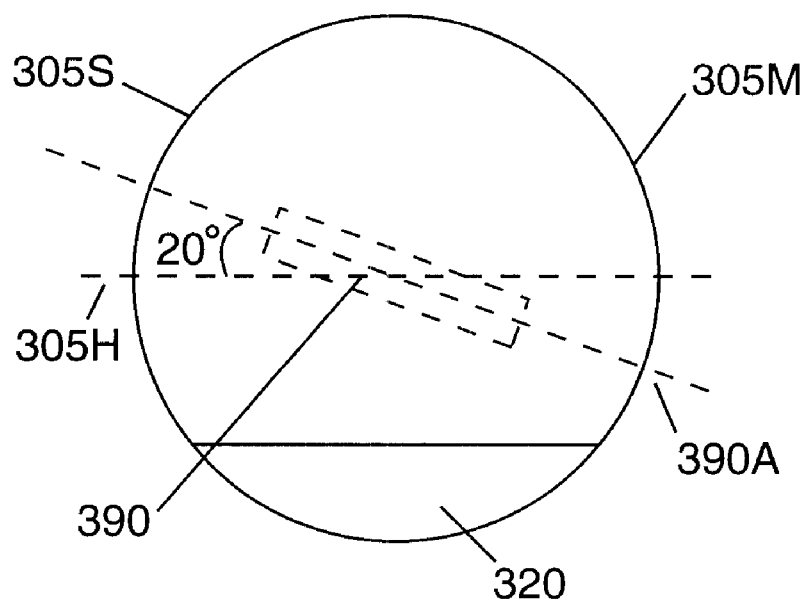

FIG. 242 illustrates a permanent magnet secured to the inside of the inner sphere.

Figure 243:
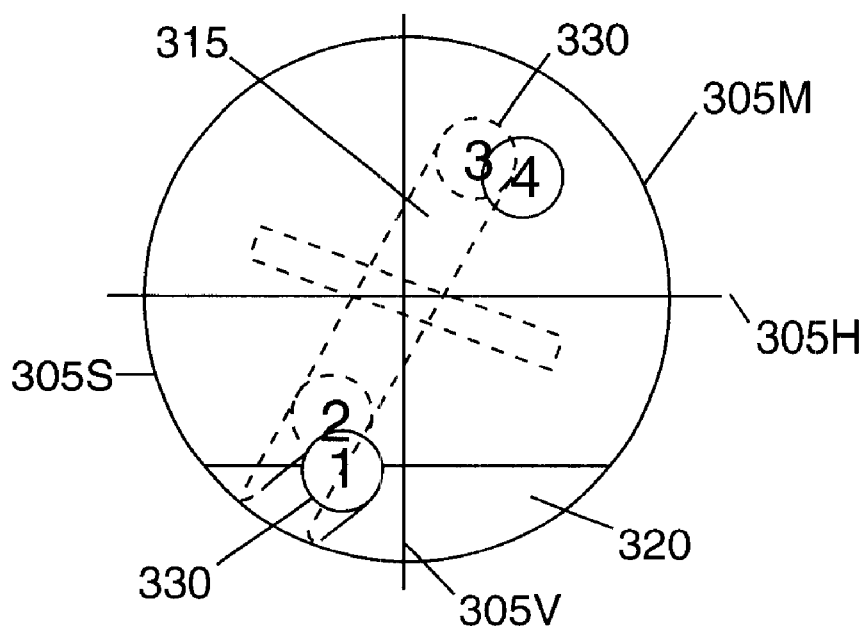

FIG. 243 illustrates position bull's eyes located on the outside of the inner spheres of FIGS. 237, 241, and 242.

FIG. 244 is a side view of a cylindrical tube supporting one of the devices of FIGS. 236–244 at one end and a lens at the other end.

FIG. 245 is a view similar to that of FIG. 7 but illustrating an inner sphere of the type having four position bull's eyes, in place.

Figure 246:
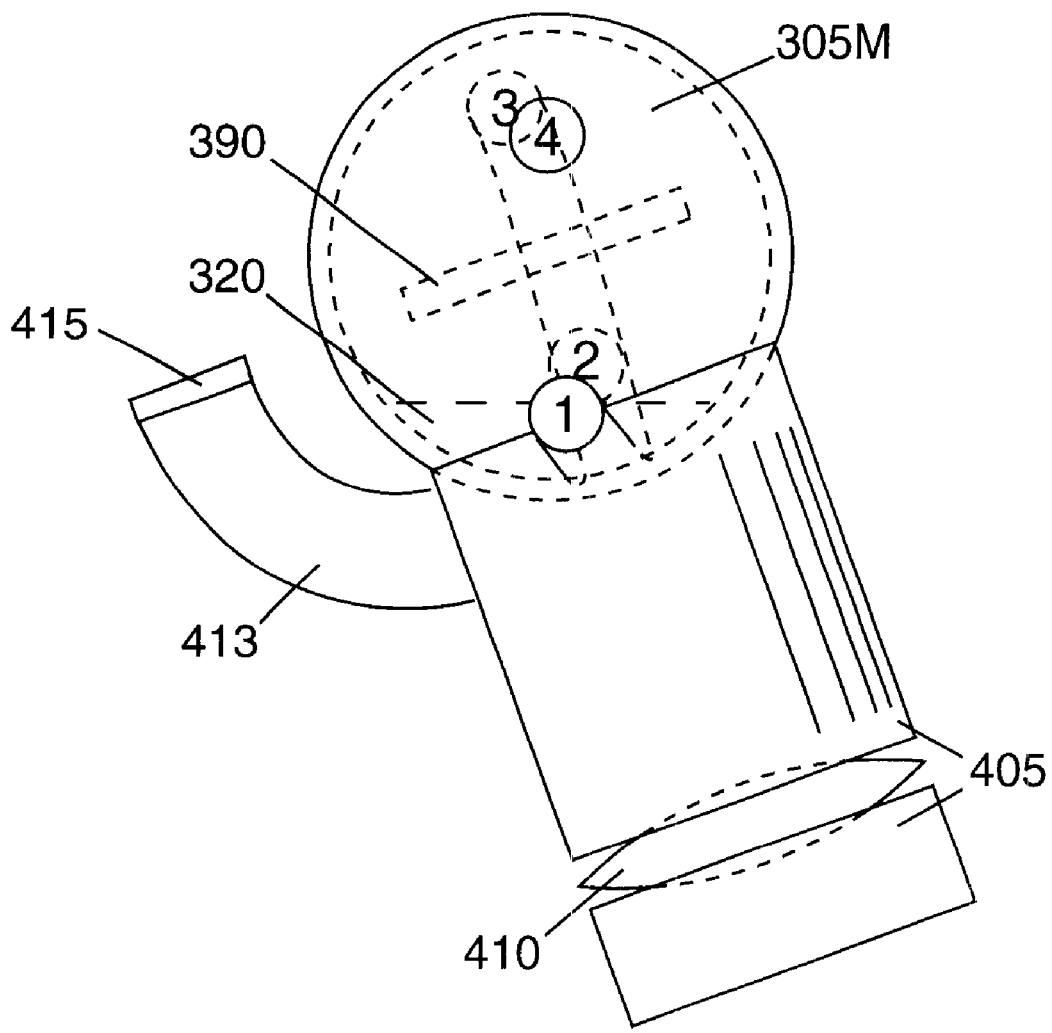

FIG. 246 is a view similar to that of FIG. 8 but illustrating the inner sphere of FIG. 246 in place.

Figure 247:
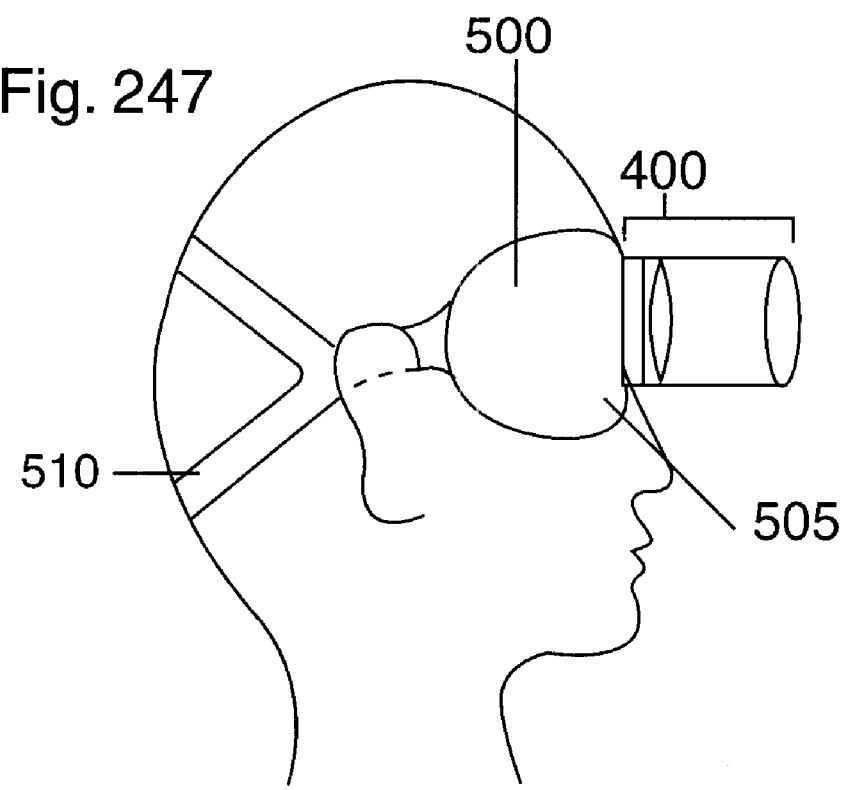
Figure 248:
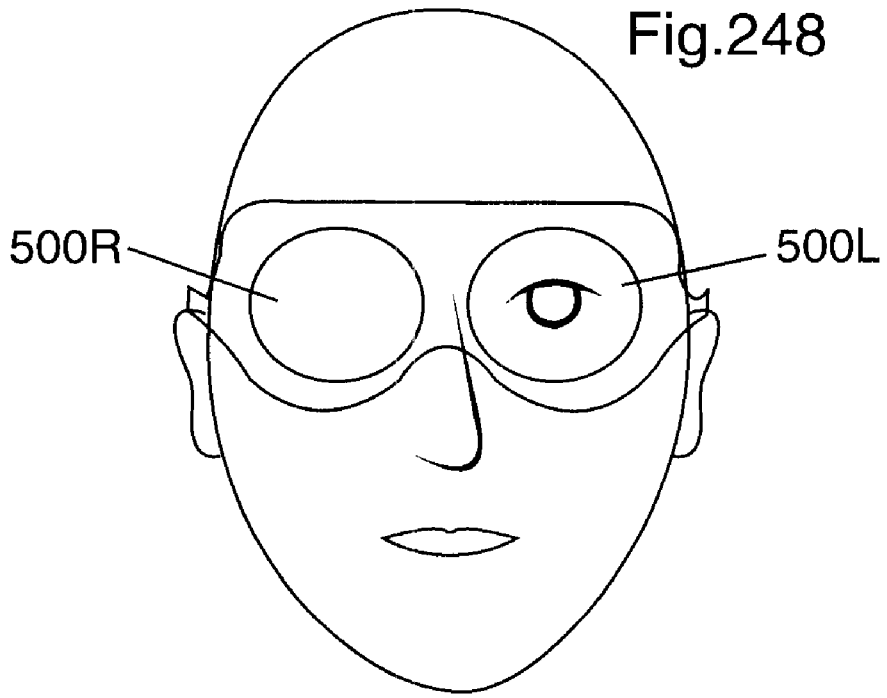

FIGS. 247 and 248 illustrate goggles for supporting the device of FIGS. 244–246.

Figure 249:
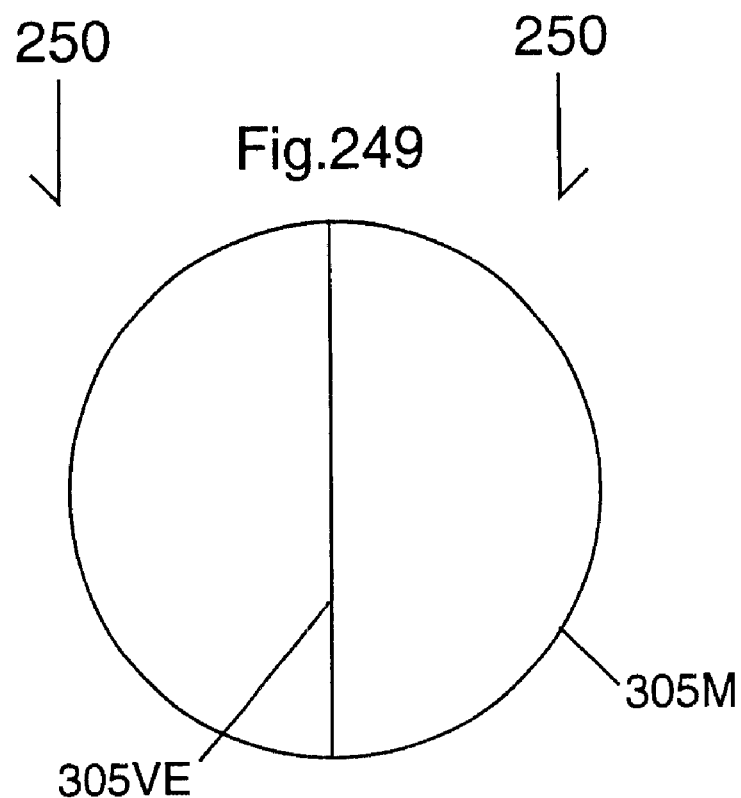

FIGS. 249 illustrates an inner sphere with its vertical equator.

Figure 250:
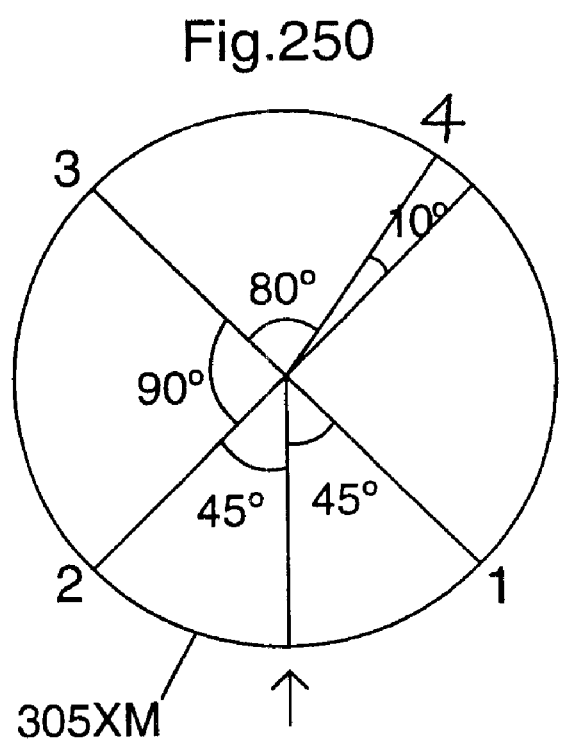

FIG. 250 is a view of FIG. 249 as seen along lines 250—250 thereof and illustrating the angular relationship of four position bull's eyes.

Figure 251:
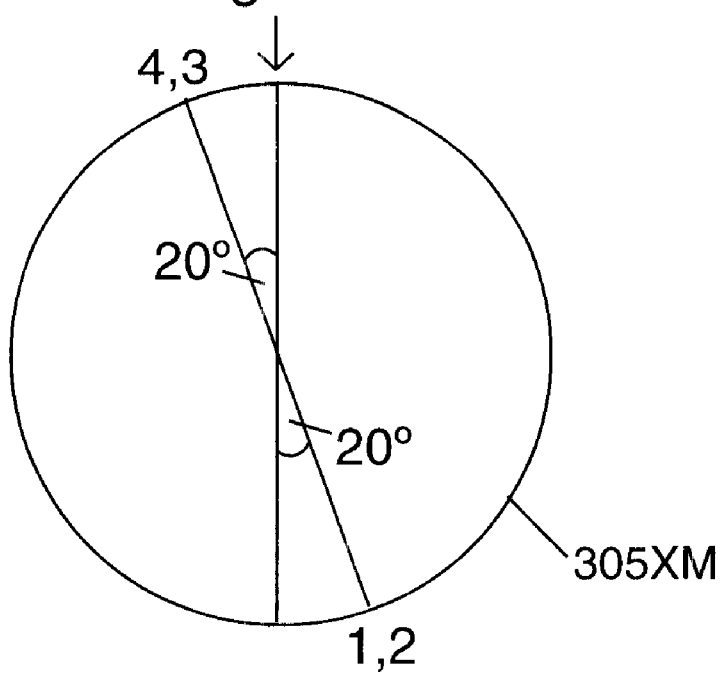

FIG. 251 is a view similar to that of FIG. 13 illustrating the angular positions of the four bull's eyes relative to the vertical equator.

Figure 252:
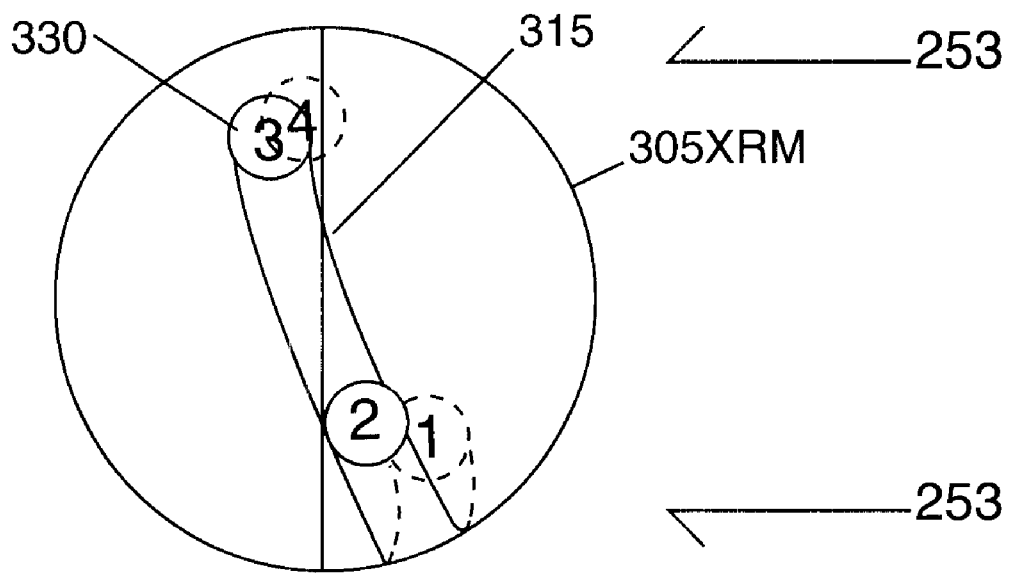

FIG. 252 is another view of the inner sphere of FIGS. 249–251 for treating left posterior SCC.

Figure 253:
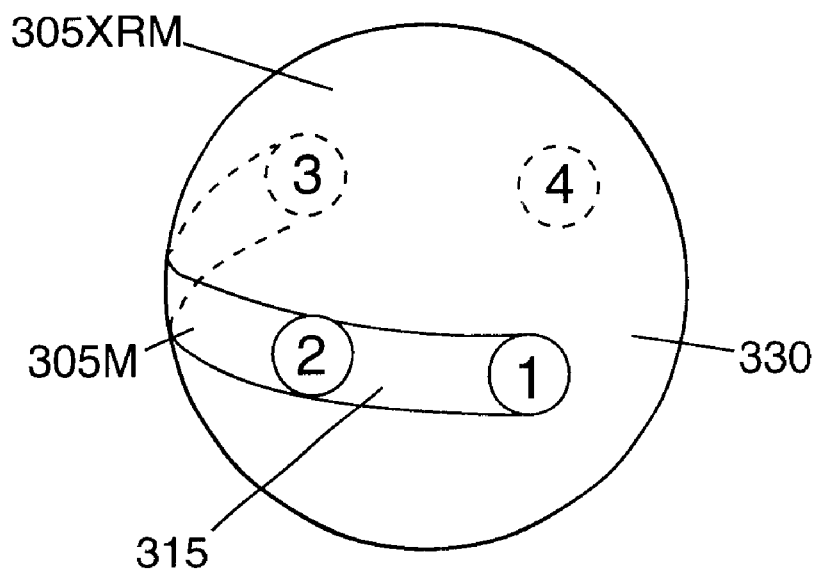

FIG. 253 is a view of the inner sphere of FIG. 252 as seen along lines 253—253 thereof.

Figure 254:
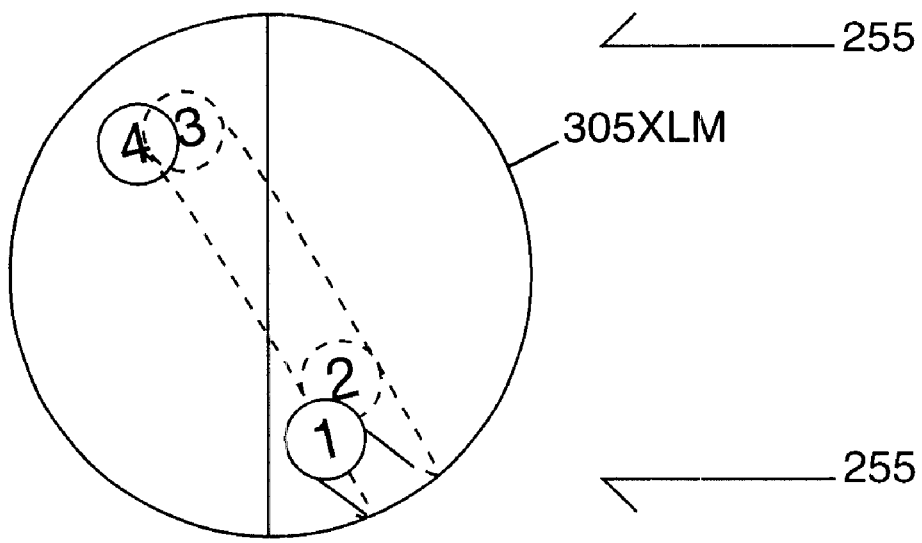

FIG. 254 is a view of an inner sphere having four position bull's eyes for treating right posterior SCC BPPV.

Figure 255:
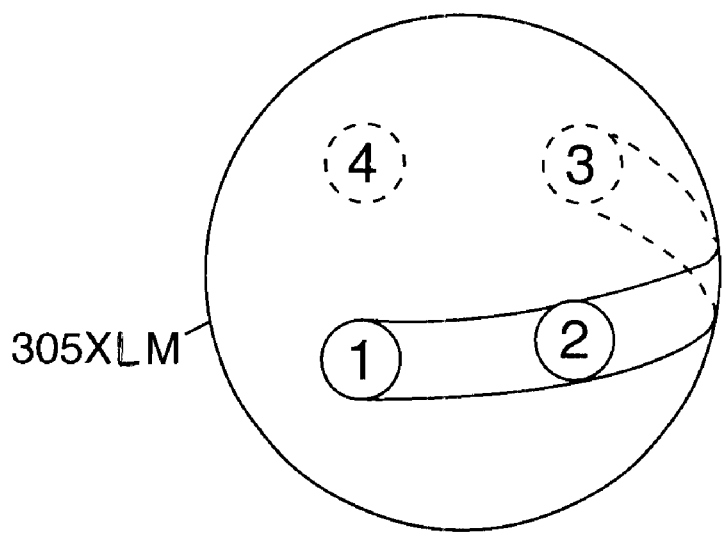

FIG. 255 is a view of FIG. 254 as seen along lines 255—255 thereof.

Figure 256:
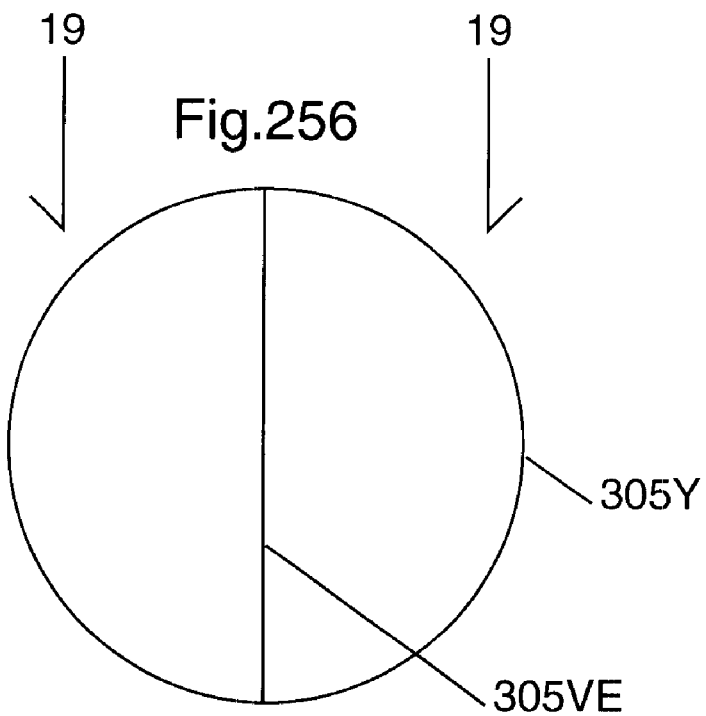

FIG. 256 illustrates an inner sphere with its vertical equator.

Figure 257:
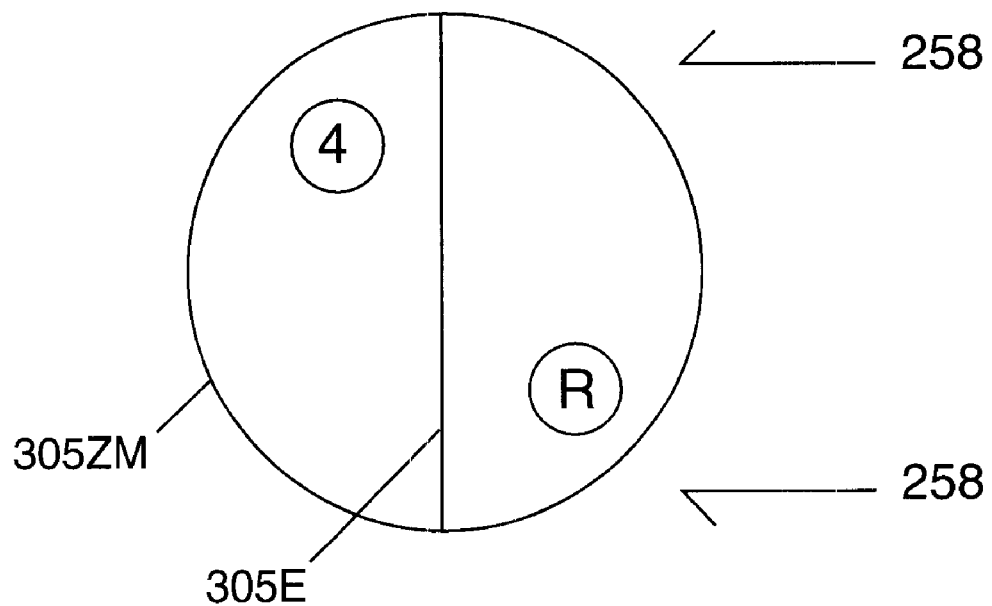

FIG. 257 is a diagnostic inner sphere having a position bull's eye No. 4 thereon.

Figure 258:
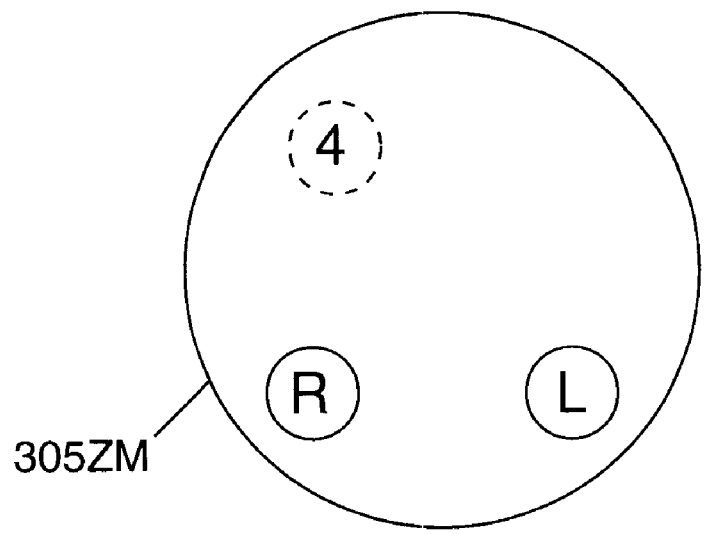

FIG. 258 is a view of FIG. 257 as seen along lines 258—258 thereof.

Figure 259:
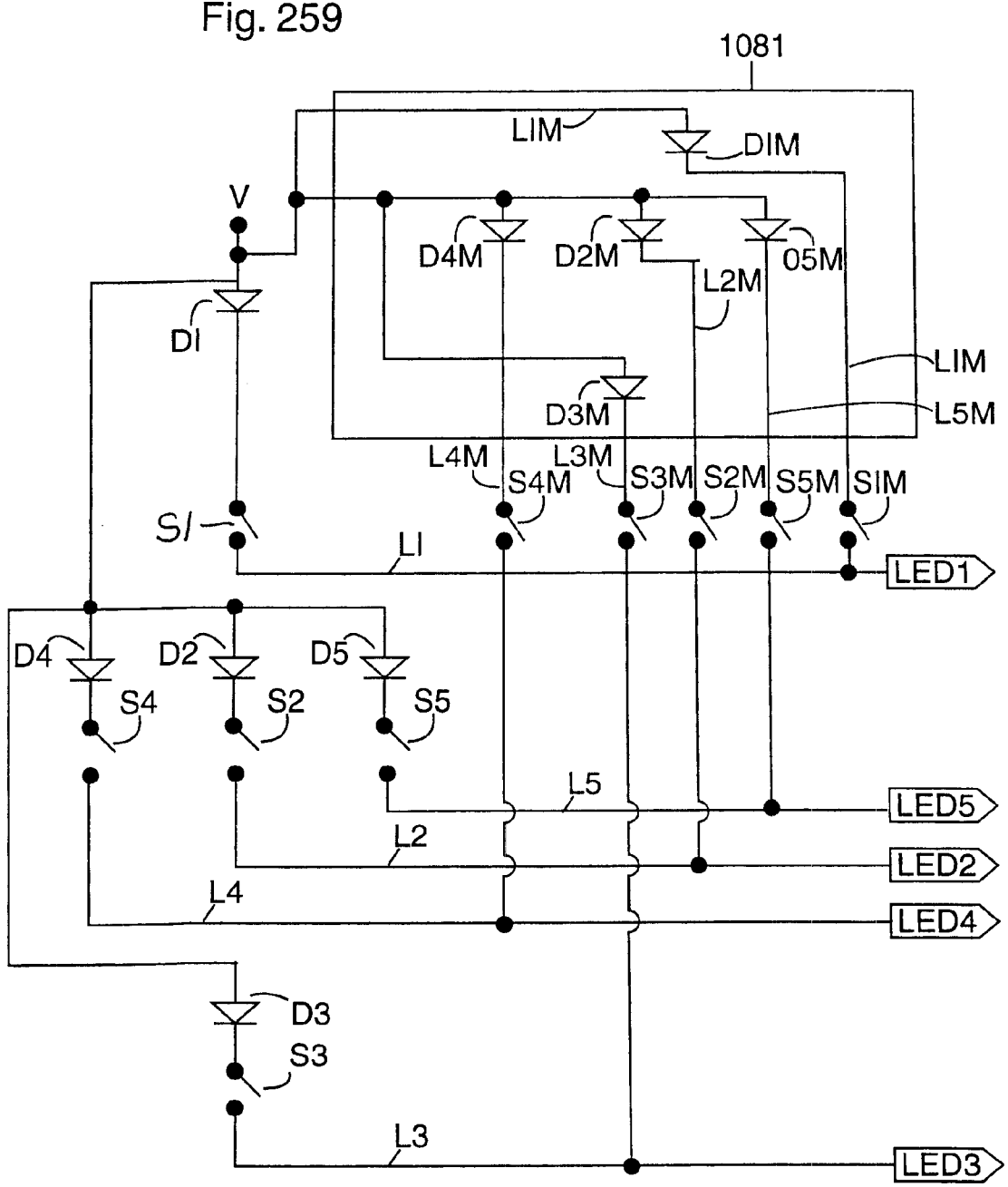

FIG. 259 illustrates a modification of the circuit of FIGS. 189A, 189B, 189C, and 189D for allowing an observer to monitor the head movement of a user of the embodiment of FIGS. 189–204.

Figure 260:
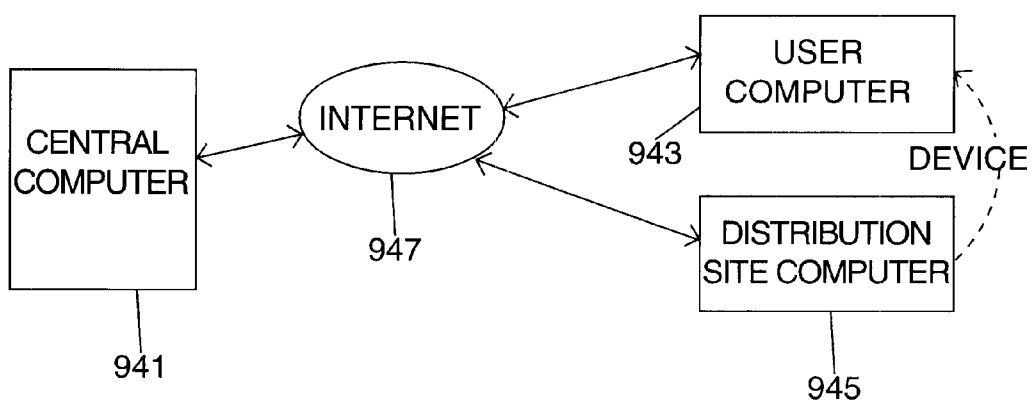

FIG. 260 is a schematic diagram showing an overview of the system for implementation of the combination of the questions and proprietary relationship of the questions to the diagnosis of BPPV, and a delivery system for the device for the treatment of BPPV.

Figure 261:
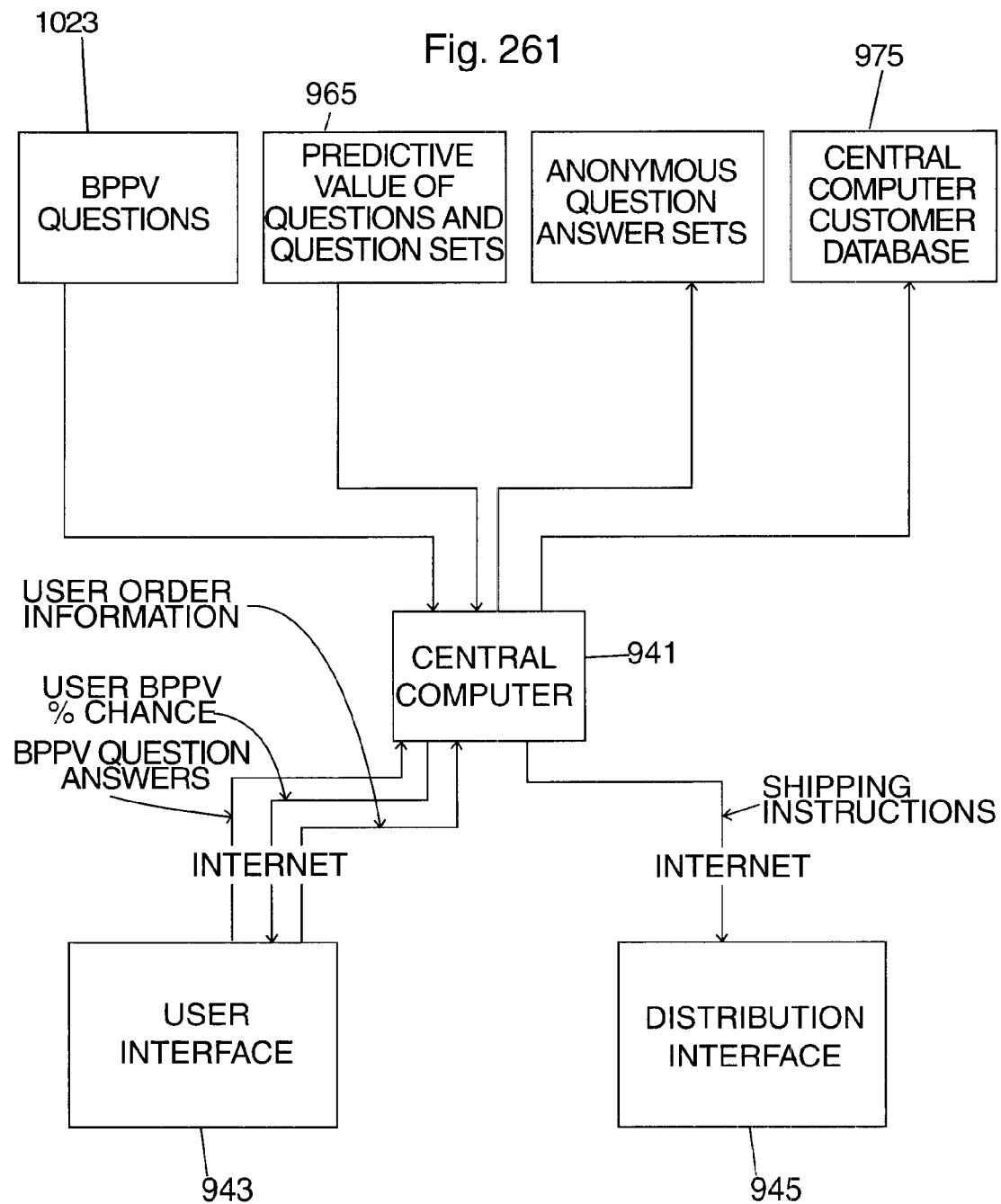

FIG. 261 is a flow chart of the system for implementation of the combination of question, question answers, proprietary relationship information and product distribution.

Figure 262:
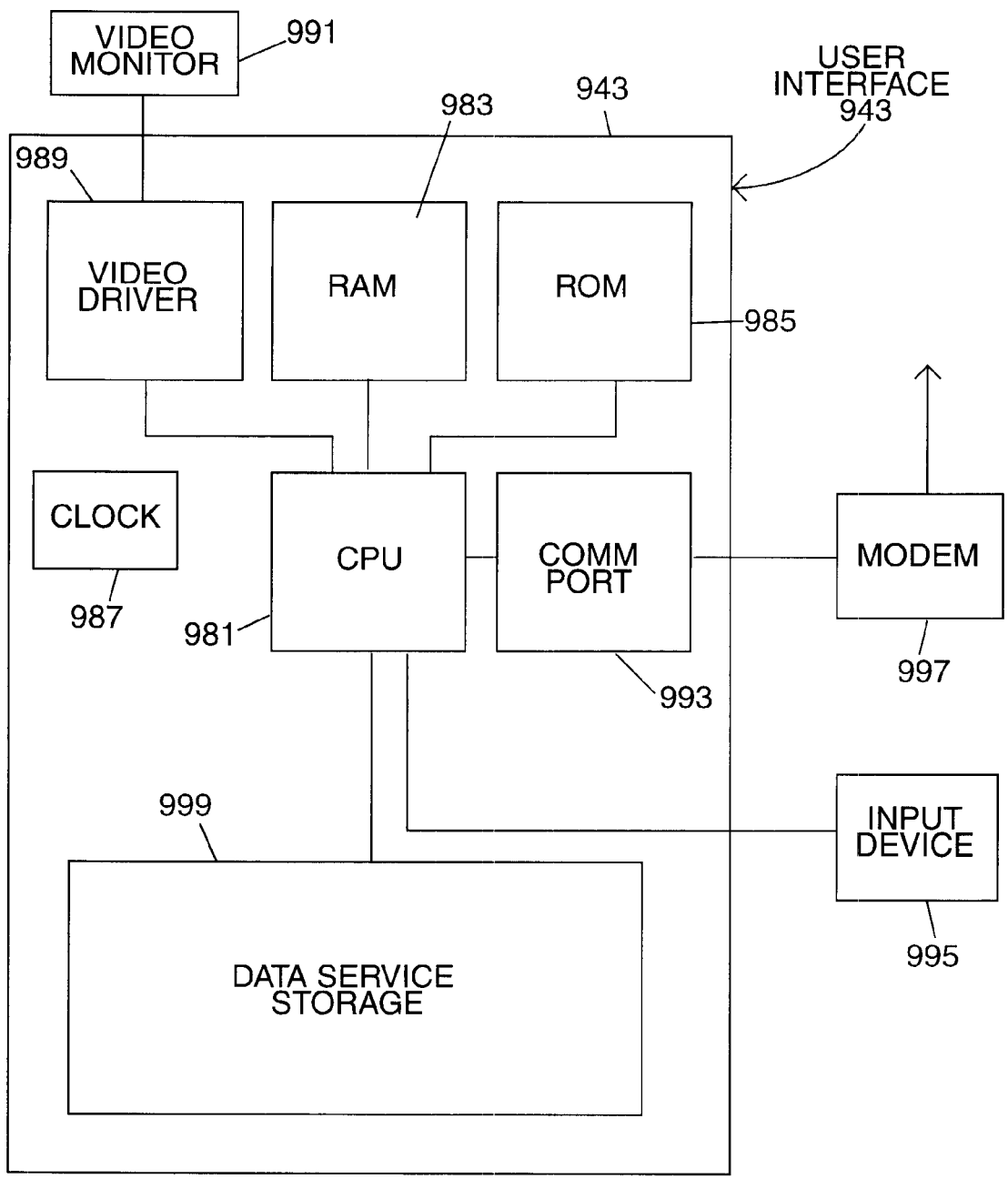

FIGS. 262 is a block diagram showing the components for the user to gain access to the diagnostic questions to determine whether the patient's symptoms are BPPV.

Figure 263:
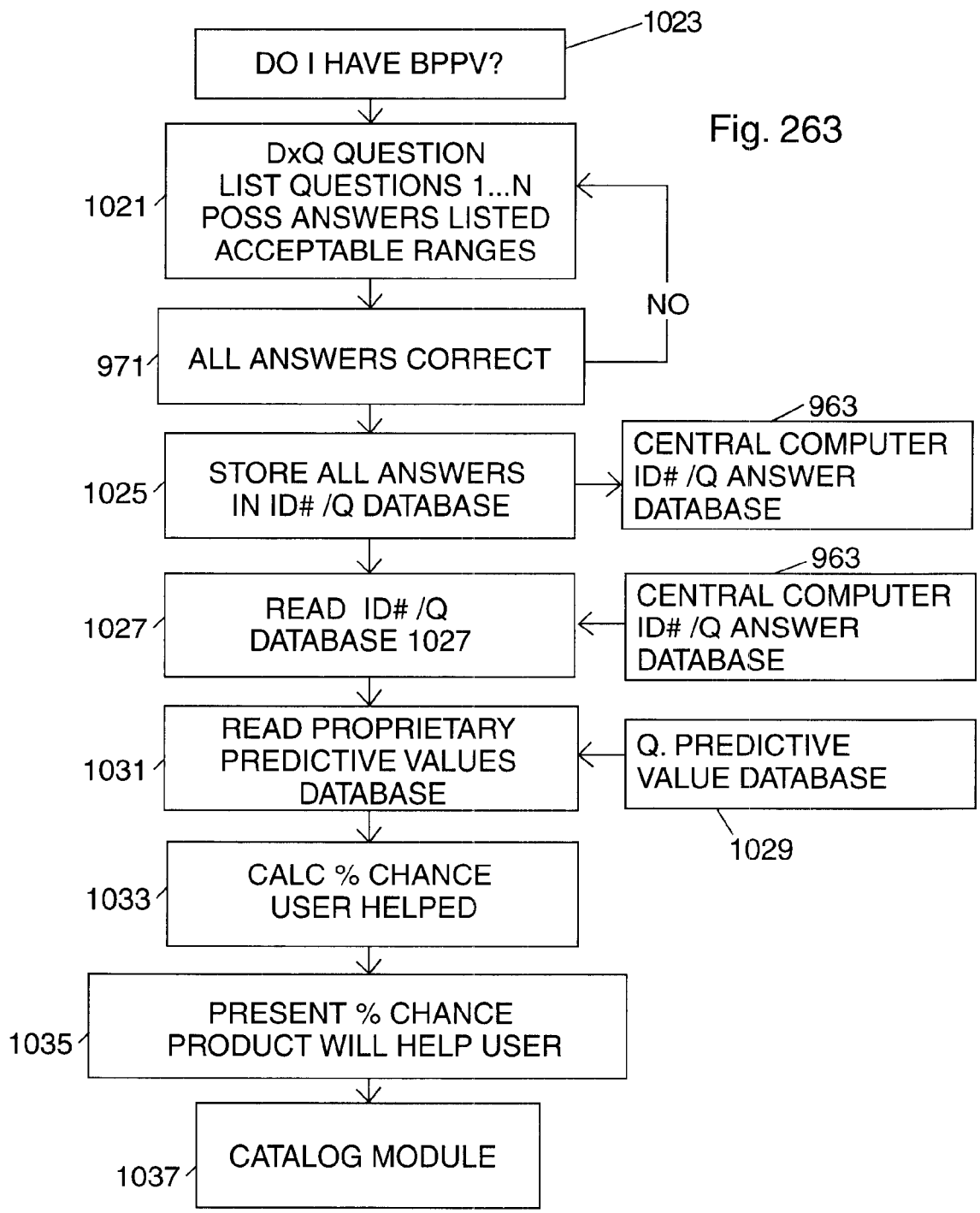

FIG. 263 is a flow diagram showing the steps performed to establish whether the user suffers from BPPV. The Dx questions are asked of the user. The predictive values of the questions and, the question set answers are combined to establish the statistical chances that the user suffers from BPPV.

Figure 264:
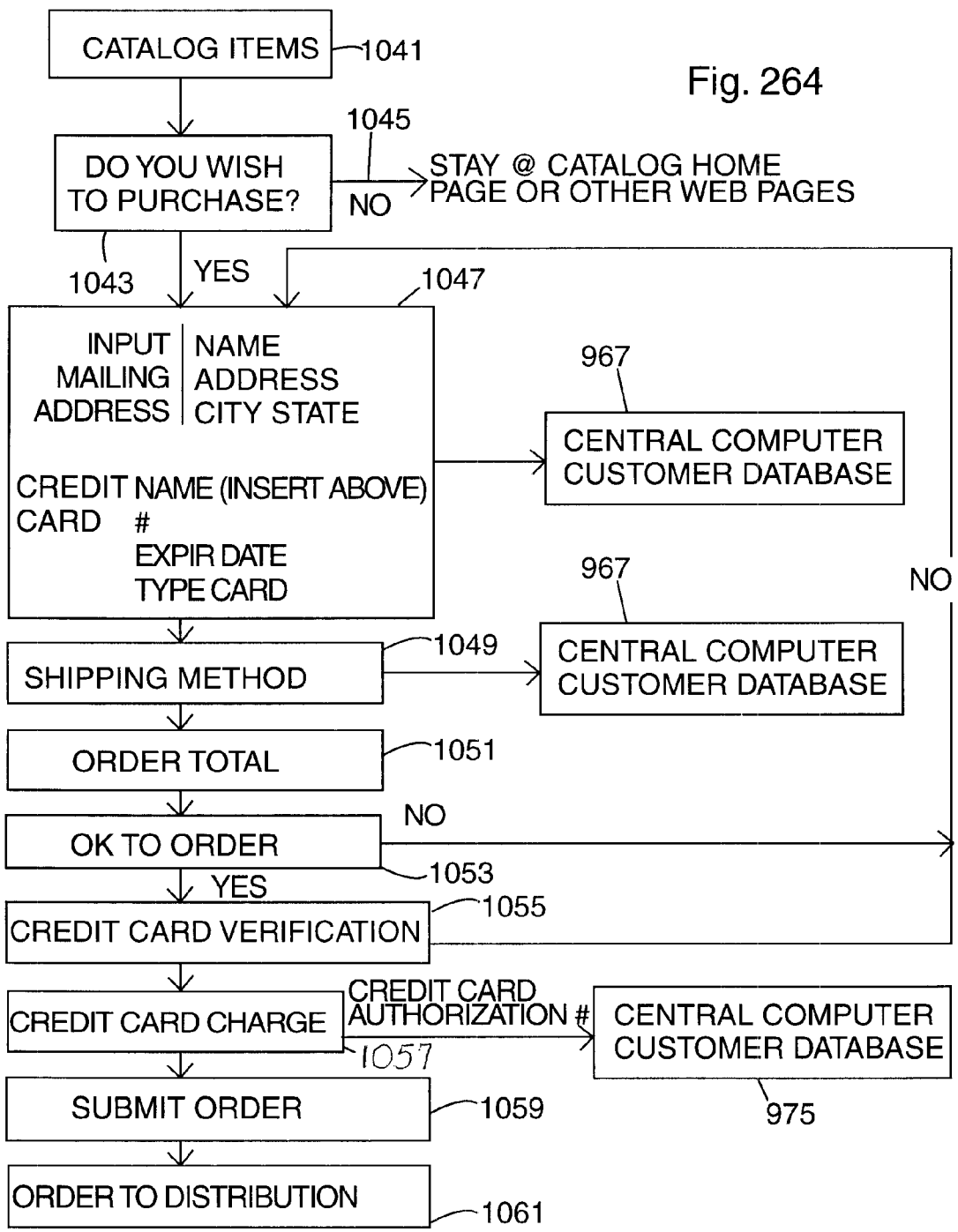

FIG. 264 is a flow diagram showing the steps performed by the user to purchase a device for the treatment of his or her BPPV.

Figure 265:
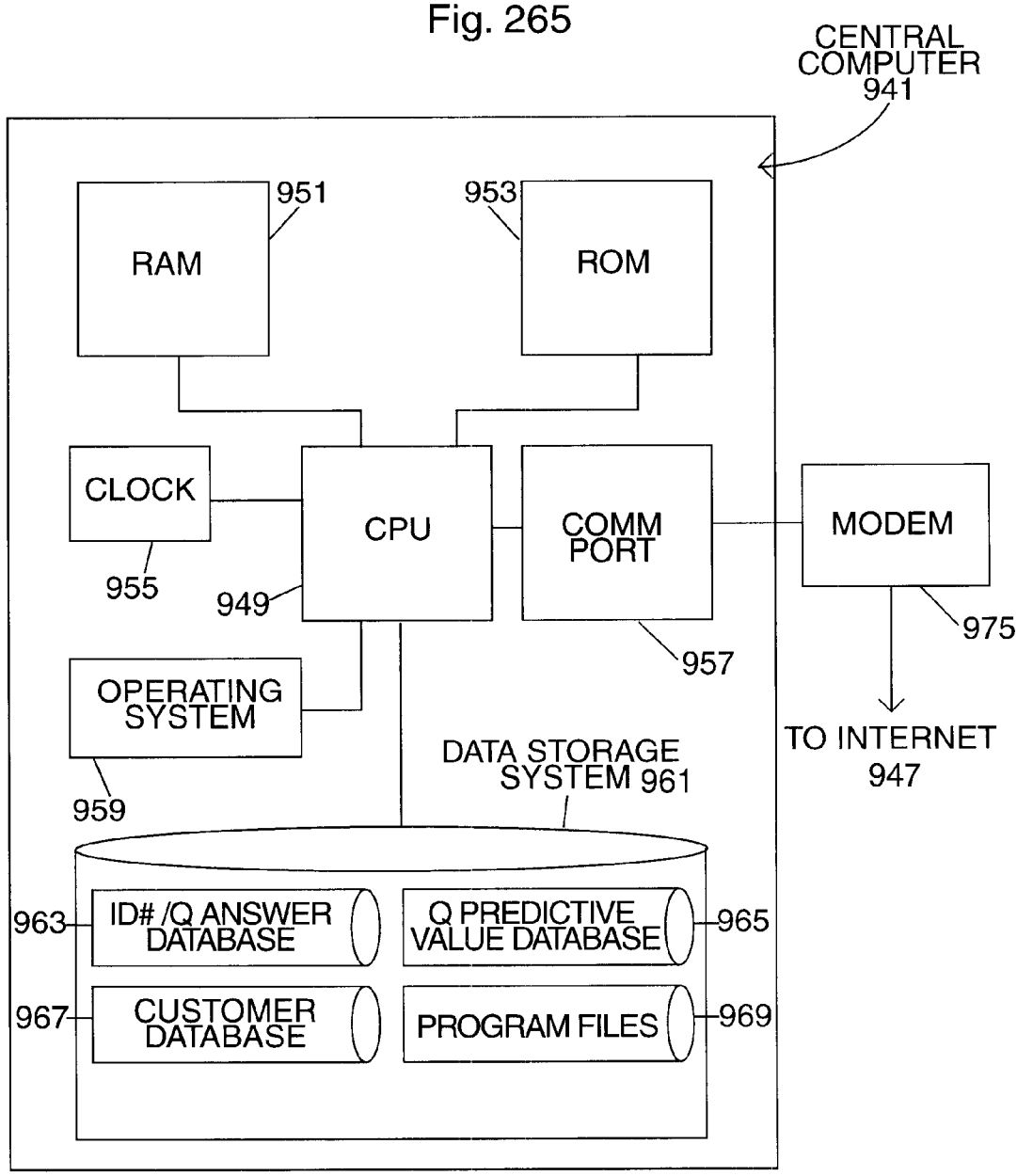

FIG. 265 is a block diagram showing the components of the central computer within which the diagnosis Dx question-answers and their proprietary values are combined to determine the users percentage chance of having BPPV.

FIG. 266 is a block diagram showing the components necessary for the distributor computer to receive the user purchase order and to ship the device to the user using the user preferred shipping method.

DESCRIPTION OF THE PREFERRED EMBODIMENTS

The invention is directed to a new system and process for the diagnosis and treatment of BPPV. In one embodiment, diagnosis may be carried out by way of a questionnaire submitted to and answered by the patient. If the answers indicate that the user has BPPV of one of the SCC, the patient is offered for sale a device which helps in the diagnosis of which SCC is involved by the loosened crystals and a device which allows the patient to perform a head maneuver to move the loosened crystals out of the involved SCC. The user may use the devices for self diagnosis and self treatment or go to a health provider with the devices for diagnosis and treatment of his BPPV. The devices of FIGS. 1–259 may be sold to the user for diagnosis and treatment of BPPV.

FIGS. 1–235 disclose devices for self-diagnostic and self-treatment BPPV which are disclosed and claimed in U.S. patent application Ser. No. 09/570,002, filed May 12, 2000. FIGS. 236–259 disclose devices which may be used [1] for self-diagnostic and self-treatment of BPPV by visual feedback to the patient, [2] used for self-diagnosis and self-treatment of BPPV by visual feedback to the patient and monitored by a health care provider or [3] in one embodiment monitored only by the health care provider for diagnosis and treatment purposes with no visual feedback to the patient.

FIGS. 260–266 disclose a system for implementing the questionnaire and answer procedure, the initial diagnosis procedure and the offer for sale and sale and shipping of the diagnosis and treatment devices.

Before a description of the devices of FIGS. 1–259 is made, there will be provided a description of the statistical method for identifying patients who will respond to the Epley maneuver for BPPV; the questionnaire and answer procedure; and the system of FIG. 260–266.

Statistical Techniques

The answers to the DxQ and DHI question sets were collected from a group of patients with vertigo, dizziness or imbalance. These patients were evaluated by a neurotologist (ear only subspecialist). Those patients who were through to have BPPV were treated with an Epley maneuver or a goggle directed Epley maneuver. Those patients for whom the maneuver relieved 70% or more of their vertigo symptoms within 1 month were selected. The DxQ and DHI question answers, and the overall improvement percents were tabulated. These data underwent statistical evaluation.

A two phase method was used to determine the best statistical method for identifying patients who will respond to Epley maneuver treatment for BPPV. The first phase is the selection of the best set of predictor questions from all those questions ask and the second is the determination of the optimal classification rule. The "step-wise linear regression"

("forward selection" strategy" was used to choose a set of questions from the combined questions of the DxQ and DHI question sets. Those questions were chosen that predict good response in vertigo resolution after the Epley maneuver treatment for BPPV. After selecting the question set which predict good Epley maneuver responses, the second phase for establishing misclassification (false positive and false negative) probabilities is used. The second technique is called the "leave one out cross evaluation". Using this technique, each subject related data set was classified as a good responder if the probability of the subject getting >=70% resolution of his symptoms using the Epley maneuver equals alpha. The value of alpha is then varied until the rule with the lowest misclassification probabilities is found.

Questionnaire Construction

The questionnaire shown below was administered to a group of patients with vertigo, dizziness or imbalance. To determine the chances that a user who is suffering dizziness/vertigo/imbalance has BPPV, two question sets were combined and administered. The first set of questions is shown below. These questions were designed to elicit clinical information which would support or not support the possibility that the patient's symptoms were BPPV. The questionnaires were completed by the patients before seeing the physician. Any answer oversight was solicited by staff before proceeding.

The use of information provided by the goggle device (for example the embodiments of FIGS. 1–26 and 236–258) in a diagnostic mode is very helpful. When the goggle device is used to guide the user's head into the right and left Dix-Hallpike positions, the presence or absence of subjective vertigo is a very statistically important piece of information. This information can be obtained by making the device sale a two stage event. The first event being the sale of the device with identification guide ball and the second event being the sale of the relief guide ball fitting for the goggle device.

Name: _____ Pt No. _____
Date: _____
Please complete the following questionnaire. All questions pertain to your dizziness/imbalance.
Please answer Y = Yes, S = Sometimes, N = No

| | | | | |
|---|---|---|---|---|
| 1. | How old are you? (Age) | ___ Yrs. | | |
| 2. | Are you male or female? | M | F | |
| 3. | Do you have physician diagnosed migraine headaches? | Y | N | |
| | a. If Y, do you have migraine headaches before or during your dizziness episodes? | Y | S | N |
| 4. | At this moment do you have better hearing in one ear than the other? | Y | N | |
| | a. If Y, which ear hears better, right or left? | R | L | |
| 5. | Does your hearing fluctuate (get better and worse)? | Y | S | N |
| | a. If Y or S, which ear fluctuates, right ear, left ear, or Unknown? | R | L | Unknown |
| 6. | How many months have you had balance or dizziness problems | ___ Months | | |
| 7. | Immediately before the beginning of your symptoms did you suffer a head blow? | Y | N | |
| 8. | Immediately before the beginning of your symptoms did you have a cold? | Y | N | |
| 9. | Have you had loss of consciousness before, during or after a dizzy episode? | Y | N | |
| 10. | Do you have a pressure or full feeling in either of your ears when you are dizzy or imbalanced? | Y | S | N |
| | a. If Y or S, is the fullness in the right ear, left ear or both ears? | R | L | Both |
| 11. | Are your symptoms more spinning or more imbalance? | Spinning Imbalance | | |
| 12. | Do you have symptoms all the time? | Y | N | |
| 13. | Do your symptoms go away when you lie down in bed? | Y | S | N |
| 14. | When you are dizzy or imbalanced, do your symptoms worsen when you turn your head quickly? | Y | S | N |
| | a. If Y or S, which direction causes dizziness right, left or both? | R | L | Both |
| 15. | If you lie on your back with your head turned to the side for 30 seconds do you become dizzy? | Y | S | N |
| | a. If Y or S, which direction causes dizziness, right, left or both? | R | L | Both |
| 16. | When you are dizzy or imbalanced, do your symptoms worsen when you look up? | Y | S | N |
| 17. | When you are dizzy or imbalanced, do your symptoms worsen when you bend down? | Y | S | N |
| 18. | When you are dizzy or imbalanced, do your symptoms worsen when you straighten up from bending down? | Y | S | N |
| 19. | Are your symptoms worse at times and better at other times? | Y | N | |
| 20. | Are your symptoms constant? | Y | N | |

-continued

| | | | | |
|---|---|---|---|---|
| 21. | When you are dizzy or imbalanced, do your symptoms worsen (even for a short period of time) when you lie down in bed? | Y | S | N |
| 22. | When laying on your back, do you get dizzy when you roll to one side or the other? | Y | S | N |
| | a. If Y or S, when you roll to the right? | Y | S | N |
| | b. If Y or S, when you roll to your left? | Y | S | N |
| | c. Which side makes you more dizzy? | R | L | Unknown |
| 23. | When you are dizzy or imbalanced, do your symptoms worsen when you sit up in bed? | Y | S | N |
| 24. | When you are dizzy or imbalanced, do you stagger while walking? | Y | S | N |
| | a. If Y or S, do you stagger to the right, left or both directions? | R | L | Both |
| 25. | When you are dizzy or imbalanced, do your symptoms worsen when you look down? | Y | S | N |
| 26. | When you are dizzy or imbalanced, do your symptoms worsen when you stand up from sitting? | Y | S | N |
| 27. | Are you only dizzy when you are standing? | Y | N | |
| 28. | When you are dizzy or imbalanced, do your symptoms worsen when you stand up from a lying position? | Y | S | N |
| 29. | Do you have physician diagnosed retinal detachment? | Y | N | |
| 30. | Do you use the internet? | Y | N | |
| 31. | When your symptoms first began, were your symptoms more spinning or more imbalance? | Spinning Imbalance | | |
| 32. | Are you completely free of your symptoms while lying in bed? | Y | S | N |
| 33. | Do your symptoms go away immediately after you lie down in bed? | Y | S | N |

The second questionnaire was the Dizziness Handicap Inventory published in the Archives of Otolaryngology[16].
Both questionnaires are administered by the methods outlined above. Characteristic responses from a patient with classic right posterior SCC BPPV would be filled out as below. Only the answer is shown.

Name: _____ Pt No. _____
Date: _____

Please complete the following questionnaire. All questions pertain to your dizziness/imbalance.
Please answer Y = Yes, S = Sometimes, N = No

| | | | |
|---|---|---|---|
| 1. | How old are you? (Age) | 43 | Yrs. |
| 2. | Are you male or female? | F | |
| 3. | Do you have physician diagnosed migraine headaches? | N | |
| | a. If Y, do you have migraine headaches before or during your dizziness episodes? | | |
| 4. | At this moment do you have better hearing in one ear than the other? | N | |
| | a. If Y, which ear hears better, right or left? | | |
| 5. | Does your hearing fluctuate (get better and worse)? | N | |
| | a. If Y or S, which ear fluctuates, right ear, left ear, or Unknown? | | |
| 6. | How many months have you had balance or dizziness problems? | 4 | Months |
| 7. | Immediately before the beginning of your symptoms did you suffer a head blow? | N | |
| 8. | Immediately before the beginning of your symptoms did you have a cold? | N | |
| 9. | Have you had loss of consciousness before, during or after a dizzy episode? | N | |
| 10. | Do you have a pressure or full feeling in either of your ears when you are dizzy or imbalanced? | N | |
| | a. If Y or S, is the fullness in the right ear, left ear or both ears? | | |
| 11. | Are your symptoms more spinning or more imbalance? | Spinning | |
| 12. | Do you have symptoms all the time? | N | |
| 13. | Do your symptoms go away when you lie down in bed? | N | |
| 14. | When you are dizzy or imbalanced, do your symptoms worsen when you turn your head quickly? | N | |
| | a. If Y or S, which direction causes dizziness right, left or both? | | |

-continued

| | | |
|---|---|---|
| 15. | If you lie on your back with your head turned to the side for 30 seconds do you become dizzy? | Y |
| | a. If Y or S, which direction causes dizziness, right, left or both? | R |
| 16. | When you are dizzy or imbalanced, do your symptoms worsen when you look up? | S |
| 17. | When you are dizzy or imbalanced, do your symptoms worsen when you bend down? | S |
| 18. | When you are dizzy or imbalanced, do your symptoms worsen when you straighten up from bending down? | S |
| 19. | Are your symptoms worse at times and better at other times? | Y |
| 20. | Are your symptoms constant? | N |
| 21. | When you are dizzy or imbalanced, do your symptoms worsen (even for a short period of time) when you lie down in bed? | Y |
| 22. | When laying on your back, do you get dizzy when you roll to one side or the other? | Y |
| | a. If Y or S, when you roll to the right? | Y |
| | b. If Y or S, when you roll to your left? | N |
| | c. Which side makes you more dizzy? | R |
| 23. | When you are dizzy or imbalanced, do your symptoms worsen when you sit up in bed? | S |
| 24. | When you are dizzy or imbalanced, do you stagger while walking? | N |
| | a. If Y or S, do you stagger to the right, left or both directions? | |
| 25. | When you are dizzy or imbalanced, do your symptoms worsen when you look down? | S |
| 26. | When you are dizzy or imbalanced, do your symptoms worsen when you stand up from sitting? | S |
| 27. | Are you only dizzy when you are standing? | N |
| 28. | When you are dizzy or imbalanced, do your symptoms worsen when you stand up from a lying position? | Y |
| 29. | Do you have physician diagnosed retinal detachment? | N |
| 30. | Do you use the internet? | N |
| 31. | When your symptoms first began, were your symptoms more spinning or more imbalance? | Spinning |
| 32. | Are you completely free of your symptoms while lying in bed? | S |
| 33. | Do your symptoms go away immediately after you lie down in bed? | N |

Characteristic answers from a patient who does not have BPPV are shown below:

Name: _____ Pt No. _____
Date: _____

Please complete the following questionnaire. All questions pertain to your dizziness/imbalance.

Please answer Y = Yes, S = Sometimes, N = No

| | | | |
|---|---|---|---|
| 1. | How old are you? (Age) | 72 | Yrs. |
| 2. | Are you male or female? | M | |
| 3. | Do you have physician diagnosed migraine headaches? | Y | |
| | a. If Y, do you have migraine headaches before or during your dizziness episodes? | Y | |
| 4. | At this moment do you have better hearing in one ear than the other? | Y | |
| | a. If Y, which ear hears better, right or left? | L | |
| 5. | Does your hearing fluctuate (get better and worse)? | Y | |
| | a. If Y or S, which ear fluctuates, right ear, left ear, or Unknown? | L | |
| 6. | How many months have you had balance or dizziness problems? | 4 | Months |
| 7. | Immediately before the beginning of your symptoms did you suffer a head blow? | N | |
| 8. | Immediately before the beginning of your symptoms did you have a cold? | Y | |
| 9. | Have you had loss of consciousness before, during or after a dizzy episode? | Y | |
| 10. | Do you have a pressure or full feeling in either of your ears when you are dizzy or imbalanced? | Y | |
| | a. If Y or S, is the fullness in the right ear, left ear or both ears? | L | |

-continued

| | | |
|---|---|---|
| 11. | Are your symptoms more spinning or more imbalance? | Imbalance |
| 12. | Do you have symptoms all the time? | Y |
| 13. | Do your symptoms go away when you lie down in bed? | Y |
| 14. | When you are dizzy or imbalanced, do your symptoms worsen when you turn your head quickly?<br>  a. If Y or S, which direction causes dizziness right, left or both? | N |
| 15. | If you lie on your back with your head turned to the side for 30 seconds do you become dizzy?<br>  a. If Y or S, which direction causes dizziness, right, left or both? | N |
| 16. | When you are dizzy or imbalanced, do your symptoms worsen when you look up? | N |
| 17. | When you are dizzy or imbalanced, do your symptoms worsen when you bend down? | N |
| 18. | When you are dizzy or imbalanced, do your symptoms worsen when you straighten up from bending down? | N |
| 19. | Are your symptoms worse at times and better at other times? | N |
| 20. | Are your symptoms constant? | Y |
| 21. | When you are dizzy or imbalanced, do your symptoms worsen (even for a short period of time) when you lie down in bed? | N |
| 22. | When laying on your back, do you get dizzy when you roll to one side or the other?<br>  a. If Y or S, when you roll to the right?<br>  b. If Y or S, when you roll to your left?<br>  c. Which side makes you more dizzy? | N |
| 23. | When you are dizzy or imbalanced, do your symptoms worsen when you sit up in bed? | N |
| 24. | When you are dizzy or imbalanced, do you stagger while walking?<br>  a. If Y or S, do you stagger to the right, left or both directions? | Y<br><br>BOTH |
| 25. | When you are dizzy or imbalanced, do your symptoms worsen when you look down? | N |
| 26. | When you are dizzy or imbalanced, do your symptoms worsen when you stand up from sitting? | N |
| 27. | Are you only dizzy when you are standing? | Y |
| 28. | When you are dizzy or imbalanced, do your symptoms worsen when you stand up from a lying position? | N |
| 29. | Do you have physician diagnosed retinal detachment? | Y |
| 30. | Do you use the internet? | N |
| 31. | When your symptoms first began, were your symptoms more spinning or more imbalance? | Imbalance |
| 32. | Are you completely free of your symptoms while lying in bed? | Y |
| 33. | Do your symptoms go away immediately after you lie down in bed? | Y |

Statistical Methods

In the preferred statistical embodiment, two basic phases are used. The first phase is the selection of the best set of predictor questions from all those questions ask, and the second is the determination of the optimal classification rule. To accomplish the first step the technique of "step-wise linear regression" ("forward selection" strategy) was used to choose a set of questions from the combined questions of the DxQ and DHI question sets. Those questions were chosen that predict good response in vertigo resolution after the Epley maneuver treatment for BPPV.

After selecting the best set of questions for predicting "good" Epley maneuver response, the second phase, that of establishing the optimal classification rule, was undertaken. Based on standard classification theory, classification rules of the following form were considered:

Classify the patient as a "good" Epley maneuver responder if P50 exceeds alpha, whereas P50 is "the established probability of 50% Epley responsive BPPV score" and that alpha is a number between zero and one.

The optimal value of alpha was chosen via the standard technique of "leave one out" cross validation. Specifically, a selection of candidate values of alpha (eg. 0.1, 0.2, 0.3 . . . , 0.9) were considered one at a time and for each, the cross validation estimates of the following criteria were obtained:

% correct=percentage correctly classified sensitivity=percentage of good responder correctly classified specificity=percentage of bad responders correctly identified false positive rate=percentage of bad responders incorrectly identified false negative rate=percentage of good responders incorrectly identified The Table below shows such figures for the hypothetical set of prediction questions. Given such a table, one simply selects the value of alpha which gives the best performance on the criteria which he deems most important (e.g. a low false positive rate and a high percentage correct).

Where the question set Model #1 contains:

Q1, Q28, Q11, Q12

Cross Validation Estimates

| Model Q Set Alpha | % correct | sens | spec | F+ | F−#1 |
|---|---|---|---|---|---|
| .20 | 63 | 53 | 10 | 38 | 0 |
| .25 | 60 | 50 | 10 | 38 | 3 |
| .30 | 69 | 50 | 19 | 28 | 3 |
| .35 | 73 | 50 | 22 | 25 | 3 |
| .40 | 74 | 50 | 24 | 24 | 3 |
| .50 | 80 | 50 | 32 | 15 | 22 |
| .60 | 28 | 60 | 32 | 15 | 25 |

In this process each question and question set is assigned a Beta value which represents its positive or negative influence upon the probability that the patient has Epley maneuver responsive BPPV. An intercept point value is also described.

As an example:

| Variables | Beta(Y) | Patient Response "X" |
|---|---|---|
| Intercept | Y0 = −.76 | |
| Q1 | Y1 = 1.13 | X1 |
| Q28 | Y28 = 2.31 | X28 |
| Q12 | Y12 = .71 | X12 |
| Q11 | Y11 = −1.90 | 811 |

Where:
Variables are the questions.

Betas are the positive and negative relevancy of the question answer to whether or not the patient will have Epley maneuver responsive BPPV.

Patient Response "X" are the patient answers. For the above questions the possible answers are:

X0=1

X1=1 if Q17 answer=Age<60
=0 if Q17 answer=Age>60

X28=1 if Q34 answer=Yes
=0 if Q34 answer=Sometimes or No

X12=1 if Q12 answer=Yes
=0 if Q12 answer=No

X11=1 if Q3 answer=Spinning
=0 if Q3 answer=Imbalance

An example would be:

X1=1 (age<60)

X28=1 (Q34=yes)

X12=0 (Q12=No)

X11=0 (Q3=imbalance)

Therefore:

Z=(−0.76)(1)+(1.13)(1)+(2.31)(1)+(0.71)(0)+(−1.90)(0)

Z=2.68

Therefore $$P50 = \frac{e^z}{(1+e^z)}$$

Where e=2.718

P50=0.935

Because of the high % correct (80%) and the low false positive rate (15%) alpha=0.5 was selected from the cross validation estimate table.

That is:
Good Epley maneuver responder will have a P50>=alpha=0.50
or
Bad Epley maneuver responder will have a P50<=alpha=0.50

Since (in this example):
P50=0.9358 which is >0.5

Then the probability that the user has BPPV which will be responsive at least 50% responsive to the Epley maneuver is 80%, with sensitivity=50%, specificity=32%, false positive rate=30% and false negative rate=22%.

In another embodiment, the a Multivariant Adaptive Regression Spline (MARS) model is to be used. In this embodiment the more general function is to be used to specify the predictors depending upon the portion (or region) of the predictor space within which the subject falls.

In another embodiment, the CART (Classification and Regression Trees) methodology can be used to accomplish the two steps of the preferred statistical embodiment but using a different methodology. The CART techniques constructs a diagram in the generic form (in generic terms w/three predictors V1, V2, and V3) "if V1=No. and V2=No and V3=No then classify as good, if V1=No and V2=No and V3=Yes then classify as poor, etc. The tree classifier is evaluated used the "leave one out cross validation" technique used in the preferred statistical embodiment.

In another embodiment the Fisher Liner Discriminant Function can be used to accomplish the two steps of the preferred statistical embodiment.

In another embodiment, Neural Networks methods can be used to solve the two steps of the preferred statistical embodiment.

Computer System and Process

The method and system of the present invention will now be discussed with reference to FIGS. 260–266. In a preferred embodiment the present invention includes a central computer, user interface, and a distributor interface. The central computer receives inquiries from users who suffer vertigo, dizziness or imbalance. The system solicits the answers to a series of questions from the user. The invention then uses the question answers and proprietary question, and question set, predictive values to computationally calculate the percentage chance that the user has benign paroxysmal positional vertigo that will be responsive to the use of the device. Rule based decision making can be used or added to the statistical methods used to determine the user's probability of responsive use of the device. Those users who will be responsive to the device are offered the opportunity to purchase the device.

DETAILED DESCRIPTION

Computer Techniques

System Architecture

The system architecture of the preferred embodiment of the apparatus and method of the present invention is illustrated with reference to FIG. 260. As shown in FIG. 260 the apparatus of this invention comprises a central computer 941, a user computer or interface 943 and a distributor computer or interface 945 (collectively the "nodes"). Each node can communicate with or be connected to the other nodes by way of the internet 947 using publicly switched phone network such as those provided by a local telephone or regional telephone company operating company. Connection may also be provided by dedicated data lines, cellular or personal communications systems ("PCS"), cable, microwave or satellite networks.

A conventional personal computer or workstation with sufficient memory and processing capacity may be used as the central controller 941 as shown in FIG. 265. In one embodiment it operates as a web server, both receiving and transmitting information. The Pentium microprocessor, such as the 100 mHz, P54C, commonly manufactured by Intel, Inc., may be used for the CPU 949. This processor employs a 32-bit architecture. Equivalent processors include Motorola 120 mHz, Howell PC 604 or Sun Microsystems 166 mHz Ultra Sparc-1.

Referring to FIG. 265, the controller 941 includes the CPU 949, a RAM 951, a ROM 953, a clock 955, a common port 957, and an operating system 959. The data storage device 961 may include a hard disk magnetic or optical storage unit as well as CD-ROM drive or flash memory. Data storage device 961 contains databases used in processing of question answers, question predictive values, customer demographics. It includes question answers 963; question predictive value database 965, customer purchase database 967, program files 969. ID number associated question answer database 963 maintains data anonymously on all users who have completed the questions. These data are stored associated with an identification number. Every time a series of questions is offered, to a user a unique identification number is offered as well. Immediately after the user indicates that all questions have been completed, at 971 in FIG. 263, the unique identification number and question answers are stored into question answer database 963. The use of this unique identification number allows the user to return to retrieve and review question answers either for correction of answers after further considering the question, communication with a support person, or for identifying serial questionnaire answer sets.

The predictive value database 965 maintains proprietary data regarding the predictive value of individual questions and sets of questions based on the correlation of question answers in patients with a clinical diagnosis of BPPV from physician consulting groups and from patient response after treatment with the device. These proprietary predictive values were determined by querying a sufficient number of new dizzy patients with an original set of predictive questions and collecting their responses to those questions. The patients were then treated using the device and objectively evaluated serially after their treatment. The predictive value of each question was determined using standard statistical techniques.

Customer database 967 contains information collected each time a customer purchases the device. This database will provide systems information for product return, processes, future product notifications, product recall, and other reasonable business functions.

Network interface including a modem 975 is the gateway to communicate with users and distribution centers through respective user 943 and distributor 945 interfaces. Conventional internal or external modems may serve as network interface 975. Network interface 975 supports modems with a baud rate from 1,200 to 56,000 but may combine such input into T1 or T3 line if more bandwidth is required. In the preferred embodiment, the network interface is connected with the Internet and/or any of the commercial on-line services such as America Online, CompuServe, or Prodigy, allowing users access to a full range of on-line connections. Several commercial electronic mail servers include the above functionality. Alternately Internet interface 975 may be configured as a voice mail interface, Web site BBS (Bulletin Board Service), or electronic mail address.

While the above embodiment describes a single computer acting as central controller 941, those skilled in the art will realize the functionality can be distributed over a plurality of computers. In one embodiment, a central controller 941 is configured in a distributed architecture, wherein the databases and processor are housed in separate units or locations. Some controllers perform the primary process functions and contain a minimum of RAM, ROM, and a general processor. Each of these controls is attached to a WAN (Wide Area Network) hub that serves as a primary communication link with other controllers and interface devices. The WAN hub may have minimal processing capability itself, serving primarily as a communications router. Those skilled in the art will appreciate that almost an unlimited number of controllers may be supported. This arrangement yields a more dynamic and flexible system, less prone to characteristic hardware failure, affecting the entire system.

FIGS. 262 and 266 disclose user interface 943 and distributor interface 945. In an exemplary embodiment they are both conventional personal computers having an input device such as a keyboard, and/or mouse, display device, such as video monitor, a processing device such as a CPU and a network interface such as a modem. These devices interface with the central computer 941. Alternately user interface and distributor interface may also be voice mail systems, or other electronic or voice communications systems. As described further in the following embodiments, devices such as fax machines or pagers are also suitable interface devices.

Referring now to FIG. 262 there is disclosed the user interface 943 which includes a central processor (CPU) 981, RAM 983, ROM 985, clock 987, video driver 989, video monitor 991, communication port 993, input device 995, modem 997, and data storage device 999. A Pentium microprocessor such as the 100 mHz P54C described above may be used for the CPU 981. Clock 987 is a standard chip based clock. Modem 997 may not require high-speed data transfer. Data storage device 999 may be a conventional magnetic based hard disk storage unit such as manufactured by Conner Peripherals.

Referring now to. FIG. 266 there is disclosed the distributor interface 945, which includes a central processor (CPU) 1001, RAM 1003, ROM 1005, clock 1007, video driver 1009, video monitor 1011, communications port 1013, input device 1015, modem 1017, and data storage device 1019. All these components may be identical to those described in connection with FIG. 262.

There are many commercial software applications that can enable the communications required by user interface 943 and distributor interface 945 the primary functionality being message creation and transmission. When the central computer 941 is configured as a web server, conventional communications software such as Netscape Navigator web browser from Netscape Corporation may be used. The user 943 and the distributor 945 may use the Netscape Navigator browser. The user will use the software to receive and answer BPPV screening questions, to receive the % chance that he has BPPV, and to send order information for the device. The distributor will use the software to receive order information and to send shipping and inventory reports for management purposes.

On-line Embodiment

Referring to FIG. 263, in one embodiment of the present invention, communications with the user take place via electronic network with the central computer 941 configured as a web server. At the web site the user logs on to the central computer and is presented with the BPPV screening questions 1021 of a questionnaire 1023 as described previously. The questions are complete by clicking the appropriate answer or by completing range-limited fill-in-the-blank questions. When all the questions have been completed and the user believes the questions are correct, the user indicates "All Questions Correct?" Yes, at 971. At 1025, the central processor stores all question answers associated with the assigned identification number to the question answer database 963. The question answers are recalled at 1027 from the question answer database 963. At 1029, the question predictive value database is queried and at 1031 BPPV screening proprietary question predictive values are recalled. At 1033, the user question answers and proprietary question predictive values are used to calculate the percentage chance that the user has BPPV which will be helped by the device. At 1035, the percent chance that the device will help the user is presented to the user in a text, graphical or multi-media manner. At this point the user has the option to go to the catalog module at 1037 of the web site. The user also has the option to move to any other portion of the website.

Referring to FIG. 264, in the preferred embodiment, a catalog function 1041 is available with graphic and/or text description of each item. Detailed information about each catalog item can be provided. The user is invited to peruse and/or select items for purchase.

A decision to purchase is made at 1043. If no purchase is desired, the user may take path 1045 to stay at the catalog home page, other web pages, etc. If the user decides to purchase and after one or more items are selected, the preferred payment method is solicited.

Payment Preferences

The user selects his preferred method of payment. Preferred methods include credit cards, personal checks, electronic funds transfer, digital money, etc. At Step 1047 the user transmits payment data corresponding to his preferred method of payment to the central computer 941. As indicated by Box 1047, such payment data might include a credit card number or bank account number. These payment methods are meant to be merely illustrative; however, as there are many equivalent methods of payment commonly known to the practitioner skilled in the art, which may also be used. As an example, if the user wants to pay by credit card, payment data would include his credit card account number, expiration date, name of the issuing institution, and credit limit. For electronic funds transfer, payment data includes the name of the payer's bank and his account number.

The central computer records the payment preference method of the user and the pertinent data regarding that payment method in the customer database 967. The central computer 941 contacts the credit card clearinghouse to get an authorization number. When the authorization number is received the central computer 941 updates the customer database 967 to indicate that payment has been made.

Another payment method involves procedures using digital cash. The central computer 941 updates the customer database 967 to indicate that payment has been made. This address might be an electronic mail address if digital cash is to be transferred by electronic mail, or it could be an Internet credit card address capable of accepting an on-line transfer of digital cash. This electronic delivery address is sent to the central controller 941 and updates the customer database balance at 967 to indicate that payment has been made.

The practice of using digital cash protocols to effect payment is well known to those skilled in the art and need not be described here in detail. For reference, one skilled in the art may refer to Daniel C. Lynch and Leslie Lundquist, *Digital Money*; John Wylie and Sons, 1996; or Seth Godin, *Presenting Digital Cash*, Sams Net Publishing, 1995.

Shipping Method

The user selects his preferred method of shipping. The preferred methods of shipping include any method of moving the product from the distribution site to the user. It is expected that depending upon the users severity of symptoms he may wish to pay for a more or less rapid delivery of the device for his use. At step 1049 the user transmits shipping information to the central computer 941 as indicated. The cost (depending upon the speed of deliver desired and the distance of the user from the closest distribution center) of the selected shipping method is shown. There are multiple equivalent shipping methods and commercial companies to perform this function commonly known to the practitioner skilled in the art.

Total Cost

The user is presented with his total cost for the device at 1051 and the shipping method that he has chosen. At 1053, when the user approves this amount of charge, the central computer 941 uses the payment preference method to collect the indicated amount. Credit card verification; credit card charge; and submit order are shown at 1055, 1057, and 1059 respectively.

Distribution

After the satisfactory completion of the charge collection is performed, instructions are forwarded to the distribution center at 1061 to ship, by the indicated method, the items selected by the user.

Off-line Embodiment

In another embodiment of the present invention the user can communicate in an off-line manner with the central computer 941. Rather than using a web-based server, the user can use electronic mail, telephone, fax machine, postal mail, or other off-line communication tools.

A user may use the telephone, for example, to answer the BPPV screening question set. The user calls the central computer 941 and is connected with an agent. The user answers the verbally relayed questions by the agent and when the question answers, entered into the computer and "questions completed" button is pushed, the agent relays the % chances the device will help the user. The user can then instruct the agent that he does or does not wish to purchase the device or other items for purchase. If the user wishes to purchase the device, the agent solicits the preferred payment and preferred shipping method information from the user and the information is entered into the computer 941. After payment has been received by the central computer 941, shipping instructions are sent to the distribution center 945.

In an alternative embodiment the user calls the central computer 941 and is connected with a conventional Interactive Voice Response Unit (IVRU) that allows the user to enter the solicited question answers to perform screening for BPPV. The user can then either continue entering interactive instructions using the touch-tones of his phone to select payment preference and shipping method and to accept the charges relayed by the telephone IRVU system. After the information has been received, the central computer 941 instructs the distribution center to ship the indicated items by the preferred shipping method to the user.

In another embodiment the user may call the central computer 941 to request a fax back or postal mail list of BPPV screening questions and answer options. After the questions have been answered, the information is delivered by fax or postal mail to the agent. The data is entered manually or in an automated manner into the central computer 941. The answered questions, the percentage chance of improvement with the device is provided to the user as well as a telephone number to use to order the device or other items for sale. The user has the option of using the telephone number provided to call the central computer and order the device using IRVU or direct connection with an agent.

Description of the Diagnosis and Treatment Devices

SBPPV

The Figures depicting the treatment positions for PBPPV treatment will be used to describe the SBPPV position sequence.

Device

The device attaches to the user's head to measure head position and to give the user visual feedback about his head position or series of head positions.

Referring to FIGS. 1–10, the device comprises three components or members 300, 400, and 500.

First Component The first component 300 comprises a clear, transparent, watertight outer sphere 302 of approximately $1^{12}/_{32}$ inches inside diameter and an outside diameter of approximately $1^{14}/_{32}$ inches. The outer sphere is made of a clear plastic and has upon it a sighting marking 306. The sighting marking is a circle approximately $3/8$ inch diameter. The thickness of the line drawing the circle is approx. $1/16$ inches thick of black or an easily visible color. Within this outer sphere is an inner sphere 305. The inner sphere has an outside diameter of approximately $1^{10}/_{32}$ inches. The inner sphere weight is approx. 0.04 lbs. It is to be understood that the dimensions and specifications of the outer and inner sphere as listed above may vary. The inner sphere is suspended in a liquid 303, water in the preferred embodiment, and is buoyancy neutral. The inner sphere has a weight 320 which maintains a vertical axis 305V in a vertical position. The inner sphere has an elongated bar magnet 390 which is a permanent magnet 390 located in the center of the sphere 305. The axis 390A of the magnet 390 is located at an angle of 20 degrees relative to a horizontal axis 305H, which is perpendicular to axis 305V. The higher end of the magnet 390 is directed toward the side 305S upon which are located the position bull's eye No. 1 and No. 2 identified by reference numeral 330.

The inner sphere has a numbered series of position bull's eyes 330 printed upon it and a path 315 from each position bull's eye to the next sequentially numbered position bull's eye. There are 3 position bull's eye configurations used on the inner sphere of the embodiment. The first is a posterior BPPV treatment configuration. The second is the horizontal BPPV treatment configuration. The third is the BPPV diagnostic configuration. The inner spheres in these three embodiments are identified by reference numerals 305X, 305Y, 305Z respectively.

The posterior BPPV treatment configuration is shown in FIGS. 11–17. FIG. 11 shows an inner sphere 305X with the vertical equator 305VE upon it. FIG. 12 shows that in the left posterior SCC BPPV treatment configuration from the user's line of sight, the position bull's eye No. 1 is 45 degrees to the right of the user's line of sight (up pointing arrow at bottom of FIG. 12); position bull's eye No. 2 is 45 degrees to the left of the user's line of sight; and the No. 3 position bull's eye is 135 degrees to the left of the user's line of sight. As seen in FIG. 13, bull's eyes No. 1 and No. 2 are 20 degrees from the vertical equator, and No. 3 is 20 degrees from the vertical equator, but in the opposite direction. These angles are determined by the equator and straight lines extended from the center of the inner sphere 305X to the position bull's eyes No. 1, No. 2, and No. 3. FIG. 14 illustrates the position bull's eyes No. 1, No. 2, and No. 3 for the left posterior SCC BPPV treatment from the perspective of FIG. 11. FIG. 15 is a view of FIG. 14 as seen along lines 15—15 thereof. FIG. 15 illustrates the position bull's eyes No. 1, No. 2, and No. 3 for the left posterior SCC BPPV treatment configuration. The inner sphere of FIGS. 14 and 15 for use for the left posterior SCC BPPV treatment is identified at 305XL.

FIGS. 16 and 17 show the location of position bull's eyes No. 1, No. 2, and No. 3 for the right posterior SCC BPPV treatment configuration. FIG. 16 illustrate the position bull's eyes No. 1, No. 2, and No. 3 for the right posterior SCC BPPV treatment configuration from the perspective of FIG. 11. FIG. 17 is a view of FIG. 16 as seen from lines 17—17thereof and illustrates the position bull's eyes No. 1, No. 2, and No. 3 for the right posterior SCC BPPV treatment configuration. The inner sphere of FIGS. 16 and 17 for use for the right posterior SCC BPPV treatment is identified at 305XR.

The horizontal BPPV treatment configuration is shown in FIGS. 18–24. FIG. 18 shows a vertical equator 305VE of an inner sphere 305Y. FIG. 19 is a view of FIG. 18 as seen along lines 19—19 thereof. In FIG. 19, position bull's eyes No. 1, No. 2, No. 3, and No. 4 are at 90 degrees from each other. Position bull's eyes No. 1 and No. 3 are on the horizontal equator and position bull's eyes No. 2, and No. 4 are on the vertical axis. As shown in FIG. 20, the position of bull's eyes No. 1 and No. 3 are on the vertical equator, and the position of bull's eyes Nos. 2 and No. 4 are 25 degrees off the vertical equator in the direction of the top of the user's head. These angles are determined by the equator and straight lines extending from the center of the sphere 305Y to No. 2 and No. 4 bull's eyes.

The location of the position bull's eyes for the treatment of right horizontal BPPV is shown in FIGS. 21 and 22. FIG. 22 is a side view depicting position bull's eye No. 3 on the vertical equator in the center of the sphere and immediately behind it, not directly visible, is position bull's eye No. 1. Position bull's eye No. 2 is at the bottom and No. 4 is at the top, each 25 degrees deviated from the vertical equator toward the head of the user. FIG. 22 is a view of FIG. 21 as seen along lines 22—22 thereof illustrating the four position bull's eyes. The inner sphere of FIGS. 21 and 22 for use for the treatment of right horizontal BPPV is identified at 305YR.

The location of the position bull's eyes for the treatment of left horizontal BPPV is shown in FIGS. 23 and 24. FIG. 23 is a side view of the inner sphere depicting the position bulls eye No. 1 on the vertical equator in the center of the sphere and immediately behind it. Not directly visible, is the position bull's eye No. 3. Position bull's eye No. 2 is at the bottom and No. 4 is at the top, each 25 degrees deviated from the vertical equator toward the head of the user. FIG. 24 is a view of FIG. 23 as seen along lines 24—24 thereof illustrating four position bull's eye. The inner sphere of FIGS. 23 and 24 for use for the treatment of left horizontal BPPV is identified at 305YL.

The third position bull's eye configuration is the diagnostic configuration of FIGS. 25 and 26. These bull's eyes are located on an inner sphere 305Z. Position bulls eye "R" is in the same position as the right posterior SCC BPPV treatment position bulls eye No. 1, FIGS. 16 and 17. Position bulls eye "L" is in the same position as the right posterior SCC BPPV treatment position bulls eye No. 2, FIGS. 16 and 17.

The second component 400 is a device which holds the first component 300 at the appropriate focal distance from the lens 410. The second component is a clear or light transmitting tube 405. By being clear it allows light to penetrate and strike the sighting mark 306 and the position bull's eye on the lens side of the inner sphere 305. The lens 410 in the preferred embodiment is a lens of 20 diopter strength. A 20 diopter lens is the best combination of magnification, depth of field, and width of field. The clear plastic tube 405 portion of the second component holds the lens-proximate surface of the inner sphere and the adjacent sighting marking 306 at the focal distance 407 of the lens 410.

FIG. 7 shows the first component 300 and the second component 400 joined and in the patient upright position. FIG. 7 depicts a magnet support surface 413 and the external magnet 415. The magnet 390 within the inner sphere 305 as well as the left posterior BPPV treatment configuration of position bull's eye is shown in FIG. 7. FIG. 8 shows the first and second components when the user is lying in the supine position with his neck extended 20 degrees. The orientation of the inner sphere 305 can be seen to be the same in FIGS. 7 and 8. Stabilization of the vertical axis of the inner sphere 305 is accomplished by the internal weight 320 within the inner sphere 305.

A permanent magnet 390 within the inner sphere 305 will orient according to the earth's magnetic field when no external magnet 415 is present. However, when the distancing component 400 and positioning component 300 combination are used without an external magnet 415, the permanent magnet 390 within the inner sphere 305 will be effected by ferrous metals (such as floor support beams) in proximity to the patient. When the external magnet is in place and the patient becomes supine with 20 degrees neck extension, the external magnet 415 aligns with the inner sphere 305 internal magnet 390 to keep the inner sphere 305 oriented in the horizontal axis. This functions particularly well because position bull's eye No. 1, position bull's eye No. 2 and position bull's eye No. 3 define a plane, the perpendicular to which is approximately 20 degrees off the horizontal equator.

The third component 500 of the device is shown in FIGS. 9 and 10. The third component 500 is a device which holds the combination of the second component 400 and the first component 300 in front of the eye of the user. The third component establishes a fixed position on the user's skull and transmits the position of the skull through the second component and the outer sphere of the first component. The third component is held to the head with a headband 510 which can be a single strap or a split strap. The headband holds the goggle-like third component over the eyes, firmly placed against the forehead, cheek, and over the bony nasal ridge. Positioning of the second component relative to the eye of the user is such that the central line of sight of the second component is approximately 32 mm lateral to the user's skull midline and at approximately the pupillary height. The distance of the second component from the eye is approximately 12–15 mm.

For diagnostic purposes the outer sphere 302 will have the diagnostic inner sphere 305Z located therein supported by the liquid 303. For treatment purposes, four outer spheres 302 will be provided, one having located therein the inner sphere 305XL supported by the liquid 303; one having located therein the inner sphere 305XR supported by the liquid 303; one having located therein the inner sphere 305YL supported by the liquid 303; and one having located therein the inner sphere 305YR supported by the liquid 303. Each component 500 has two eye openings 500L and 500R for the left and right eyes. Each sphere combination (302, 305Z), (302, 305XL), (302, 305XR), (302, 305YL), (302, 305YR) will be separately coupled to a component 400 to form five different component combinations 400 (302, 305Z), 400 (302, 305XL), 400 (302, 305XR), 400 (302, 305YL), 400 (302, 305YR) each of which may be removably coupled to the left or right openings 500L or 500R of the goggles 500.

Method to Use Device.

To diagnose right posterior and semicircular canal BPPV. The user is instructed to follow the following procedure using the device of FIGS. 1–10.

The user is instructed to sit on the floor and/or mat and put the goggles over his eyes in such a manner that the outer clear watertight sphere sighting mark 306 is clearly seen, as shown in FIG. 27. The diagnostic first component combination 400 (302, 305Z) is in place coupled to the desired eye opening of the goggles 400.

The user is instructed to lie supine in position "R", FIG. 28.

The pillow is rolled lengthwise and used longitudinally under the spine from C5 to L1. He is instructed to place the pillow on the mat behind him such that the pillow will be positioned under his upper thoracic spine (not under his shoulders). He is then instructed to lie backward upon the pillow and floor. The user is now instructed to find the positioning bull's eye "R", FIG. 25, 26, and position it within the sighting mark. He is to stay in this position for 30 seconds or until his dizziness resolves.

Sit on the floor and/or mat with goggles over the eyes, FIG. 27.

The user is instructed to return to the upright sitting position and wait for his dizziness to resolve.

Lie supine in position "L", FIG. 29.

The pillow is rolled lengthwise and placed longitudinally under the spine from C5 to L1. The user is instructed to place the pillow on the mat behind him such that the pillow will be positioned under his upper thoracic spine (not under his shoulders). He is instructed to lie backward upon the pillow and floor. The user is now instructed to find the position bull's eye "L" (FIGS. 25, 26) and position it within the sighting marker 306. He is to stay in this position for 30 seconds or until his dizziness resolves.

Return to the sitting position, FIG. 27.

The user is instructed to sit upright. He is instructed to remove the goggles, wait 30 seconds or until his dizziness resolves.

The user is instructed to determine whether placing his head in the position such that "R" is within the sighting marking causes more dizziness than placing his head in the position such that "L" is within the sighting mark. The position which causes the greatest symptoms of dizziness is the ear that is affected by the posterior semicircular canal BPPV.

Method for Posterior SCC BPPV Treatment

Treat Right Posterior SCC BPPV:

Sit on the Floor and/or mat with goggles over eyes (FIG. 30) using the component combination 400 (302, 305XR).

The user is instructed to sit on the floor or on a mat and put the goggles over his eyes in such a manner that the outer clear watertight ball sighting mark 306 is clearly seen.

Lie supine in head position No. 1 (FIG. 31).

The pillow is rolled lengthwise and placed longitudinally under the spine from C5 to L1. The user is instructed to place a pillow on the mat behind him such that the pillow will be positioned under his upper thoracic spine (not under his shoulders). He then is instructed to lie backward upon the pillow and floor. The user is now instructed to find the positioning bull's eye No. 1 (FIGS. 16, 17) and position it within the sighting marker (head position No. 1). He is to stay in this position for thirty seconds or until his dizziness resolves.

Lie Supine in head position No. 2 (FIG. 32).

The user then moves his head such that the printed path 315 on the inner sphere is kept within the sighting marking and he moves his head until the No. 2 positioning bull's eye (FIG. 17) is seen within the sighting marking (head position No. 2). He is instructed to stay in his position for thirty seconds or until the dizziness resolves.

Lie on left side with head turned downward 135 degrees (FIG. 33) (head position No. 3).

He now is instructed to roll upon his left side and simultaneously follow the printed path 315 within the target sighting marking to the positioning bull's eye No. 3 (FIGS. 16, 17) (head position No. 3). He is instructed to remain in this position for thirty second or until the dizziness resolves.

Roll into crawl position (FIG. 34).

The user is instructed to keep his head in the head position 3 (FIGS. 16, 17) and roll toward the left side into a crawl position as shown in FIG. 34. He is instructed to remain in this position for thirty second or until any dizziness resolves.

Come up to a kneeling position (FIG. 35).

The user is instructed to raise his torso into a kneeling position and steady himself for thirty seconds or until the dizziness resolves.

Either repeat the procedure or remove the goggles. If the user was dizzy during the positioning sequence, the user now is instructed to repeat the maneuver. If there was no dizziness during the maneuver sequence; the user is instructed to stop the maneuvers and remove the goggles.

Treat Left Posterior SCC BPPV:

Sit on the floor and/or mat with goggles over eyes (FIG. 36) using the component 400 (302, 305XL).

The user is instructed to sit on the floor or on a mat and put the goggles over his eyes in such a manner that the outer clear watertight ball sighting mark is clearly seen.

Lie supine in head position No. 1 (FIG. 37).

The pillow is rolled lengthwise and place longitudinally under the spine from C5 to L1. The user is instructed to place a pillow on the mat behind him such that the pillow will be positioned under his upper thoracic spine (not under his shoulders). He then is instructed to lie backward upon the pillow and floor. The user now is instructed to find the positioning bull's eye No. 1 (FIGS. 14, 15) and position it within the sighting marker (head position No. 1). He is to stay in this position for thirty seconds or until his dizziness resolves.

Lie Supine in head position No. 2 (FIG. 38).

The user then moves his head such that the printed path 315 on the inner sphere is kept within the sighting marking and he moves his head until the No. 2 positioning bull's eye (FIGS. 14, 15) is seen within the sighting marking (head position No. 2). He is instructed to stay in this position for thirty seconds or until the dizziness resolves.

Lie on right side with head turned downward 135 degrees (FIG. 39). Head position No. 3.

The user now is instructed to roll upon his right side simultaneously follow the printed path 315 within the target sighting marking to the positioning bull's eye No. 3 (FIGS. 14, 15) Head position No. 3. He is instructed to remain in this position for thirty seconds or until the dizziness resolves.

Roll into crawl position (FIG. 40).

The user is instructed to keep his head in the head position No. 3 (FIGS. 14, 15) and roll toward the right side into a crawl position, as shown in FIG. 40. He is instructed to remain in this position for thirty seconds or until any dizziness resolves, as shown in FIG. 40.

Come up to a kneeling position (FIG. 41).

The user is instructed to raise his torso into a kneeling position and steady himself for thirty seconds or until the dizziness resolves.

Either repeat the procedure or remove the goggles. If the user was dizzy during the positioning sequence, the user is now instructed to repeat the maneuver. If there was no dizziness during the positioning sequence, the user is instructed to stop the maneuvers and remove the goggles.

Treat Right Horizontal Semicircular Canal BPPV.

Sit on the floor and/or mat with goggles over the eyes, FIG. 42, using the component combination 400 (300, 305YR).

The user is instructed to sit on the floor on a mat and put the goggles over his eyes in such a manner that the outer clear watertight sphere sighting mark is clearly seen. The right horizontal semicircular canal treatment first component (300, 305 YR) is in place. The user is to have the right horizontal SCC BPPV first component in place.

Lie supine in position No. 1, FIG. 43.

The user is instructed to lie backward upon the mat or floor. He is instructed to find the position bull's eye No. 1, FIGS. 21, 22 and position it within the sighting marker. He is to stay in this position for 30 seconds or until the dizziness resolves.

Lie in position No. 2. FIG. 44.

The user moves his head such that the printed path 315 on the inner ball is kept within the sighting marking and moves his head until the No. 2 position bull's eye, FIGS. 21, 22, is seen within the sighting marking. He is instructed to stay in position for 30 seconds or until the dizziness resolves. This position involves flexion of the neck 25 degrees while in a classic supine position.

Lie supine in position No. 3. FIG. 45.

The user now is instructed to move his head such that the printed path on the inner ball is: kept within the sighting marking, and moves his head until positioning bull's eye No. 3 is seen within the sighting marking (FIGS. 21, 22). He is instructed to stay in this position for 30 seconds or until the dizziness resolves.

Lying on his stomach with his head turned 180 degrees from classic supine, FIG. 46.

The user now is instructed to roll onto his stomach, keeping the positioning bull's eye No. 3 within the sighting marking. He is instructed to follow the printed path within the sighting marking to position bull's eye No. 4 (position No. 4). He is instructed to stay in this position for 30 seconds or until the dizziness resolves. In this position the patient is in a classic prone position with his neck flexed 25 degrees, FIG. 46.

Get into a crawl position, FIG. 47.

The user is instructed to keep his head in position No. 4 (FIGS. 21, 22) and, keeping his head in such a position that portion bull's eye No. 4 remains in the sighting marking, come to a crawl position. He is instructed to remain in this position, with his head such that position bull's eye No. 4 remains in the sighting mark for 30 seconds or until the dizziness resolves.

Come up to the kneeling position, FIG. 48.

The user is instructed to raise his torso into a kneeling position and steady himself for 30 seconds or until the dizziness resolves.

Either repeat or remove the goggles.

If the user is dizzy during the maneuver sequence, the user is now instructed to repeat the maneuver. If there is no dizziness during the maneuver sequence, the user is instructed to stop the maneuvers and remove the goggles.

Treat Left Horizontal Semicircular Canal BPPV.

Sit on the floor and/or mat with goggles over the eyes, FIG. 49, using the component combination 400 (302, 305YL).

The user is instructed to sit on the floor on a mat and put the goggles over his eyes in such a manner that the outer clear watertight sphere sighting mark is clearly seen. The user is to have the left horizontal SCC BPPV treatment first component in place.

Lie supine in position No. 1, FIG. 50.

The user is instructed to lie backward upon the mat or floor. He is instructed to find the position bull's eye No. 1, FIGS. 23, 24 and position it within the sighting marker. He is to stay in this position for 30 seconds or until the dizziness resolves.

Lie in position No. 2. FIG. 51.

The user moves his head such that the printed path on the inner ball is kept within the sighting marking and moves his head until the No. 2 position bull's eye, FIGS. 23, 24, is seen within the sighting marking. He is instructed to stay in position for 30 seconds or until the dizziness resolves. This position involves flexion of the neck 25 degrees while in a classic supine position.

Lie supine in position No. 3. FIG. 52.

The user now is instructed to move his head such that the printed path on the inner ball is kept within the sighting marking, and moves his head until positioning bull's eye No. 3 is seen within the sighting marking (FIGS. 23, 24). He is instructed to stay in this position for 30 seconds or until the dizziness resolves.

Lying on his stomach with his head turned 180 degrees from classic supine, FIG. 53.

The user now is instructed to roll onto his stomach, keeping the positioning bull's eye No. 3 within the sighting marking. He is instructed to follow the printed path within the sighting marking to position bull's eye No. 4 (position No. 4). He is instructed to stay in this position for 30 seconds or until the dizziness resolves. In this position the patient is in a classic prone position with his neck flexed 25 degrees, FIG. 53.

Get into a crawl position, FIG. 54.

The user is instructed to keep his head in position No. 4 (FIGS. 23, 24) and, keeping his head in such a position that position bull's eye No. 4 remains in the sighting marking, come to a crawl position. He is instructed to remain in this position, with his head in a position such that bull's eye No. 4 is in the sighting marking and remains in the sighting marked for 30 seconds or until the dizziness resolves.

Come up to the kneeling position, 55.

The user is instructed to raise his torso into a kneeling position and steady himself for 30 seconds or until the dizziness resolves.

Either repeat or remove the goggles.

If the user is dizzy during the maneuver sequence, the user is now instructed to repeat the maneuver. If there is no dizziness during the maneuver sequence, the user is instructed to stop the maneuvers and remove the goggles.

Treat Right Superior SCC BPPV:

Sit on the Floor and/or mat with goggles over eyes (FIG. 36) using the component combination 400 (302, 305XL).

The user is instructed to sit on the floor or on a mat and put the goggles over his eyes in such a manner that the outer clear watertight ball sighting mark is clearly seen. The user is to have the left posterior SCC BPPV treatment first component in place.

Lie supine in the head position No. 1 (FIG. 37).

The pillow is rolled lengthwise and placed longitudinally under the spine from C5 to L1. The user is instructed to place a pillow on the mat behind him such that the pillow will be positioned under his upper thoracic spine (not under his shoulders). He then is instructed to lie backward upon the pillow and floor. The user now is instructed to find the positioning bull's eye No. 1 (FIGS. 14, 15) and position it within the sighting marker (head position No. 1). He is to stay in this position for thirty seconds or until his dizziness resolves.

Lie Supine in head position number 2 (FIG. 38).

The user then moves his head such that the printed path on the inner ball is kept within the sighting marking and he moves his head until the No. 2 positioning bull's eye (FIGS. 14, 15) is seen within the sighting marking. He is instructed to stay in this position for thirty seconds (head position No. 1) or until the dizziness resolves.

Lie on right side with head turned downward 135 degrees (FIG. 39). Head position No. 3.

The user now is instructed to roll upon his right side and simultaneously follow the, printed path within the target sighting marking to the positioning bull's eye No. 3 (FIGS. 14, 15). He in instructed to remain in this position for thirty seconds or until the dizziness resolves.

Roll into crawl position (FIG. 40).

The user is instructed to keep his head in the head position 3 (FIGS. 14, 15) and roll toward the right side into a crawl position. He is instructed to remain in this position, as shown in FIG. 40, for thirty seconds or until any dizziness resolves.

Come up to a kneeling position (FIG. 41).

The user is instructed to raise his torso into a kneeling position and steady himself for thirty seconds or until the dizziness resolves.

Either repeat the procedure or remove the goggles. If the user was dizzy upon going from the crawl to the kneeling positions, the user now is instructed to repeat the maneuver. If there was no dizziness when the user goes from the crawling to the kneeling positions, the user is instructed to stop the maneuvers and remove the goggles.

Treat Left Superior SCC BPPV:

Sit on the Floor and/or mat with goggles over eyes (FIG. 30) using the component combination 400 (302, 305XR).

The user is instructed to sit on the floor or on a mat and put the goggles over his eyes in such a manner that the outer clear watertight ball sighting mark is clearly seen. The user is to have the right posterior SCC BPPV treatment first component in place FIG. 30.

Lie supine in head position number 1 (FIG. 31).

The pillow is rolled lengthwise and placed longitudinally under the spine from C5 to L1. The user is instructed to place a pillow on the mat behind him such that the pillow will be positioned under his upper thoracic spine (not under his shoulders). He then is instructed to lie backward upon the pillow and floor. The user now is instructed to find the positioning bull's eye No. 1 (FIGS. 16, 17) and position it within the sighting marker (head position No. 1). He is to stay in this position for thirty seconds or until his dizziness resolves.

Lie Supine in head position number 2 (FIG. 32).

The user then moves his head such that the printed path on the inner sphere is kept within the sighting marking and he moves his head until the No. 2 positioning bull's eye (FIGS. 16, 17) is seen within the sighting marking (head position No. 2). He is instructed to stay in this position for thirty seconds or until the.dizziness resolves.

Lie on left side with head turned downward 135 degrees (FIG. 33). Head position No. 3.

The user is now instructed to roll upon his left side and simultaneously follow the printed path within the target sighting marking to the positioning bull's eye No. 3 (FIGS. 16, 17) (head position No. 3). He in instructed to remain in this position for thirty seconds or until the dizziness resolves.

Roll into crawl position (FIG. 34).

The user is instructed to keep his head in the head position 3 (FIG. 34) and roll toward the left side into a crawl position, as shown in FIG. 34. He is instructed to remain in this position for thirty seconds or until any dizziness resolves.

Come up to a kneeling position (FIG. 35).

The user is instructed to raise his torso into a kneeling position and steady himself for thirty seconds or until the dizziness resolves.

Either repeat the procedure or remove goggles. If the user was dizzy upon going from the crawl to the kneeling positions, the user is now instructed to repeat the maneuver. If there was no dizziness when the user goes from the crawling to the kneeling position, the user is instructed to stop the maneuvers and remove the goggles.

Detailed description of the left posterior semicircular canal BPPV treatment showing body positions and goggle apparatus using magnet embodiment.

Principles in Action. Reference is Made to FIGS. 56–87.

When the sighting mark has within it a position bull's eye or position bull's eye path FIG. 65, 70, 75, 80 then the internal 390 and external 415 magnets are aligned, FIGS. 64, 69, 74, 79 and they form an axis D. This axis D is in a 20 degree top of head down relationship to the horizontal plane. The long axis of the head S in FIGS. 57, 67, 72, 77 is in a 20 degree top-of-head-down relationship with the horizontal plane. Hence axis D and axis S are parallel.

The plane defined by the position bull's eye and their path is perpendicular to the magnet axis D, FIGS. 59, 64, 69, 74, 79, 84. The long axis of the user's head S is parallel to the axis D. Since axis D is parallel to axis S and since the bull's eye defined plane is perpendicular to axis D then the bull's eye defined plane is perpendicular to axis S. If the relationship between the users head and the goggle device is constant then when the position bull's eye or position bull's eye path is kept within the target sighting mark and the head is rotated from position bull's eye to No. 1 to position bull's eye No. 3, the maneuver will be correctly completed.

One of the difficult aspects of the maneuver is to keep the head in the 20-degree plane during the transition from head position 2 to head position 3. In this transition the user goes from the lying on his back in a neck extended position to lying on his side in a neck flexed (or chin tucked) position. During this transition there is a period during which the neck must be extended downward to keep the long axis of the head downward by 20 degrees. This occurs as the user is rolling onto the shoulder opposite the ear being treated. The visual feedback is necessary to keep the long axis of the head correctly positioned.

It is also necessary to have visual feedback for the user while the user's head is in position 3 and the user is transitioning from the face downward position while lying on his side head position No. 3 to the crawl position. Maintaining the head in the same position is difficult without visual feedback.

FIGS. 56–60 show the user in the start position sitting up with a pillow placed to support and elevate his back. The external magnet 415 is vertical in the same axis as the longitudinal axis S of the head, FIG. 57. The user can see no markings within the target sighting mark, FIG. 60. The internal magnet is centered within the inner sphere and has a 20-degree angle to the horizontal. The plane defined by the position bull's eyes is perpendicular to the internal magnet axis D.

FIGS. 61–65 show the user lying on his back with his head turned to the left 45 degrees and his neck extended 20 degrees. In this position, FIG. 61, the external magnet can be seen to be aligned with the internal magnet, FIG. 64, and the target sighting mark has within it the position bull's eye No. 1, FIGS. 64, 65. Whenever the target sighting mark has within it the plane defined by the position bull's eye, that is, has a position bull's eye or the position bull's eye path within it, the internal and external magnets will be aligned and the user's head will be at a 20 degrees top-of-head-down angle to the horizontal plane. The key to successfully performing a successful maneuver is to maintain this head long axis orientation during the rotation of the head in the plane defined by the position bull's eyes.

FIGS. 66–70 show the user lying on his back with his head turned to the right 45 degrees, FIGS. 66 and 67, with his neck extended 20 degrees. The user has kept the position bull's eye path within the target sighting mark and has turned his head 90 degrees to the right, FIGS. 66, 67 such that he has the position bull's eye No. 2 in the target sighting mark, FIG. 70.

FIG. 71–75 show that the user has rolled 90 degrees from head position No. 2 to head position No. 3, FIG. 73, onto the right side and has turned his face downward at a 45 degree angle to horizontal, FIG. 71. He has also gone from a neck extended, FIGS. 66, 67 to a neck flexed (chin tucked toward chest) position, FIGS. 71, 72. This requires that the user not only transition from neck extension to neck flexion but do so while rolling onto his right shoulder. The user must, in the middle of this transition, bend his neck laterally to maintain the top-of-head downward angle relative to the horizontal plane. This is accomplished by keeping the bull's eye path within the target sighting mark during the movement.

FIGS. 76–80 show that the user has maintained the same head position, FIGS. 73, 74, 75, 78, 79, 80 and has moved from a right side down position, FIGS. 71, 72, to the crawl position, FIGS. 76, 77.

FIGS. 81–85 show the user having moved from the crawl to the kneeling positions, FIGS. 81, 82. The external magnet is returned to the vertical position, FIG. 84. The user no longer sees any position bull's eye in the target sighting mark, FIG. 85. The user is now looking at the opposite side of the inner sphere, FIG. 84, than the side which he saw in the start sitting position, FIG. 59.

FIG. 86 shows the 180 degree rotation of the user's head around the interior magnet axis D seen end on for treatment of left posterior SCC BPPV.

FIG. 87 shows a view of the complete sequence of head positions for left posterior SCC BPPV treatment from the point of view in line with the magnet axis D, 20 degrees top-of-head-down from the horizontal. In FIG. 87I the back of the user's head in the sitting position is seen. In FIG. 87II the user lies down with 20 degree neck extension allowing the magnet axis D to be seen end on and turns his head 45 degrees to the left (head position No. 1). He then maintains the neck extension and turns his head 90 degrees to the right to head position No. 2, FIG. 87III. He turns his head to the right another 90 degrees while maintaining the top of the head down 20 degrees bending his neck laterally 20 degrees, rolls onto this right shoulder and flexes his neck (chin toward chest) 20 degrees, FIG. 87IV. Maintaining the head position No. 3, FIG. 87IV, the user moves into a crawl position, FIG. 87V. The user moves from a crawl position to the kneeling position, FIG. 87VI. In the kneeling position, FIG. 87V, the axis of the inner sphere magnet 390 is seen end on with the position bull's eye visible.

Other Embodiments

First Component
Inner Ball Structure Variations
Horizontal Axis Magnetic Control As in the previously discussed embodiment this device attaches to the user's head to reflect head position and to give the user visual feedback about this head position or series of head positions.

In the previously discussed embodiment the external magnet 415 provides horizontal axis orientation when the patient lies down and especially when the patient lies supine with 20 degrees of neck extension, FIG. 8. When the patient is sitting, FIG. 88, the external magnet is approximately perpendicular to the axis of the inner sphere internal magnet 390, FIG. 88. In order to keep the internal magnet 390 oriented approximately in the horizontal plane in the sitting position, additional magnets can be placed on the second component 405. By keeping the inner sphere oriented in the position shown in FIG. 88 in the sitting position, instructions can be presented to the user on the surface of the inner sphere 305. This additional magnet or magnets orient the inner sphere 305, in the sitting position, by creating a horizontal axis magnetic entrapment system. FIG. 88 shows the second component 400 and first component 300 with additional magnets 416R and 416L attached to both sides of the clear plastic tube 405B of the second component 400. These additional magnets ensure that the axis of the inner sphere magnet 390 and hence the inner sphere is oriented as shown in FIG. 88 relative to axis of the tube 405 when the user is in the sitting position. When the user lies in a supine position with 20 degrees of neck extension, as shown in FIG. 89, the magnets 416 R, 416 L become perpendicular to the long axis of the inner sphere magnet 390. In such a configuration the magnets 416 R and 416 L cease to significantly affect the inner sphere magnet 390, but the external magnet 415 rotates into direct alignment with the axis of the inner sphere magnet 390 such that the external magnet 415 keeps the inner sphere oriented for the posterior semicircular canal treatment maneuver.

In another embodiment, as shown in FIG. 90, the axis of the inner sphere magnet 390 can be located parallel to the flat surface of the weight 320 such that it will be oriented in the horizontal plane (horizontal at all times). When the first component inner sphere 305 is fitted with a horizontal internal magnet 390 and is attached to the second component 400 as shown in FIG. 91, the internal magnet 390 is optimally aligned to be affected by the earth's magnetic field. The device can be used when no surrounding ferrous objects are within 15 feet of the user to disrupt the inner sphere magnet orientation with the earth's magnet field. Additionally this configuration allows any three dimensional head position to be determined based on the configuration of positional bull's eyes printed on the outer surface of the inner sphere.

In another embodiment, as shown in FIG. 93, when the inner sphere of the first component is configured with horizontal permanent magnet 390, but the device is intended to be used in the presence of ferrous objects, an external magnet 492 not attached to the device but located close 61 to the device and which is strong enough to create a magnetic field that can effect magnet 390, can be effective in correctly orienting the internal magnet 390 and hence the inner sphere 305.

Horizontal Axis Control by Entrapment

In another embodiment, horizontal axis control of the inner sphere 305 can occur by an entrapment device. This device attaches to the user's head to measure head position and to give the user visual feedback about his head position or series of head positions.

FIG. 94 shows an inner sphere 305 within a clear, transparent, water-tight outer sphere configuration 302 for the first component 300, with the inner sphere 305 being buoyancy neutral, suspended in a fluid (water) 303 being enclosed in a watertight outer sphere 302. In this embodiment, the inner sphere 305 has an entrapment protrusion 340 which is fixed to the inner sphere 305 and extends radially outward therefrom. The entrapment protrusion 340 fits within an entrapment slot 350. Entrapment slot 350 and entrapment protrusion 340 are covered by an entrapment cover 355, which keeps the outer sphere watertight. FIG. 96 shows a cutaway view of the entrapment slot 350 in one configuration. Entrapment slot configurations are shown in FIGS. 96–101. The orientation of the entrapment protrusion 340 is shown in FIG. 94. The entrapment protrusion extends outward approximately 4 mm along a line which begins at the center of the inner sphere and is elevated 20 degrees relative to the horizontal axis. A line extending perpendicular through the plane formed by the position bull's eyes No. 1, No. 2, and No. 3 extends approximately in the line of the entrapment protrusion 340.

The entrapment slot 350 has an arcuate length 350L which defines a 45 degree angle relative to the center of the outer sphere 302. That is $((pi)(d)/8)$ is approximately the best entrapment slot length; where pi=3.1416, d=diameter of the sphere in which the entrapment slot 350 is placed. FIG. 104 shows the orientation of the center of the sighting mark 306 and the center of the entrapment slot 350 when the patient is lying in a supine position with his neck extended 20 degrees and the sagittal plane of his skull perpendicular to the horizon. (In FIG. 104 the entrapment slot 350 is shown extending 22.5 degrees on each side of the protrusion 340). In this position, the entrapment protrusion is in the axis about which the head is rotated to perform the maneuver for the removal of the otoconial crystals from the posterior SCC for the relief of posterior SCC BPPV. The center of the sighting mark 306 in the supine position, head extended 20 degrees, lies approximately in the plane formed by position bull's eyes No. 1, No. 2, No. 3. The line of the entrapment protrusion 340 is approximately perpendicular to this plane.

Referring to FIG. 104, a line from the center of the inner sphere to the center of the entrapment slot and a line from the center of the inner sphere to any of the position bull's eyes or points along the path are at approximately a 90 degree angle. When the user lies supine and head extended 20 degrees, the center of the sighting mark is at a 90 degree angle to the axis of the entrapment protrusion.

When the user rises from supine with 20 degree neck extension to a classic supine position, FIG. 107, the center of the sighting mark moves to the bottom of the inner sphere and the center of the entrapment slot moves to a horizontal position. Because the entrapment slot is approximately 45 degrees in width, in FIG. 104, the entrapment protrusion will have moved to approximately the top end of the entrapment slot, but the inner sphere will not have moved.

When the user rises from a classic supine position to a sitting upright position, FIG. 108, the inner sphere is rotated in the plane formed by the center of the inner sphere, the entrapment protrusion and the center of the weight in the inner sphere. During this position change, the inner sphere is rotated approximately 87.5 degrees.

The placement of the position bull's eyes for the treatment of post SCC BPPV, FIGS. 11–17, and the method of treatment for post SCC BPPV when the inner sphere horizontal axis is controlled by the entrapment embodiment is like the method used in the embodiment of FIG. 30–41. The placement of the position bull's eye (R and L) for BPPV diagnostic technique and the method for post BPPV when inner sphere horizontal axis is controlled by the entrapment embodiment is like the method used in embodiment FIGS. 27–29. The entrapment embodiment cannot be used to treat horizontal BPPV Rx.

Detailed description of the left posterior semicircular canal BPPV treatment showing body positions and goggle apparatus using entrapment embodiment.

Principles in Action. Reference is Made to FIGS. 109–142

When the sighting mark has within it a position bull's eye or position bull's eye path, FIGS. 117, 122, 127, 132, then the entrapment protrusion 340 is free to move within the entrapment slot 350 and will tend to seek its free floating axis orientation of 20 degrees from the horizontal, FIGS. 117, 122, 127, 132. When the sighting mark has within it a position bull's eye or position bull's eye path 117, 122, 127, 132 then the long axis S of the head. FIGS. 115, 120, 125, 130 is in a 20 degree top-of-head-down relationship with the horizontal plane.

The plane defined by the position bull's eyes is approximately perpendicular to the axis of the entrapment protrusion FIGS. 112, 117, 122, 127, 132, 137, 139. When the target sighting mark has within it either a positioning bull's eye or the position bull's eye path then the long axis S of the user's head is parallel to the entrapment protrusion defined axis i.e. 20 degrees from the horizontal. If the relationship between the users head and the goggle device is constant, then when the position bull's eye or position bull's eye path is kept within the target sighting mark and the head is rotated 180 degrees from position bull's eye to No. 1 to position bull's eye No. 3, the maneuver will be correctly completed.

One of the difficult aspects of the maneuver is to keep the head in the 20 degree top-of-head-down plane during the transition from head position No. 2, FIGS. 119, 120 to head position No. 3, FIGS. 124, 125. In this transition, the user goes from the lying on his back in a neck extended position, FIGS. 119, 120, to lying on his right side in a neck flexed (or chin tucked) position FIGS. 124, 125. During this transition there is a period during which the neck must be bent laterally and downward to keep the long axis of the head top-of-head-downward by 20 degrees. This occurs as the user is rolling onto his shoulder opposite the ear being treated. The visual feedback is necessary to keep the long axis of the head position correct.

It is also necessary to have visual feedback to the user while the user's head is kept in head position No. 3, FIGS. 124, 125, 129, 130, but the user is transitioning from the face downward position while lying on his right side, FIGS. 124, 125, to the crawl position, FIG. 129, 130. Maintaining the head in the same position is difficult without visual feedback.

FIGS. 109–113 show the user in the start position sitting up with a pillow placed to support and elevate his back, FIGS. 109, 110. The user can see no markings within the target sighting mark FIG. 113. The user's eye, the target sighting mark and the center of the inner sphere are located along the horizontal axis. A line from the center of the target sighting mark. to the center of the inner sphere and a line from the center of the entrapment slot to the inner sphere form a 90 degree angle. A line from the center of the inner sphere weight 320 to the center of the inner sphere and a line from the entrapment protrusion to the center of the inner sphere form an angle of 110 degrees. The entrapment slot forms a 45 degrees arc. Therefore from the center of the entrapment slot to the end furthest from the target sighting mark is a 22.5 degrees arc. A horizontal line passing through the center of the user's pupil, through the center of the target sighting mark and through the center of the inner sphere and a line passing through the center of the weight 320 and the center of the inner sphere form an angle of 2.5 degrees. The center of the weight is below the horizontal line.

FIGS. 114–118 show the user lying on his back with his head turned to the left 45 degrees and his neck extended 20 degrees. During the lying down process, the user moves his head and the attached target sighting mark backward. When the head has been rotated backward toward horizontal 87.5 degrees, the weight 320 has reached its lowest point and the inner sphere ceases to be moved in the vertical plane by the inner sphere entrapment protrusion and the outer sphere entrapment slot interaction. The user lies down and extends his neck 20 degrees and the target sighting mark moves another 22.5 degrees and comes to have within it either the position bull's eye or the position bull's eye path. At this time the entrapment protrusion is in the center of the entrapment slot. So long as the target sighting mark stays on a position bull's eye or position bull's eye path, the entrapment protrusion will move vertical freely within the entrapment slot, except during a brief period in the transition from head position No. 2 to head position No. 3. Since the plane defined by the three position bull's eye is perpendicular to the entrapment protrusion axis DP, the user can now rotate his head in the plane defined by the position bull's eyes. By rotating his head 180 degrees in the plane defined by the position bull's eye from head position No. 1 to head position No. 3, the post SCC BPPV treatment maneuver can be successfully accomplished.

In FIG. 117, the entrapment protrusion can be seen to be moving freely within the entrapment slot and the target sighting mark has within it the position bull's eye No. 1, FIGS. 117, 118. Whenever the target sighting mark is in the plane defined by the position bull's eyes, the entrapment protrusion will be moving freely vertically within the entrapment slot and the user's head will be at a 20 degrees top-of-head-down angle to the horizontal plane. The key to successfully performing a maneuver is to maintain his head long axis S orientation during the rotation of the head in the plane defined by the position bull's eyes.

FIGS. 119–123 show the user lying on his back with his head turned to the right 45 degrees, FIGS. 119, 120 with his neck extended 20 degrees. The user has kept the position bull's eye path within the target sighting mark and has turned his head 90 degrees to the right, FIGS. 119, 120, such that he has the position bull's eye No. 2 in the target sighting mark, FIG. 123.

FIGS. 124–128 show that the user has rolled 90 degrees from position No. 2, FIG. 121, to position No. 3, FIG. 126, onto his right side and has turned his face downward at a 45 degree angle to horizontal, FIGS. 124, 125. He has also gone from a neck extended, FIGS. 114, 115, 119, 120, to a neck flexed (chin tucked toward chest) position, FIGS. 124, 125, This requires that the user not only transition from neck extension to neck flexion but do so while rolling onto his right shoulder. In the middle of this transition the user must bend his neck laterally to maintain the top-of-head downward angle relative to the horizontal plane. This is accomplished by keeping the bull's eye path within the target sighting mark during the movement.

FIGS. 124, 125, 129, 130, show that the user has maintained the same head position, FIGS. 126, 127,128, 131, 132, 133, and has moved from a right side down position, FIGS. 124, 125, to the crawl position, FIGS. 129, 130.

FIGS. 129, 130, 134–140 show the user having moved from the crawl, FIGS. 129, 130, to the kneeling position, FIGS. 134, 135. As the user moves from the crawl to the kneeling position, several changes occur in the device. When the user raises his head 22.5 degrees from the neck-flexed position, FIG. 132, the entrapment protrusion comes to rest on the entrapment slot end most distant from the target sighting mark, FIG. 107. As the user raises his head to the upright (vertical) position, FIGS. 137, 139, the line from the center of gravity of the weight is raised to slightly above the horizontal position. The user is now looking at the opposite side of the inner sphere, FIG. 137, than the side which he saw in the start sitting position FIG. 139. If the user raises his head or certainly when the user begins to lie on his back to repeat the maneuver, the weight will move downward and rotate the inner sphere around the axis of the entrapment protrusion and move the inner sphere outer surface which is closest to the weight into the user's line of sight, FIG. 139.

FIG. 141 shows the 180 degree rotation of the user's head around the entrapment protrusion axis seen end on for treatment of left posterior SCC BPPV.

FIG. 142 shows a view of the complete sequence of head positions for left posterior SCC BPPV treatment from the point of view in line with the entrapment protrusion axis 20 degrees from the horizontal. In FIG. 142I, the back of the user's head in the sitting position is seen. In FIG. 142II, the user lies down with 20-degree neck extension allowing the entrapment protrusion axis to be seen end on and turns his head 45 degrees to the left (Head position No. 1). He then maintains the neck extension and turns his head 90 degrees to the right to head position No. 2, FIG. 142 III. He turns his head to the right another 90 degree while maintaining the top-of-head-down 20 degrees extending his neck laterally 20 degrees, rolls onto his right shoulder and flexes his neck 20 degrees into head position No. 3, FIG. 142 IV. Maintaining the head position No. 3, FIG. 142 IV, the user moves into a crawl position FIG. 142 V. The user moves from a crawl position to the kneeling position FIG. 142 VI.

Inner Sphere Marking Variations

Figure 145:
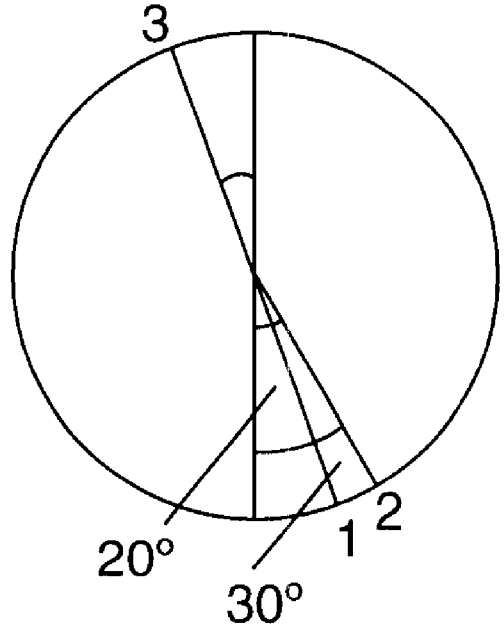
Figure 146:
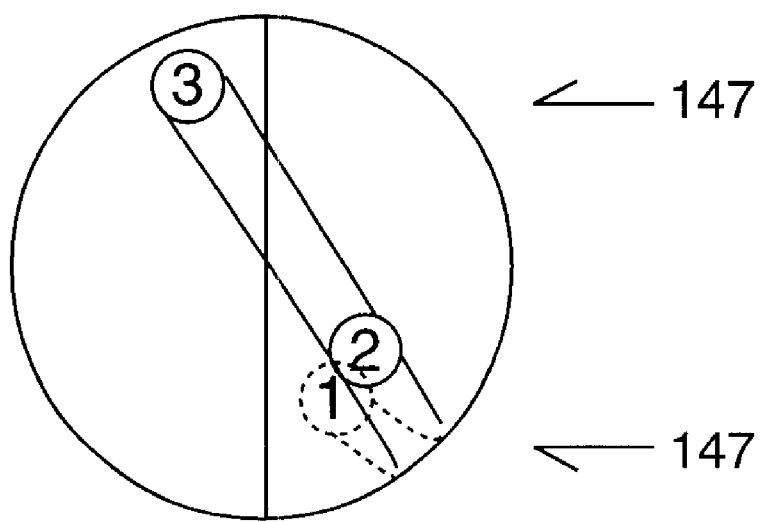
Figure 147:
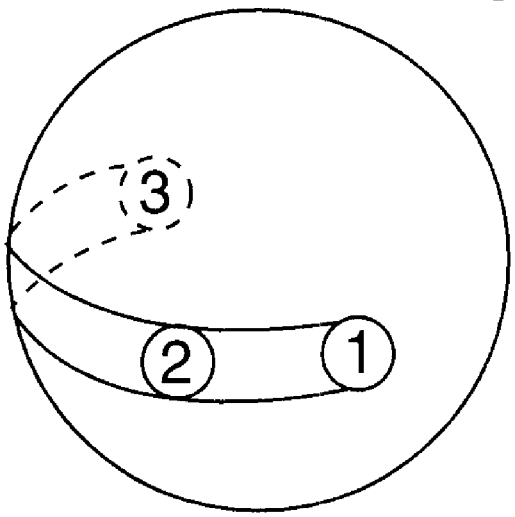
Figure 148:
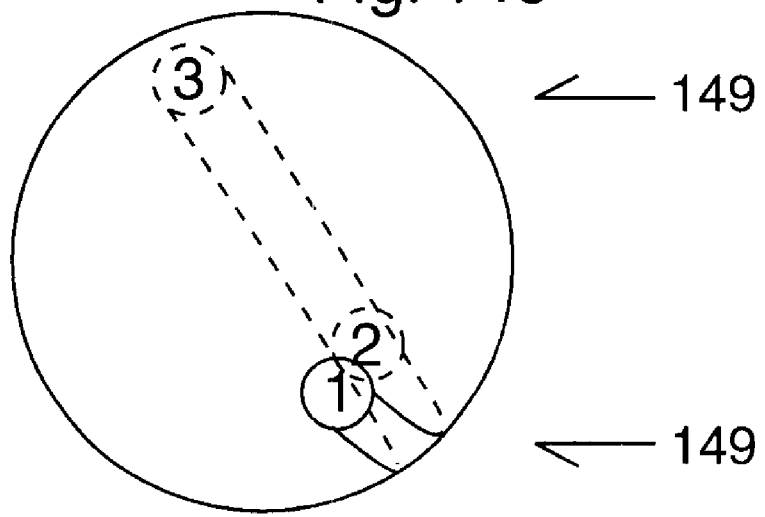

Referring to FIGS. 143–149, there will be described inner sphere marking variations. As previously described under PBPPV observations, the best sequence of head positions for clearing crystals from the posterior canal is the position sequence that would cause position No. 2 to have the top of the patient's head pointed directly downward. Moving the position bull's eye No. 2 to a position that requires greater neck extension in position No. 2 of posterior SCC BPPV treatment will increase the effectiveness of the maneuver. FIG. 143 illustrates an inner sphere 305 with a vertical equator 305VE. FIG. 144 is a view of FIG. 143 as seen along lines 144—144 thereof and illustrating the angular relationship of the three position bull's eyes. The position bull's eye No. 1 is 45 degrees from the vertical equator 305VE. The position bull's eye No. 2 is 45 degrees from the vertical equator on the opposite side from the bull's eye position No. 1. The position bull eye No. 3 is 135 degrees from the vertical equator on the same side of the vertical equator 305VE as position bull's eye No. 2. FIG. 145 shows the orientation of position bull's eyes No. 1, No. 2, and No. 3 relative to the vertical equator shown in FIG. 143. As previously noted, position No. 1 bull's eye is 20 degrees from the equator measured by the equator and a line from the center of the ball to position No. 1. Position No. 2 bull's eye is 30 degrees from the equator as measured from the equator and the line drawn from the center of the inner sphere to position No. 2. Position No. 3 is 20 degrees from the vertical equator measured by a line from the center of the inner sphere to the position bulls eye No. 3. Position bulls eye No. 3 is on the opposite side of the vertical equator from positions No. 1 and No. 2. FIGS. 146 and 147 show this location modification of position bull's eye No. 2. The increase in the extension of the neck during the transition from Position No. 1 to Position No. 2 increases the effectiveness of the posterior SCC BPPV crystal moving maneuver. Clinically it is difficult to find patients whose necks are limber enough to perform this greater than 20 degree extension in position No. 2, but for those who are able to extend further in position No. 2 than 20 degrees, it makes the maneuver more effective. FIGS. 146 and 147 show the same change in position bull's eye No. 2 for right posterior BPPV treatment first component. FIGS. 148 and 149 show the same change in position bull's eye No. 2 for left posterior BPPV treatment first component. The angular position No. 2 of the inner sphere 305 of the embodiment of FIGS. 18–24 may be modified in a similar manner.

Other Embodiments

First Component

Hanging Object Device

Referring now to FIGS. 150–165, there will be described a hanging object device which attaches to the user's head to measure head position and to give the user visual feedback about his head position or series of head positions.

Referring first to FIGS. 150 and 151, the first component 600 comprises a clear, transparent, plastic, hollow, outer sphere 602. From the top inside of the sphere 602, within the outer sphere is a indicator suspension rod 604 which extends from the dead top center 602C of the sphere 602 to the sphere mid-point 605. A flexible indicator suspension string 609 has one end attached to the mid point 606. An indicator 611 is attached to the other end of the string 609. The indicator suspension string 609 and indicator 611 are free to move, with the indicator being an object that will be controlled by gravity.

The hanging object device first component 600 is located within the second component 405. In FIG. 151, the sphere 602 is shown partially in the tube 405. The clear plastic tube second component 405 holds the hanging object sphere center 605 at the focal distance of the 20 diopter lens 410. The diameter outside of the hanging object device 600 is approximately equal to the inside diameter of the second component clear plastic tube 405. It is to be understood that the length of the tube 405 will be sufficient such that the full diameter of the sphere 602 will be located in the tube 405 with the center 605 at the focal length of the lens 410. In this configuration the user must be able to visualize the entire circumference of the hanging object device 600 in order to follow the indicator 611 movement within the sphere 602.

There are three spheres 602 used in this embodiment. One sphere 602D is used for diagnostic purposes and two spheres 602TR and 602TL are used for treatment purposes. All three spheres are hollow and have a transparent outer wall and have the indicator suspension rod 604, string 609 and indicator 611 of FIG. 150 and all three spheres will fit in a holding tube 405 as shown in FIG. 151. The diagnostic position mark configuration is shown in FIGS. 153–157. The treatment mark configuration for the treatment of right posterior SCC BPPV is shown in FIGS. 162, and 163 and for left posterior SCC BPPV is shown in FIGS. 164 and 165.

As in the preferred embodiment described previously, the orientation of the position marks and the numbering of the position marks can be arranged such that the hanging object device can be used to guide the user through head position sequences which will 1) position the head in classic Dix Hallpike diagnostic positions for right and left posterior SCC BPPV, 2) guide the user through the head position sequences which will allow the loosened crystals to fall out of the right or left posterior SCC resolving the symptoms of posterior SCC BPPV, or 3) guide the users through the head positions sequences which will allow the loosened crystals to fall out of the right or left horizontal SCC resolving the symptoms of horizontal SCC BPPV.

Hanging Object Device Position Mark Configuration

Diagnostic Position Mark Configuration

The locations of the position marks used in the hanging object device that will guide the user into the classic Dix Hallpike positions to help in the diagnosis of posterior SCC BPPV and to help differentiate right posterior SCC BPPV from left posterior clear SCC BPPV are shown in FIGS. 152–157. FIG. 152 shows the clear sphere 602D with a vertical equator 602VE. FIG. 153 is a view of FIG. 152 seen along lines 153—153 thereof. FIG. 153 indicates that from a top view, with the arrow 615 at the bottom of FIG. 153 showing the user's view of the R and L markers, each of these is 45 degrees to the right and left, respectively, of the line of sight of the user. FIGS. 154 uses the orientation of FIG. 152. FIG. 155 is a view of FIG. 154 as seen along lines 155—155 thereof. FIG. 155 indicates that the R and L position markings are 20 degrees above the horizontal equator 602HE. FIG. 156 shows the position marks of R and L from the users view on the outer sphere of the hanging object device. The lines 617 and 619 show the path the user is instructed to cause the indicator 611 to follow in his head motion to cause his head to come into the right and left Dix Hallpike diagnostic position. FIG. 157 is a view of FIG. 156 as seen along lines 157—157 thereof. FIG. 157 is the view of the R and L position marks shown in FIG. 156.

Hanging Object Device Position Mark Configuration

Posterior SCC BPPV Treatment Position Mark Configuration

The locations of the position marks used to guide the user's head through the sequence of positions which will cause the loosened crystals to fall out of the right and left posterior semicircular canals and hence resolve the symptoms of BPPV are shown in FIGS. 158–165. In FIGS. 158–161 the treatment sphere is identified at 602T. FIG. 158 shows the clear sphere 602T with a vertical equator. FIG. 159 is a view of FIG. 158 as seen along lines 159—159. FIG. 159 shows, from a top perspective, the orientation of position marks No. 1, No. 2, and No. 3. The arrow at the bottom of FIG. 159 shows the user's line of sight 621. FIG. 159 shows the orientation from the top of the right posterior semicircular canal treatment position marks. Position mark No. 1 is 45 degrees to the right of the viewer's perspective, where the angle is formed by the user's line of sight and a line from the center of the sphere to the position mark No. 1; position mark No. 2 is 45 degrees to the left of the user's line of sight, where the angle is formed by the user's line of sight and a line from the center of the sphere to the position mark No. 2 which is 45 degrees to the left. Position mark No. 1 and position mark No. 2 are 90 degrees from each other. Position mark No. 3 is 135 degrees to the left of the user's line of sight on the back side of the clear sphere. Treatment of the left posterior semicircular canal BPPV orientation is reversed such that position mark No. 1 is 45 degrees to the left of the user's line of sight and position mark No. 2 is 45 degrees to the right of the user's line of sight and position mark No. 3 is 135 degrees to the right of the user's line of sight. FIG. 160 again shows the same vertical equator diagram as FIG. 158 with FIG. 161 being a view of FIG. 160 as seen along lines 161—161 thereof. FIG. 161 indicates that position marks No. 1 and No. 2 in both right and left posterior semicircular canal BPPV treatment configurations are 20 degrees above the horizontal equator 602HE where the angle is formed by the user's line of sight and a line from the center of the sphere to the position marks No. 1 and No. 2; and position mark No. 3 is 20 degrees below the horizontal equator, whereby the angle is formed by the user's line of sight and line from the center of the sphere to the position mark No. 3.

FIG. 162 indicates the specific layout of the specific position mark location configuration on sphere 602TR for the treatment of right posterior semicircular canal BPPV. The perspective of FIG. 162 is the perspective of the user's line of sight 621 in FIG. 159. It shows position mark No. 1, 20 degrees above the horizontal equator 602HE and 45 degrees to the right of the user's line of sight. Position mark No. 2 is 20 degrees above the horizontal equator 602HE and 45 degrees to the left of the user's line of sight. Position mark No. 3 is 135 degrees to the left of the user's line of sight and 20 degree below the horizontal equator. Lines 607, indicate the path between mark Nos. 1, 2, and 3. FIG. 163 is a view of FIG. 162 as seen along lines 163—163 thereof. FIG. 163 shows position marks No. 1 and No. 2, 20 degrees above the equator 603HE, 90 degrees from each other. Position mark No. 2 is 45 degrees to the right of the user's line of sight. It shows position mark No. 3, 45 degrees to the left (See FIG. 163) of the user's line of sight and 20 degrees below the horizontal equator. The angle between position mark Nos. 2 and 3 is 90 degrees. FIG. 164 shows the position mark location configuration for the sphere 602TL of the hanging object device left posterior BPPV treatment position mark configuration. FIG. 164 is the view of the user's line of sight. In FIG. 164, position mark No. 1 is 20 degrees above the horizontal equator and 45 degrees to the left of the viewer's line of sight. Position mark No. 2 is 45 degrees to the right of the user's line of sight and 20 degrees above the horizontal equator. Position mark No. 3 is 20 degrees below the horizontal equator and 135 degrees to the right of the user's line of sight. Lines 607 indicate the path between mark Nos. 1, 2, and 3. FIG. 165 is a view of FIG. 164 as seen along lines 165—165 thereof FIG. 165 shows the position mark No. 1, 20 degrees above and 45 degrees to the right of the user's line of sight. Position mark No. 2 is 135 degrees to the right and 20 degrees above the horizontal equator. Position mark 3 is 135 degrees to the left of the user's line of sight and 20 degrees below the horizontal equator.

Hanging Object Device Method Description

Diagnostic Method Description

To diagnose the right and left posterior semicircular canal BPPV using the hanging object device.

The user is instructed to sit on the floor and/or mat and put the goggles over his eyes (with the combination 400, 602D in place) in such a manner that the clear sphere 602D, the position marks "R" and "L", and the indicator 611 are clearly seen, FIG. 27.

The user is instructed to lie supine in position "R", FIG. 28.

The pillow is rolled lengthwise and used longitudinally under the spine from C5 to L1. The user is instructed to place the pillow on the mat behind him such that the pillow will be positioned under his upper thoracic spine (not under this shoulder). He then is instructed to lie backward upon the pillow and the floor. The user is instructed to find the positioning mark "R", FIG. 156. The user is now instructed to find the indicator 611 and move his head such that he positions the indicator 611 proximate to position mark "R". He is to stay in this position for 30 seconds or until his dizziness resolves.

Sit on the floor and/or mat with goggles over his eyes, FIG. 27. The user is instructed to return to the upright sitting position and wait for his dizziness to resolve.

Lie supine in position "L", FIG. 29.

The pillow is rolled lengthwise and laid longitudinally under the spine from C5 to L1. He is instructed to place the pillow on the mat behind him such that the pillow will be placed under his upper thoracic spine (not his shoulder). He is instructed to lie backward upon the pillow and floor. The user is now instructed to find the indicator 611 and move his head such that the indicator 611 is positioned proximate to the position "L". He is to stay in this position for 30 seconds or until his dizziness resolves.

Return to sitting position, FIG. 27.

The user is instructed to sit upright. He is instructed to remove the goggles, wait 30 seconds or until his dizziness resolves.

The user is instructed to determine whether placing his head in the position such that the indicator 611 is approximate to the position mark "R" causes more dizziness than placing his head in the position such that the indictor 611 is proximate to "L" position mark. If the user has greater dizziness when the indicator 611 is proximate to "L", then the left posterior SSC is effected by BPPV. If the user has more dizziness when the indictor 611 is proximate to the "R" then the right posterior SCC is effected by BPPV.

Method For Posterior SCC BPPV Treatment

Treat Right Posterior SCC BPPV:

Sit on the floor and/or mat with goggles over eyes (FIG. 30) and the right posterior SCC hanging device treatment sphere 602TR in place.

The user is instructed to sit on the floor or on a mat and put the goggles over this eyes in such a manner that the clear outer sphere 602TR and the indicator 611 are clearly seen. The right posterior SCC BPPV treatment first component is 602TR in place.

Lie supine in position No. 1 (FIG. 31).

The pillow is rolled lengthwise and placed longitudinally under the spine from C5 to L1. The user is instructed to place a pillow on the mat behind him such that the pillow will be positioned under his upper thoracic spine (not under his shoulders). He is then instructed to lie backward upon the pillow and floor. The user now is instructed to visually find the indicator 611 (FIG. 150) and position it at position marking No. 1, FIGS. 162, 163. He is to stay in this position for thirty seconds or until his dizziness resolves.

Lie supine in position No. 2 (FIG. 32).

The user then moves his head such that the indicator 611 moves along the printed path 607 on the outer sphere until the indicator 611 moves to position marking No. 2. He is instructed to stay in this position for thirty second or until the dizziness resolves.

Lie on left side with head turned downward 135 degrees (FIG. 33).

The user now is instructed to roll upon his left side and simultaneously move his head such that the indicator 611 follows the printed path 607 to the position marking No. 3. He is instructed to remain in this position for thirty seconds or until the dizziness resolves.

Roll into crawl position (FIG. 34).

The user is instructed to move his head such that the indicator 611 stays aligned with the position mark No. 3, (FIGS. 162, 163) and roll toward his left side into a crawl position. He is to remain in this position for thirty seconds or until any dizziness resolves.

Come up to a kneeling position (FIG. 35).

The user is instructed to raise his torso into a kneeling position and steady himself for thirty second or until the dizziness resolves.

Either repeat or move goggles.

If the user was dizzy upon going from the crawl to the kneeling positions, the user is now instructed to repeat the maneuver. If there was no dizziness when the user goes form the crawling to the kneeling positions, the user is instructed to stop the maneuvers and remove the goggles.

Treat Left Posterior SCC BPPV:

Sit on the floor and/or mat with goggles over eyes (FIG. 36) and the left posterior SCC hanging device treatment sphere 602TL (FIGS. 164, 165) in place.

The user is instructed to sit on the floor or on a mat and put the goggles over this eyes in such a manner that the clear outer sphere 602TL and the indicator 611 are clearly seen. The left posterior SCC BPPV treatment first component 602TL is in place.

Lie supine in position No. 1 (FIG. 37).

The pillow is rolled lengthwise and placed longitudinally under the spine from C5 to L1. The user is instructed to place a pillow on the mat behind him such that the pillow will be positioned under his upper thoracic spine (not under this shoulders). He is then instructed to lie backward upon the pillow and floor. The user now is instructed to visually find the indicator 611 (FIG. 150) and position it at position marking No. 1, FIGS. 164, 165. He is to stay in this position for thirty seconds or until his dizziness resolves.

Lie supine in position No. 2 (FIG. 38).

The user moves his head such that the indicator 611 moves along the printed path 607 on the outer sphere until the indicator moves to position marking No. 2. He is instructed to stay in this position for thirty seconds or until the dizziness resolves.

Lie on right side with head turned downward 135 degrees (FIG. 39).

The user now is instructed to roll upon his right side and simultaneously move his head such that the indicator 611 follows the printed path 607 to the position marking No. 3 (FIGS. 164, 165). He is instructed to remain in this position for thirty seconds or until the dizziness resolves.

Roll into crawl position (FIG. 40).

The user is instructed to move his head such that the indicator 611 stays aligned with the position mark No. 3 (FIGS. 164, 165) and roll toward his right side into a crawl position. He is instructed to remain in this position for thirty seconds or until any dizziness resolves.

Come up to a kneeling position (FIG. 41).

The user is instructed to raise his torso onto a kneeling position and steady himself for third seconds or until the dizziness resolves.

Either repeat or remove goggle. If the user was dizzy upon going from the crawl to the kneeling positions, the user is now instructed to repeat the maneuver. If there was no dizziness when the user goes form the crawling to the kneeling position, the user is instructed to stop the maneuvers and remove the goggles.

Other Embodiments

First Component

Sand Particles in Tube Device

Referring to FIGS. 166–170, the device attaches to the user's head to reflect head position and to give the user visual feedback about his head position or series of head positions.

The device comprises a hollow torodial shaped tube 651 having a transparent wall 651T which contains a liquid 652 in which are located sand particles 653 or other types of particles or crystals. The sand particles can be used to give the user visual feedback about his head position for the diagnosis of post BPPV and the differentiation of right from left post BPPV, or his head position to allow the resolution of symptoms of right or left posterior SCC BPPV. The liquid may be water. The device 651 is mounted within the second component 400 as shown in FIGS. 167 and 168. FIG. 162 is a side view. FIG. 168 is a top view. In these Figures the clear plastic tube 405 and the 20 diopter lens 410 could be the same as in the preferred embodiment. The outer diameter of the toroid 651 is approximately equal to the inside diameter of the clear plastic tube 405.

For treatment of the right posterior SCC BPPV the second component 400 is configured in the following manner. From a top view FIG. 168, for use in the right posterior BPPV treatment the toroid 651R is located in the cylindrical tube 405 at an angle of 45 degrees relative to the axis of the member 405 with the distal edge of the toroid located close to the left side of the tube 405 as shown in FIG. 168. Thus the sand in the tube device 651 is aligned at 45 degrees from the line of the sight of the user. The position of the toroid 651 furthest from the user is positioned closest to the left side of the second component.

For treatment of left posterior SCC BPPV, the second component 400 is configured in the following manner. From a top view, FIG. 169, for use in the left posterior BPPV treatment, the toroid 651L is located in the cylindrical member 405 at an angle of 45 degrees relative to the axis of the member 405 with the distal edge of the toroid located to the right side of the member 405 as shown in FIG. 169. Thus the sand in the tube device 651 is aligned at 45 degrees from the line of the sight of the user. The portion of the tube circle furthest form the user is positioned closest to the right side of the second component.

For purposes of instruction, the sand in the tube device is divided into four 90 degrees areas. These areas are shown in FIG. 170. Area A is the bottom quadrant, Area B is the quadrant closest to the users eye. Area C is the top quadrant of the tube and Area D is the quadrant furthest from the user's eye.

Method for Posterior SCC BPPV Treatment

Treat Right Posterior SCC BPPV:

Sit on the floor and/or mat with goggles over eyes (FIG. 30).

The components 405, 651R will be coupled to the goggles 500.

The user is instructed to sit on the floor or on a mat and place the tube 651R configured for right posterior SCC BPPV treatment over his eyes in such a manner that the sand in the tube 651R is clearly seen.

Lie supine in position No. 1 (FIG. 31).

The pillow is rolled lengthwise and placed longitudinally under the spine from C5 to L1. The user is instructed to place a pillow on the mat behind him such that the pillow will be positioned under his upper thoracic spine (not under this shoulders). He then is instructed to lie backward upon the pillow and floor. The user is now instructed to extend his neck to allow the crystals to fall from the A area FIG. 170 of the tube 651R in the sand device into the B area of the 651R tube. He is to stay in this position for thirty seconds or until his dizziness resolves.

Lie supine in position No. 2 (FIG. 32).

The user then moves his head, keeping his neck extended, such that the crystals fall from B area to the top or C FIG. 170 area of the tube 651R. He is instructed to stay in this position for thirty seconds or until the dizziness resolves.

Lie on left side with head turned downward 135 degrees (FIG. 33).

The user now is instructed to keep his neck extended and to roll upon his left side and cause the crystals to fall from the C FIG. 170 area of the tube 651R into the D area of the tube 651R. He is instructed to remain in this position for thirty seconds or until the dizziness resolves.

Roll into crawl position (FIG. 34).

The user is instructed to keep his head in the position described immediately above then roll toward the left side into a crawl position. He is instructed to remain in this position for thirty seconds or until any dizziness resolves.

Come up to a kneeling position (FIG. 35).

The user is instructed to raise his torso into a kneeling position and steady himself for thirty seconds or until the dizziness resolves.

Either repeat or remove goggle. If the user was dizzy during the maneuver sequence, the user is now instructed to repeat the maneuver. If there was no dizziness during the maneuver sequence, the user is instructed to stop the maneuvers and remove the goggles.

Treat Left Posterior SCC BPPV:

Sit on the floor and/or mat with goggles over eyes (FIG. 36).

The components 405, 651L will be coupled to the goggles 500.

The user is instructed to sit on the floor on a mat and place the 651L configured for left posterior SCC BPPV treatment FIG. 169 over his eyes in such a manner that the sand in the tube 600L first component is clearly seen.

Lie supine in position No. 1 (FIG. 37).

The pillow is rolled lengthwise and place longitudinally under the spine form C5 to L1. The user is instructed to place a pillow on the mat behind him such that the pillow will be positioned under his upper thoracic spine (not under his shoulders). He then is instructed to lie backward upon the pillow and floor. The user is now instructed to extend his neck to allow the crystals to fall from the A area FIG. 170 of the 651L tube in the sand device into the B area FIG. 170 of the tube. He is to stay in this position for thirty seconds or util his dizziness resolves.

Lie supine in position No. 2 (FIG. 38).

The user then moves his head, keeping his neck extended, such that the crystals fall from B area FIG. 170 to the top or C area of the tube 651L. He is instructed to stay in this position for thirty seconds or until the dizziness resolves.

Lie on right side with head turned downward 135 degrees (FIG. 39).

The user now is instructed to keep his neck extended and in contact with the floor and to roll upon his right side and cause the crystals to fall from the C area FIG. 170 of the tube 651L into the D area of the tube. He is instructed to remain in this position for thirty seconds or until the dizziness resolves.

Roll into crawl position (FIG. 40).

The user is instructed to keep his head in the position described immediately above and roll toward the right side into a crawl position. He is instructed to remain in this position for thirty seconds or until any dizziness resolves.

Come up to a kneeling position (FIG. 41).

The user is instructed to raise his torso into a kneeling position and steady himself for thirty seconds or until the dizziness resolves.

Either repeat or remove goggle. If the use was dizzy upon going from the crawl to the kneeling positions, the user is now instructed to repeat the maneuver. If there was no dizziness when the user goes from the crawl to the kneeling position, the user is instructed to stop the maneuvers and remove the goggles.

Other Embodiment
First Component
Rolling Ball Embodiment

Referring to FIGS. 171–188, there will be described a rolling ball device which attaches to the user's head to measure head position and to give the user visual feedback about his head position or series of head positions. Diagrams 171–188 show the ridge path as solid lines on the foreground side of the sphere and ridge pair paths on the background side of the sphere as dotted, recognizing that all ridge pair paths are on the inner surface of the outer sphere.

In this embodiment the outer treatment sphere comprises a clear, transparent, plastic hollow sphere 700 as shown in FIG. 172. Within this clear outer sphere is a smaller inner sphere or ball 710. The inside diameter of the outer sphere is approximately 1½ inches. The outside diameter of the inner sphere 710 is approximately ¼ inch. It is to be understood that these dimensions may vary. The inner sphere is free to roll around within the outer sphere. On the outside surface of the outer clear sphere are printed position bull's eye which are marked "1", "2", and "3". On the inner surface of this clear plastic sphere are pairs of ridges 720A and 720B which outline or define a path 720P of travel for the small inner sphere 710.

The ridges 720A and 720B are approximately 5 mm apart and approximately 1 mm in height. It is to be understood that these dimensions may vary. In order to complete the maneuver, the user is to position his head such that he can maneuver the small inner sphere into an entrance 721 between the ridge pair near position bull's eye No. 1 and then move the ball along the ridge pair from position bull's eye No. 1 to No. 2, and to No. 3, pausing at each position bull's eye for his dizziness to resolve and then out of the ridge pair opening 723 on the opposite side of position bull's eye No. 3 from position bull's eye No. 2.

This ridge pair has the functional characteristic that as the inner sphere is moved along the ridge pair, if the user gets too far out of the head position maneuver sequence, the inner sphere will escape from the ridge pair track and the user will have to restart the maneuver by moving his head such that the inner sphere returns to position No. 1, where the inner sphere can reenter the ridge pair path and the maneuver can be repeated until it is performed properly. Additionally the height of the ridges can vary from one area of the ridge pair path to another. That is, in the portions of the maneuver in which positioning is less critical, the ridge pair path height can be higher, but in areas where head position is critical the ridge height can be lower. This allows the device to have head position maneuver tolerances built into the device.

The sphere 700 sits within the second component 405 shown in FIG. 174. The clear plastic tube second component 405 holds the rolling ball outer sphere center 700C, FIG. 172, at the focal distance of the 20 diopter lens 410. The diameter of the rolling ball outer sphere 700 is approximately equal to the inside diameter of the second component clear plastic tube 405. In this configuration the user must be able to visualize the entire circumference of the rolling ball device 700 in order to follow the inner sphere's 710 movement within the outer sphere.

The origination of the position marks and numbering of the position marks on the outer sphere 700 of the rolling ball embodiment are arranged such that the rolling ball embodiment is used to guide the user through head position sequences which will 1) position the head in classic Dix-Hall Pike positions for diagnosis of right or left posterior semicircular canal; 2) guide the head into classic Dix-Hall Pike positions for diagnostic differentiation of right posterior semicircular canal BPPV vs. left posterior semicircular canal BPPV, or 3) guide the user's head through head position sequences which will allow the loosened crystals to fall out of the right or left posterior semicircular canal, resolving the symptoms of posterior semicircular canal BPPV.

Rolling ball embodiment position mark configuration.
Diagnostic position mark configuration, The locations of the position marks used in the rolling ball device that will guide the user into the classic Dix-Hall Pike positions to help in the diagnosis of posterior semicircular canal BPPV and to help differentiate right from left posterior semicircular canal BPPV are shown in FIGS. 175–180. FIGS. 175–180 illustrate a hollow outer diagnostic sphere 700D with inside ridges 720AD and 720BD forming a path 720PD for an inner ball or sphere 700D. FIG. 175 shows the clear outer sphere 700D with a vertical equator 700DVE. FIG. 176 is a view of FIG. 175 as seen along lines 176–176 thereof. In FIG. 176, the arrow at the bottom of the figure is the user's view of the "R" and "L" markings. From the perspective of FIG. 176, the "R" marking is 45 degrees to the right of the user's line of sight and the "L" marking is 45 degrees to the left of the user's line of sight. FIG. 177 has the orientation of FIG. 175.

FIG. 178 indicates that the "R" and "L" position markings are 20 degrees above the horizontal equator 700DHE.

FIG. 178 is a view of FIG. 177 as seen along lines 178—178 thereof. The 20 degree angle is formed between a line between the center of the horizontal equator and a line that extends from the center of the ball to the positions "R" and "L". FIG. 179 shows the position marks "R" and "L" from the user's point of view from the outer surface of the sphere 700. The dotted lines show the raised ridge pair path 720P of the clear plastic outer sphere 700. The inner sphere must enter the ridge pair 720P at the bottom or near the bottom of the clear outer sphere at 720DE and roll along the path to the "R" position mark or "L" position mark. FIG. 180 is a view of FIG. 179 as seen along lines 180—180 thereof. In FIG. 180, the right mark is behind and in line with the left mark and is not shown. It again shows that the "R" and "L" markings are 20 degrees above the horizontal equator as demonstrated in FIG. 178.

Rolling ball device position mark configuration.
Posterior semicircular canal BPPV treatment position mark configuration.

The locations of the position marks used to guide the user's head through the sequence of positions which will cause the loosened crystals to fall out of the right and left posterior semicircular canals and resolve the symptoms of BPPV are shown in FIGS. 181–188. FIG. 181 shows the clear plastic outer sphere 700 with the vertical equator 700VE. FIG. 182 shows the horizontal plane orientation of position marks No. 1, No. 2, and No. 3. FIG. 182 is a view of FIG. 181 as seen along lines 182—182. The arrow at the bottom of FIG. 182 indicates the user's line of sight. In right posterior semicircular canal BPPV configuration, shown as an example in FIG. 182, position Nos. 1 mark is 45 degrees to the right of the line formed by the user's line of sight and a line going from the center of the sphere to the position mark No. 1. Position mark No. 2 is 45 degrees to the left of the user's line of sight. The 45 degree angle is formed between the line of sight of the user and a line going from the center of the sphere to the position No. 2. Position No. 3 is 135 degrees to the left of the user's line of sight. FIG. 183 shows the clear plastic outer sphere 700 with the vertical equator 700VE. FIG. 184 is a view of FIG. 183 as seen along lines 184–181 thereof. FIG. 184 shows that position marks No. 1 and No. 2 in both right and left posterior semicircular canal BPPV treatment configuration are 20 degrees above the horizontal equal when the 20 degrees is measured between the horizontal equator 700HE and the line going from the center of the sphere to the position marks No. 1 and No. 2. Position mark No. 3 is 20 degrees below the horizontal equator as measured by an angle between the horizontal equator and a line going from the center of the sphere to the position mark No. 3.

FIG. 185 shows the position marking configuration for right posterior semicircular canal BPPV treatment. Position No. 1 with its associated ridge pair opening is seen 20 degrees above the equator and 45 degrees to the right of the line of sight of the user. Position No. 2, within the ridge pair path, is 45 degrees to the left of the line of sight of the user and 20 degrees above the horizontal equator. Position No. 3 is 135 degrees to the left of the line of sight of the user and 20 degrees below the horizontal equator. The ridge pair path opens after position mark No. 3. FIG. 186 is a view of FIG. 185 as seen along lines 186—186 thereof. In FIG. 186, the position mark No. 1 is immediately behind the position mark No. 2 and 20 degrees above the horizontal equator. The position mark No. 1 is 135 degrees to the right of the user's line of sight. Position mark No. 2 is 20 degrees above the horizontal equator and 45 degrees to the right of the line of sight of the user. Position mark No. 3 is 45 degrees to the left of the line of sight of the user and 20 degrees below the horizontal path.

The left posterior semicircular canal BPPV treatment configuration is shown in FIG. 187. In this Figure, position mark No. 1 is 45 degrees to the left of the line of sight of the user and 20 degrees above the horizontal equator. It is surrounded by a ridge pair path with an opening into the ridge pair path left of the position mark No. 1. The position mark No. 2 is 45 degrees to the right of the line of sight of the user and 20 degrees above the horizontal equator. It is surrounded by a ridge pair path. The ridge pair path leads to the position mark No. 3. Position mark No. 3 is 135 degrees to the right of the line of sight of the user and 20 degrees below the horizontal equator. FIG. 188 is a view of FIG. 187 as seen along lines 188—188 thereof FIG. 188 shows position mark No. 3, 20 degrees below the horizontal equal and 45 degrees to the left of the line of sight of the user.

Rolling Ball Embodiment Method
Method for Posterior SCC BPPV Treatment

Treat right posterior SCC BPPV: The components 405, 700R will be coupled to goggles 500.

Sit on the floor and/or mat with goggles over eyes (FIG. 30).

The user is instructed to sit on the floor or on a mat and put the goggles with the rolling ball embodiment first component 700R for right posterior SCC BPPV treatment configuration over his eyes in such a manner that the clear sphere 700R and inner sphere 710 are clearly visible.

Lie supine in position No. 1 (FIG. 31).

The pillow is rolled lengthwise and placed longitudinally under the spine from C5 to L1. The user is instructed to place a pillow on the mat behind him such that the pillow will be positioned under his upper thoracic spine (not under his shoulders). He then is instructed to lie backward upon the pillow and floor. The user now is instructed to move his head such that the inner sphere enters at 721 the ridge pair path 720P and moves to position mark No. 1. He is to stay in this position for thirty seconds or until his dizziness resolves.

Lie supine in position No. 2 (FIG. 32).

The user then moves his head such that the inner sphere 710 rolls along the ridge pair path 720P from the position mark No. 1 to position mark No. 2. He is instructed to stay in this position for thirty second or until the dizziness resolves.

Lie on left side with head turned downward 135 degrees (FIG. 33).

The user now is instructed to roll upon his left side and simultaneously move his head such that the inner sphere 710 rolls along the ridge pair path 720P from position mark No. 2 to position mark No. 3. He is instructed to remain in this position for thirty seconds or until the dizziness resolves.

Roll into crawl position (FIG. 34).

The user is instructed to keep his head in a constant position with the inner sphere 710 at position mark No. 3 while moving from lying on left side to a crawl position. He is instructed to remain in this position for thirty seconds or until any dizziness resolves.

Come up to a kneeling position (FIG. 35).

The user is instructed to raise his torso into a kneeling position and steady himself for thirty seconds or until the dizziness resolves.

Either repeat or remove goggle. If the user was dizzy during the maneuver sequence, the user now is instructed to repeat the maneuver. If there was no dizziness during the maneuver sequence, the user is instructed to stop the maneuvers and remove the goggles.

Treat left posterior SCC BPPV: The components 405, 700L will be coupled to goggles 500.

Sit on the floor and/or mat with goggles over eyes (FIG. 36).

The user is instructed to sit on the floor or on a mat and put the goggles with the rolling ball embodiment first component 700L FIGS. 187, 188 for left posterior SCC BPPV treatment configuration over his eyes in such a manner that the outer clear sphere 700L and inner sphere 710 are clearly visible.

Lie supine in position number 1 (FIG. 37).

The pillow is rolled lengthwise and placed longitudinally under the spine from C5 to L1. The user is instructed to place a pillow on the mat behind him such that the pillow will be positioned under his upper thoracic spine (not under his shoulders). He then is instructed to lie backward upon the pillow and floor. The user now is instructed to move his head such that the inner sphere 710 enters at 721 the ridge pair path 720P and moves to position mark No. 1. He is to stay in this position for thirty seconds or until his dizziness resolves.

Lie Supine in position number 2 (FIG. 38).

The user then moves his head such that the inner sphere 710 rolls along the ridge pair path from the position mark No. 1 to position mark No. 2. He is instructed to stay in this position for thirty seconds or until the dizziness resolves.

Lie on right side with head turned downward 135 degrees (FIG. 39)

The user now is instructed to roll upon his right side and simultaneously move his head such that the inner sphere 710 rolls along the ridge pair path from position mark No. 2 to position mark No. 3. He is instructed to remain in this position for thirty seconds or until the dizziness resolves.

Roll into crawl position (FIG. 40).

The user is instructed to keep his head in a constant position with the inner sphere 710 at position mark No. 3 while moving from lying on right side to a crawl position.

He is instructed to remain in this position for thirty seconds or until any dizziness resolves.

Come up to a kneeling position (FIG. 41).

The user is instructed to raise his torso into a kneeling position and steady himself for thirty seconds or until the dizziness resolves.

Either repeat or remove goggle. If the user was dizzy during the maneuver sequence, the user now is instructed to repeat the maneuver. If there was no dizziness during the maneuver sequence, the user is instructed to stop the maneuvers and remove the goggles.

Electronic Configuration Embodiment

This device attaches to the user's head to measure or determine head position and to give the user visual feedback about his head position or series of head positions.

Introduction

A method of measuring three dimensions of spatial orientation is described herein. The specific application is to measure the orientation of a patient's head as he/she under goes treatment for dizziness. The procedure is to measure gravitational acceleration to ascertain attitude and illuminate indicators to direct the patient's head motion. This apparatus comprises an embedded computer, and two accelerometers, each being capable of measuring two dimensions of static acceleration, and a means of displaying motion cues to the patient. Spatial attitude is measured by the declination of the head and rotation about the declination axis.

Hardware Description

FIGS. 189A, 189B, 189C, 189D diagram the electronic circuitry used to measure spatial orientation and operate the Light Emitting Diodes (LED). The circuitry is partitioned into five sections labeled:

Gravity Sensors, 803 comprising sensors U1 and U2

Selection and Routing system 805,

Micro Controller 807,

Patient Display 809,

Voltage Regulator 811

Some connections between the sections are indicated by connector flags, e.g. T1CLK.

Various micro chips are referenced by "U" numbers. Chips U3 through U5 and U7 are industry standard parts manufactured by several major manufacturers, such as Motorola U4 and U5 are type 4013 D flip flops.

Gravity Sensors

Acceleration is measured in two planes XY, and YZ by acceleration sensors U1 and U2. See FIG. 191. Each sensor measures two 90 degree components in the earth's gravity field. The measurements are a function of the orientation of U1 and U2 in the earth's gravity field. Analog Devices Inc., manufactures the ADXL202 sensor. The ADXL202 is a low cost 2 axis accelerometer capable of measuring static gravity field. Three dimensional measurements are made with a pair of these sensors.

Rotation is measured in the XY plane and declination is measured in the YZ plane. See FIG. 191. The raw acceleration information for the two planes is referenced by Rx, Ry for the rotation plane and Dy and Dz for the declination plane. Acceleration data are encoded in a pulse format.

FIG. 190 illustrates the format of the sensor outputs and the sequence involved in interpreting the pulses. The X, Y, Z trace is typical for the three axis and is representative of one of the Rx, Ry, Dx, Dy pulse measurements which will be obtained. Separate X, Y, Z traces can be depicted for each of the Rx, Ry, Dy, Dz measurements made. Each pulse output is periodic over the interval T0 through T2. Acceleration is represented by the duration of the interval T0–T1 as a percentage of the total interval T0–T2. This format is commonly referred to as "duty cycle" encoding.

$$\text{Acceleration}=(T1-T0)\,(T2-T0) \tag{1}$$

The sensors are set to a T0–T2 interval of ten milliseconds. Resistors R1 and R2 set this interval. The bandwidth of the sensor outputs is limited to 10 Hz by capacitors C1–C4. This bandwidth (response time) is adequate for the measurement of head motion.

Selection and Routing

The four Rx, Ry, Dy, Dz pulses are sequentially selected by U3 and routed to the micro controller through gates U6A and U6B. The controller specifies which channel is selected by inputs to $S_0$ and $S_1$ of U3.

The purpose of the routing logic is to separate the two intervals, ($T_1-T_0$ and $T_2-T_0$) and route a stream of pulses to counters contained in the controller. Refer to FIGS. 189A, 189B, 189C, 189B and 190. Time measurements are accomplished by counting the precision pulses ($T_1$CLK and $T_2$CLK). The clock pulses are sourced from the ALE output of U8, and divided by 2 by U5B, resulting in a 500 kilohertz (kHz) clock, (two microsecond pulse spacing).

The micro controller starts a measurement by asserting ENAB CNT. The COUNT flip flop is set by ENAB CNT. The T2GATE flip flop is set at the beginning (T0) of the period and is reset at the end of the period T2 by ACK. The presence of T2GATE, and COUNT gate the 500 kHz clock into the counter inputs, T2CLK. Simultaneously T1GATE and COUNT gate the 500 kHz clock to the T1CLK counter. When the T0–T2 interval ends, flip flop U4B is set signaling data is ready (DAT RDY). The micro controller acknowledges by issuing ACK which resets the gating circuitry.

A complete set of measurements requires 40 milliseconds. Processing the data requires approximately 50 milliseconds. The display is updated at about 10 Hz. The patient should not perceive a delay between head motion and LED feedback.

Micro Controller

Atmel manufactures the AT89S53 micro controller. This device incorporates an industry standard 8051 architecture, implemented with low power CMOS technology. The device contains an 8 bit micro processor, 12 Kbytes of flash memory, two counters, and four byte wide input/output ports. A 12 MegaHz crystal clocks the internal operations. A one MegaHz external timing pulse (ALE) is derived from the 12 MegaHz crystal. Device U5B divides the ALE pulses by two resulting in a precision 500 kHz pulse stream.

The control program is stored internally in flash memory. Flash memory can be re-programmed as opposed to "one time programmable" memories that are "burned" into memory. The software contains the control parameters including angles and dwell times.

Initial conditions are set when Power is turned on R3 and C5 create a RESET pulse which causes the controller to start execution at the beginning of the program. A procedure is selected from a set of four procedures by switches S2 through S5.

Diagnostic Left (DIAG L): Switch S2

Diagnostic Right (DIAG R): Switch S3

Left Post SCC BPPV Treatment (LP SCC): Switch S4

Right Post SCC BPPV Treatment (RP SCC): Switch S5

Calibration is required for the sensor inputs because each sensor has different sensitivities and offset values. A calibration procedure is performed during the manufacturing process. The calibration constants are embedded in the software and are referred to as OFFSET and SCALE values for each channel and allow the measurements made during the treatment process to be converted into sin and cos angles of rotation and declination.

Patient Display

Five Light Emitting Diodes (LED) D1, D2, D3, D4, D5 indicate the required motion action. Declination motion is indicated by UP and DOWN, while RIGHT and LEFT indicate the rotation motion. Dwell position is indicated by the STOP indicator. One or two LED's will always be on. The motion indicators are arranged as shown in FIG. 192. The goggle device is shown in FIGS. 201–204.

Voltage Regulator

The sensor outputs are affected to the power supply voltage. A precision regulator U7 manufactured by National Semiconductor, fixes the supply voltage at a constant five volt level. This device is a low power chip designed for battery operated equipment. Power is sourced from a small 6 volt battery. Lithium cells are preferred, for weight and performance reasons. Battery life is extended by turning the unit off with S1 when not in use.

Software Description

The objective is to lead the patient's head through four specific paths, diagnostic left and right, right post SCC BPPV treatment and left post SCC BPPV treatment, pausing where he/she dwells for a time. The path is specified by a set of angles defining the rotation and declination path the head is to follow as specified in Table 1, diagnosis, Table 2, right post SSC BPPV treatment, and Table 3, left post SCC BPPV treatment. The complete process is divided into four user selectable procedures as described above.

Data Structure

A path is specified by twelve pairs of angles, where each pair represents a marker along the selected path. Table I shows the data for two diagnostic procedures.

TABLE 1

Diagnostic Procedure

| | Diagnostic | | | |
|---|---|---|---|---|
| | Diagnostic left | | Diagnostic right | |
| Step | Rotation | Declination | Rotation | Declination |
| 1 | 90 | 90 | 90 | 90 |
| 2 | 94 | 80 | 86 | 80 |
| 3 | 98 | 70 | 82 | 70 |
| 4 | 102 | 60 | 78 | 60 |
| 5 | 106 | 50 | 74 | 50 |
| 6 | 110 | 40 | 70 | 40 |
| 7 | 114 | 30 | 66 | 30 |
| 8 | 118 | 20 | 62 | 20 |
| 9 | 122 | 10 | 58 | 10 |
| 10 | 126 | 0 | 54 | 0 |
| 11 | 130 | 350 | 50 | 350 |
| 12 | 135 | 340 | 45 | 340 |

The last step (12), is the dwell position. The patient remains in the dwell position to allow time for the particles to reposition. Two paths are represented in Table 1. The first path is diagnostic left where the patient begins in a sitting position and gradually reclines while rotating his/her head to the left to the 135 degrees position and declining to 340 degrees (20 degrees below horizontal). Diagnostic right begins in the sitting position and ends with the head right at 45 degrees declining again to 340 degrees.

Tables 2 and 3 are paths for the two SCC treatment procedures. As with the diagnostic procedure, step twelve is the dwell state for these as well.

TABLE 2

Right Position SCC BPPV Treatment Paths
Right Post SCC BPPV Treatment

| | Position No. 1 | | Position No. 2 | | Position No. 3 | | Position No. 4 | |
|---|---|---|---|---|---|---|---|---|
| Step | Rotation | Declination | Rotation | Declination | Rotation | Declination | Rotation | Declination |
| 1 | 90 | 90 | 45 | 340 | 135 | 340 | 225 | 340 |
| 2 | 86 | 80 | 53 | 340 | 143 | 340 | 225 | 351 |
| 3 | 82 | 70 | 61 | 340 | 151 | 340 | 225 | 2 |
| 4 | 78 | 60 | 69 | 340 | 159 | 340 | 225 | 13 |
| 5 | 74 | 50 | 77 | 340 | 167 | 340 | 225 | 35 |
| 6 | 70 | 40 | 85 | 340 | 175 | 340 | 225 | 24 |
| 7 | 66 | 30 | 93 | 340 | 183 | 340 | 225 | 35 |
| 8 | 62 | 20 | 101 | 340 | 191 | 340 | 225 | 46 |
| 9 | 58 | 10 | 109 | 340 | 199 | 340 | 225 | 57 |
| 10 | 54 | 0 | 117 | 340 | 207 | 340 | 225 | 79 |
| 11 | 50 | 350 | 125 | 340 | 215 | 340 | 270 | 90 |
| 12 | 45 | 340 | 135 | 340 | 225 | 340 | 270 | 90 |

TABLE 3

Left Position SCC BPPV Treatment Paths
Left Post SCC BPPV Treatment

| | Position No. 1 | | Position No. 2 | | Position No. 3 | | Position No. 4 | |
|---|---|---|---|---|---|---|---|---|
| Step | Rotation | Declination | Rotation | Declination | Rotation | Declination | Rotation | Declination |
| 1 | 90 | 90 | 135 | 340 | 45 | 340 | 315 | 340 |
| 2 | 94 | 80 | 127 | 340 | 37 | 340 | 315 | 351 |
| 3 | 98 | 70 | 119 | 340 | 29 | 340 | 315 | 2 |
| 4 | 102 | 60 | 111 | 340 | 21 | 340 | 315 | 13 |
| 5 | 106 | 50 | 103 | 340 | 13 | 340 | 315 | 35 |
| 6 | 110 | 40 | 95 | 340 | 5 | 340 | 315 | 24 |
| 7 | 114 | 30 | 87 | 340 | 357 | 340 | 315 | 35 |
| 8 | 118 | 20 | 79 | 340 | 349 | 340 | 315 | 46 |
| 9 | 122 | 10 | 71 | 340 | 341 | 340 | 315 | 57 |
| 10 | 126 | 0 | 63 | 340 | 333 | 340 | 300 | 79 |
| 11 | 130 | 350 | 55 | 340 | 325 | 340 | 285 | 90 |
| 12 | 135 | 340 | 45 | 340 | 315 | 340 | 270 | 90 |

Time Considerations

Movement through a path is not timed. The patient is prompted only to rotate and/or tilt the head while moving to the next dwell position. When the head reaches position 12, a thirty second dwell interval begins. Some persons may have difficulty maintaining a fixed position. For this reason, short term excursions outside the dwell zone are timed by the shake timer. Shake time defines an allowable time to stay out of the dwell zone before restarting the dwell period. Three seconds are allowed for the shake time. If shake time is exceeded the dwell time is re-started.

Math Model

The math model shown in FIG. 191 shows how angles are defined. The declination angle is defined as a vector through the center of the head extending through the center of rotation for the head. When the head is in the sitting position, the declination angle is 90 degrees. At rest (supine) position (face looking up while reclining on back), the declination angle is 0 degrees. Tilting the head 20 degrees below the 0 degrees mark, results in a declination angle of 340 degrees.

The head is rotated about the declination vector. Rotation is measured by an angle in the XY plane, where looking up is 90 degrees, to the right is 0 degrees, and to the left is 180 degrees. As the declination angle changes, so does the XY plane. To compute the real rotation angle, the XY plane must be referred back to a vertical plane. This is accomplished by first determining the declination angle DECz, then computing a normalization factor ROT NORM to be applied to the observed X and Y vectors. This factor is computed by:

$$ROT\ NORM=1.00\ \cos(DECz) \tag{2}$$

Calibration and Calculation Details

FIGS. 231A–233A and 231B–233B show relative timing for three spatial orientations used to establish the calibration values for the sensor. The values measured during calibration become constants describing the specific properties of the sensor. Each sensor has a set of unique constants. The constants are stored in the computer memory and are used to calculate the actual orientation angles for the sensor. FIGS. 234A, 234B and 235A, 235B depict the sensor output for 45 degrees and 335 degrees orientation. Detailed calculations will be performed for these orientations.

Referring to FIGS. 231A and 231B, note the arrows (upper left), representing the acceleration vectors for the sensor. For this discussion, it is assumed that the plane of rotation is parallel to the gravitational field, so correction for declination is not required. In FIG. 213B, the broad arrow pointing upward near the middle of the Ry line points to a reference time noted as Tos.

The objective of the calibration procedure is to measure the duty cycle for the two angular extremes; 90 degrees and 270 degrees, and the midpoint, at 0 degrees. The duty cycle at the midpoint Tos, is used as a reference for the calculations. Variations about the reference are proportional to the angular variation about the zero degree reference. The reference at zero degrees is referred to as the "offset", somewhat analogous to the term "basis" used in some financial calculations to evaluate the performance of an investment instrument.

For discussion, focus upon the Ry vector (FIGS. 231A, 231B), which is oriented parallel to the gravity field. At this position, the value will be a maximum value, that is, the time from T0 to T1 is maximum. Thus, there has been established the output from the sensor associated with highest output that can be expected, which is 100% of the gravity field. This value defines the 90 degrees sensor output.

When the sensor is rotated clockwise to a position shown in FIGS. 232A, 232B, the Ry vector is normal to the gravity field. The zero degree position (Tos) is chosen as the reference for calculations. This means variations of Ry above this point are considered as movement in the counterclockwise direction toward 90 degrees. Ry duty cycles less than Tos are considered to be movement in the clockwise direction.

The last calibration point for the Ry vector is at 270 degrees where the sensor experiences 100% negative gravitational acceleration, meaning the sensor is physically inverted. The value read at this point represents the minimum extreme for the sensor output. Note that the duty cycle (FIGS. 233A, 233B) is now less than the reference Tos. The sensor output is linear, so there now is enough information to calculate the sensor orientation for any duty cycle.

The micro controller reads the sensors by counting a precision pulse stream that is gated by the Ry pulse. The period, or, cycle time is gated by the T2 GATE. The precision pulse stream has a rate of 500,000 pulses per second. The cycle time (T0 to T2), is 0.01 second. So there is a period measurement of 500,000×0.01 second=5000 counts. At zero degrees, midpoint, as shown in FIGS. 232, 232B, the sensor will be near 50% duty cycle, therefore the Tos output count will be 2500 counts. The sensor output varies ±12.5% (of period) from Tos for ±90 degrees changes, resulting in a range of ±0.125×5000, or ±625 counts. It is expected that T1CLK will be somewhere between 1875 and 3125 counts. The duty cycle extremes will be different for each sensor, but remain constant for each sensor. A perfect sensor operated under the aforementioned conditions will have a set of constants such as:

Constant Value Where it came from
  RyOFFSET (Tos): 2500 [Count at 0 degrees]
  RyMaxCount at 90 degrees 3125 [Count at 90 degrees= 2500+625]
  RyMinCount at 270 degrees 1875 [Count at 270 degrees=2500−625]

The ±625 variation about 2500 (Tos) is proportional to the sine of the rotation angle. The maximum value for the sine is 1.00, hence the scale factor is calculated by scaling the 625 count span to 1 by:

RySCALE=1/625=0.0016

Calculation of an Angle
  Case 1: 45 degrees

With the constants Tos and RySCALE, there can be calculated an angle for a dwell time. A 45 degrees rotation is depicted in FIGS. 234A, 234B. Note that T0 T1 time exceeds the T0–Tos time, so it is known that the angle is between 0 and 90 degrees. At 45 degrees, the output will be sin(45)×RySCALE.

First it is found out what the sensor would produce at 45 degrees

Ry Count=RyOFFSET+sin(RotAngle)×RySCALE
  Ry Count=2500+0.707×625
  Ry Count=2942

This is the count that will be received from the sensor for Ry at 45 degrees.

To convert this number into an angle, first remove the offset:

Ry=Ry−ROFFSET
  Ry=2942−2500=442

Next the number is scaled to get a sine sin(RyAngle)=442×0.016=0.707

To find the Rotation angle, take the arcsine

ROT=arcsine(0.707)=45 degrees
  Case 2: 325 (−25 degrees)

At 335 degrees, the sensor will output

Ry Count=RyOFFSET+sin(ROT Angle)×RySCALE
  Ry Count=2500+(−0.4226)×625=2500−264=2236 counts Given this count from Ry, the angle can be found the by Ry=Ry−RyOFFSET
  Ry=2236−2500=−264

Scaling

Ry=−264×0.0016=−0.4224

Finding the angle

Ry=arcsine (−0.4224)=24.98°

Transposing to the reference frame (FIG. 191 Math Model)

Ry=360−25=335°

Control Flow

Refer to FIGS. 193–200 for the flow charts describing the software operations. Starting with RESET at 821 in FIG. 193, the flow initializes the system at 822 then goes into a continuous loop beginning at operation 823 consisting of reading the switches and sensors, determining what procedure to follow, calculating the angles and optimizing the choice of which vector to use. At 824–827 switches S2–S5 (See FIG. 189C) are scanned to determine which procedure to follow. Initialization at 822 includes Clear Counters. Reset Router, DEC POS=FALSE, ROT POS=FALSE, SHAKETIMER=FALSE, ALL LED OFF, PROCEDURE=0. Each procedure is defined by a table of data that specifies a path, and dwell position.

All procedures follow the same set of rules, the difference being the data table associated with the selected procedure. After determining the current spatial orientation, a test for subsequent action is performed. If a dwell position is not detected, then the patient is directed to the next position according to the path in the data table. If dwell conditions exist, the dwell time is monitored as well as continued maintenance of the position indicators.

Operation

The control loop begins at the OPERATION connector 823, FIG. 193B. The procedure switches are scanned. When a switch is activated, the current procedure is terminated, and the new one begins immediately. Raw data for the procedure is loaded at 828–831 into the active array and the number of paths for the procedure is updated. The following procedures are carried out at 828–831: Load Diag L Tables (Number of Paths=1; Load Diag R Tables (Number of Paths=1; Load RPSCC Tables (Number of Paths=4; Load RPSCC Tables (Number of Paths=4.

At 832 the following parameters are set. Operate=True; Pathname=1; Stepnum=1; ROTMAX=ROTn+RDEL; ROTMIN=ROTn−RDEL; DECMAX=DECn+DDEL; DECMIN=DECn−DDEL wherein RDEL and DDEL are the limits of tolerance which may be ±3 degrees. At 833 OPERATE is tested to determine if switch, polling is to continue.

Read Accelerometers

Beginning with Read Accelerometers, raw acceleration values Rx, Ry, Dy, Dz are read at 842 by the internal counters of the micro controller. The duty cycle for each axis is calculated at 842 by the equation (1) described previously. The axis values are converted into actual acceleration vectors using the offset and scaling constants obtained at calibration. At 843, the sensor offset values referred to previously and defined at R Offset and D Offset are subtracted from the pulse values Rx, Ry, Dy, Dz and the resulting values are multiplied by the scale of factors R Scale and D Scale to allow the resulting pulse values to be converted to sin and cos of orientation angles to obtain the orientation of the sensors in the earth's gravity field. At 844 and 845, the declination angles are computed from each of the declination sensors, e.g. one for the Y axis (DECy)=A COS (Dy) and one for the Z axis (DECz=A SIN (Dz), wherein A COS is the arc cos and A SIN is the arc sin. ROTx and ROTy would be identical for a perfect sensor. However, accuracy of the computed angles is dependent upon the orientation. In this respect each sensor measures two components of gravity. Initially one component is parallel to the gravity axis while the other is normal to the gravity axis. The vector normal to gravity is most sensitive. As rotation continues, X sensitivity diminishes, while Y sensitivity improves. Choosing the most sensitivity vector improves overall performance.

At 844 the normalizing factor is calculated by:

$$At\ ROT\ NORM=1.00\ COS(DECz)$$

This factor is used to multiply the Rx and Ry values which converts them to normal rotation. The rotation angle ROTx, is computed by taking the arc cosine of the normalized cosine vector Rx, $$ROTx=A\ COS(Rx\times ROT\ NORM) \qquad (3)$$

Similarly, the rotation angle ROTy is computed from the vector Ry by taking the arc sin of the normalized sin vector Ry, $$ROTy=A\ SIN(Ry\times ROT\ NORM) \qquad (4)$$

Select R Vector

Using the X vector results ROTx, for reference, one of the two angle solutions is selected to define the rotation angle. The choice is made by the flow shown in FIG. 195 beginning with Select Vector 851 and continuing from 852–858. Accuracy for both vectors is about equal in the regions near the switch points. FIG. 196 represents a decision model wherein the y and x components are selected between the angles shown.

Pathfinder

This segment beginning at 861 in FIGS. 197A, 197B guides the patient through the path specified in the data table. FIGS. 187A and 197B are connected by 197L1. At 862, if step 12 is the current step, then a dwell position exists, and the flow is directed to the dwell test 881. Otherwise, the rotation and declination angles are tested against the maximum and minimum limits and the appropriate LED is activated to keep the head within the path limits. Acceptable limit conditions are signaled by ROT OK at 867 and DEC OK 872. When both conditions are satisfied, the step number is incremented at 874 and the guidance process continues until step 12 is reached. When step 12 entered the flow is directed to the dwell test 881.

Referring again to FIGS. 197A, 197B, the rotation is tested against the minimum limit at 863 (ROT−ROTMN) and against the maximum limit at 865 (ROT−ROTMAX). If rotation is below the minimum the right LED is turned off and the left LED is turned on at 864.

At 865 rotation is tested against the maximum limit (ROT−ROTMAX). If the rotation is above the maximum, the right LED is turned on and the left LED is turned off at 866. If the rotation is OK at 867 (ROT OK) the path goes to 868 where the declination is tested against the minimum limit (DEC−DECMIN). If declination is below minimum at 869, the up LED is turned on and the down LED is turned off. At 870 the declination is tested against the maximum limit, (DEC−DECMAX). If the declination is above maximum at 871, the up LED is turned off and the down LED is turned on. If the Declination is OK at 872 (DEC OK=TRUE) and the Rotation is OK at 873 (ROT OK=TRUE), the path goes to the increment step at 874 where DEC OK is set equal it False; ROT OK is set equal to False; and the Minimum and Maximum parameters are updated.

If step 12 is not reached at 862, the path goes back to operate at 823. If step 12 is reached, the path goes to Dwell Test at 881.

Dwell Test

A dwell condition exists when the rotation and declination angles fall within a window specified in step 12, +5°, for instance, the dwell window for Diagnostic left (table 1) would be 130°<Rotation<140°

335°<Declination<345°.

Referring to FIG. 198, at 882 and 884, the first two tests compare the declination (DEC) to the specified value, DEC (12). At 883 and 884, if declination is not inside the limits DEC (12)−5 and DEC (12)+5, the UP or DOWN LED is illuminated. If both upper and lower limit conditions are met, the UP and DOWN indicators are turned off. At 886, status bit, DEC POS, is set true to indicate the declination angle is within limits.

At 887 and 889, the rotation angle (ROT) is compared to the current specified angle ROT (12). At 888 and 890, the LEFT or RIGHT indicators are activated if ROT is not within the specified limits ROT (12)–RDEL and ROTC (12)+RDEL. For example, when ROT is within limits, the LEFT and RIGHT LED are turned off, and a status bit, ROTPOS at 891, is set true to indicate the rotation angle is within limits. The path goes to Dwell Time 892.

Dwell Time

Reference is made to FIGS. 199A and 199B which are connected by 199L1. This segment of code sets and monitors the timer for dwell time. Another timer, referred to as the SHAKE timer is maintained to measure short excursions outside the window (e.g. 3 seconds). If the patient gets lost and the SHAKE timer times out, the dwell timer is reset at 899 so the cycle can be repeated until the proper dwell time is completed. The SHAKE timer is re-started when ROTPOS or DECPOS cease to be true.

When ROTPOS and DECPOS are true, a status bit, DWELL, is set true to indicate the dwell condition has been recognized. The STOP indicator is turned on and the dwell timer is started when the dwell condition is first recognized.

When the dwell interval is completed as detected by the dwell time-out test, the PATHNUM index is incremented to the next path, ROTPOS, DECPOS and DWELL are set to false and the STOP LED is turned off. If PATHNUM exceeds the pre-determined number of dwell states, then the procedure is finished and the COMPLETE segment is entered.

Referring again to FIGS. 199A, 199B, at 893 and 895 ROTPOS and DECPOS are determined whether they are true. If both are true, the user is in the desired position, the shake timer is reset at 897 and shaking is set equal to FALSE. If either ROT POS or DEC POS is false, the user has moved out of the limits for the dwell position. If this "out of limit" condition has been detected previously, the SHAKING bit is true. 894 tests this bit to determine if the condition has been recognized. If not, then the SHAKING bit is set to TRUE and the SHAKE TIMER is started in 896. If the condition has been recognized, flow is directed to 898. At 898 the SHAKE timer is tested for timeout. The timer for example may time out in 10 seconds. If it does time out, that means that the user is still out of position for an undesired time period and the Dwell Timer is reset at 899. If the user is in a dwell state (Dwell True at 900), the Dwell timer times out at 902 and the path number is incremented at 903. In addition at 903, the following parameters are set Stop LED=OFF; DEC POS=FALSE; ROTPOT=FALSE; DWELL=FALSE. At 905 a determination is made whether the Path number is greater than the number of paths. If true, the path goes to complete 906. If not true, the path goes back to operate 823. At 900, if the dwell state has not been detected, the path goes to 901 where the following parameters are set: Dwell=True; Stop=True; Start Dwell Timer, Stop LED=On. From 901 and 902 (if the dwell timer has not timed out), the path goes to 904 where the dwell timer is incremented and the path goes to OPERATE 823.

Complete

This segment has the sole purpose of indicating a successful completion of the procedure. All five of the LED are flashed at a one second period. The controller will continue in this loop until turned off, or one of the procedure buttons is activated. The procedures at 907–910 are Turn On All LED; Delay 0.5 second; Turn Off All LED; Delay 0.5 second respectively.

Referring to FIGS. 201–204, the goggles are identified at 921. FIG. 201 illustrates the view the user will have when the goggles are in place over his or her eyes. Member 923 depicts the system 800 of FIGS. 189A, 189B, 189C, 189D. Member 925 is a battery for supplying electrical power to the system 800. Four push button switches S2, S3, S4, and S5 are employed to control the system 800. Member 933 is a strap for use for securing the goggles to a person's head with the LEDs D1–D5 in front of one of the eyes of the person.

Electronic Embodiment

Electronic Embodiment Method

Diagnostic Method

Method to Use Device.

To diagnose right posterior semicircular canal BPPV.

Figures 206A, 206B:
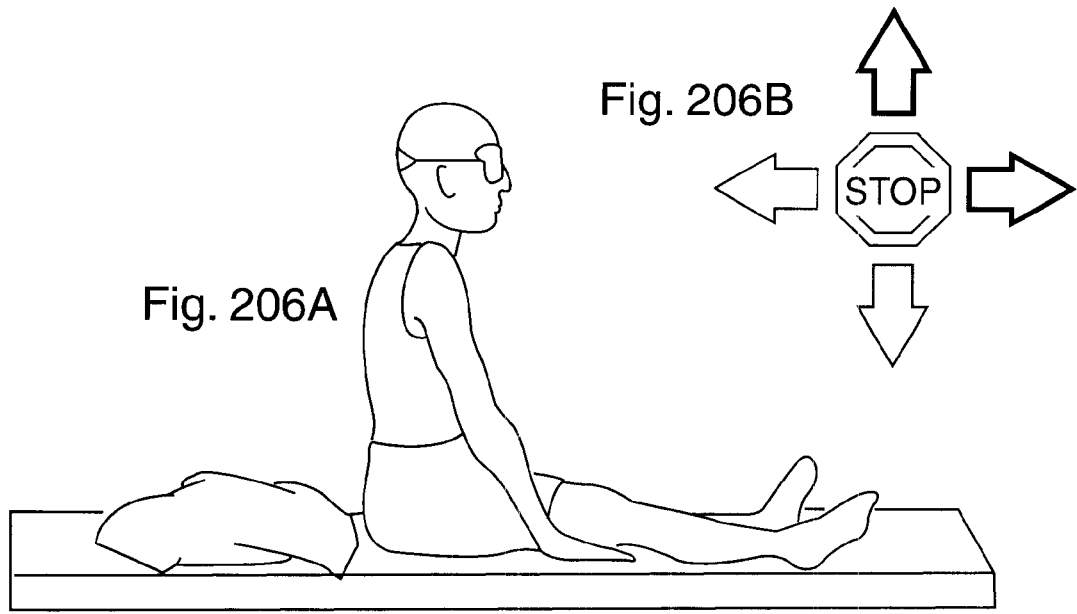
Figures 209A, 209B:
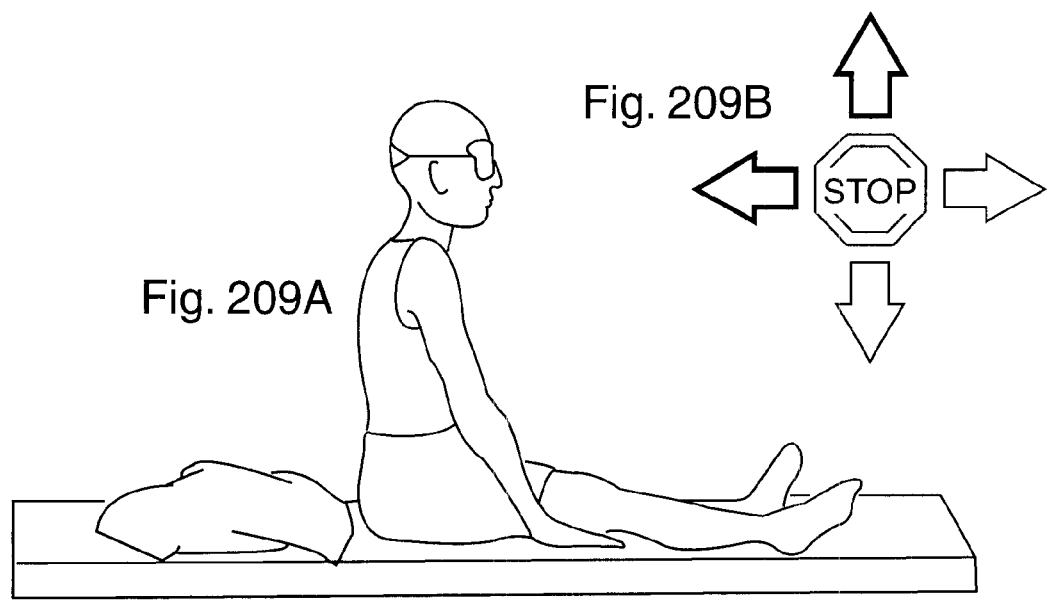

The user is instructed to sit on the floor and/or mat as shown in FIG. 206A and put the goggles 921 over his eyes in such a manner that the LED screen is clearly seen.

Figures 205A, 205B:
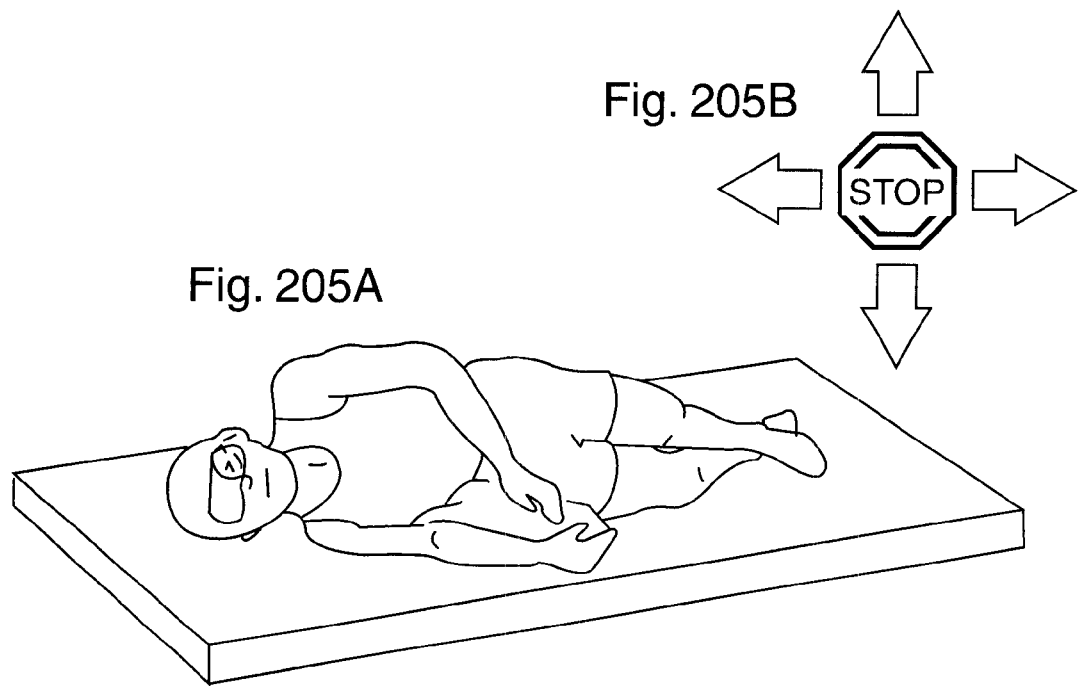

The user is instructed to lie supine in position "R", FIG. 205A.

The pillow is rolled lengthwise and used longitudinally under the spine from C5 to L1. The user is instructed to place the pillow on the mat behind him such that the pillow will be positioned under his upper thoracic spine (not under his shoulders). He is then instructed to push the center button S3 of the four goggle buttons. He is instructed to follow the head direction indicated by the LED arrows 206B. The up D1 and right D5 arrows will blink and the user will lie backward upon the pillow and floor. The user is to extend his neck until the up arrow D1 ceases flashing and he is instructed to turn his head to the right until the right arrow D5 ceases flashing. When both up and right arrows cease flashing, the "stop" indicator will light, FIG. 205B. The user is instructed to stay in this position until the stop indicator is no longer lighted (for 30 seconds).

After 30 seconds in the right Dix Hallpike position, FIG. 205A the down D3 and left D4 arrows will blink FIGS. 207A, 207B. The user will sit upward, flexing his neck and turning his head to the left until he reaches the sitting and forward looking position. When the user reaches the upright position, the downward flashing arrow will cease to flash and when the head is turned straight ahead, the left pointing arrow will cease to flash and the stop indicator D2 will light up FIG. 208B. The user is instructed to remain in the upright sitting position while the stop indicator is lighted and wait for his dizziness to resolve FIGS. 208A, 208B.

To diagnose the left posterior semicircular canal BPPV.

Figures 210A, 210B:
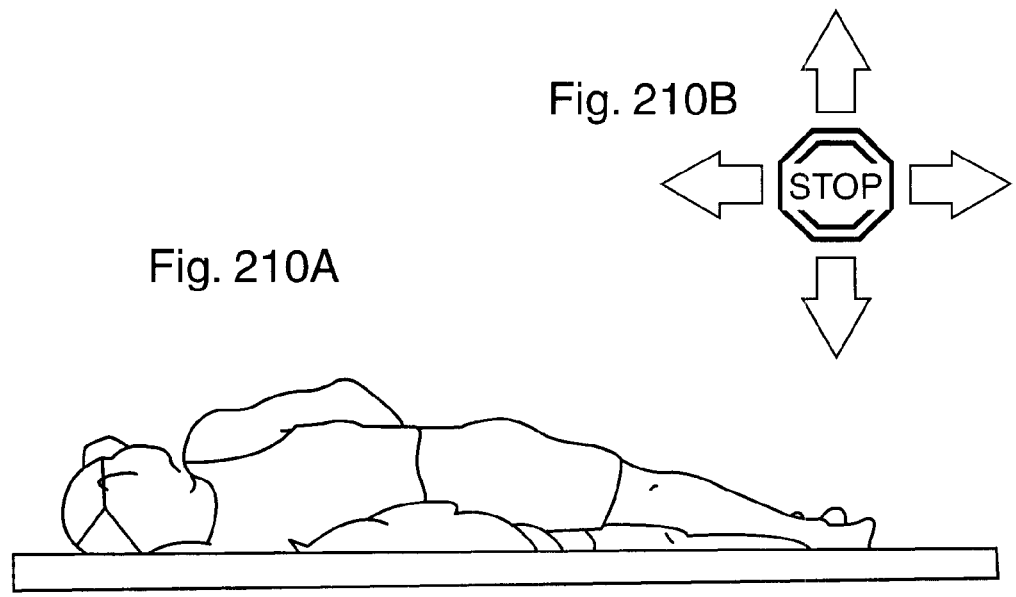
Figures 211A, 211B:
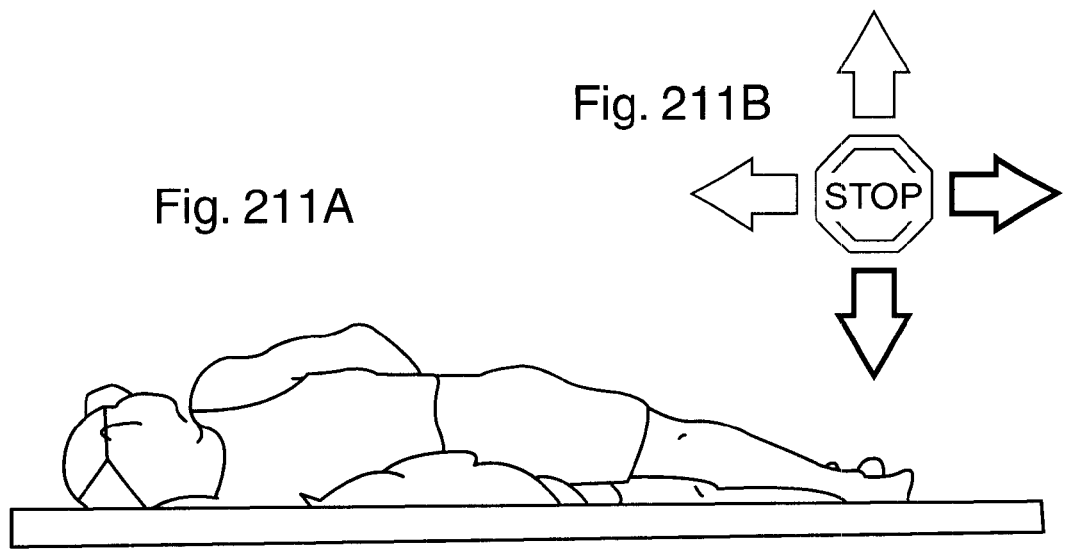
Figures 212A, 212B:
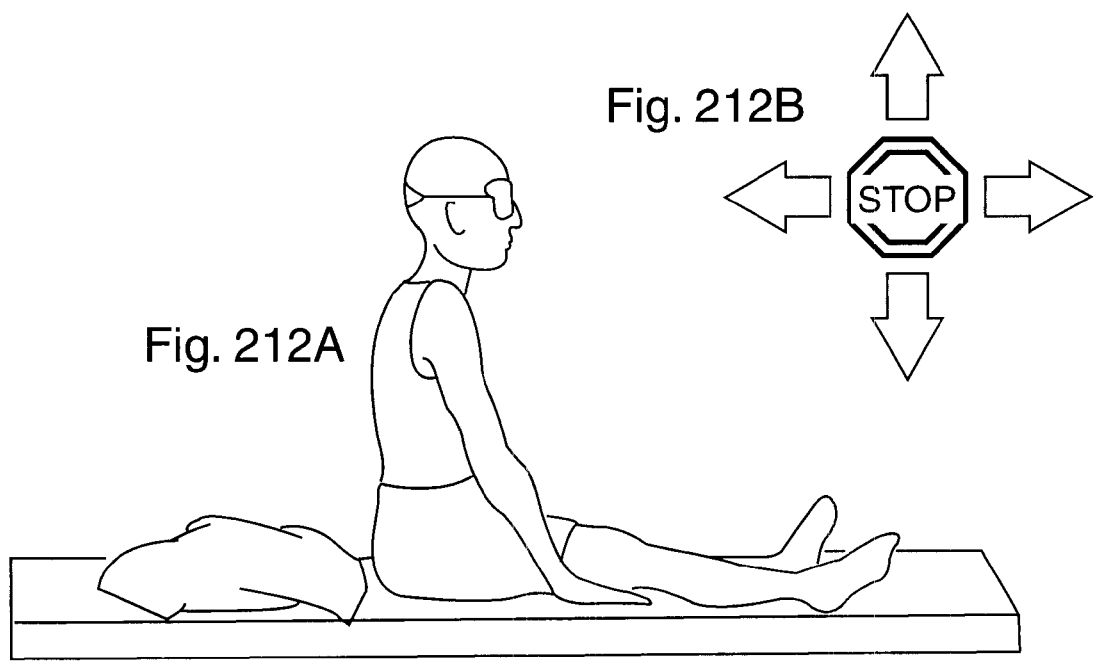

Lie supine in position "L", FIG. 210A.

The user will push the button S2. The up D1 and left D4 arrows will begin to blink, FIGS. 209A, 209B and the user will lie backward upon the pillow and floor. The user is to extend his neck until the up arrow ceases flashing and he is instructed to turn his head to the left until the left arrow ceases flashing. When both up and left arrows cease flashing, the "stop" indicator will light, FIG. 210B. After 30 seconds in the left Dix Hallpike position, FIGS. 210A and 210B, the down D3 and right D5 arrows will blink, FIGS. 211A, 211B. The user will sit upward, flexing his neck and turning his head to the right until he reaches the sitting and forward looking position. When the user reaches the upright position, the down flashing arrow will cease to flash and when the head is turned straight ahead the right pointing arrow will cease to flash and the stop indicator will light up. The user is instructed to remain in the upright sitting position and wait for his dizziness to resolve, FIGS. 212A, 212B. He is instructed to remove the goggles, wait 30 seconds or until his dizziness resolves.

The user is instructed to determine whether placing his head in the position such that the right ear is more downward, causes more dizziness than placing his head in the position such that the left ear is more downward. The ear downward position which causes the greatest symptoms of dizziness is the ear that is affected by the posterior semicircular canal BPPV.

Method for Posterior SCC BPPV Treatment

Treat Right Posterior SCC BPPV:

Sit on the Floor and/or mat with goggles over eyes FIG. 213A.

The user is instructed to sit on the floor or on a mat and put the goggles over his eyes in such a manner that the LED is clearly seen, FIG. 213A.

Lie supine in position number 1 (FIG. 214A).

Pillow is rolled lengthwise and placed longitudinally under the spine from C5 to L1. He is instructed to place a pillow on the mat behind him such that the pillow will be positioned under his upper thoracic spine (not under his shoulders). He is then instructed to push the right most of buttons S5. He is instructed to follow the head direction indicated by the LED arrows. The up D1 and right D5 arrows will blink, FIG. 213B, and the user will lie backward upon the pillow and floor. The user is to extend his neck until the up arrow ceases flashing and he is instructed to turn his head to the right until the right arrow ceases flashing. When both up and right arrows cease flashing, the "stop" indicator will light up, FIG. 214B. The user is instructed to stay in this position until the stop indicator is no longer lit (for 30 seconds), FIG. 214A.

Lie Supine in position number 2 FIG. 215A.

The user is instructed to follow the head direction indicated by the LED arrows, FIGS. 215A, 215B. The up D1 and left D5 arrows will blink and the user will turn his head to the left while keeping his neck extended. So long as the user keeps his neck extended enough that the head is extended equal to or more than 20 degrees below horizontal, the up arrow will not flash. The user is to extend his neck until the up arrow ceases flashing and he is instructed to turn his head to the left until the left arrow ceases flashing. When both up and left arrows cease flashing, the "stop" indicator will light up, FIGS. 216A, 216B. The user is instructed to stay in this position until the stop indicator is no longer lit (for 30 seconds), FIGS. 217A, 217B.

Lie on left side with head turned downward 135 degrees (FIG. 218A).

The user is instructed to follow the head direction indicated by the LED arrows, FIG. 217B. The up D1 and left D4 arrows will blink and the user will turn his head to the left while keeping his neck extended. So long as the user keeps his neck extended enough that the head is extended equal to or more than 20 degrees below horizontal, the up arrow will not flash. The user is to extend his neck until the up arrow ceases flashing and he is instructed to turn his head to the left until the left arrow ceases flashing. In order to follow the head position instructions given by the flashing light the user will roll onto his left side. When both up D1 and left D4 arrows cease flashing, the "stop" indicator will light up, FIGS. 218A, 218B. The user is instructed to stay in this position until the stop indicator is no longer lit (for 30 seconds), FIG. 218A.

Roll into crawl position FIG. 219A.

The user is instructed to keep his head in the position 3, FIG. 218A and roll his body toward the left side into a crawl position. The 4 LED directional arrows will prompt the user what direction his head must be moved to be kept in the constant position. He is instructed to remain in this position for thirty seconds or until any dizziness resolves, FIG. 219A.

Come up to a kneeling position FIG. 221A.

The user is instructed by the flashing up arrow FIG. 220B to raise his head and torso into the kneeling forward looking position and steady himself for thirty seconds or until the dizziness resolves, FIGS. 220A, 221A.

Either repeat or remove goggle. If the user was dizzy during the maneuver sequence, the user is now instructed to repeat the maneuver. If there was no dizziness during the maneuver sequence, the user is instructed to stop the maneuvers and remove the goggles.

Method for Posterior SCC BPPV Treatment

Treat Left Posterior SCC BPPV:

Sit on the Floor and/or mat with goggles over eyes FIG. 222A.

The user is instructed to sit on the floor or on a mat and put the goggles over his eyes in such a manner that the LED is clearly seen, FIG. 222A.

Figure 223A:
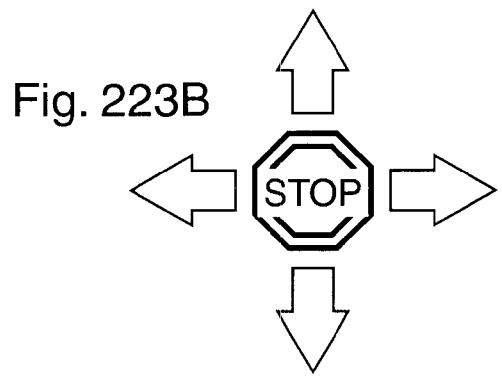
Figure 223B:
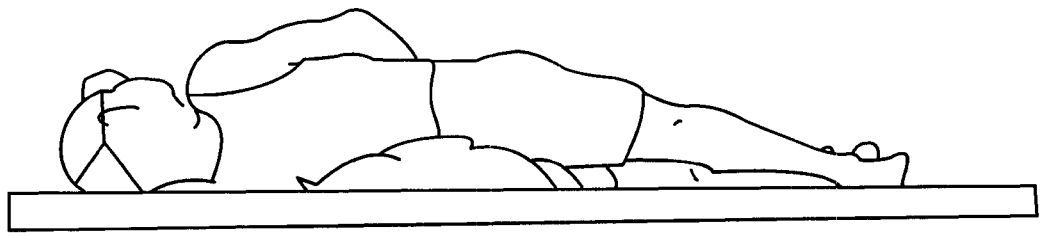

Lie supine in position number 1, FIG. 223A. Pillow is rolled lengthwise and placed longitudinally under the spine from C5 to L1. The user is instructed to place a pillow on the mat behind him such that the pillow will be positioned under his upper thoracic spine (not under his shoulders). He is then instructed to push the goggle button S4. He is instructed to follow the head direction indicated by the LED arrows. The up D1 and left D4 arrows will blink FIG. 222B and the user will lie backward upon the pillow and floor. The user is to extend his neck until the up arrow ceases flashing and he is instructed to turn his head to the left until the left arrow ceases flashing. When both up and left arrows cease flashing, the "stop" indicator will light up, FIGS. 223A, 223B. The user is instructed to stay in this position until the stop indicator is no longer lit (for 30 seconds), FIGS. 224A, 224B.

Lie Supine in position number 2 FIG. 226A.

Figure 224A:
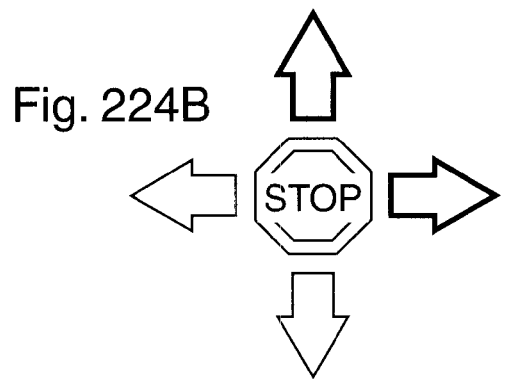
Figure 224B:
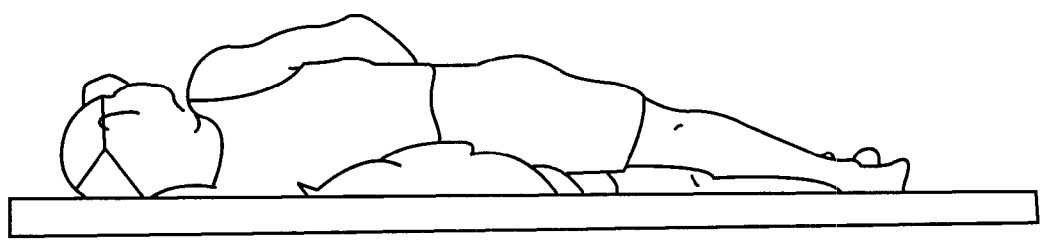
Figures 229A, 229B:
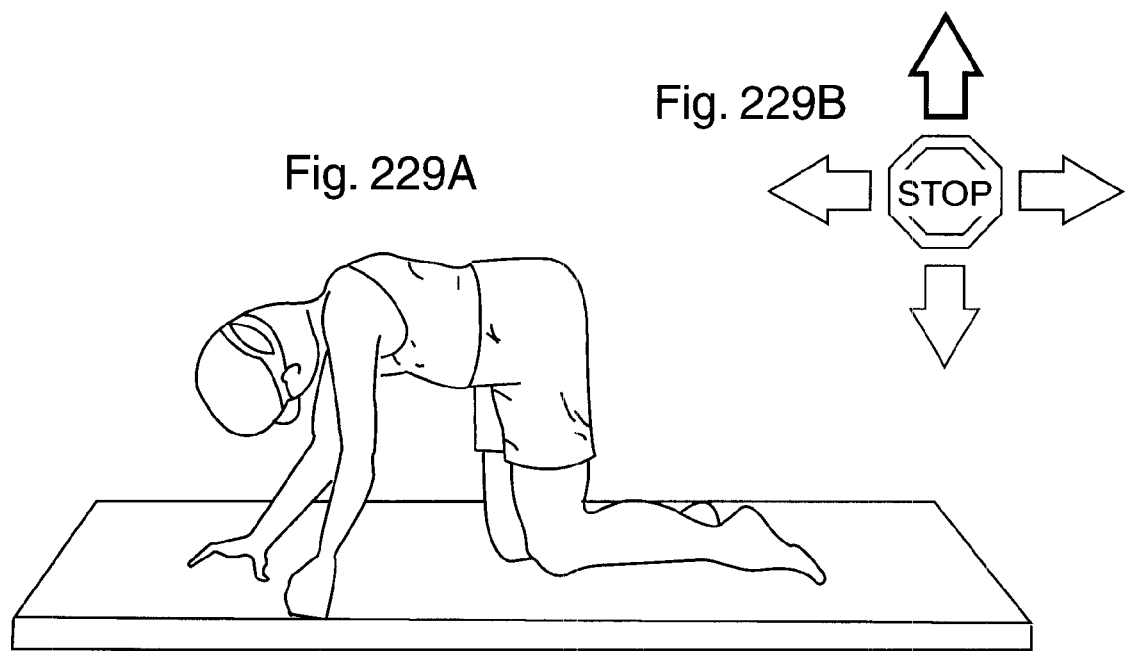

The user is instructed to follow the head direction indicated by the LED arrows, FIGS. 224A, 224B. The up D1 and right D5 arrows will blink and the user will turn his head to the right while keeping his neck extended. So long as the user keeps his neck extended enough that the head is extended equal to or more than 20 degrees below horizontal, the up arrow will not flash. The user is to extend his neck until the up arrow ceases flashing and he is instructed to turn his head to the right until the right arrow ceases flashing. When both up and right arrows cease flashing, the "stop" indicator will light up, FIGS. 225A, 225B. The user is instructed to stay in this position until the stop indicator is no longer lit (for 30 seconds), FIGS. 226A, 226B.

Lie on left side with head turned downward 135 degrees (FIG. 227A).

The user is instructed to follow the head direction indicated by the LED arrows, FIGS. 226A, 226B. The up D1 and right D5 arrows will blink and the user will turn his head to the right while keeping his neck extended. So long as the user keeps his neck extended enough that the head is extended equal to or more than. 20 degrees below horizontal, the up arrow will not flash. The user is to extend his neck until the up arrow ceases flashing and he is instructed to turn his head to the right until the right arrow ceases flashing. In order to follow the head position instructions given by the flashing light, the user will roll onto this right side. When both up and right arrows cease flashing, the "stop" indicator light up,. FIGS. 227A, 227B. The user is instructed to stay in this position until the stop indicator is no longer lit (for. 30 seconds).

Roll into crawl position FIG. 228A.

The user is instructed to keep his head in the position 3, FIGS. 227A, 227B and roll his body toward the right side into a crawl position. The 4 LED directional arrows will prompt the user what direction his head must be moved to be kept in the constant position. He is instructed to remain this position for thirty seconds or until any dizziness resolves, FIGS. 228A, 228B.

Figures 230A, 230B:
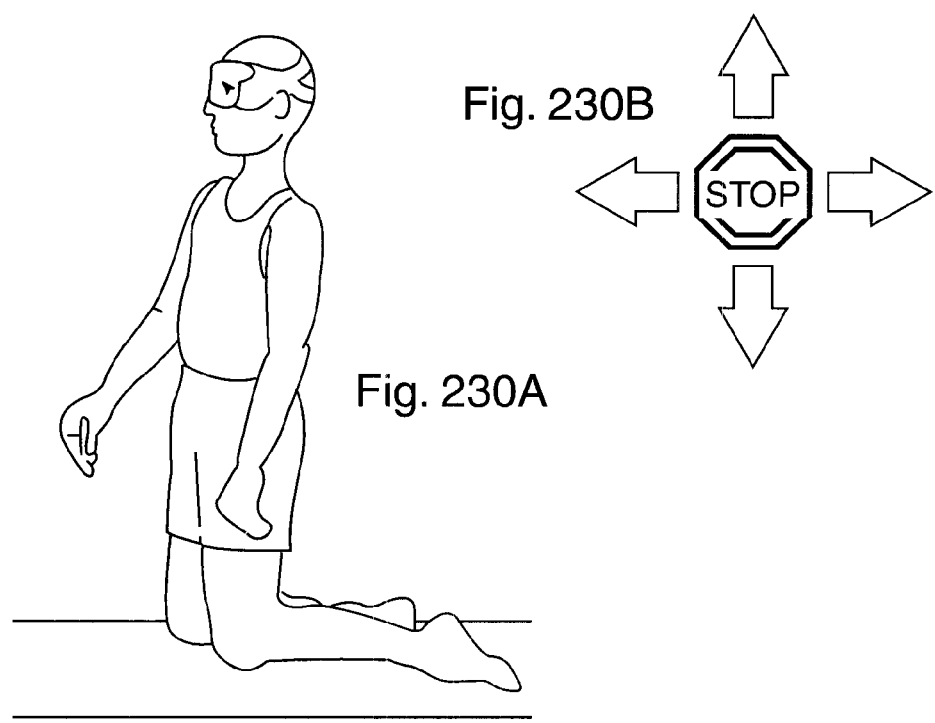

Come up to a kneeling position FIG. 230A.

The user is instructed by the flashing up arrow (FIGS. 229A, 229B) to raise his head and torso into the kneeling forward looking position and steady himself for thirty seconds or until the dizziness resolves, FIGS. 230A, 230B.

Either repeat or remove goggle. If the user was dizzy during the maneuver sequence, the user is now instructed to repeat the maneuver. If there was no dizziness during the maneuver sequence, the user is instructed to stop the maneuvers and remove the goggles.

Referring now to FIGS. 236–258 the devices shown therein are similar to the devices of FIGS. 1–26 but have been modified. In FIGS. 1–2 and 236–258, the same reference numerals shown therein identify the same components. The outer sphere 302M is the same as outer sphere 302 but the outer sphere 302M has observer markings on its outer surface. The inner sphere 305M is the same as the inner sphere 305 but has an observers position bulls eye 4 as described below.

The user sighting mark 306 of FIG. 236 is on the horizontal equator directly in the user's line of sight in all outer sphere versions. The outer sphere versions (302XRM, 302XLM, 302ZM) have additional outer sphere markings. The posterior BPPV outer sphere configurations as shown in FIGS. 236, 237, and 238. FIG. 236 shows an outer sphere from the user's point of view with the user's sighing mark 306 in the center of the user's line of sight. The observer sighting markings are all on the horizontal equator of the outer sphere when the user is in the sitting position. FIG. 238 shows FIGS. 236 from the point of view of arrows A—A. FIG. 238 shows a posterior BPPV outer sphere diagnostic configuration 302ZM. Transparent observers sighting markers 306.5L and 306.5R are shown in FIG. 238 on the horizontal equator. Marker 306.5L is 100 degrees to the right of the user's line of sight shown by the user's sighting mark 306. The observer sighting mark 306.5R is 190 degrees to the right of the user's line of sight.

The posterior BPPV treatment outer sphere configurations are shown in FIGS. 239 and 240. FIG. 239 shows the right posterior BPPV treatment outer sphere configuration viewed from superiorly as seen along arrows A—A in FIG. 236. The user sighting mark 306 is directly in the user's line of sight shown by the upward directed arrow at the bottom of the FIG. 239. The observer's sighting marks are all on the horizontal equator. The transparent observer's sighting mark 306XR1 is 100 degrees to the left of the user's point of view. The observer's transparent sighting mark 306XR2 is 190 degrees to the left of the user's line of sight. The observer's transparent sighting mark 306XR3 is 280 degrees to the left of the user's line of sight. The observer sighting marks are connected by a path 1071R. The path runs along the horizontal equator of the outer sphere from one observer sighting mark to the next. The path 1071R should stay aligned with the position bulls eye No. 4 as the user moves his head to move the outer sphere about the inner sphere during the right posterior BPPV treatment maneuver. During the right posterior BPPV treatment maneuver, position bulls eye No. 4 of the inner sphere should be seen by the observer within sighting mark 306XR1 (head position #1) for 30 seconds; as movement continues, then within sighting mark 306XR2 (head position #2) for 30 seconds; and as movement continue then within sighting mark 306XR3 (head position #3) for 30 seconds. The patient should then raise his torso from the crawl position to the kneeling position completing the Epley maneuver sequence.

FIG. 240 shows the left posterior BPPV treatment outer sphere configuration viewed from superior as seen along arrows A—A in FIG. 236. The user sighting mark 306 is directly in the user's line of sight shown by the upward directed arrow at the bottom of the FIG. 240. The observer's sighing marks are all on the horizontal equator. The observer's transparent sighting mark 306XL1 is 100 degrees to the right of the user's point of view. The observer's transparent sighting mark 306XL2 is 190 degrees to the right of the user's line of sight. The observer's transparent sighting mark 306XL3 is 280 degrees to the right of the user's line of sight. The observer sighting marks are connected by a path 1071L. The path runs along the horizontal equator of the outer sphere from one observer sighting mark to the next. The path 1071L should stay aligned with the position bulls eye No. 4 as the user moves this head to move the outer sphere about the inner sphere during the left position BPPV treatment maneuver. During the left posterior BPPV treatment maneuver, position bulls eye No. 4 of the inner sphere should be seen by the observer within 306XL1 (Head position #1) for 30 seconds; as movement continues, then within sighting mark 306XL2 (head position #2) for 30 seconds; and as movement continues, within the sighting mark 306XL3 (head position #3) for 30 seconds. The patient should then raise his torso from the crawl position to the kneeling position completing the Epley maneuver sequence.

Referring to FIGS. 241–246 and 249–256 within each outer sphere is an inner sphere 305M. The inner sphere is suspended in a liquid 303, water in the preferred embodiment, and is buoyancy neutral. The inner sphere has a weight 320, which maintains a vertical axis 305V in a vertical position. The inner sphere has an elongated bar magnet 390 which is a permanent magnet 390 located in the center of the sphere 305M. The axis 390A of the magnet 390 is located at an angle of 20 degrees relative to a horizontal axis 305H, which is perpendicular to axis 305V. The higher end of the magnet 390 is directed toward the side 305S upon which are located the position bulls eye No. 1 and No. 2.

The inner sphere has a numbered series of position bulls eyes 330 printed upon it and a path 315 from each position bulls eye to the next sequentially numbered position bulls eye for bulls eye positions 1, 2, and 3. The posterior BPPV treatment inner spheres each have a bulls eye No. 4 which is not connected to the other bulls eyes by the path 315. There are two types of position bulls eye configurations used on the inner sphere of the embodiment. The first is a posterior BPPV treatment configuration. The second is the BPPV diagnostic configuration. The inner spheres in these two embodiments are identified by reference numerals 305XM and 305ZM respectively.

The posterior BPPV treatment configuration is shown in FIGS. 249–256. FIG. 249 shows an inner sphere 305XM with the vertical equator 305VE upon it. FIG. 250 shows that in the right posterior SCC BPPV treatment configuration from the user's line of sight, the position bulls eye No. 1 is 45 degrees to the right of the user's line of sight (up pointing arrow at bottom of FIG. 250); position bulls eye No. 2 is 45 degrees to the left of the user's line of sight; and the No. 3 position bulls eye is 135 degrees to the left of the user's line of sight. The No. 4 position bulls eye is 215 degrees to the left of the user's line of sight. As seen in FIG. 251 bulls eyes No. 1 and No. 2 are 20 degrees from the vertical equator, and No. 3 and No. 4 are 20 degrees from the vertical equator, but in the opposite direction. These angles are determined by the equator and straight lines extended from the center of the inner sphere 305XM to the position bulls eyes No. 1, Nos. 2, No. 3, and No. 4. FIG. 252 illustrates the position bulls eyes No. 1, No. 2, No. 3 and No. 4 for the right posterior SCC BPPV treatment from the perspective of FIG. 249. FIG. 253 is a view of FIG. 252 as seen along lines 253—253 thereof. FIG. 253 illustrates the position bulls eyes No. 1, No. 2, No. 3, and No. 4 for the right posterior SCC BPPV treatment configuration. The inner sphere of FIGS. 252 and 253 for use for the right posterior SCC BPPV treatment is identified at 305XRM.

FIGS. 254 and 255 show the location of position bulls eyes No. 1, No. 2, No. 3, and No. 4 for the left posterior SCC BPPV treatment configuration. FIG. 254 illustrates the position bulls eye No. 1, No. 2, No. 3, and No. 4 for the left posterior SCC BPPV treatment configuration from the perspective of FIG. 249. FIG. 255 is a view of FIG. 254 as seen from lines 255—255 thereof and illustrates the position bulls eyes No. 1, No. 2, No. 3, and No. 4 for the left posterior SCC BPPV treatment configuration. The inner sphere of FIGS. 254 and 255 for use for the right posterior SCC BPPV treatment is identified at 305XLM.

The third position bulls eye configuration is the diagnostic configuration of FIGS. 257 and 258. These bulls eyes are located on an inner sphere 305ZM. Positions bulls eye "R" is in the same position as the right posterior SCC BPPV treatment position bulls eye No. 1, FIGS. 254 and 255. Position bull eye "L" is in the same position as the left posterior SCC BPPV treatment position bulls eye No. 2, FIGS. 254 and 255. Position bulls eye No. 4 is in the same position as position as the left posterior SCC BPPV treatment position bulls eye No. 4 FIGS. 254 and 255.

The device 400 for holding the modified sphere 305M of component 300 at the appropriate focal distance from the lens 410 is identified at 400 in FIG. 244 and is the same as the device of FIG. 6. The modification of the device 400 which includes the external magnet 215 is shown in FIGS. 245 and 246 and is the same as the device of FIGS. 7 and 8. The third component 500 which holds the combination of the second component 400 and the first component 300 in the front of the eye of the user is shown in FIGS. 247 and 248 and is the same as that shown in FIGS. 9 and 10.

For diagnostic purposes the outer sphere 302ZM will have the diagnostic inner sphere 305ZM located therein supported by the liquid 303. For treatment purposes, two outer spheres 302XLM and 302XRM will be provided, 302XLM having located therein the inner sphere 305XLM supported by the liquid 303; 302XRM having located therein the inner sphere 305XRM supported by the liquid 303. Each component 500 has two eye openings 500L and 500R for the left and right eyes. Each sphere combination (302ZM, 305ZM), (302XLM, 305XLM), (302XRM, 305XRM) will be separately coupled to a component 400 to form three different component combinations 400 (302ZM, 305ZM), 400 (302XLM, 305XLM), 400 (302XRM, 305XRM) each of which may be removably coupled to the left or right openings 500L or 500R of the goggles 500.

METHOD TO USE DEVICE

To diagnose right and left posterior semicircular canal BPPV. The user is instructed to follow the following procedure.

The user is instructed to sit on the floor and/or mat and put the goggles over his eyes in such a manner that the outer clear watertight sphere sighting mark 306 is clearly seen, as shown in FIG. 27. The diagnostic first component combination 400 (302ZM, 305ZM) is in place coupled to the desired eye opening of the goggles 500.

The user is instructed to lie supine in position "R", FIG. 28.

The pillow is rolled lengthwise and used longitudinally under the spine from C5 to L1. He is instructed to place the pillow on the mat behind him such that the pillow will be positioned under his upper thoracic spine (not under his shoulders). He is then instructed to lie backward upon the pillow and floor. The user is now instructed to find the positioning bulls eye "R", FIG. 257, 268, and position it within the user sighting mark 306. The observer looks at the surface of the outer sphere 302ZM at the observer sighting mark 306.5R. If the bulls eye No. 4 is not in the center of the sighting mark 306.5R the observer is to coach the user to attain the correct head position. He is to stay in this position for 30 seconds or until his dizziness resolves.

Sit on the floor and/or mat with goggles over the eyes, FIG. 27.

The user is instructed to return to the upright sitting position and wait for his dizziness to resolve.

Lie supine in position "L", FIG. 29.

The pillow is rolled lengthwise and placed longitudinally under the spine from C5 to L1. The user is instructed to place the pillow on the mat behind him such that the pillow will be positioned under his upper thoracic spine (not under his shoulders). He is instructed to lie backward upon the pillow and floor. The user is now instructed to find the position bulls eye "L" (FIGS. 25, 26) and position it within the user sighting marker 306. The observer looks at the surface of the outer sphere 302ZM at the observer sighting mark 306.51. If the bulls eye No. 4 is not in the center of the sighting mark 306.51 the observer is to coach the user to attain the correct head position. He is to stay in this position for 30 seconds or until his dizziness resolves.

Return to the sitting position, FIG. 27.

The user is instructed to sit upright. He is instructed to remove the goggles, wait 30 seconds or until his dizziness resolves. The user is instructed to determine whether placing his head in the position such that "R" is within the user sighting marking causes more dizziness than placing his head in the position such that "L" is within the user sighting mark. The position which causes the greatest symptoms of dizziness is the ear that is affected by the posterior semicircular canal BPPV.

METHOD FOR POSTERIOR SCC BPPV TREATMENT

Treat Right Posterior SCC BPPV:

Sit on the floor and/or mat with goggles over eyes (FIG. 30) using the component combination 400 (302XRM, 305XRM).

The user is instructed to sit on the floor or on a mat and put the goggles over his eyes in such a manner that the outer clear watertight ball user sighting mark 306 is clearly seen.

Lie supine in head position No. 1 (FIG. 31).

The pillow is rolled lengthwise and placed longitudinally under the spine from C5 to L1. The user is instructed to place a pillow on the mat behind him such that the pillow will be positioned under his upper thoracic spine (not under his shoulders). He then is instructed to lie backward upon the pillow and floor. The user is now instructed to find the positioning bulls eye No. 1 (FIGS. 252, 253) and position it within the user sighting marker 306 (head position No. 1). The observer is to note if the inner sphere position bulls eye No. 4 is in the center of the observer sighting mark 306XR1. If not, the observer is to coach the user to attain the correct head position. The user is to stay in this position for thirty seconds or until his dizziness resolves.

Lie supine in head position No. 2 (FIG. 32).

The user then moves his head such that the printed path 315 on the inner sphere is kept within the user sighting marking 306 and he moves his head until the No. 2 positioning bulls eye (FIG. 255) is seen within the user sighting marking 306 (head position no. 2). The observer is to note if the inner sphere position bulls eye No. 4 stays in the outer sphere path 1071R from 306XR1 to 306XR2. The observer is to note if inner sphere position bulls eye No. 4 is in the center of the observer sighting mark 306XR2. If not the observer is to coach the user to attain the correct head position. The user is instructed to stay in this position for thirty seconds or until the dizziness resolves.

Lie on left side with head turned downward 135 degrees (FIG. 33) (head position No. 3).

He now is instructed to roll upon his left side and simultaneously follow the printed path 315 within the user sighting marking 306 to the positioning bulls eye No.: 3 (FIGS. 254, 255) (head position No. 3). The observer is to note if the inner sphere position bulls eye No. 4 stays in the outer sphere path 1071R from 306XR2 to 306XR3. The observer is to note if inner sphere position bulls eye No. 4 is in the center of the observer sighting mark 306XR3. The user is instructed to remain in this position for thirty second or until the dizziness resolves.

Roll into crawl position (FIG. 34).

The user is instructed to keep his head in the head position 3 (FIGS. 254, 255) and roll toward the left side into a crawl position as shown in FIG. 34. The observer is to note if inner sphere position bulls eye No. 4 stays in the center of the observer sighting mark 306XR3 as the user rolls into the crawl position. The user is instructed to remain in this position for thirty second or until any dizziness resolves.

Come up to a kneeling position (FIG. 35).

The user is instructed to raise his torso into a kneeling position and steady himself for thirty seconds or until the dizziness resolves.

Either repeat the procedure or remove the goggles. If the user was dizzy during the positioning sequence, the user now is instructed to repeat the maneuver. If there was no dizziness during the maneuver sequence, the user is instructed to stop the maneuvers and remove the goggles.

Treat Left Posterior SCC BPPV:

Sit on the floor and/or mat with goggles over eyes (FIG. 36) using the component 400 (302XLM, 305XLM).

The user is instructed to sit on the floor or on a mat and put the goggles over his eyes in such a manner that the outer clear watertight ball user sighting mark is clearly seen.

Lie supine in head position No. 1 (FIG. 37).

The pillow is rolled lengthwise and place longitudinally under the spine from C5 to L1. The user is instructed to place a pillow on the mat behind him such that the pillow will be positioned under his upper thoracic spine (not under his shoulders). He then is instructed to lie backward upon the pillow and floor. The user now is instructed to find the positioning bulls eye No. 1 (FIGS. 254, 255) and position it within the user sighting marker (head position No. 1). The observer is to note if the inner sphere position bull eye No. 4 is in the center of the observer sighting mark 306XL1. If not the observer is to coach the user to attain the correct head position. The user is to stay in this position for thirty seconds or until his dizziness resolves.

Lie supine in head position No. 2 (FIG. 38).

The user then moves his head such that the printed path 315 on the inner sphere is kept within the user sighting marking 306 and he moves his head until the No. 2 positioning bulls eye (FIGS. 252, 253) is seen within the user sighting marking (head position No. 2). The observer is to note if the inner sphere position bulls eye No. 4 stays in the outer sphere path 1071L from 306XL1 to 306XL2. The observer is to note if inner sphere position bulls eye No. 4 is in the center of the observer sighting mark 306XL2. If not the observer is to coach the user to attain the correct head position. The user is instructed to stay in this position for thirty seconds or until the dizziness resolves.

Lie on right side with head turned downward 135 degrees (FIG. 39). Head position No. 3.

The user now is instructed to roll upon his right side simultaneously follow the printed path 315 within the user sighting marking 306 to the positioning bulls eye No. 3 (FIGS. 254, 255) (head position No. 3). The observer is to note if the inner sphere-position bulls eye No. 4 stays in the outer sphere path 1071L from 306XL2 to 306XL3. The observer is to note if inner sphere position bulls eye No. 4 is in the center of the observer sighting mark 306XL3. If not the observer is to coach the user to obtain the correct head position. The user is instructed to remain in this position for thirty seconds or until the dizziness resolves.

Roll into crawl position (FIG. 40).

The user is instructed to keep his head in the head position No. 3 (FIGS. 254, 255) and roll toward the right side into a crawl position, as shown in FIG. 40. The observer is to note if the inner sphere position bulls eye No. 4 stays in the center of the observer sighting mark 306XL3 as the user rolls into the crawl position. The user is instructed to remain in this position for thirty seconds or until any dizziness resolves, as shown in FIG. 40.

Come up to a kneeling position (FIG. 41).

The user is instructed to raise his torso into a kneeling position and steady himself for thirty seconds or until the dizziness resolves.

Either repeat the procedure or remove the goggles. If the user was dizzy during the positioning sequence, the user is now instructed to repeat the maneuver. If there was no dizziness during the positioning sequence, the user is instructed to stop the maneuvers and remove the goggles.

Referring now to FIG. 259, there will be described a monitor system of the system of FIGS. 189A, 189B, 189C, and 189D. The LED's D1, D2, D3, D4, and D5 are the same as those of FIGS. 189D and 201 which are mounted on the goggles 921 of FIGS. 201. Switches S1, S2, S3, S4, S5 will be provided in the leads L1, L2, L3, L4, and L5 respectively. Also provided are LED's D1M, D2M, D3M, D4M, and D5M which are coupled in parallel to LED's D1, D2, D3, D4, and D5 respectively by flexible leads L1M, L2M, L3M, L4M, and L5M. Thus when either one of D1, D2, D3, D4, D5 is on or off the parallel D1M, D2M, D3M, D4M, D5M will be on or off also. The LED's D1M, D2M, D3M, D4M, D5M are mounted on a support 1081 which may be supported on a desk or table for a care provider such as a physician or paramedic to monitor. The leads L1M, L2M, L3M, L4M, and L5M will be flexible and long enough such that they will not interfere with the head movement of the patient while the patient is carrying out the desire head movement. Leads L1M, L2M, L3M, L4M, and L5M have switches S1M, S2M, S3M, S4M, and S5M coupled therein. If switches S1, S2, S3, S4, S5 and S1M, S2M, S3M, S4M, S5M are closed, there will be feedback information to the patient and the same information presented to the care provider when the patient is performing the head maneuver. Thus the care provider can help the patient correctly perform the head positioning maneuvers. If switches S1, S2, S3, S4, S5 are closed and switches S1M, S2M, S3M, S4M, S5M are open, feedback information will be provided only to the patient. If switches S1, S2, S3, S4, S5 are open and switches S1M, S2M, S3M, S4M, S5M are closed, head positioning information will be provided only to the care provider whereby the care provider can monitor and instruct the patient in carrying out the positioning maneuvers.

References

1. Fife T: Recognition and Management of Horizontal Canal Benign Positional Vertigo. Am J Otolaryngology 19:345–351, 1998.
2. Takegoshi H, Ito K, Mizuno M, Mizutani J. Horizontal variant of benign paroxysmal positional vertigo. Equilibrium Research (Japan) 1996; 55: 12–9.
3. Brandt T, Daroff R., Physical Therapy for Benign Paroxysmal Positional Vertigo. Arch. Otolaryng 106: August, 1980, pp. 484–485.
4. Semont A, Freyss G, Vitte E. Curing BPPV with a liberatory maneuver. Adv. Otorhinolaryng 1988; 42:290–3.
5. Norre M. Rational of Rehabilitation Treatment for Vertigo. Am J Otol, 8:31–35, 198.
6. Norre M. Rehabilitation Treatment for Vertigo and Related Syndromes. CRC Critical Reviews of Physical Medicine, 2:101–120, 1990.
7. Norre M and Beckers, A. Vestibular Habituation Training. Specificity of Adequate Exercise. Arch Otolaryng Head Neck Surgery, 114:883–886, 1988.
8. Epley J. Caveats in particle repositioning for treatment of canalithiasis (BPPV), Operative Techniques in Otolaryngology-Head and Neck Surgery Vol. 8, No. 2 (June) 1997, pp. 68–76.
9. Epley J. The canalith repositioning procedure: For treatment of benign paroxysmal positional vertigo. Otolaryngology Head and Neck Surgery 107:3 September 1992, pp. 399–404.
10. Harvey S, Hain T, Adameic J. Modified Liberatory Maneuver: Effective Treatment for Benign Paroxysmal Positional Vertigo Laryngoscope 104 October, 1994, pp. 1206–1212.
11. Katsarkas A. Paroxysmal Positional Vertigo: An Overview and the deposits repositioning maneuver. Am J Otolaryngology 16:6, pp. 725–730.
12. Lempert T, Wosley C, Davies R, Gresty M, Bronstein A. Three hundred sixty-degree rotation of posterior semicircular canal for treatment of benign positional vertigo: A placebo-controlled trial. Neurology 49; September 97, pp, 729–33.
13. McClure J. Horizontal canal BPV. The Jour Otolaryng 14:130–135.
14. Nutti D, Vannucchi P, Pagnini O. Benign Paroxysmal Positional Vertigo of the Horizontal Canal: a form of canalithiasis with variable clinical features. J Vestib Res 1996;6: 176–84.
15. Herdman S. Treatment of Benign Paroxysmal Positional Vertigo. Physical Therapy 70:6 June 1990:381–388.
16. Jacobson G P, Newman C W. The development of the Dizziness Handicap Inventory. Arch Otolaryngol Head Neck Surg Vol 116, April 1990 pp 424–427.
17. Fielder H, Denholm S W, Lyons R A, Fielder C P. Measurement of health status in patients with vertigo. Clinics of Otolaryngology 1996; 21:122–126.
18. McKenna L, Hallam R S, Hinchcliffe R. Clinics of Otolaryngology 1991; 16:452–456. The problems of psychological disturbance in neurotology patients.
19. Goldberg D (1978). Manual of the General Health Questionnaire. National Foundation for Educational Research Slough (Apparently a British general health questionnaire).
20. Yardley L, Owen N, Nazareth I, Luxon L. The prevalence and presentation of dizziness in a general practice community sample of working age people. British Journal of General Practice 1998; 48:1131–1135.
21. Abu-Arafeh I, Russell G. Paroxysmal vertigo as a migraine equivalent in children: a population based study. The Journal Cephalgia 1995; 15:22–25. Oslo.
22. Honrubia V, Bell T S, Harris M R, Baloh R W, Fische L M. Quantitative evaluation of dizziness characteristics and impact on quality of life. American Journal of Otology 1996; 17:595–602.
23. Savundra P A, Sutherland R, Freeman J, Carter J, Coelho A, Davies R A, Luxon L N. Cawthome-Cooksey exercises in relaxation therapy in the management of vertigo due to labyrinthine dysfunction. Journal of Audiology and Medicine in Press 1997.
24. Busis S. Neurotologic diagnoses. Acta Otolaryngologica (Stockholm). Supplement 209, 1965. (FAX'ed req to cpy whole thing on Nov. 29, 1999 to circ desk).
25. Sheehy J L. The dizzy patient. Archives of Otolaryngol 1967; 86:44–45.
26. Mira E, Buizza A, Magenes G, Manfrin M, Schmid R. Expert systems as a diagnostic aid in otoneurology. Otorhinolaryngology (Journal for Oto-Rhino-Laryngology and Its Related Specialties.) 1990; 52:96–103.
27. Mira E, Schmid R. Zanocco P, et al: Nouveaux supports informatises a l'exploration de la fonction vestibulaire. II. Un systeme expert pour la classification des vertiges. Acta Oto-Rhino-Laryng Belg 1987; 41:1010–1020.
28. Schmid R, Zanocco P, Buizza A, et al: An Expert system for the classification of dizziness and vertigo; in Fox J, Fieschi M, Engelbrecht R (eds): AIME 87, Lecture Notes in Medical Informatics, Berlin, Springer, 1987, vol 33, pp 45–53.
29. Mira E, Schmidt R, Zanocco P, Buizza A, Magenes G, Manfrin M. A computer based consultation system (Expert system) for the classification and diagnosis of dizziness. Advances in Oto-Rhino-Laryngology 1988; 42:77–80.
30. Auramo Y, Juloha M, Pyykko I. The expert system for the computer aided diagnosis of dizziness and vertigo. Medical Informatics 1993; 18, #4:293–305.
31. Kentala E, Pyykko Y, Auramo Y, Juhola M. Reasoning in Expert System ONE for Vertigo Work Up. Acta Otolaryngol (Stockh) 1995; Suppl 520; 207–208.
32. Kentala E. Characteristics of Six Otologic Diseases Involving Vertigo. Am J Otol. 1996; 17:883–892.
33. Gavilan C, Gallegro J, Gavilan J. 1990, Carrusel: An expert system for vestibular disorders. Acta Otolaryngologica, 110, 161–167. (ask Linda at TCOM interlibrary loans to reorder on Nov. 29, 1999).

I claim:

1. A method of performing a statistical determination as to whether a person has benign paroxysmal positional vertigo of any of the semicircular canals based upon answers provided by a person to questions stored in a central computer systems located at a distance spaced from said person comprising the steps of:

carrying out communication by said person to access said central computer system to obtain said questions stored in said central computer system, communicating said questions to said person, answering said questions and communicating said answered questions to said central computer system, evaluating the answers to said questions and determining the percentage chance that said person has benign paroxysmal positional vertigo of any of the semicircular canals, communicating to said person, the percentage chance that said person has benign paroxysmal positional vertigo which would be responsive to canalith repositioning maneuvers directed to any of the semicircular canals, if it is determined that said person would be responsive to canalith repositioning maneuvers, based on said percentage chance, communicating to said person an offer to sell to said person an apparatus which will guide the head positioning of said person to allow the diagnosis of which membranous semicircular canal is involved if said answers do not indicate the involved membranous canal.

2. A method of performing a statistical determination as to whether a person has benign paroxysmal positional vertigo of any of the semicircular canals based upon answers provided by a person to questions stored in a central computer systems located at a distance spaced from said person comprising the steps of:

carrying out communication by said person to access said central computer system to obtain said questions stored in said central computer system, communicating said questions to said person, answering said questions and communicating said answered questions to said central computer system, evaluating the answers to said questions and determining the percentage chance that said person has benign paroxysmal positional vertigo of any of the semicircular canals, communicating to said person, the percentage chance that said person has benign paroxysmal positional vertigo, which would be responsive to canalith repositioning maneuvers directed to any of the semicircular canals, if it is determined that said person would be responsive to canalith repositioning maneuvers, based on said percentage chance, communicating to said person an offer to sell to said person an apparatus which will guide the head positioning of said person through canalith repositioning maneuvers directed to the removal of otoconia from the involved membranous semicircular canal.

3. A method of performing a statistical determination as to whether a person has benign paroxysmal positional vertigo of any of the semicircular canals based upon answers provided by a person to questions stored in a central computer systems located at a distance spaced from said person comprising the steps of:

carrying out communication by said person to access said central computer system to obtain said questions stored in said central computer system, communicating said questions to said person, answering said questions and communicating said answered questions to said central computer system, evaluating the answers to said questions and determining the percentage chance that said person has benign paroxysmal positional vertigo of any of the semicircular canals, communicating to said person, the percentage chance that said person has benign paroxysmal positional vertigo which would be responsive to canalith repositioning maneuvers directed to any of the semicircular canals, if it is determined that said person would be responsive to canalith repositioning maneuvers, based on said percentage chance, communicating to said person an offer to sell to said person an apparatus which will guide the head positioning of said person to allow the diagnosis of which membranous semicircular canal is involved if said answers do not indicate the involved membranous canal and an apparatus which will guide the head of said person through canalith repositioning maneuvers directed to the removal of otoconia from the involved membranous semicircular canal.

4. The method of claim 1, wherein:

if said person wishes to purchase said apparatus, arranging for payment of said apparatus by said person and arranging for the shipment of said apparatus to said person.

5. The method of claim 2, wherein:

if said person wishes to purchase said apparatus, arranging for payment of said apparatus by said person and arranging for the shipment of said apparatus to said person.

6. The method of claim 3, wherein:

if said person wishes to purchase said apparatus, arranging for payment of said apparatus by said person and arranging for the shipment of said apparatus to said person.

7. The method of any of claims 1, 2, 3, 4, 5, or 6, wherein:

said person has access to a user computer wherein, said communications by said person with said central computer system are carried out with the aid of said user computer.

8. The method of any of claims 4, 5, or 6, wherein:

said person has access to a user computer wherein, said communications by said person with said central computer system are carried out with the aid of said user computer, arrangements for payment of said apparatus by said person and arrangements for shipment of said apparatus to said person are carried with the aid of a distributor computer.

9. The method of any of claims 1, 2, 3, 4, 5, or 6, wherein:

said person has access to a user computer wherein said communications by said person with said central computer system are carried out with the aid of said user computer and said communications between said user computer and said central computer system are carried out by the use of internet connections.

10. A system for performing a statistical determination of the percentage chance as to whether a person has benign paroxysmal positional vertigo of any of the semicircular canals, comprising:

a computer having a storage system, a computer program stored in said storage system including a series of questions pertinent to benign paroxysmal positional vertigo and which are accessible by a person and which are to be answered by a person, said computer program includes means for analyzing the answers provided by the person and for communicating to the person the percentage- chance that the person has benign paroxysmal positional vertigo, and an apparatus which will guide the head positioning of said person to allow the diagnosis of which membranous semicircular canal is involved if said answers do not indicate the involved membranous canal.

11. The system of claim 10, wherein said apparatus comprises:

a hollow outer housing having a sighting mark thereon, an inner member and a liquid located in said outer housing with said liquid supporting said inner member such that said outer housing can move relative said inner member, a left indicia and a right indicia formed on said inner member at spaced apart positions, a support means having first and second opposite ends, said second end of said support means being coupled to said outer housing such that said sighting mark can be seen from said first end of said support means, means for coupling said support means to a persons head next to an eye of the person to allow the person to see said sighting mark and to move said outer housing with the persons head to allow the person to see each of said indicia at different positions of the person's head.

12. A system for performing a statistical determination of the percentage chance as to whether a person has benign paroxysmal positional vertigo of any of the semicircular canals, comprising:

a computer having a storage system, a computer program stored in said storage system including a series of questions pertinent to benign paroxysmal positional vertigo and which are accessible by a person and which are to be answered by a person, said computer program includes means for analyzing the answers provided by the person and for communicating to the person the percentage chance that the person has benign paroxysmal positional vertigo, and an apparatus which will guide the head positioning of said person to allow the resolution of benign paroxysmal positional vertigo.

13. The system of claim 10, comprising:

an apparatus which will guide the head of said person through canalith repositioning maneuvers directed to the removal of otoconia from the involved membranous semi-circular canal.

14. A system for performing a statistical determination of the percentage chance as to whether a person has benign paroxysmal positional vertigo of any of the semicircular canals, comprising:

a computer having a storage system, a computer program stored in said storage system including a series of questions pertinent to benign paroxysmal positional vertigo and which are accessible by a person and which are to be answered by a person, said computer program includes means for analyzing the answers provided by the person and for communicating to the person the percentage chance that the person has benign paroxysmal positional vertigo, and an apparatus which will guide the head of said person through canalith repositioning maneuvers directed to the removal of otoconia from the involved membranous semi-circular canal.

\* \* \* \* \*